United States Patent
Barbas, III et al.

(10) Patent No.: US 8,765,920 B2
(45) Date of Patent: Jul. 1, 2014

(54) TYROSINE BIOCONJUGATION THROUGH AQUEOUS ENE-LIKE REACTIONS

(75) Inventors: Carlos F. Barbas, III, Solana Beach, CA (US); Hitoshi Ban, Atagoyama (JP); Julia Gavrilyuk, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/518,353

(22) PCT Filed: Dec. 23, 2010

(86) PCT No.: PCT/US2010/062101
§ 371 (c)(1),
(2), (4) Date: Jul. 30, 2012

(87) PCT Pub. No.: WO2011/079315
PCT Pub. Date: Jun. 30, 2011

(65) Prior Publication Data
US 2012/0289682 A1    Nov. 15, 2012

Related U.S. Application Data

(60) Provisional application No. 61/289,979, filed on Dec. 23, 2009.

(51) Int. Cl.
*C07K 16/00*  (2006.01)
*C12P 21/08*  (2006.01)
*C07D 249/00* (2006.01)

(52) U.S. Cl.
CPC .................................. *C07D 249/00* (2013.01)
USPC ..................... 530/409; 530/391.3; 530/391.7; 548/363.4; 548/363.6

(58) Field of Classification Search
CPC .................................................... C07D 249/00
See application file for complete search history.

(56) References Cited

U.S. PATENT DOCUMENTS

| 3,141,023 A | 7/1964 | Bousquet |
| 2004/0115207 A1 | 6/2004 | Irwin et al. |

FOREIGN PATENT DOCUMENTS

| JP | 4 005287 A | 1/1992 |
| WO | WO 01/85685 A1 | 11/2001 |
| WO | WO 2007/141389 A1 | 12/2007 |
| WO | WO 2008/134761 A2 | 11/2008 |

OTHER PUBLICATIONS

Baran et al., Org. Lett., vol. 5, No. 11, 2003, also in the ISR of the ISA dated Jun. 21, 2012.*
Kinart et al., Catalysis Letters vol. 103, Nos. 3-4, Oct. 2005. As in the IDS dated Sep. 18, 2013.*
Ayers et al., "Effector-Sensitive Cross-Linking of Phosphorylase *b* Kinase by the Novel Cross-Linker 4-Phenyl-1,2,4-Triazoline-3,5-Dione," *Biochem. J.* (1998), 331:137-141.
Baran et al., "The First Method for Protection-Deprotection of the Indole 2,3-π. Bond," *Org. Lett.* (2003), 5(11):1999-2001, American Chemical Society.
Gao et al., "Regio- and Diastereoselective Ene Reaction of 4-Phenyl-1,2,4-triazoline-3,5-dione with Chiral Allylic Alcohols and their Derivatives," *J. Org. Chem.* (1999), 64:2194-2201, American Chemical Society.
Joshi et al., "A Three-Component Mannich-Type Reaction for Selective Tyrosine Bioconjugation," *J Am. Chem. Soc.* (2004), 126:15942-15943, American Chemical Society.
Mallakpour et al., "A Novel One-pot Synthesis of 4-Substituted 1,2,4-Triazolidine-3,5-Diones", *Synlett* (2007), 8:1255-1256.

(Continued)

*Primary Examiner* — Marcela M Cordero Garcia
*Assistant Examiner* — Kaipeen Yang
(74) *Attorney, Agent, or Firm* — DLA Piper LLP (US)

(57) ABSTRACT

A new and versatile class of cyclic diazodicarboxamides that reacts efficiently and selectively with phenols and the phenolic side chain of tyrosine through an Ene-like reaction is reported. This mild aqueous tyrosine ligation reaction works over a broad pH range and expands the repertoire of aqueous chemistries available for small molecule, peptide, and protein modification. The tyrosine ligation reactions are shown to be compatible with the labeling of native enzymes and antibodies in buffered aqueous solution. This reaction provides a novel synthetic approach to bispecific antibodies. This reaction will find broad utility in peptide and protein chemistry and in the chemistry of phenol-containing compounds.

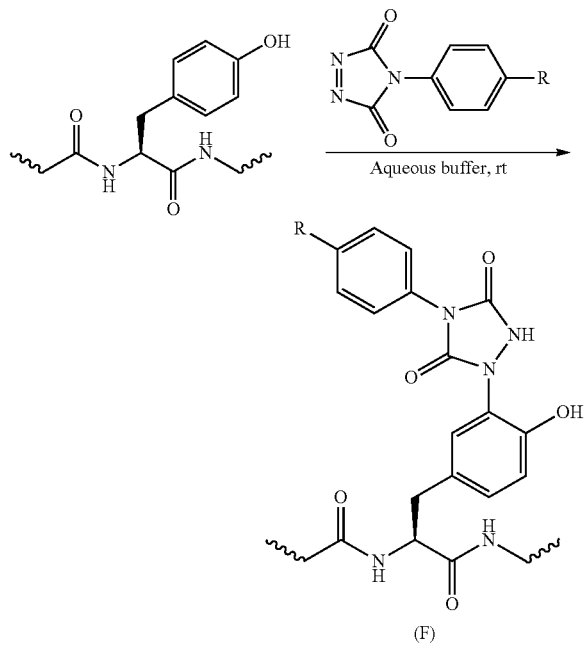

8 Claims, 23 Drawing Sheets

(56) References Cited

OTHER PUBLICATIONS

Bausch et al., "Proton, Electron, and Hydrogen Atom Transfers from Ions, Radicals, and Radical Ions Derived from Substituted Urazoles and Triazolinediones", *J. Org Chem*, (1992), 57(4):1118-1124.

Nifontov et al., "Interaction of Aromatic Diazo Derivatives with N-Acetyltyrosine Methylamide", *Khimiko-Farmatsevticheskii Zhurnal*, (1990), 24(8):53-55.

Luisada-Opper et al., "Azoproteins IV The Coupling Reaction of p-diazobenzoic Acid and its Methyl Ester with Native and with Urea-Treated Bovine Serum Albumin", *J.Bio Chem*, (1963), 238:143-145.

Kinart et al., "Studies on the Catalysis by Lithium Perchlorate of Reactions of Aromatic Amines with Diethyl Azodicarboxylate and Naphthalen-2-ol with 4-Phenyl-1,2,4-Triazoline-3,5-Dione", *Catalysis Letters*. (2005). 103(3-4):185-189.

Theis et al., "Diazo Compounds and Azides. LII. Stable Azomethine Imine Dipoles from Diazo Compounds and 3H-1,2,4-Triazole-3,5(4H)-Diones", *Chemische Berichte*, (1985), 118(1):28-41.

European Search Report (ESR) from application No. 10840202.5 (Aug. 13, 2013).

* cited by examiner

TYROSINE BIOCONJUGATION THROUGH AQUEOUS ENE-LIKE REACTIONS

CROSS-REFERENCE TO RELATED APPLICATIONS

This application is a 35 USC §371 National Stage application of International Application No. PCT/US2010/062101 filed Dec. 23, 2010, now pending; which claims the benefit under 35 USC §119(e) to U.S. Application Ser. No. 61/289,979 filed Dec. 23, 2009. The disclosure of each of the prior applications is considered part of and is incorporated by reference in the disclosure of this application.

FIELD OF THE DISCLOSURE

The present disclosure generally relates to the field of bioconjugation of proteins, and particularly, to methods for bioconjugating tyrosine residues through an aqueous Ene-like reaction.

BACKGROUND OF THE DISCLOSURE

Bioconjugation is the process of coupling two biomolecules together in a covalent linkage. Common types of bioconjugation chemistry are amine coupling of lysine amino acid residues (typically through amine-reactive succinimidyl esters), sulfhydryl coupling of cysteine residues (via a sulfhydryl-reactive maleimide), and photochemically initiated free radical reactions, which have broader reactivity. The product of a bioconjugation reaction is a bioconjugate. The most common bioconjugations are coupling of a small molecule (such as biotin or a fluorescent dye) to a protein, or protein-protein conjugations, such as the coupling of an antibody to an enzyme. Other less common molecules used in bioconjugation are oligosaccharides, nucleic acids, synthetic polymers such as polyethylene glycol (a.k.a. PEG a.k.a. polyethylene oxide) and carbon nanotubes.

Bioconjugation methods rely heavily on chemoselective modification of native protein functional groups. Lysine and cysteine side chains are the most commonly functionalized amino acids. However, the high abundance of lysine on protein surfaces makes site-specific modification challenging. In contrast, cysteines are rare and are most often found in disulfide linked pairs in proteins in their natural environment. Labeling at this amino acid typically requires reduction of the target disulfide followed by reaction with a reagent like maleimide. Recently significant attention has been paid to the bioorthogonal modification of the aromatic amino acid side chains of tryptophan and tyrosine. Tyrosine modification in mild, biocompatible, metal-free conditions has been studied using Mannich-type additions to imines. These modifications, however, are subject to retro-Mannich type reactions. Therefore, there remains a need in the art for new methods for bioconjugation by modifying tyrosine residues in proteins.

SUMMARY OF THE DISCLOSURE

The disclosure provides an orthogonal bioconjugation strategy based on modifying tyrosine residues in peptides and proteins. This strategy is based on the reactivity of diazodicarboxylate-related molecules and tyrosine through an efficient aqueous Ene-like reaction. This new and efficient tyrosine ligation reaction and its utility in the preparation of small molecule, peptide, enzyme, and antibody conjugates is provided herein.

In one embodiment the disclosure provides compounds having Formula I:

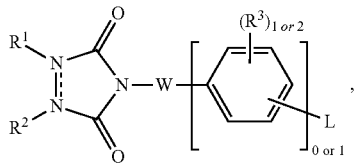

or a pharmaceutically acceptable salt thereof, wherein:
$R^1$ and $R^2$ are each H when

is a single bond, and $R^1$ and $R^2$ are each absent when

is a double bond;
W is independently a direct bond or is O;
$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3's}$ form a cyclic or heterocyclic ring, wherein each $R^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;
L is independently H, $N_3$, $CH_3$, C≡CH, C≡CHN$_3$, CH=CHN$_3$, $CH_2CH_2N_3$, $O(CH_2)N_3$, $C_6H_5$, $COCH_3$, $OCH_2C$=CH, $OCH_2COCH_3$, $OCOCF_3$, or X—[$CH_2CH_2$—Y]$_n$—(CH$_2$)$_q$—N$_3$;
X and Y are each independently $CH_2$, O, NH, S, NHCO or CONH; and
n and q are each independently an integer from 0 to 12.

In another embodiment the disclosure provides compounds having Formula IX:

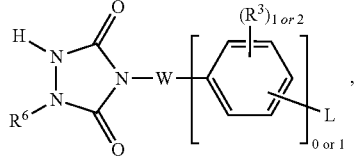

or a pharmaceutically acceptable salt thereof, wherein:
W is independently a direct bond or is O;
$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3's}$ form a cyclic or heterocyclic ring, wherein each $R^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;
L is independently H, $N_3$, $CH_3$, C≡CH, C≡CHN$_3$, CH=CHN$_3$, $CH_2CH_2N_3$, $O(CH_2)N_3$, $C_6H_5$, $COCH_3$, $OCH_2C$=CH, $OCH_2COCH_3$, $OCOCF_3$, or X—[$CH_2CH_2$—Y]$_n$—(CH$_2$)$_q$—N$_3$;

X and Y are each independently CH$_2$, O, NH, S, NHCO or CONH;

n and q are each independently an integer from 0 to 12; and

R$^6$ is a tyrosine moiety or a tyrosine residue in a peptide or a protein.

In another embodiment the disclosure provides compounds having Formula IX, wherein the tyrosine moiety is N-acyl tyrosine methylamide, or H-Gly-Gly-Tyr-OH; and the tyrosine residue in a peptide or a protein is in Chymotrypsinogen A, Myoglobin, Bovine Serum Albumin (BSA), or toci-noic acid.

In another embodiment the disclosure provides methods for chemoselectively modifying a moiety containing the amino acid tyrosine by reacting a compound of Formula X with a compound of Formula XI to provide a compound of Formula XII, thereby modifying the moiety containing the amino acid tyrosine:

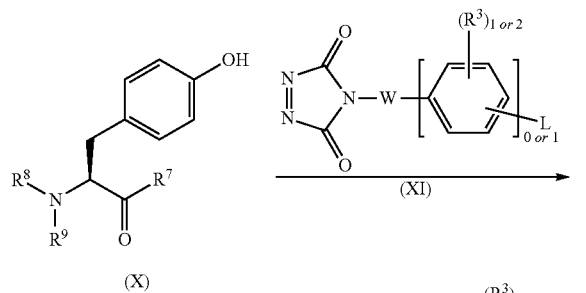

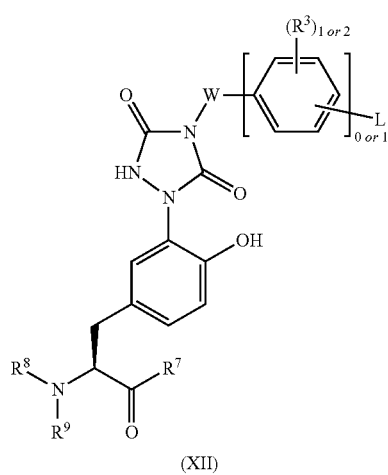

wherein:

W is independently a direct bond or is O;

R$^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two R$^{3's}$ form a cyclic or heterocyclic ring, wherein each R$^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, N$_3$, CH$_3$, C≡CH, C≡CHN$_3$, CH=CHN$_3$, CH$_2$CH$_2$N$_3$, O(CH$_2$)N$_3$, C$_6$H$_5$, COCH$_3$, OCH$_2$C≡CH, OCH$_2$COCH$_3$, OCOCF$_3$, or X—[CH$_2$CH$_2$—Y]$_n$—(CH$_2$)$_q$—N$_3$;

X and Y are each independently CH$_2$, O, NH, S, NHCO or CONH;

n and q are each independently an integer from 0 to 12;

R$^7$, R$^8$ and R$^9$ are each independently hydrogen, hydroxyl, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy, substituted or unsubstituted alkylaryl, substituted or unsubstituted alkylheteroaryl, or R$^7$, R$^8$ and R$^9$ are in a tyrosine residue of a peptide or a protein.

In another embodiment the disclosure provides methods for producing a herceptin antibody with binding specificity for ErbB-2 and integrin αvβ3 by:

a) cyclizing a compound of Formula XX with a cyclic RGD peptide of Formula XXI to form a 1,4-triazole compound of Formula XXII;

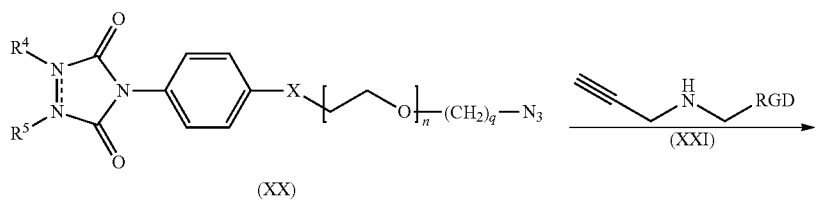

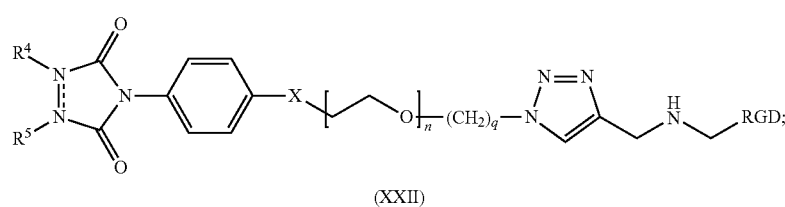

b) converting the

single bond in the compound of Formula XXII to a

double bond to provide a compound of Formula XXIII:

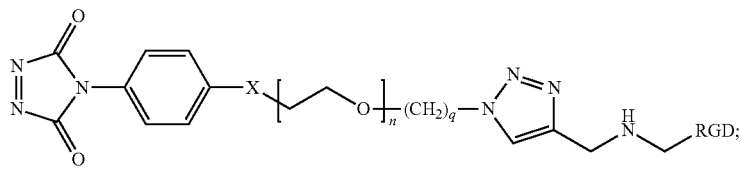

(XXIII)

c) conjugating the compound of Formula XXIII with Herceptin to provide the Herceptin antibody of Formula XXIV:

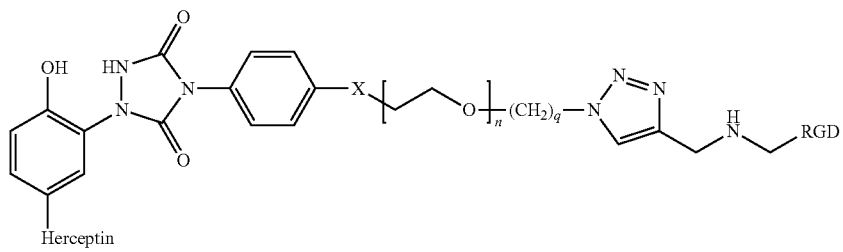

(XXIV)

wherein:
X and Y are each independently $CH_2$, O, NH, S, NHCO or CONH; and n and q are each independently an integer from 0 to 12; wherein the compound of Formula XXIV has binding specificity for ErbB-2 and integrin $\alpha v\beta 3$.

In another embodiment the disclosure provides methods for producing a multi-specific antibody with binding specificity for binding peptides, polypeptides, and organic compounds by:

a) cyclizing a compound of Formula XX with a peptide of Formula XXV to form a 1,4-triazole compound of Formula XXVI;

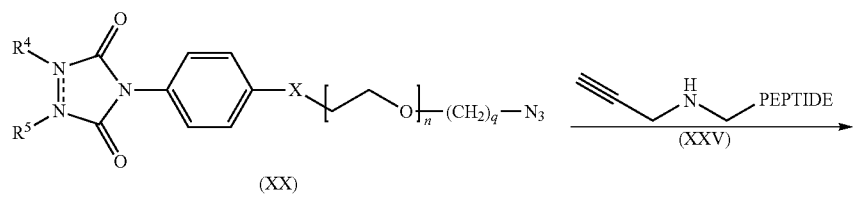

(XX)     (XXV)

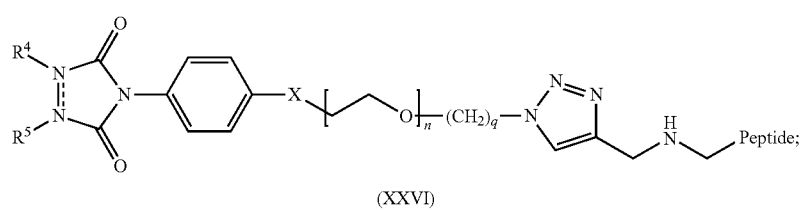

(XXVI)

b) converting the

single bond in the compound of Formula XXVI to a

double bond to provide a compound of Formula XXVII:

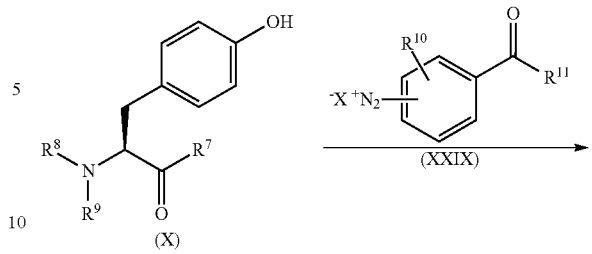

(XXVII)

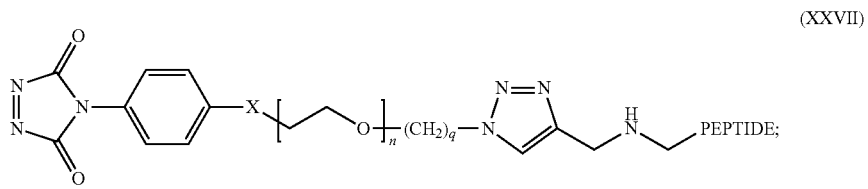

c) conjugating the compound of Formula XXVII with Herceptin to provide the Herceptin antibody of Formula XXVIII:

(XXVIII)

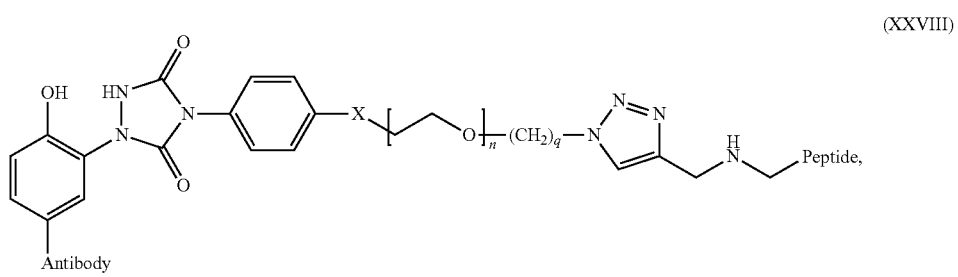

wherein:

X and Y are each independently $CH_2$, O, NH, S, NHCO or CONH; and n and q are each independently an integer from 0 to 12; wherein the compound of Formula XIV has multi-specific antibody binding specificity for binding peptides, polypeptides, and organic compounds.

In another embodiment the disclosure provides methods for site-specific tyrosine labeling at a specific site on human IgG heavy chain proteins by exposing human IgG heavy chain proteins to o-benzaldehyde diazonium hexafluorophosphate.

In another embodiment the disclosure provides methods for chemoselectively modifying a moiety containing the amino acid tyrosine by:

a) reacting a compound of Formula X with a compound of Formula XXIX to provide a compound of Formula XXX; and -continued

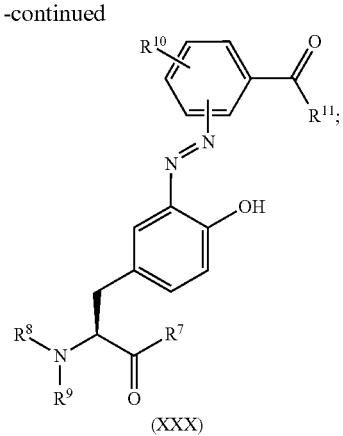

(XXX)

b) reacting the compound of Formula XXX with a compound of Formula XXXI to provide a compound of Formula XXXII;

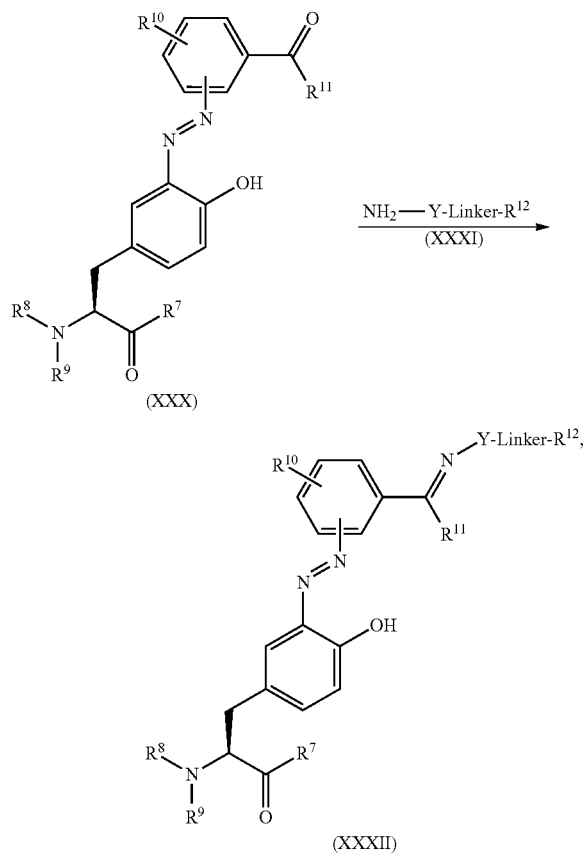

wherein:

X⁻ is independently F⁻, Cl⁻, Br⁻, I⁻, ClO$_4^-$, NO$_3^-$, HSO$_3^-$, PF$_6^-$ or BF$_4^-$;

Y is independently NH or O;

$R^7$, $R^8$ and $R^9$ are each independently hydrogen, hydroxyl, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy, substituted or unsubstituted alkylaryl, substituted or unsubstituted alkylheteroaryl, or $R^7$, $R^8$ and $R^9$ are in a tyrosine residue of a peptide or a protein;

$R^{10}$ is independently hydrogen, halogen, nitro, cyano, trifluoromethyl, substituted or unsubstituted alkyl or alkyl, substituted or unsubstituted alkoxy or alkoxy, substituted or unsubstituted aryl or aryl substituted, substituted or unsubstituted aryloxy or aryloxy, substituted or unsubstituted heteroaryl or heteroaryl substituted, substituted or unsubstituted heteroaryloxy or heteroaryloxy;

$R^{11}$ is independently hydrogen, alkyl, alkoxy, phenoxy, or alkylaryloxy;

$R^{12}$ is independently small organic molecule, fluorescence unit, enzyme, peptide or antibody;

Linker is $(CH_2)_l$-A-$[CH_2CH_2-Z]_m$—$(CH_2)_n$—B;

A and B are each independently bond, C(=O), CONH or NHCO;

Z is independently CH$_2$ or O; and l, m, and n are each independently an integer from 0 to 12.

In another embodiment the disclosure provides a compound having Formula XXXIII:

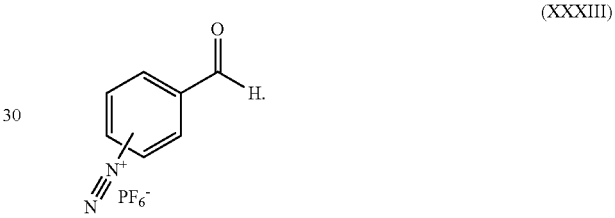

In another embodiment the disclosure provides methods for bioconjugating momomethyl auristatin E (MMAE) to a cancer targeting monoclonal antibody (mAb) to provide a bioconjugated mAb by reacting the compound of Formula XXXV with a monoclonal antibody (mAb) to provide the bioconjugated mAb:

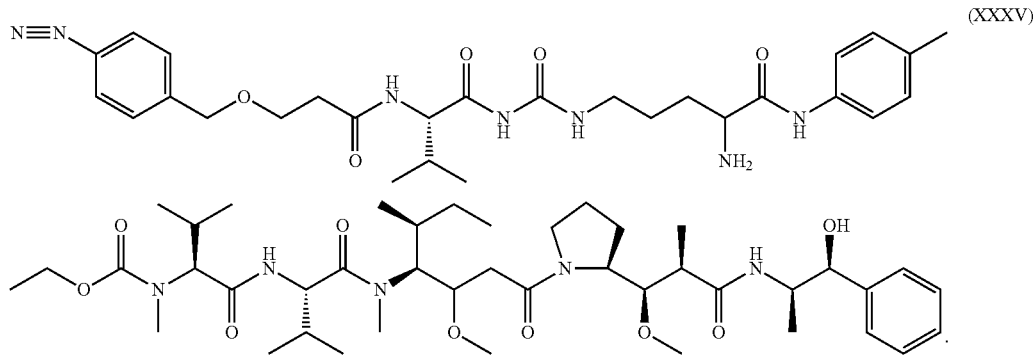

In another embodiment the disclosure provides methods for bioconjugating momomethyl auristatin E (MMAE) to a cancer targeting monoclonal antibody (mAb) to provide a bioconjugated mAb by reacting the compound of Formula XXXVI with a monoclonal antibody (mAb) to provide the bioconjugated mAb:

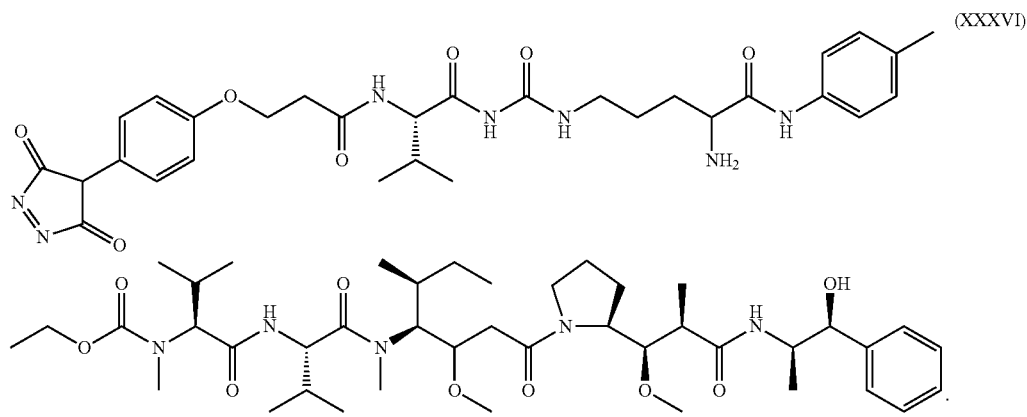

(XXXVI)

In another embodiment the disclosure provides methods for chemoselectively modifying a glucaon-like protein receptor (GLP-1R) agonist by reacting a GLP-1R agonist with a compound of Formula XI:

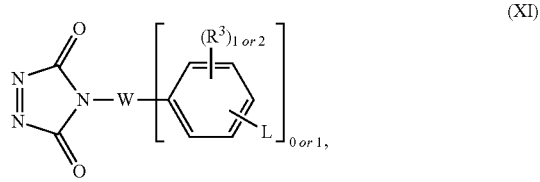

(XI)

wherein:

W is independently a direct bond or is O;

$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3\prime s}$ form a cyclic or heterocyclic ring, wherein each $R^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, $N_3$, $CH_3$, $C\equiv CH$, $C\equiv CHN_3$, $CH\equiv CHN_3$, $CH_2CH_2N_3$, $O(CH_2)N_3$, $C_6H_5$, $COCH_3$, $OCH_2C\equiv CH$, $OCH_2COCH_3$, $OCOCF_3$, or $X-[CH_2CH_2-Y]_n-(CH_2)_q-N_3$;

X and Y are each independently $CH_2$, O, NH, S, NHCO or CONH;

n and q are each independently an integer from 0 to 12.

In another embodiment the disclosure provides methods for chemoselectively modifying a glucaon-like protein receptor (GLP-1R) agonist by reacting a GLP-1R agonist with a compound of Formula XXVII:

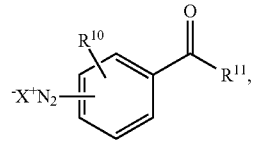

(XXVII)

wherein:

$X^-$ is independently $F^-$, $Cl^-$, $Br^-$, $I^-$, $ClO_4^-$, $NO_3^-$, $HSO_3^-$, $PF_6^-$ or $BF_4^-$;

$R^{10}$ is independently hydrogen, halogen, nitro, cyano, trifluoromethyl, substituted or unsubstituted alkyl or alkyl, substituted or unsubstituted alkoxy or alkoxy, substituted or unsubstituted aryl or aryl substituted, substituted or unsubstituted aryloxy or aryloxy, substituted or unsubstituted heteroaryl or heteroaryl substituted, substituted or unsubstituted heteroaryloxy or heteroaryloxy; and $R^{11}$ is independently hydrogen, alkyl, alkoxy, phenoxy, or alkylaryloxy.

In another embodiment the disclosure provides methods for chemoselectively modifying a glucaon-like protein receptor (GLP-1R) agonist, further comprising reacting the modified GLP-1R agonist with a compound of Formula XXXI:

$$NH_2-Y-Linker-R^{12}$$ (XXXI), wherein:

Y is independently NH or O;

$R^{12}$ is independently small organic molecule, fluorescence unit, enzyme, peptide or antibody;

Linker is $(CH_2)_2-A-[CH_2CH_2-Z]_m-(CH_2)_n-B$;

A and B are each independently bond, $C(=O)$, CONH or NHCO;

Z is independently $CH_2$ or O; and l, m, and n are each independently an integer from 0 to 12.

BRIEF DESCRIPTION OF THE DRAWINGS

Various features and advantages of the present disclosure will become more apparent by describing in detail exemplary embodiments thereof with reference to the attached drawings in which.

Figure 1:
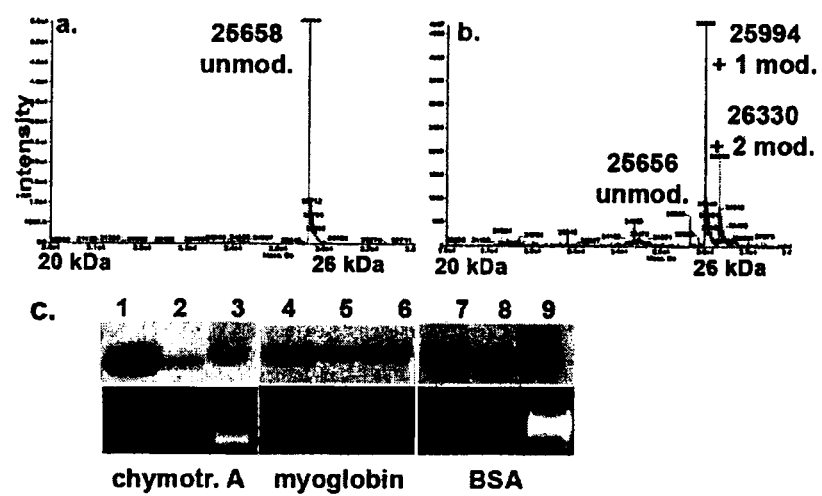
FIG. 1 illustrates the ESI-MS analysis of purified samples containing (a) unmodified chymotrypsinogen A; (b) chymotrypsinogen A modified with oxidized linker 7; and (c) Gel stained with coomassie blue (top) and under UV light (bottom): lane 1, unmodified chymotrypsinogen A; lane 2, chymotrypsinogen A/11; lane 3, chymotrypsinogen A/9; lane 4, unmodified myoglobin; lane 5, myoglobin/11; lane 6, myoglobin/9; lane 7, unmodified BSA; lane 8, BSA/11; and lane 9, BSA/9.

As used herein, the terms "alkyl" and "alkylene" are interchangeable depending on the placement of the "alkyl" or "alkylene" group within the molecule.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. As used herein, the terms "heteroalkyl" and "heteroalkylene" are interchangeable depending on the placement of the "heteroalkyl" or "heteroalkylene" group within the molecule.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively. As used herein, the terms "cycloalkyl" and "cycloalkylene" are interchangeable depending on the placement of the "cycloalkyl" or "cycloalkylene" group within the molecule. As used herein, the terms "heterocycloalkyl" and "heterocycloalkylene" are interchangeable depending on the placement of the "heterocycloalkyl" or "heterocycloalkylene" group within the molecule.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. As used herein, the terms "haloalkyl" and "haloalkylene" are interchangeable depending on the placement of the "haloalkyl" or "haloalkylene" group within the molecule.

The term "aryl" means, unless otherwise stated, a polyunsaturated, aromatic, hydrocarbon substituent which can be a single ring or multiple rings (from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. For example, pyridine N-oxide moieties are included within the description of "heteroaryl." A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively. As used herein, the terms "aryl" and "arylene" are interchangeable depending on the placement of the "aryl" and "arylene" group within the molecule. As used herein, the terms "heteroaryl" and "heteroarylene" are interchangeable depending on the placement of the "heteroaryl" and "heteroarylene" group within the molecule.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" referrers to a carbon or heteroatom.

The term "oxo" as used herein means an oxygen that is double bonded to a carbon atom.

Each of the above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R''' and R'''' are each independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are each independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from at least the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present disclosure may exist as salts. The present disclosure includes such salts. Non-limiting examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogen-phosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science, 66:1-19 (1977)). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

As used herein, the phrase "treating cancer" refers to providing a therapeutic benefit to the cancer patient, e.g. the therapy extends the mean survival time of patients, increases the percentage of patients surviving at a given timepoint, extends the mean time to disease progression, reduces or stabilizes tumor burden or improves quality of life for the patient or any of the above, for example. While not wanting to be bound by a particular theory, some of the compounds of the disclosure may be cytostatic and therefore have activity directly on the tumor cells.

The present disclosure also provides articles of manufacture comprising packaging material and a pharmaceutical composition contained within the packaging material, wherein the packaging material comprises a label which indicates that the pharmaceutical composition can be used for treatment of disorders and wherein the pharmaceutical composition comprises a compound according to the present disclosure.

The present disclosure also provides pharmaceutical compositions comprising at least one disclosure compound in an amount effective for treating a disorder (e.g., cancer), and a pharmaceutically acceptable vehicle or diluent. The compositions of the present disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure also include amine salts formed by the protonation of an amino group with suitable organic acids, such as p-toluenesulfonic acid, acetic acid, and the like. Additional excipients which are contemplated for use in the practice of the present disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the disclosure compounds are included in the present disclosure.

The disclosed pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present disclosure. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The pharmaceutical compositions for the administration of the compounds of this embodiment either alone or in combination with other agents, e.g., chemotherapeutic, may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

The compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether .beta.-cyclodextrin, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the present disclosure are employed. (For purposes of this application, topical application shall include mouthwashes and gargles).

The disclosure compounds may also be administered in combination with an anti-inflammatory, antihistamines, chemotherapeutic agent, immunomodulator, therapeutic antibody or a kinase inhibitor, e.g., a tyrosine or a serine/threonine, or a lipid kinase inhibitor or PI3 kinase family members, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxel), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-demethoxydaunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774, which targets epidermal growth factor; antibodies targeting integrin receptors, such as Vitaxin (also known as MEDI-522), and the like. Classes of anticancer agents suitable for use in compositions and methods of the present disclosure include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 1) hematopoietic growth factors; 12) agents that induce tumor cell differentiation (e.g., all-transretinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present disclosure may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NTHEs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with disclosure compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

The term antibody as used in this disclosure is meant to include intact molecules of polyclonal or monoclonal antibodies, as well as fragments thereof, such as Fab and F(ab').sub.2, Fv and SCA fragments which are capable of binding an epitopic determinant. When other therapeutic agents are employed in combination with the compounds of the present disclosure they may be used for example in amounts as noted in the Physician Desk Reference (PDR) or as otherwise determined by one of ordinary skill in the art.

In the treatment or prevention of conditions described herein, an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was preferred at 0.1 mg/kg/day while another was effective at about 1.0 mg/kg/day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. There may be a period of no administration followed by another regimen of administration. Preferably, administration of the compound is closely associated with the schedule of a second agent administration. For example, administration can be prior to, simultaneously with or immediately following administration of additional agents.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, the disclosure provides a method for reducing the tumor burden in a subject, comprising administering to a subject in need thereof an effective amount of chemotherapeutic agent in combination with an disclosure compound. In an illustrative example, the method includes use of at least one of the disclosure compounds with a chemotherapeutic agent. It should be understood that the tumor burden in a subject can be reduced prior to treatment with a compound of the disclosure through surgical resection, chemotherapy, radiation treatment or other methods known to those of skill in the art.

As used herein, "drug" is any therapeutic compound or molecule including but not limited to nucleic acids, small molecules, polypeptide or peptide, etc., The term "drug" also includes simple binding peptides, such as peptides that bind to ang2 and VEGF, or any other defined target. The peptide may be any medically or diagnostically useful peptide or protein of small to medium size (i.e. up to about 75 kDa). The mechanisms of improved polypeptide absorption are described in U.S. Pat. No. 5,661,130 to Meezan et al., the reference of which is hereby incorporated in its entirety. The present disclosure can be mixed with all such peptides, although the degree to which the peptides benefits are improved may vary according to the molecular weight and the physical and chemical properties of the peptide, and the particular surfactant used. Examples of polypeptides include antibodies, such as monoclonal antibodies, insulin like growth factor-I (IGF-I or Somatomedin-C), insulin, calcitonin, leptin, hGH, human parathyroid hormone (PTH) or active fragments thereof, such as but not limited to PTH 1-31 (Ostabolin C™), PTH 1-34 and PTH 3-34, melatonin, GLP-1 or Glucagon-like peptide-1, GiP, OB-3 peptide, pituitary adenylate cyclase neuropeptide-activating polypeptide (PACAP), GM-1 ganglioside, nerve growth factor (NGF), D-tryp6)-LHRH, nafarelin, FGF, VEGF, VEGF antagonists, Leuprolide, interferon-alpha, interferon-beta, interferon-gamma, low molecular weight heparin, PYY, LHRH, LH, GDNF, G-CSF, Ghrelin antagonists, Ghrelin, KGF, Imitrex, Integrelin, Nesiritide, Sandostatin, cetrorelix acetate, ganirelix acetate, bivalirudin, zafirlukast, Exanitide, pramlintide acetate, vasopressin, desmopressin, glucagon, ACTH, GHRH and analogs, oxytocin, corticotropin releasing hormone, TRHrh, atrial natriuretic peptide, thyroxine releasing hormone, FSH, prolactin, Tobramycin, Triptorelin, Goserelin, Fuzeon, Hematide, Buserelin, Octreotide, Gonadorelin, Felypressin, Deslorelin, Vasopressin, 8-L-Arg, Eptifibatide, GM-CSF, EPO, Interleukin-11, Endostatin, Angiostatin, N-acetyl oxyntomodulin 30-37, Oxyntomodulin, Ularitide, Xerecept, Apo A-IV, rNAPc2, Secretin, Thymopentin, Neuromedin U, Neurotensin, Thrombospondin-1 inhibitors, FGF-18, FGF-20, FGF-21, Elcatonin Acetate, Antide Acetate, Dynorphin A (1-13) Acetate, Sincalide, Thymopentin Acetate, Thymosin alpha1 acetate (Thymalfasin), Fertirelin Acetate, CRF Acetate, CRF (ovine), Hisrelin, Thymalfasin, Ecallantide, Oxycortin, Urocortin, Arixtra, Spiegelmer nucleotide aptamers, CGRP (calcitonin gene related protein), Urocortin, Amylin, IL-21, melanotan, valpreotide, ACV-1 neuropathic pain peptide, gastrin, gastrin releasing peptide (GRP), gastrin releasing peptide-like peptides, or epidermal growth factor. Also, see Table I.

In one aspect, antibodies are included as proteins in the compositions and methods of the disclosure, including functional fragments thereof. "Antibodies" as used herein includes polyclonal and monoclonal antibodies, chimeric, single chain, and humanized antibodies, as well as Fab fragments, including the products of an Fab or other immunoglobulin expression library. Antibodies which consists essentially of pooled monoclonal antibodies with different epitopic specificities, as well as distinct monoclonal antibody preparations are provided. Monoclonal antibodies are made by methods well known to those skilled in the art. The term antibody as used in this disclosure is meant to include intact molecules as well as fragments thereof, such as Fab and F(ab')$_2$, Fv and SCA fragments which are capable of binding an epitopic determinant on a protein of interest. An Fab fragment consists of a mono-valent antigen-binding fragment of an antibody molecule, and can be produced by digestion of a whole antibody molecule with the enzyme papain, to yield a fragment consisting of an intact light chain and a portion of a heavy chain. An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner. An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds. An Fv fragment is defined as a genetically engineered fragment containing the variable region of a light chain and the variable region of a heavy chain expressed as two chains. (5) A single chain antibody ("SCA") is a genetically engineered single chain molecule containing the variable region of a light chain and the variable region of a heavy chain, linked by a suitable, flexible polypeptide linker.

As used herein, a "monoclonal antibody" may be from any origin, such as mouse or human, including a chimeric antibody thereof. Additionally, the antibody may be humanized.

Examples of monoclonal antibodies (as named by the World Health Organization in International Nonproprietary Names (INN) for Biological and Biotechnological Substances publications; the number corresponding to the INN List including the antibody) include those of mouse origin including: abagovomab (95), afelimomab (80), altumomab (80), anatumomab mafenatox, (86) arcitumomab (74), bectumomab (81), besilesomab (92), biciromab (66), capromab (80), detumomab (80), dorlimomab aritox (66), edobacomab (80), edrecolomab (74), elsilimomab (89), enlimomab (80), enlimomab pegol (77), epitumomab (82), epitumomab cituxetan (89), faralimomab (81), gavilimomab (84), ibritumomab tiuxetan (86), igovomab (86), imciromab (66), inolimomab (80), lemalesomab (86), maslimomab (66), minretumomab (80), mitumomab (82), nacolomab tafenatox (80), nerelimomab (81), odulimomab (81), oregovomab (86), satumomab (81), sulesomab (86), taplitumomab paptox (84), technetium ($^{99m}$Tc) fanolesomab (86), technetium ($^{99m}$Tc) nofetumomab merpentan (81), technetium, ($^{99m}$Tc) pintumomab (86), telimomab aritox (66), tositumomab (80), vepalimomab (80), zolimomab aritox (80); those of human origin including: adalimumab (85), adecatumumab (90), atorolimumab (80), belimumab (89), bertilimumab (88), denosumab (94), efungumab (95), exbivirumab (91), golimumab (91), ipilimumab (94), iratumumab (94), lerdelimumab (86), lexatumumab (95), libivirumab (91), mapatumumab (93), metelimumab (88), morolimumab (79), nebacumab (66), ofatumumab (93), panitumumab (91), pritumumab (89), raxibacumab (92), regavirumab (80), sevirumab (66), stamulumab (95), ticilimumab (95), tuvirumab (66), votumumab (80), zalutumumab (93), zanolimumab (92), ziralimumab (84); those of chimeric origin including: abciximab (80), basiliximab (81), bavituximab (95), cetuximab (82), clenoliximab (77), ecromeximab (87), galiximab (89), infliximab (77), keliximab (81), lumiliximab (90), pagibaximab (93), priliximab (80), rituximab (77), teneliximab (87), vapaliximab (87), volociximab (93); and those of humanized origin including: alemtuzumab (83), apolizumab (87), aselizumab (88), bapineuzumab (93), bevacizumab (86), bivatuzumab (86), cantuzumab mertansine (89), cedelizumab (81), certolizumab pegol (90), daclizumab (78), eculizumab (87), efalizumab (85), epratuzumab (82), erlizumab (84), felvizumab (77), fontolizumab (87), gemtuzumab (83), inotuzumab ozogamicin (92), labetuzumab (85), lintuzumab (86), matuzumab (88), mepolizumab (81), motavizumab (95), natalizumab (79), nimotuzumab (94), ocrelizumab (95), omalizumab (84), palivizumab (79), pascolizumab (87), pertuzumab (89), pexelizumab (86), ranibizumab (90), reslizumab (85), rovelizumab (81), ruplizumab (83), sibrotuzumab (86), siplizumab (87), sontuzumab (94), tadocizumab (94), talizumab (89), tefibazumab (92), tocilizumab (90), toralizumab (87), trastuzumab (78), tucotuzumab celmoleukin (95), urtoxazumab (90), visilizumab (84), yttrium $^{90}$Y tacatuzumab tetraxetan (93).

The terms peptide, polypeptide and protein may be used interchangeably herein, or a peptide, polypeptide or variant thereof. As used herein, the term "polypeptide" is interpreted to mean a polymer composed of amino acid residues, e.g. Ala, Arg, Asn, Asp, Cys, Glu, Gln, His, Ile, Leu, Lys, Met, Phe, Pro, Ser, Thr, Trp, Tyr, and Val, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides. "Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well-known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, AD Pribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS-STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs. 1 12 in POSTTRANSLATIONAL COVALENT MODIFICATION OF PROTEINS, B. C. Johnson, Ed., Academic Press, New York (1983); Seifter et al., Meth. Enzymol. 182:626 646 (1990) and Rattan et al., Protein Synthesis: Posttranslational Modifications and Aging, Ann. N.Y. Acad. Sci. 663: 48 62 (1992). Polypeptides may be branched or cyclic, with or without branching Cyclic, branched and branched circular polypeptides may result from post-translational natural processes and may be made by entirely synthetic methods, as well.

As used herein, the term "agent" is interpreted to mean a chemical compound, a mixture of chemical compounds, a sample of undetermined composition, a combinatorial small molecule array, a biological macromolecule, a bacteriophage peptide display library, a bacteriophage antibody (e.g., scFv) display library, a polysome peptide display library, or an extract made from biological materials such as bacteria, plants, fungi, or animal cells or tissues. Suitable techniques involve selection of libraries of recombinant antibodies in phage or similar vectors. See, Huse et al. (1989) Science 246:

1275 1281; and Ward et al. (1989) Nature 341: 544 546. The protocol described by Huse is rendered more efficient in combination with phage display technology. See, e.g., Dower et al., WO 91/17271 and McCafferty et al., WO 92/01047.

As used herein, the term "isolated" is interpreted to mean altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

As used herein, the term "variant" is interpreted to mean a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

Tyrosine Bioconjugation

In one embodiment the disclosure provides compounds having Formula I:

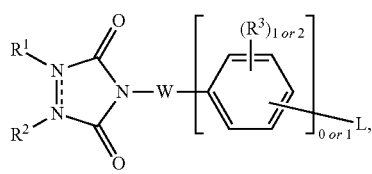
(I)

or a pharmaceutically acceptable salt thereof, wherein:
$R^1$ and $R^2$ are each H when

is a single bond, and $R^1$ and $R^2$ are each absent when

is a double bond;
W is independently a direct bond or is O;
$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3's}$ form a cyclic or heterocyclic ring, wherein each $R^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, $N_3$, $CH_3$, $C\equiv CH$, $C\equiv CHN_3$, $CH=CHN_3$, $CH_2CH_2N_3$, $O(CH_2)N_3$, $C_6H_5$, $COCH_3$, $OCH_2C\equiv CH$, $OCH_2COCH_3$, $OCOCF_3$, or $X-[CH_2CH_2-Y]_n-(CH_2)_q-N_3$;

X and Y are each independently $CH_2$, O, NH, S, NHCO or CONH; and n and q are each independently an integer from 0 to 12.

In another embodiment the disclosure provides compounds having Formula I, wherein the compound of Formula I has Formula II, III, IV, or V:

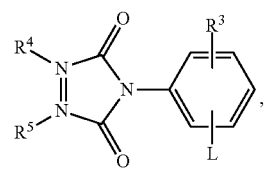
(II)

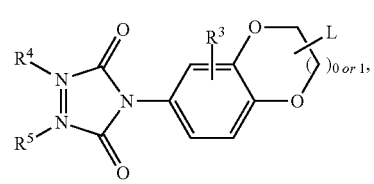
(III)

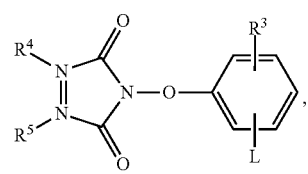
(IV)

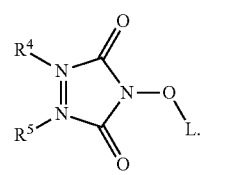
(V)

In another embodiment the disclosure provides compounds having Formula I, wherein the compound of Formula I has Formula VI:

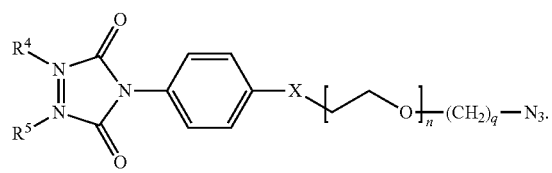
(VI)

In another embodiment the disclosure provides compounds having Formula I, wherein the compound of Formula VI has Formula VII or Formula VIII:

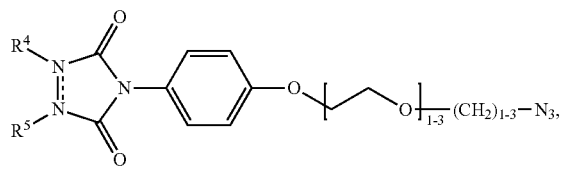
(VII)
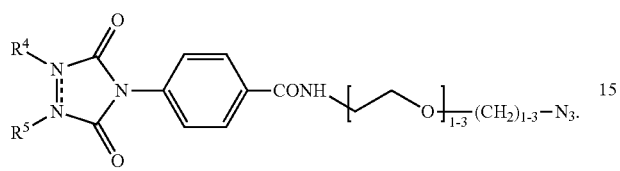
(VIII)
In another embodiment the disclosure provides compounds having Formula I, wherein the compound of Formula I is any one of the following compounds:
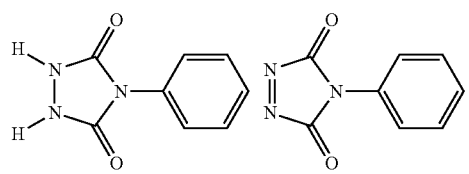
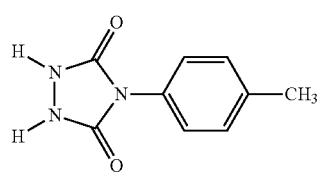
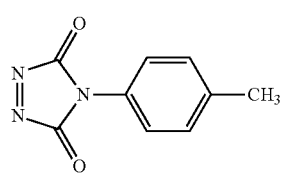
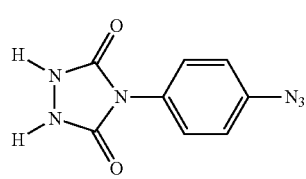
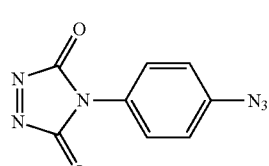
-continued
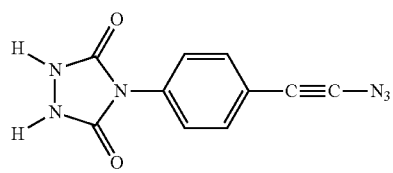
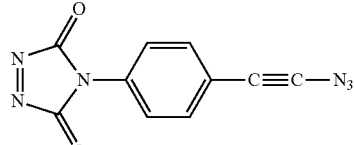
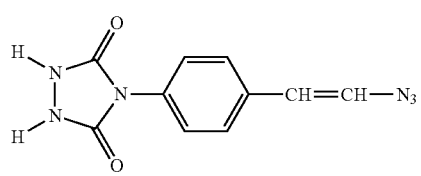
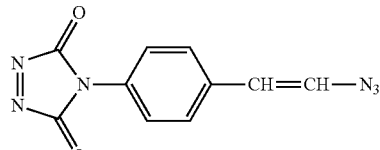
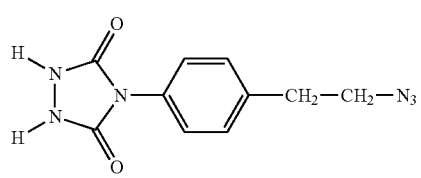
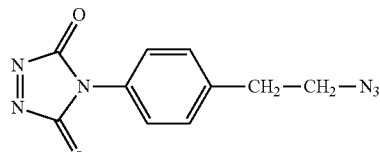
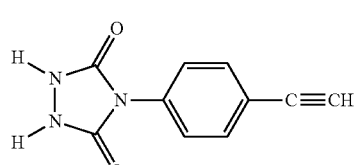
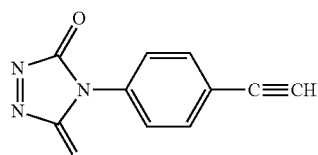
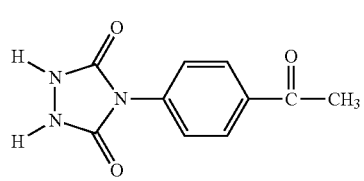

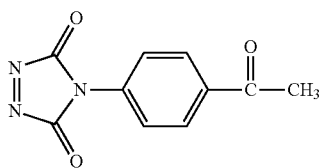

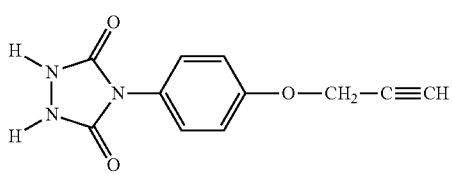

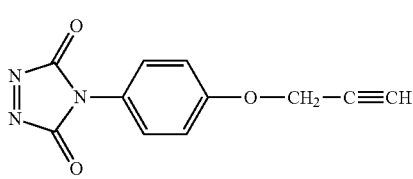

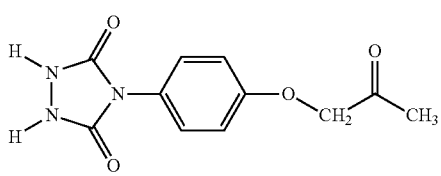

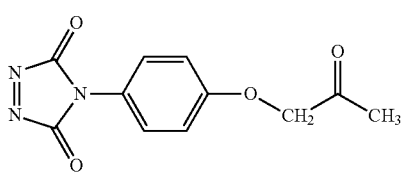

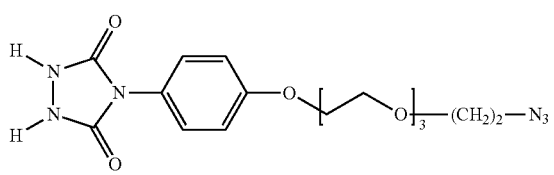

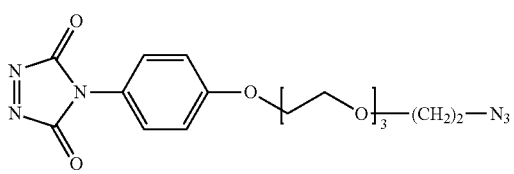

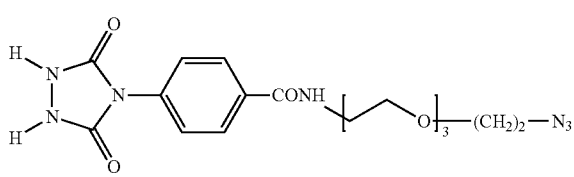

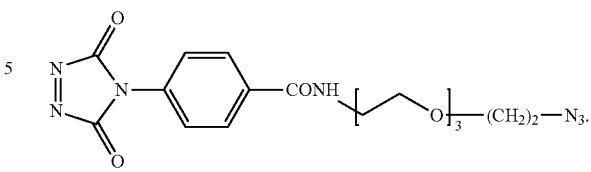

In another embodiment the disclosure provides compounds having Formula IX:

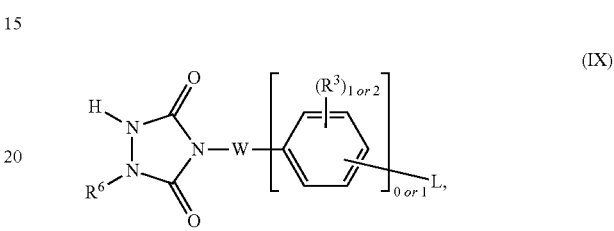

(IX)

or a pharmaceutically acceptable salt thereof, wherein:

W is independently a direct bond or is O;

$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3's}$ form a cyclic or heterocyclic ring, wherein each $R^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, $N_3$, $CH_3$, $C{\equiv}CH$, $C{\equiv}CHN_3$, $CH{=}CHN_3$, $CH_2CH_2N_3$, $O(CH_2)N_3$, $C_6H_5$, $COCH_3$, $OCH_2C{\equiv}CH$, $OCH_2COCH_3$, $OCOCF_3$, or X—[$CH_2CH_2$—Y]$_n$—($CH_2)_q$—$N_3$;

X and Y are each independently $CH_2$, O, NH, S, NHCO or CONH;

n and q are each independently an integer from 0 to 12; and $R^6$ is a tyrosine moiety or a tyrosine residue in a peptide or a protein.

In another embodiment the disclosure provides methods for treating a subject having cancer comprising administering a compound of Formula IX to the subject, thereby treating the cancer.

In another embodiment the disclosure provides compounds having Formula IX, wherein the tyrosine moiety is N-acyl tyrosine methylamide, or H-Gly-Gly-Tyr-OH; and the tyrosine residue in a peptide or a protein is in Chymotrypsinogen A, Myoglobin, Bovine Serum Albumin (BSA), or tocinoic acid.

In another embodiment the disclosure provides compounds having Formula IX, wherein the compound of Formula IX is any one of the following compounds:

37
5
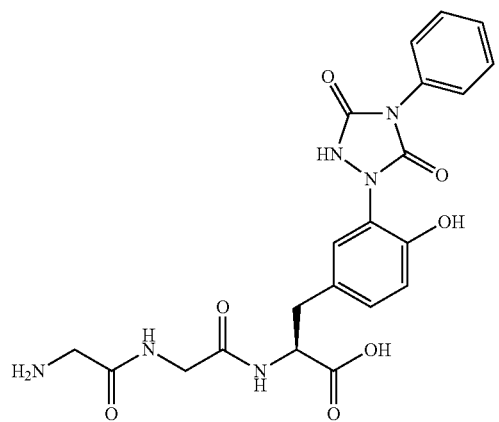
38
6
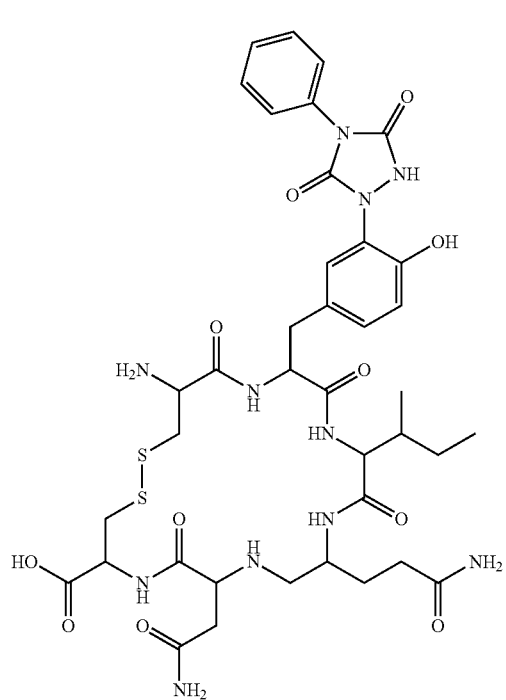
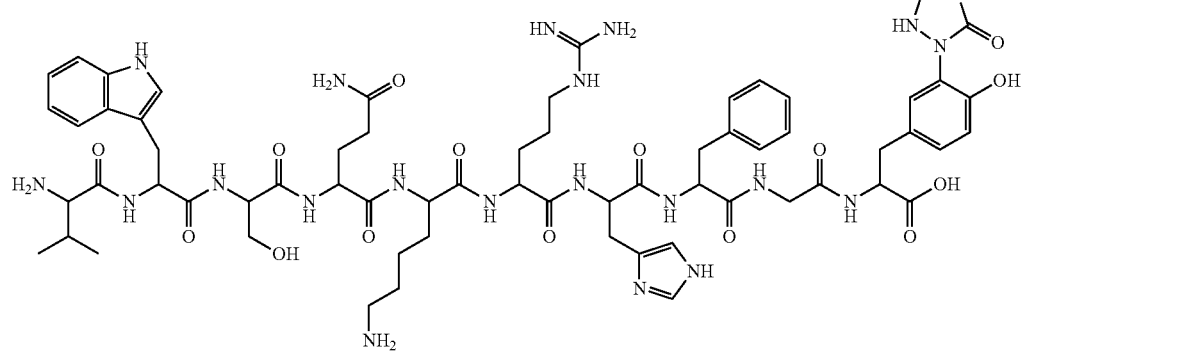
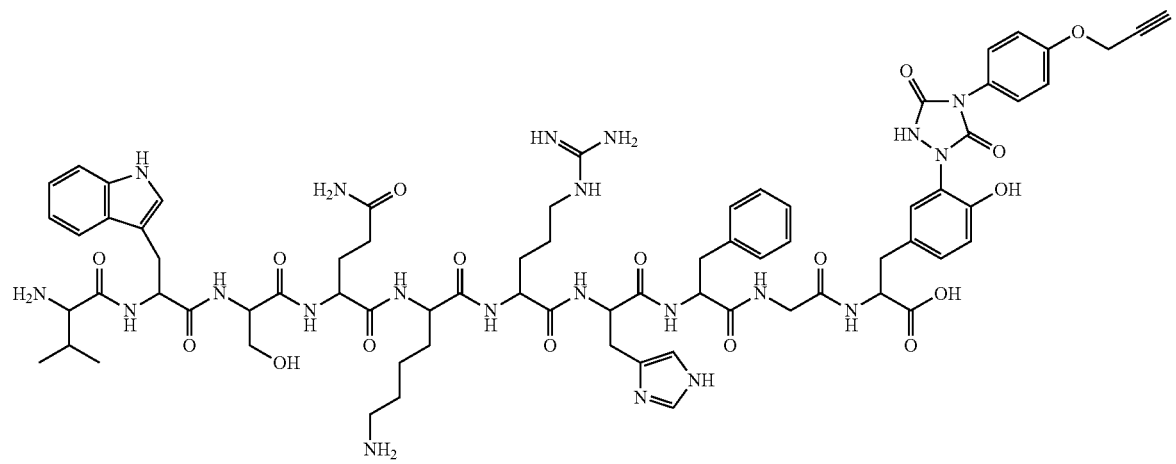

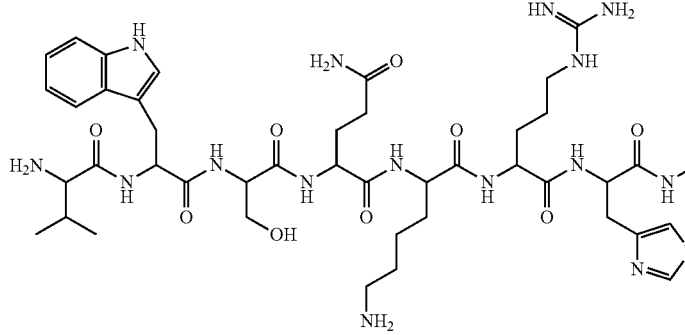

In another embodiment the disclosure provides methods for chemoselectively modifying a moiety containing the amino acid tyrosine by reacting a compound of Formula X with a compound of Formula XI to provide a compound of Formula XII, thereby modifying the moiety containing the amino acid tyrosine:

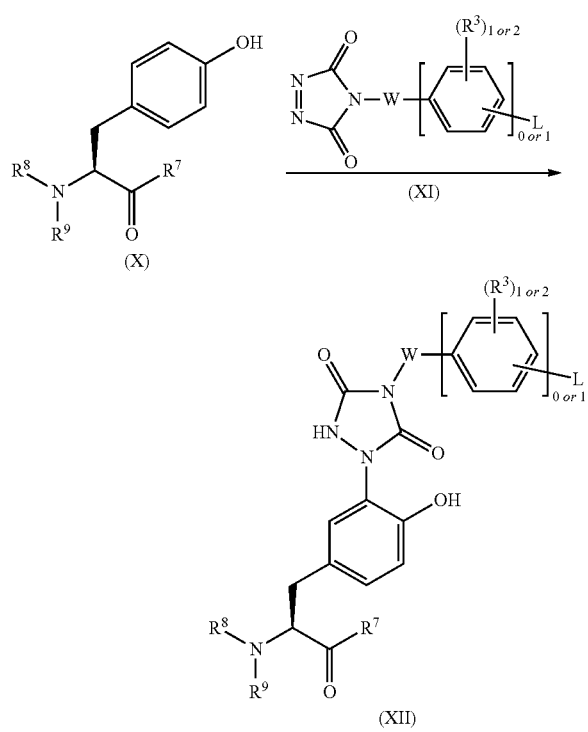

wherein:

W is independently a direct bond or is O;

$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3's}$ form a cyclic or heterocyclic ring, wherein each $R^3$ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, $N_3$, $CH_3$, C≡CH, C≡$CHN_3$, CH=$CHN_3$, $CH_2CH_2N_3$, $O(CH_2)N_3$, $C_6H_5$, $COCH_3$, $OCH_2C$≡CH, $OCH_2COCH_3$, $OCOCF_3$, or X—$[CH_2CH_2$—$Y]_n$—$(CH_2)_q$—$N_3$;

X and Y are each independently $CH_2$, O, NH, S, NHCO or CONH;

n and q are each independently an integer from 0 to 12;

$R^7$, $R^8$ and $R^9$ are each independently hydrogen, hydroxyl, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy, substituted or unsubstituted alkylaryl, substituted or unsubstituted alkylheteroaryl, or $R^7$, $R^8$ and $R^9$ are in a tyrosine residue of a peptide or a protein.

In another embodiment the disclosure provides methods for chemoselectively modifying a moiety containing the amino acid tyrosine by reacting a compound of Formula X with a compound of Formula XI to provide a compound of Formula XII, wherein the compound of Formula X has Formula XIII, XIV, XV, or XVI:

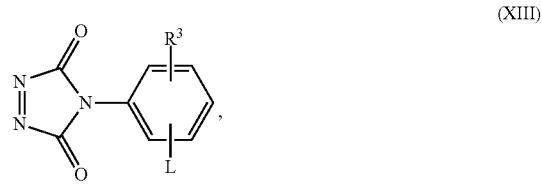

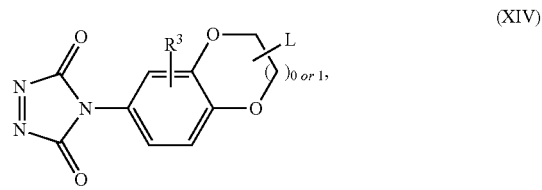

-continued

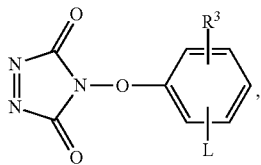
(XV)

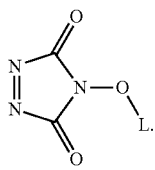
(XVI)

In another embodiment the disclosure provides methods for chemoselectively modifying a moiety containing the amino acid tyrosine by reacting a compound of Formula X with a compound of Formula XI to provide a compound of Formula XII, wherein the compound of Formula XI has Formula XVII:

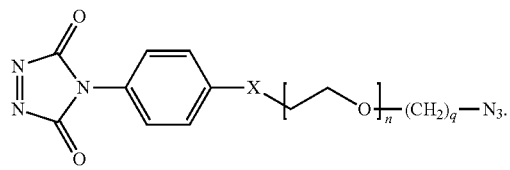
(XVII)

In another embodiment the disclosure provides methods for chemoselectively modifying a moiety containing the amino acid tyrosine by reacting a compound of Formula X with a compound of Formula XI to provide a compound of Formula XII, wherein the compound of Formula XVII has Formula XVIII or Formula XIX:

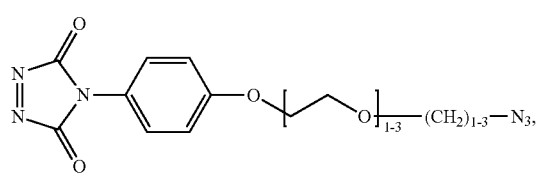
(XVIII)

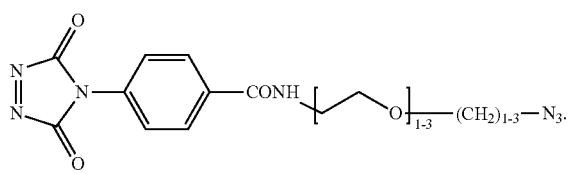
(XIX)

In another embodiment the disclosure provides methods for chemoselectively modifying a moiety containing the amino acid tyrosine by reacting a compound of Formula X with a compound of Formula XI to provide a compound of Formula XII, wherein the compound of Formula XI is any one of the following compounds:

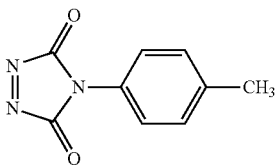

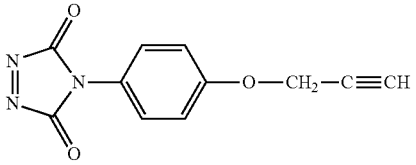

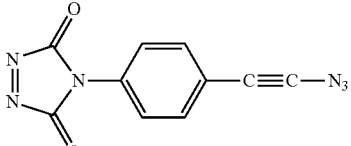

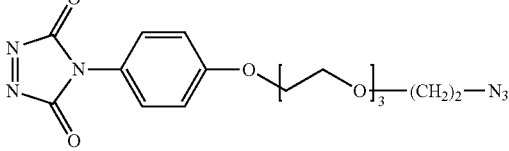

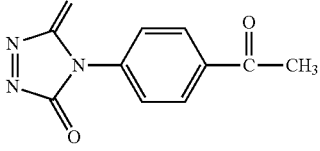

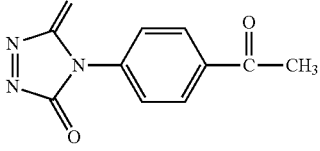

In another embodiment the disclosure provides methods for chemoselectively modifying a moiety containing the amino acid tyrosine by reacting a compound of Formula X with a compound of Formula XI to provide a compound of Formula XII, wherein the compound of Formula X is N-acyl tyrosine methylamide or H-Gly-Gly-Tyr-OH; and the tyrosine residue of a peptide or a protein is in Chymotrypsinogen A, Myoglobin, Bovine Serum Albumin (BSA), or Tocinoic acid.

In another embodiment the disclosure provides methods for chemoselectively modifying a moiety containing the amino acid tyrosine by reacting a compound of Formula X with a compound of Formula XI to provide a compound of Formula XII, wherein the compound of Formula XII is any one of the following compounds:

43                                      44
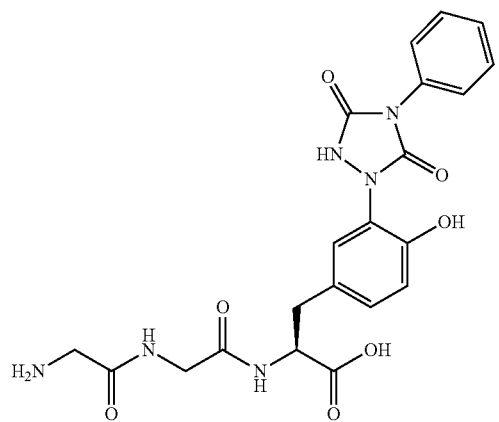
5
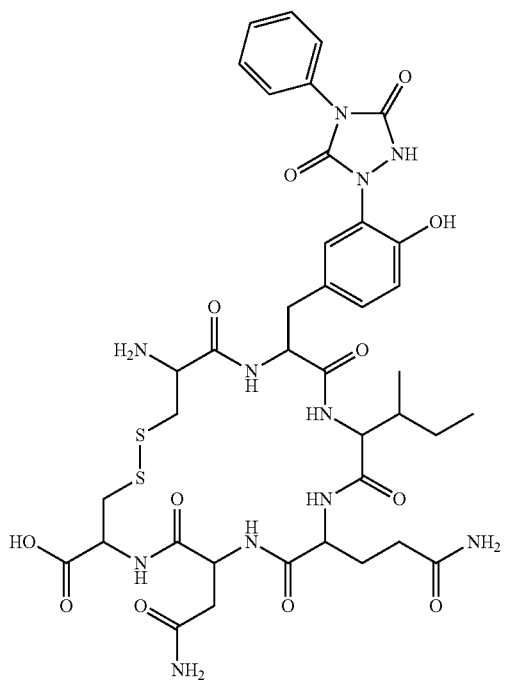
6
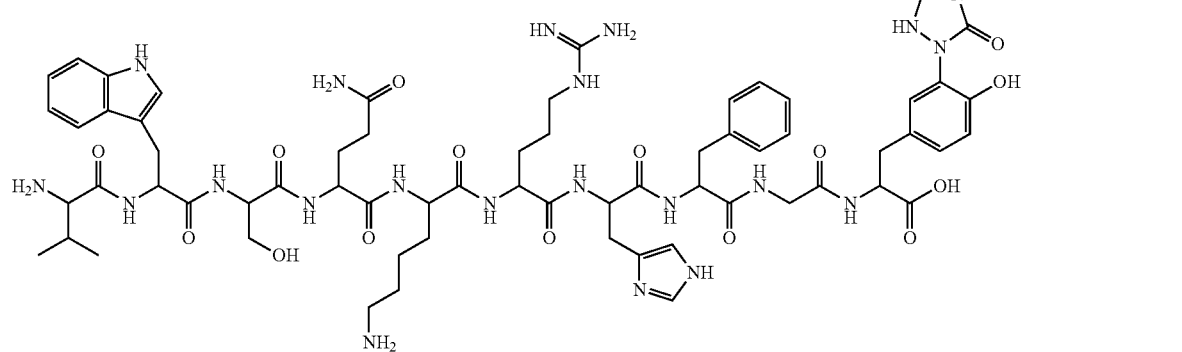
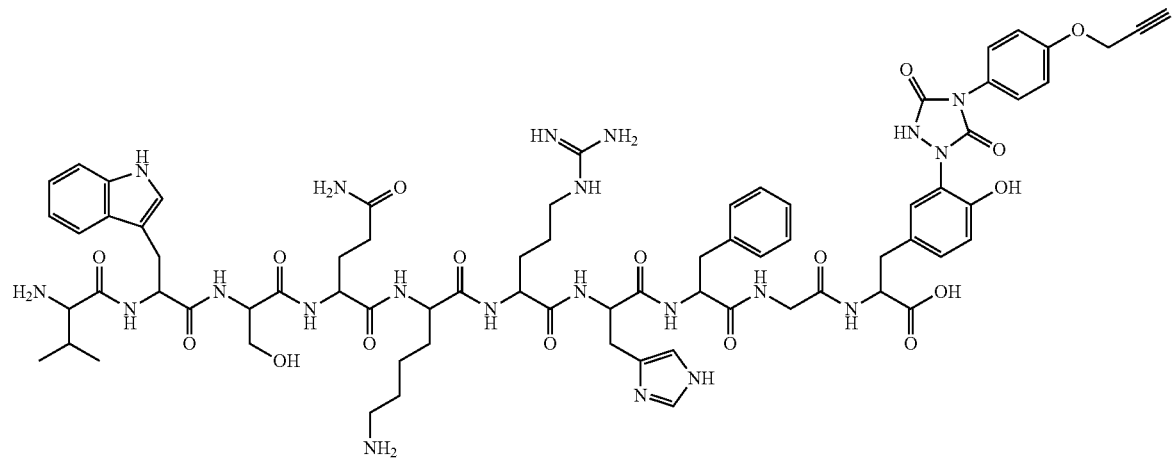

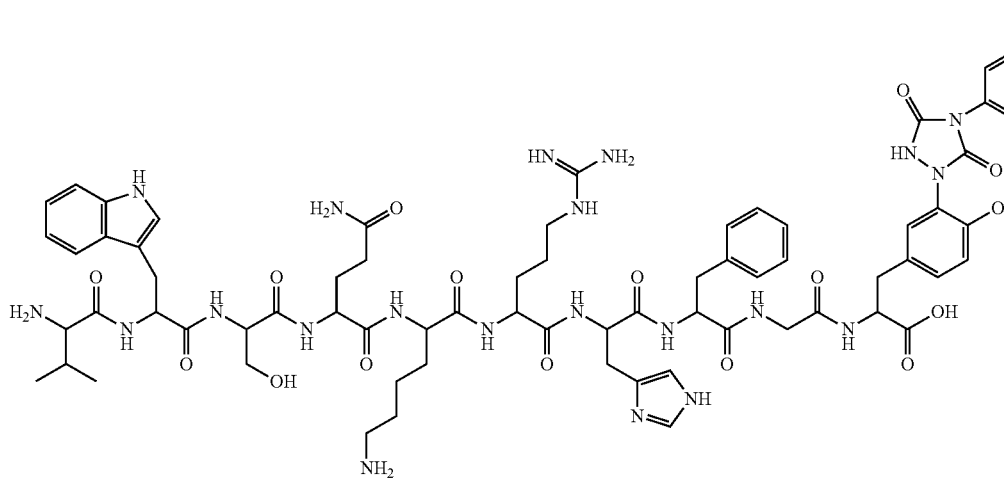
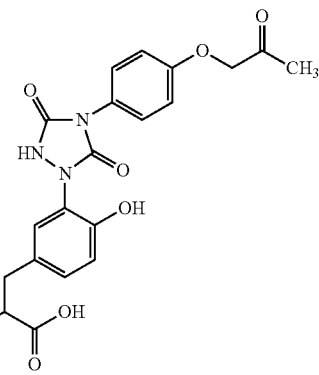

In another embodiment the disclosure provides methods for chemoselectively modifying a moiety containing the amino acid tyrosine by reacting a compound of Formula X with a compound of Formula XI to provide a compound of Formula XII, wherein the reaction occurs in an aqueous media at a pH between 2 and 10.

In another embodiment the disclosure provides methods for chemoselectively modifying a moiety containing the amino acid tyrosine by reacting a compound of Formula X with a compound of Formula XI to provide a compound of Formula XII, wherein the aqueous media is a phosphate buffer at about a pH of 7.4.

In another embodiment the disclosure provides methods for chemoselectively modifying a moiety containing the amino acid tyrosine by reacting a compound of Formula X with a compound of Formula XI to provide a compound of Formula XII, wherein the reaction occurs in a mixed organic/aqueous media.

In another embodiment the disclosure provides methods for producing a herceptin antibody with binding specificity for ErbB-2 and integrin αvβ3 by:

a) cyclizing a compound of Formula XX with a cyclic RGD peptide of Formula XXI to form a 1,4-triazole compound of Formula XXII;

b) converting the

single bond in the compound of Formula XXII to a

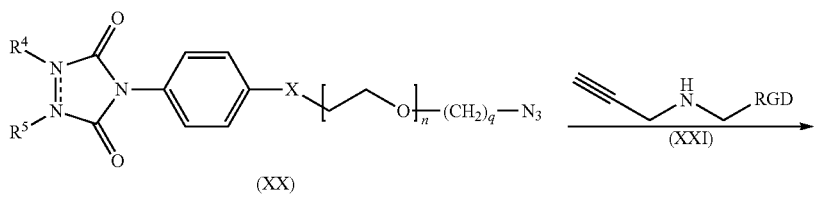

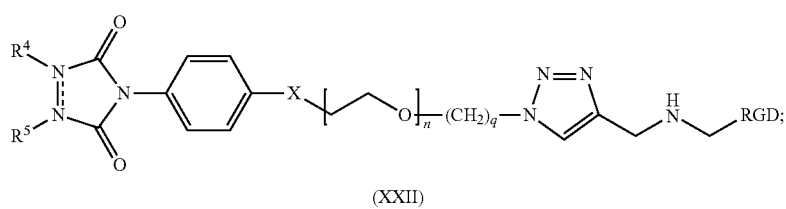

double bond to provide a compound of Formula XXIII:

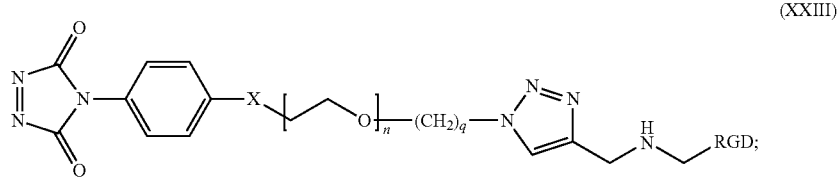
(XXIII)

c) conjugating the compound of Formula XXIII with Herceptin to provide the Herceptin antibody of Formula XXIV:

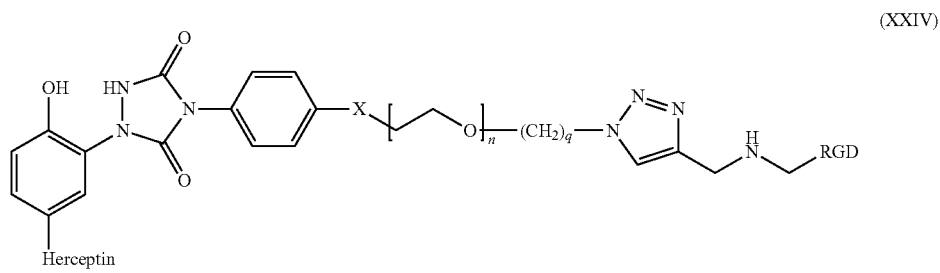
(XXIV)

wherein:
X and Y are each independently $CH_2$, O, NH, S, NHCO or CONH; and
n and q are each independently an integer from 0 to 12;
wherein the compound of Formula XXIV has binding specificity for ErbB-2 and integrin $\alpha v\beta 3$.

In another embodiment the disclosure provides methods for producing a multi-specific antibody with binding specificity for binding peptides, polypeptides, and organic compounds by:

a) cyclizing a compound of Formula XX with a peptide of Formula XXV to form a 1,4-triazole compound of Formula XXVI;

b) converting the

single bond in the compound of Formula XXVI to a

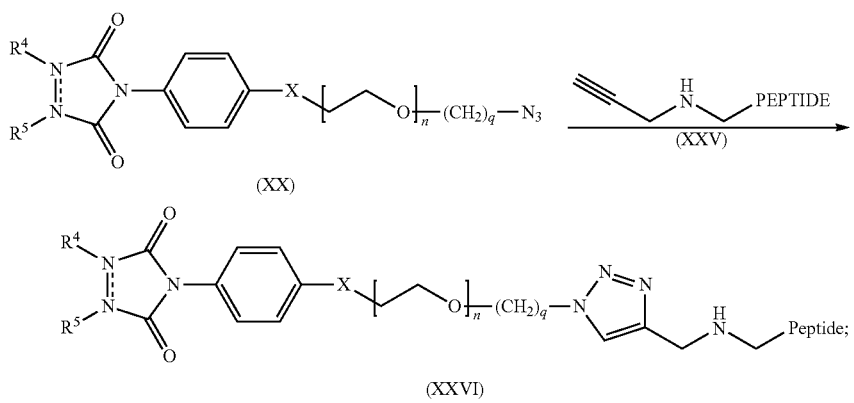

double bond to provide a compound of Formula XXVII:

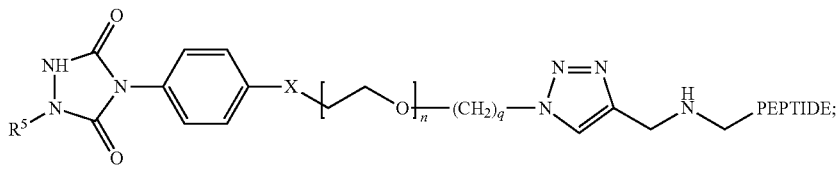
(XXVII)

c) conjugating the compound of Formula XXVII with Herceptin to provide the Herceptin antibody of Formula XXVIII:

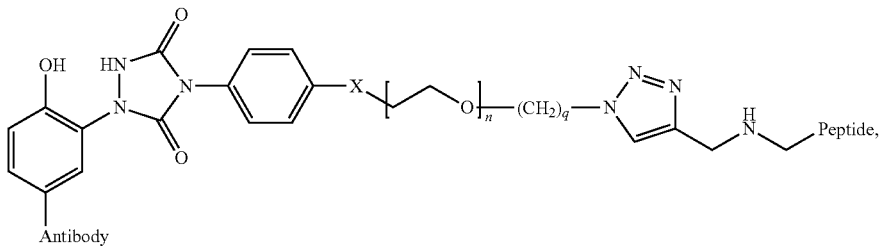
(XXVIII)

wherein:

X and Y are each independently $CH_2$, O, NH, S, NHCO or CONH; and n and q are each independently an integer from 0 to 12; wherein the compound of Formula XIV has multi-specific antibody binding specificity for binding peptides, polypeptides, and organic compounds.

In another embodiment the disclosure provides methods for site-specific tyrosine labeling at a specific site on human IgG heavy chain proteins by exposing human IgG heavy chain proteins to o-benzaldehyde diazonium hexafluorophosphate.

In another embodiment the disclosure provides methods for site-specific tyrosine labeling at a specific site on human IgG heavy chain proteins, wherein the specific site on the human IgG heavy chain protein is at the $CH_2$ domain of the heavy chain tyrosine 319 residue according to Kabat numbering.

In another embodiment the disclosure provides methods for site-specific tyrosine labeling at a specific site on human IgG heavy chain proteins, wherein the human IgG heavy chain protein is an antibody.

In another embodiment the disclosure provides methods for site-specific tyrosine labeling at a specific site on human IgG heavy chain proteins, wherein the antibody is herceptin, rutuxan or erbitux.

In another embodiment the disclosure provides methods for chemoselectively modifying a moiety containing the amino acid tyrosine by:

a) reacting a compound of Formula X with a compound of Formula XXIX to provide a compound of Formula XXX; and

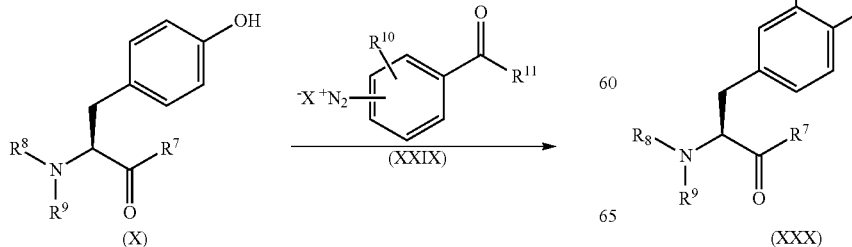

-continued

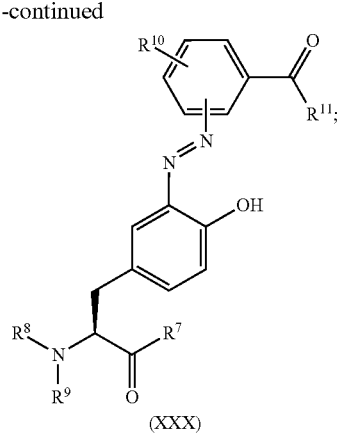
(XXX)

b) reacting the compound of Formula XXX with a compound of Formula XXXI to provide a compound of Formula XXXII;

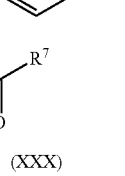

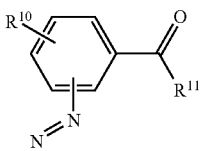
(XXXI)

-continued

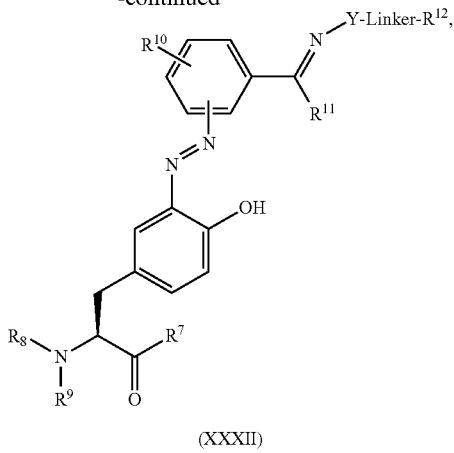

(XXXII)

wherein:

X⁻ is independently F⁻, Br⁻, ClO₄⁻, NO₃⁻, HSO₃⁻, PF₆⁻ or BF₄⁻;

Y is independently NH or O;

$R^7$, $R^8$ and $R^9$ are each independently hydrogen, hydroxyl, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy, substituted or unsubstituted alkylaryl, substituted or unsubstituted alkylheteroaryl, or $R^7$, $R^8$ and $R^9$ are in a tyrosine residue of a peptide or a protein;

$R^{10}$ is independently hydrogen, halogen, nitro, cyano, trifluoromethyl, substituted or unsubstituted alkyl or alkyl, substituted or unsubstituted alkoxy or alkoxy, substituted or unsubstituted aryl or aryl substituted, substituted or unsubstituted aryloxy or aryloxy, substituted or unsubstituted heteroaryl or heteroaryl substituted, substituted or unsubstituted heteroaryloxy or heteroaryloxy;

$R^{11}$ is independently hydrogen, alkyl, alkoxy, phenoxy, or alkylaryloxy;

$R^{12}$ is independently small organic molecule, fluorescence unit, enzyme, peptide or antibody;

Linker is $(CH_2)_l\text{-A-}[CH_2CH_2\text{—}Z]_m\text{—}(CH_2)_n\text{—B}$;

A and B are each independently bond, C(=O), CONH or NHCO;

Z is independently CH₂ or O; and l, m, and n are each independently an integer from 0 to 12.

In another embodiment the disclosure provides methods for chemoselectively modifying a moiety containing the amino acid tyrosine, wherein the compound of Formula XXIX has Formula XXXIII:

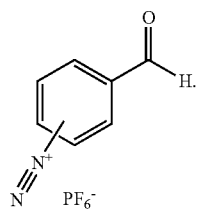

(XXXIII)

In another embodiment the disclosure provides methods for chemoselectively modifying a moiety containing the amino acid tyrosine, wherein the compound of Formula XXXIII has Formula XXXIV:

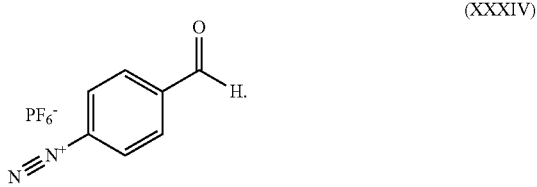

(XXXIV)

In another embodiment the disclosure provides a compound having Formula XXXIII:

(XXXIII)

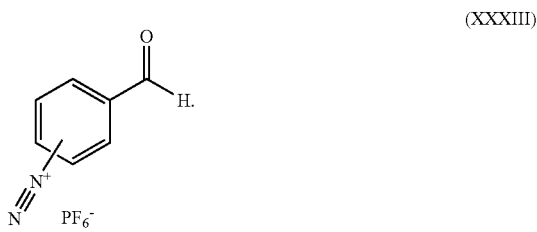

In another embodiment the disclosure provides a compound having Formula XXXIII, wherein the compound of Formula XXVIII has Formula XXXIV:

(XXXIV)

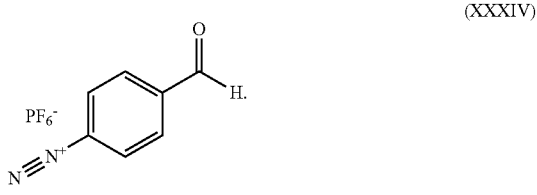

In another embodiment the disclosure provides methods for bioconjugating momomethyl amistatin E (MMAE) to a cancer targeting monoclonal antibody (mAb) to provide a bioconjugated mAb by reacting the compound of Formula XXXV with a monoclonal antibody (mAb) to provide the bioconjugated mAb:

(XXXV)

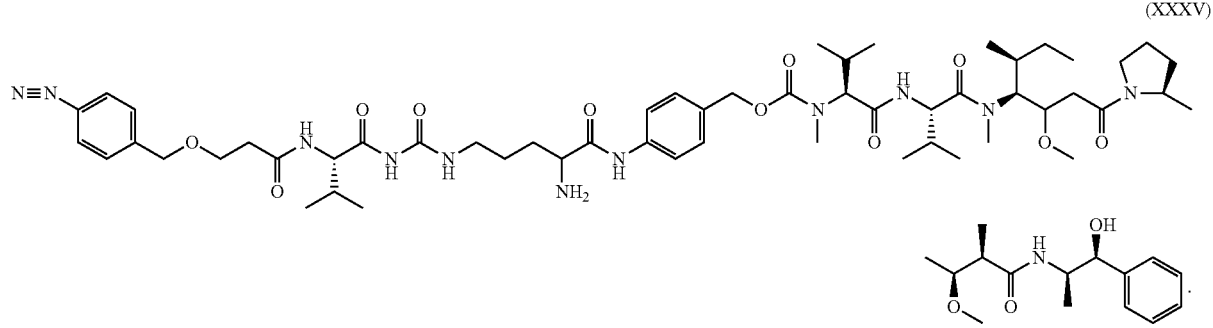

In another embodiment the disclosure provides methods for bioconjugating momomethyl auristatin E (MMAE) to a cancer targeting monoclonal antibody (mAb) to provide a bioconjugated mAb, wherein the monoclonal antibody (mAb) is CD22, CD30, CD33, GPNMB or ErbB2.

In another embodiment the disclosure provides methods for bioconjugating momomethyl auristatin E (MMAE) to a cancer targeting monoclonal antibody (mAb) to provide a bioconjugated mAb by reacting the compound of Formula XXXVI with a monoclonal antibody (mAb) to provide the bioconjugated mAb:

$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two $R^{3's}$ form a cyclic or heterocyclic ring, wherein each $R^3$ is optionally independently substituted with 1 to 3 groups selected from halogen, (XXXVI)

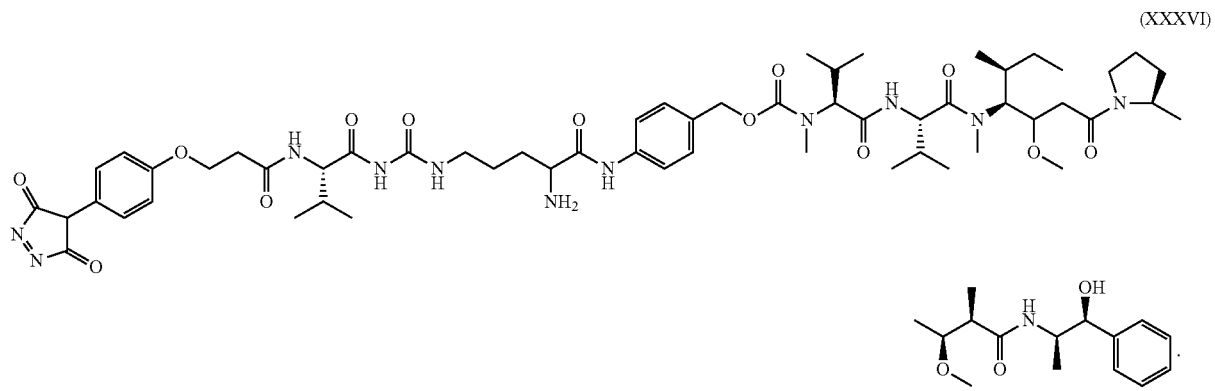

In another embodiment the disclosure provides methods for bioconjugating momomethyl auristatin E (MMAE) to a cancer targeting monoclonal antibody (mAb) to provide a bioconjugated mAb, wherein the monoclonal antibody (mAb) is CD22, CD30, CD33, GPNMB or ErbB2.

In another embodiment the disclosure provides methods for chemoselectively modifying a glucaon-like protein receptor (GLP-1R) agonist by reacting a GLP-1R agonist with a compound of Formula XI:

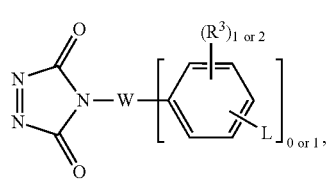

wherein:
W is independently a direct bond or is O;

carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, $N_3$, $CH_3$, C≡CH, C≡CHN$_3$, CH=CHN$_3$, $CH_2CH_2N_3$, $O(CH_2)N_3$, $C_6H_5$, $COCH_3$, $OCH_2C≡CH$, $OCH_2COCH_3$, $OCOCF_3$, or X—[$CH_2CH_2$—Y]$_n$—($CH_2$)$_q$—$N_3$;

X and Y are each independently $CH_2$, O, NH, S, NHCO or CONH;

n and q are each independently an integer from 0 to 12.

In another embodiment the disclosure provides methods for chemoselectively modifying a glucaon-like protein receptor (GLP-1R) agonist, wherein the GLP-1 agonist is Exenatide, Liraglutide or Taspoglutide.

In another embodiment the disclosure provides methods for chemoselectively modifying a glucaon-like protein receptor (GLP-1R) agonist by reacting a GLP-1R agonist with a compound of Formula XXXVIII:

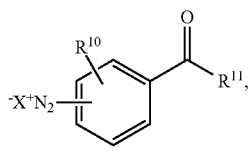

(XXXVIII)

wherein:

$X^-$ is independently $F^-$, $Cl^-$, $Br^-$, $I^-$, $ClO_4^-$, $NO_3^-$, $HSO_3^-$, $PF_6^-$ or $BF_4^-$;

$R^{10}$ is independently hydrogen, halogen, nitro, cyano, trifluoromethyl, substituted or unsubstituted alkyl or alkyl, substituted or unsubstituted alkoxy or alkoxy, substituted or unsubstituted aryl or aryl substituted, substituted or unsubstituted aryloxy or aryloxy, substituted or unsubstituted heteroaryl or heteroaryl substituted, substituted or unsubstituted heteroaryloxy or heteroaryloxy; and $R^{11}$ is independently hydrogen, alkyl, alkoxy, phenoxy, or alkylaryloxy.

In another embodiment the disclosure provides methods for chemoselectively modifying a glucaon-like protein receptor (GLP-1R) agonist, further comprising reacting the modified GLP-1R agonist with a compound of Formula XXXI:

   (XXXI), wherein:

Y is independently NH or O;

$R^{12}$ is independently small organic molecule, fluorescence unit, enzyme, peptide or antibody;

Linker is $(CH_2)_l$-A-$[CH_2CH_2-Z]_m$—$(CH_2)_n$—B;

A and B are each independently bond, C(=O), CONH or NHCO;

Z is independently $CH_2$ or O; and l, m, and n are each independently an integer from 0 to 12.

In another embodiment the disclosure provides methods for chemoselectively modifying a glucaon-like protein receptor (GLP-1R) agonist, wherein the GLP-1 agonist is Exenatide, Liraglutide or Taspoglutide.

Substituted phenols react with highly reactive electrophiles such as diazodicarboxylates in organic solvents in the presence of activating protic or Lewis acid additives. However, rapid decomposition of the diazodicarboxylate reagents in aqueous media and/or low reactivity toward phenols makes them unsuitable for bioconjugation. Acyclic diazodicarboxylate reagents are dramatically activated in Ene reactions by interaction with cationic species such as protons or metal ions. Cyclic diazodicarboxamides like 4-phenyl-3H-1,2,4-triazole-3,5(4H)-dione (PTAD), however, are not similarly activated and this reactivity difference presents an opportunity for aqueous chemistry.

A preliminary survey was conducted on the reactivity and stability of diazodicarboxylate and diazodicarboxamide reagents for the reaction with N-acyl tyrosine methyl amide 1 in aqueous buffer. As shown in Scheme 1, this study revealed that the decomposition of acyclic diazodicarboxylates in aqueous media was faster than the desired reaction with 1, whereas acyclic diazodicarboxamides were stable but not reactive enough. Ultimately, PTAD 2 provided the desired reactivity and stability.

Scheme 1. Model Tyrosine Ligation Reaction

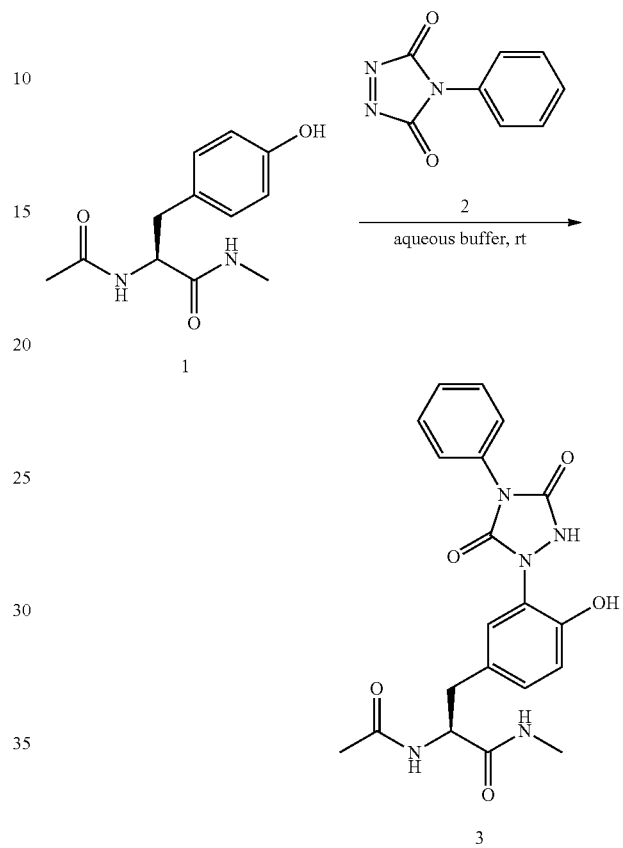

As a model for peptide labeling, N-acyl tyrosine methylamide 1 modification with PTAD 2 in mixed organic/aqueous media necessitated by the solubility characteristics of 1 was studied. In sodium phosphate buffer, pH 7/$CH_3CN$ (1:1), peptide 1 reacted rapidly (the reaction was complete within 5 minutes) with 1.1 equivalent of PTAD to provide 3 in 65% isolated yield. With the addition of 3.3 equivalents of PTAD, quantitative modification could be obtained. The buffer concentration did not significantly affect the reaction and, notably, the reaction did not proceed in $CH_3CN$ alone. This type of reaction has not been reported to occur under such mild aqueous media conditions.

Next, the chemoselectivity of this Ene-like reaction was studied with a defined collection of N-acyl methyl amides of histidine, tryptophan, serine, cysteine, and lysine. Significantly, only tryptophan and lysine yielded products detectable by $^1$H NMR. It is important to note that the indole of tryptophan reacted equally sluggishly with PTAD when the reaction was performed in neat organic solvent or in mixed aqueous media suggesting that aqueous conditions dramatically activate the phenolic group of tyrosine for the reaction. Competition experiments with an equimolar mixture of N-acyl methyl amides of tyrosine and tryptophan or tyrosine and lysine resulted in selective modification of tyrosine in 55% and 58% conversion, respectively, with no detectable modification of other amino acid amides. Similarly, when an equimolar mixture of all six amino acid amides was treated with PTAD, only the tyrosine modification (39% conversion) was observed by ¹H NMR, indicating that this reagent/reaction exhibits a high degree of chemoselectivity.

Given the inherent reversibility of the reaction between the related cyclic diazodicarboxamide 4-methyl-1,2,4-triazoline-3,5dione and indoles, the next concern was the relative stability of the C—N bond formed in the products. As shown in Scheme 2, p-cresol was used as a model phenol.

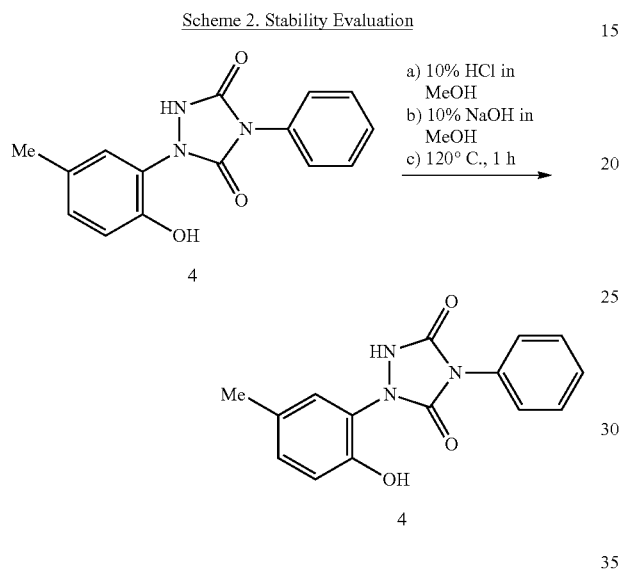

Compound 4, the product of the reaction of p-cresol and PTAD, was subjected to both strongly acidic and basic conditions for 24 hours at room temperature or high temperature (120° C.) for 1 hr. The C—N bond was found to be stable under these conditions and starting material was recovered in 89% yield following acid treatment and quantitatively recovered following base and heat treatments. These conditions are extremely harsh for a peptide or protein. This study suggests that the 1,2,4-triazolidine-3,5-dione linkage is hydrolytically and thermally stable; more robust than maleimide-type conjugations, which are prone to elimination, or Mannich-type conjugations where retro-Mannich reactions would be expected.

The Ene-like reaction was also evaluated using a variety of peptides to assess the applicability of this approach in peptide chemistry. The acyclic tripeptide H-Gly-Gly-Tyr-OH reacted rapidly with PTAD 2 in phosphate buffer, pH 7/CH₃CN (1:1) to provide product 5 in 85% isolated yield. As shown in Scheme 3, the reaction of the small cyclic peptide (Ile³)-pressinoic acid (tocinoic acid) with PTAD provided product 6, which was confirmed by LCMS and HRMS analyses. No bis-addition products were observed. These experiments demonstrated the chemoselectivity of this reaction and its application to peptide chemistry and suggests that cyclic diazodicarboxamides like PTAD should possess the reactivity and chemoselectivity required for complex protein modifications.

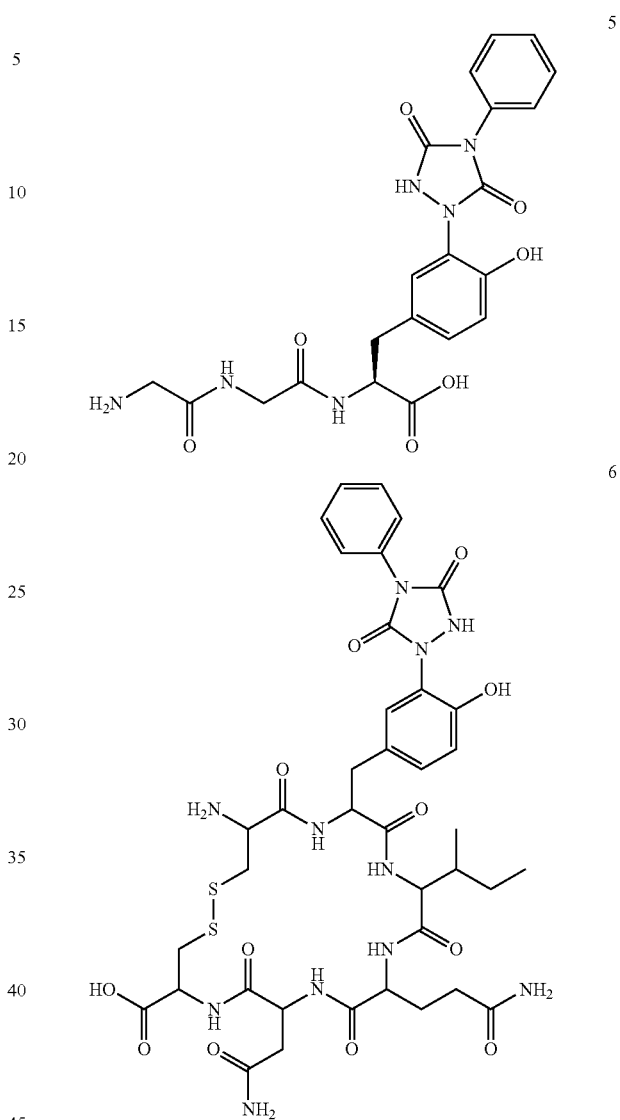

In order to explore the potential of this reaction for protein functionalization, several functionalized PTAD analogs were prepared. As shown in Scheme 4, azide containing linkers 7 and 8 were prepared as stable and synthetically versatile precursors with utility in click chemistry and as intermediates in the synthesis of 9 and 10. Differentially functionalized PTAD reagents were chosen to study whether reactivity of these reagents could be tuned with electronic effects. Reduction of the azide functionality and reaction with the commercially available NHS-activated 5- and 6-carboxy-X-rhodamine (ROX) provided the corresponding amide products. Oxidation to the corresponding cyclic diazodicarboxamides 9 and 10 was done with NBS and pyridine in N,N-dimethylformamide. To evaluate nonspecific and non-covalent attachment of highly hydrophobic ROX reagents to protein, the non-reactive rhodamine alkyne 11 was prepared and used as a negative control reagent.

Scheme 4. Linkers And Rhodamine Dye Reagents

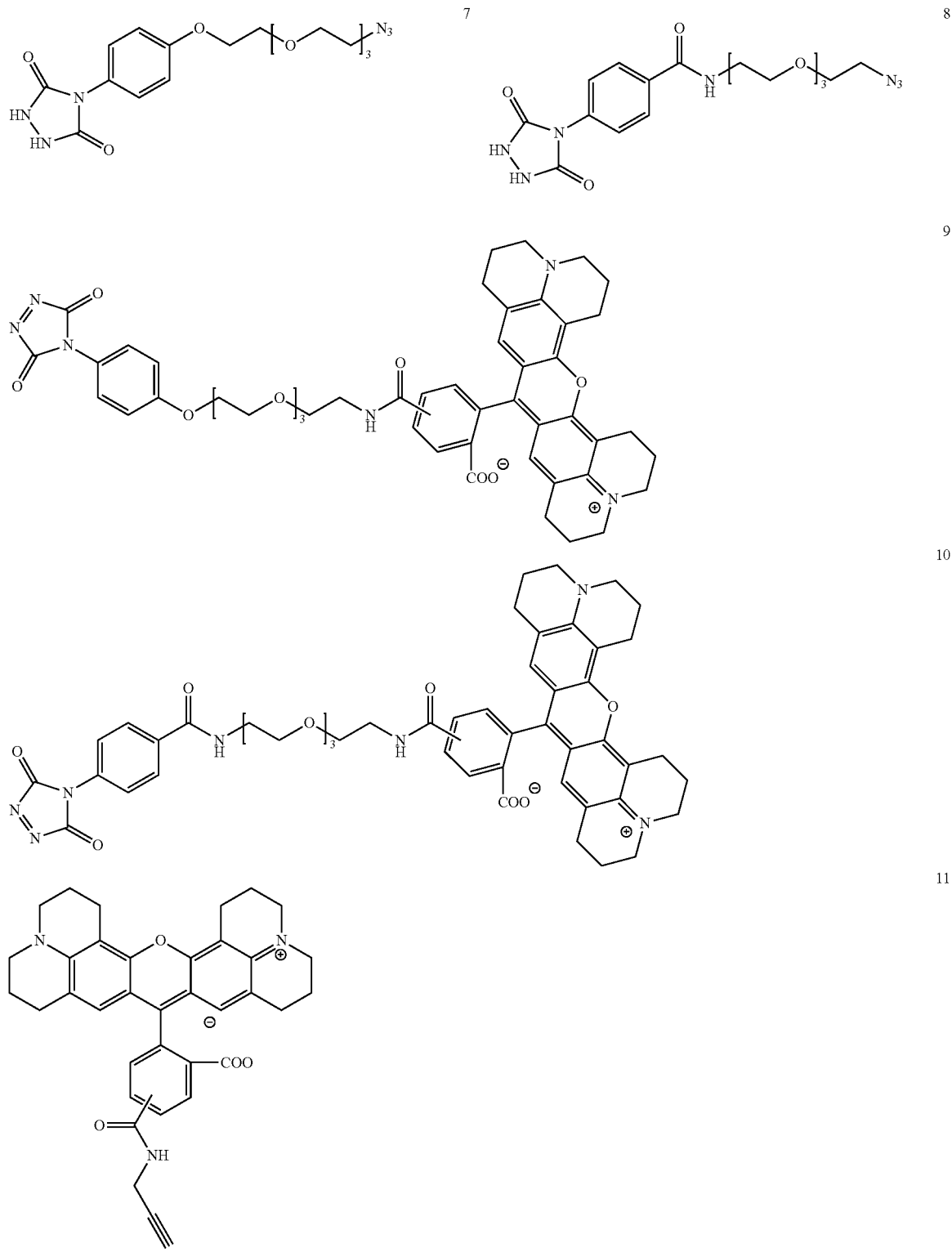

Chymotrypsinogen A, bovine serum albumin (BSA), and myoglobin from equine heart were chosen as model protein systems as these proteins have different tyrosine and tryptophan contents and side chain accessibilities. Protein labeling was studied at the physiological pH 7.4 in phosphate buffer with a minimal amount of N,N-dimethylformamide, needed to prepare and deliver the labeling reagent. The final concentration of N,N-dimethylformamide in the reaction mixture was 1 to 5%. PTADs 9 and 10 were studied at concentrations ranging from 1 mM to 10 mM and the results are provided in Table 1, Protein Modification Study.

TABLE 1

Protein Modification Study

| # | Protein[a] | Reagent concentration, mM | Labeling with reagent 9, % | Labeling with reagent 10, % |
|---|---|---|---|---|
| 1 | Chymotrypsinogen A | 1 | 56 | 35 |
| 2 | Chymotrypsinogen A | 5 | 72 | 54 |
| 3 | Chymotrypsinogen A | 10 | 81 | 60 |
| 4 | Myoglobin | 1 | 6 | 13 |
| 5 | Myoglobin | 5 | 6 | 13 |
| 6 | Myoglobin | 10 | 8 | 16 |
| 7 | BSA | 1 | 85 | 53 |
| 8 | BSA | 5 | 96 | 65 |
| 9 | BSA | 10 | 96 | 68 |
| 10 | Chymotrypsinogen A | 10[c] | 3 | 3 |
| 11 | Myoglobin | 10[c] | 3 | 3 |
| 12 | BSA | 10[c] | 4 | 4 |

[a]Protein concentration was kept at 30 µM in phosphate butter, pH 7.4.
[b]Conversion was calculated based on UV-vis absorption for extensively desalted and dialyzed sample. Average conversion of two independent experiments is shown.
[c]Reagent 11 was used as a negative control.

As shown above in Scheme 4, an assessment of the reaction conversion was done by UV analysis following dialysis in buffer to remove unbound dye. Reagent 9 provided up to 81% labeling of chymotrypsinogen A and up to 96% labeling of BSA. Myoglobin was labeled with reagent 9 at 6-8%. The background nonspecific and noncovalent association of rhodamine dye 11 to proteins accounted for 3-4% labeling in this assay. Reagent 10 was expected to be more reactive and less stable in aqueous media than 9 given the electron withdrawing linker; it yielded 60% labeling of chymotrypsinogen A, 68% labeling of BSA, and 16% modification of myoglobin. Tryptic digest and subsequent ESI-MS analysis of the fragments of all proteins modified with reagents 9 and 10 confirmed covalent modification of chymotrypsinogen A at Y228 and BSA at Y355 and Y357. Reagent 10 modified myoglobin at W15 at a very low level, consistent with the results of the small molecule study. Although some modifications of myoglobin with 9 were detected, the degree of labeling was too low to identify the site. As shown in FIG. 1, the covalent modification of proteins was confirmed using a gel-based assay, MALDI-TOF, and ESI analysis. Chymotrypsinogen A retained its enzymatic activity following labeling consistent with the mild nature of the reaction (see supporting information).

The BSA labeling with 9 over a wide pH range (pH 2 to pH 10) was also studied. This study found significant protein labeling at all pHs. Up to 54% labeling was observed at pH 2 with labeling ranging from 85% to 98% between pH 7 and 10. Thus, the tyrosine ligation reaction is applicable over a wide pH range.

The tyrosine ligation reaction may be useful for the bioconjugation of a wide variety of functionalities onto protein surfaces. As shown in Scheme 5, an integrin binding cyclic RGD peptide containing an alkyne, 12, was prepared. Cu(I)-mediated cycloaddition reaction with intermediate 7 followed by oxidation with NBS/Py provided the labeling reagent, which was then reacted with the therapeutic antibody herceptin [(a) 7, Cu, $CuSO_4$.; and (b) i) NBS, Py, N,N-DMF; ii) herceptin in phosphate buffer, pH 7.4].

Scheme 5. Preparation Of Her/RGD Construct

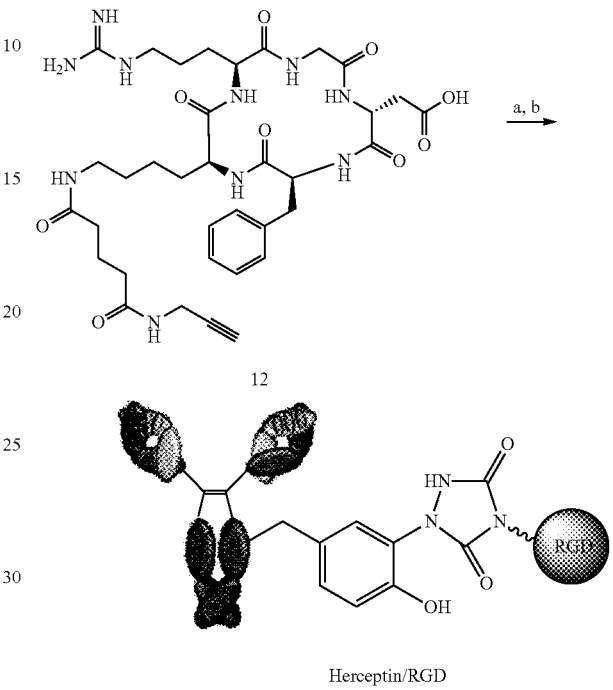

Herceptin/RGD

Figure 2:
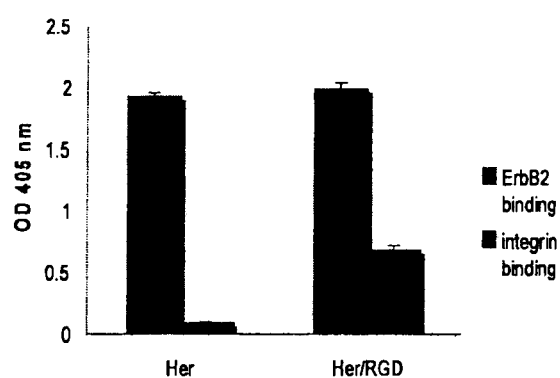
FIG. 2 illustrates the binding of ErbB2 and integrin αvβ3 to the antibody herceptin and herceptin/RGD conjugate.

The resulting herceptin/RGD conjugate was purified and characterized by MALDI-TOF MS. ErbB-2 and integrin αvβ3 binding ELISA as shown in FIG. 2. This demonstrate that modification of the antibody herceptin through tyrosine conjugation did not impair its ability to bind to ErbB-2, while introduction of the cyclic RGD peptide allowed the antibody conjugate to bind integrin αvβ3 recognition, thereby providing a new chemical route to antibodies with multiple specificities.

Thus, the disclosure provides a new and versatile class of cyclic diazodicarboxamides that react selectively with phenols and the phenol side chain of tyrosine through an Ene-like reaction. This mild aqueous reaction works over a broad pH range and expands the repertoire of aqueous chemistries available for small molecule, peptide, and protein modifications. This reaction provides broad utility in protein chemistry and in the chemistry of phenol-containing compounds.

In another aspect the disclosure further provides reagents and methods for site-specific tyrosine labeling at a specific site on human IgG heavy chain proteins using a novel aromatic diazonium salt reagent, o-benzaldehyde diazonium hexafluorophosphate shown below:

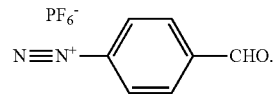

It has been found that using this azo labeling agent, unexpectedly provides for the site specific modification of human antibody IgG1 molecules at the CH2 domain of the heavy chain. More specifically, heavy chain Tyrosine 319, according to Kabat numbering, is specifically labeled with this reagent. Three therapeutic antibodies; herceptin, rituxan, and erbitux were examined. All three were specifically labeled at this single site following treatment with this reagent. This finding has important implications for the development of specific antibody conjugates for therapeutic and diagnostic purposes. For example, amino acid specific labeling is important for diagnostic applications, tools applications, and therapeutic applications. This reagent has two functionalized groups: the azo moiety that recognizes the amino acid tyrosine in one material; and the aldehyde moiety that links to another material via a linker such as hydrazine or hydroxyamine. The reagent may be used for selective tyrosine bioorthogonal modification among small molecules and/or macro molecules, such as medicines, peptides, enzymes and antibodies. This site specific labeling of human IgG1 molecules at a single residue on the heavy chain has many uses in multispecific, multifunctional, drug conjugates, radiolabeled antibodies. Conservation of this residue in other isotypes suggests that it might be targeted in antibodies other than IgG1's. This reagent may be prepared from commercially available starting material in one step and has acceptable stability for long term storage.

Biomolecule reporters, ketone, azide and alkyne, have taken on significance to produce novel biomolecules with pioneer discovery of bioorthogonal chemical reaction on oxime/hydrazone formation, Staudinger ligation and triazole formation. It is well established that these unnatural functional groups can be introduced successfully into target biomolecules by biological techniques such as enzymatic modification or genetic encoding. However, these biological methods sometimes suffer from low yields, taking long time and need of special labor to develop appropriate enzymes and/or tRNAs. On the other hand, bioconjugation, which can introduce unnatural functional groups into native proteins chemically, has been under investigation. The key development in this area, is a bioorthogonal chemical reaction which proceeds rapidly and chemoselectively under physiological acceptable conditions. However, the reaction conditions are severely limited to preserve the original protein's biological activity. The reaction is performed in aqueous media, with a narrow pH window, at low temperatures and at low concentrations. Besides, native proteins have a lot of amino acid possessing reactive functional group such as Arg, Lys, Ser, Cys, Asn, Asp, His, Trp and Tyr. Therefore, it is challenging for chemists to modify a specific amino acid in such a reactive amino acid pool by strictly limited conditions.

Lysine and cysteine side chains are the most commonly functionalized amino acids for bioconjugation. However, the high abundance of lysine on protein surface makes site-specific modification difficult. In contrast, cysteine is rare and most often present in disulfide linked pairs in proteins in their natural environment. For the modification, pretreatment by reduction to cleave the disulfide bond is typically required followed by reaction with a reagent like maleimide. Recently great attention has been paid to the bioorthogonal modification of aromatic amino acid side chains of tryptophan and tyrosine. Among nucleophilic amino acids in proteins, tyrosine has unique reactivity contributed by phenol possessing pKa 10 acidic proton. The reaction with nucleophile in basic condition proceeds at oxygen atom like alkyration or acylation. The reaction in acidic condition proceeds at carbon atom on aromatic ring like ene-reaction. Tyrosine bioorthogonal modifications at carbon atom in mild, biocompatible, metal-free conditions were reported using Mannich-type addition to imines. (However, the tyrosine modification with in situ formed imines revealed the limitation of using an excess of highly reactive formaldehyde. Tryptophan side chains and reduced disulfides form formaldehyde adducts under the reaction conditions. The alternative tyrosine modification with cyclic imines gave the uncontrollable double adduct of cyclic imine. As shown in Scheme 6, it has now been found that using the reactivity of diazodicarboxylate-related molecules, creates an efficient aqueous ene-type reaction as an orthogonal bioconjugation strategy. Thus, the present disclosure provides new and efficient chemical methods for the introduction of biomolecule reporters into small molecules, peptides, and proteins by tyrosine ligation reaction.

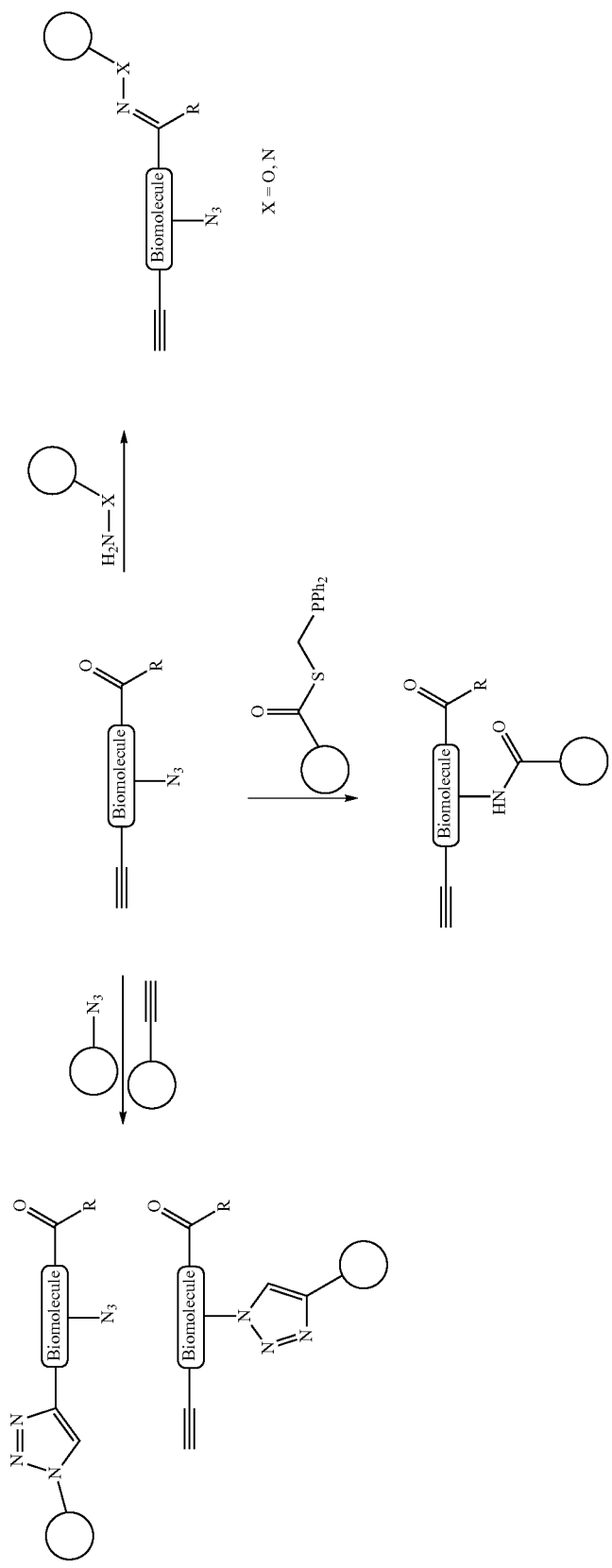
Scheme 6. Biomolecule Reporters For Bioorthogonal Reaction

Substituted phenols can react with highly reactive electrophiles such as diazodicarboxylates in organic solvents in the presence of activating protic or Lewis acid additives. However, highly reactive diazodicarboxylate reagents are rapidly decomposed in aqueous media and stable diazodicarboxyamide reagents in aqueous media are low reactive toward phenols. Their high reactivity however, has made them unsuitable for bioconjugation. Acyclic diazodicarboxylate reagents are dramatically activated in ene-reaction by the interaction with cationic species such as protons or metals. By contrast, cyclic diazodicarboxyamide like 4-phenyl-3H-1,2,4-triazole-3,5 (4H)-dione (PTAD) are not similarly activated by protic or Lewis acid additives. On the other hand, the hydroxyl functional group on phenol cannot be activated under acidic condition but instead, is activated under basic condition due to its acidic proton. A survey of the reactivity and stability of diazodicarboxylate and diazodicarboxyamide was conducted in which resulted in the finding of a new type of ene-reaction of PTAD with phenol activated by buffer conditions. Scheme 7 illustrates the PTAD linker to linker of a phenolic group of compound/peptide or protein followed by addition of aldolase antibody that then reacts through the lactam.

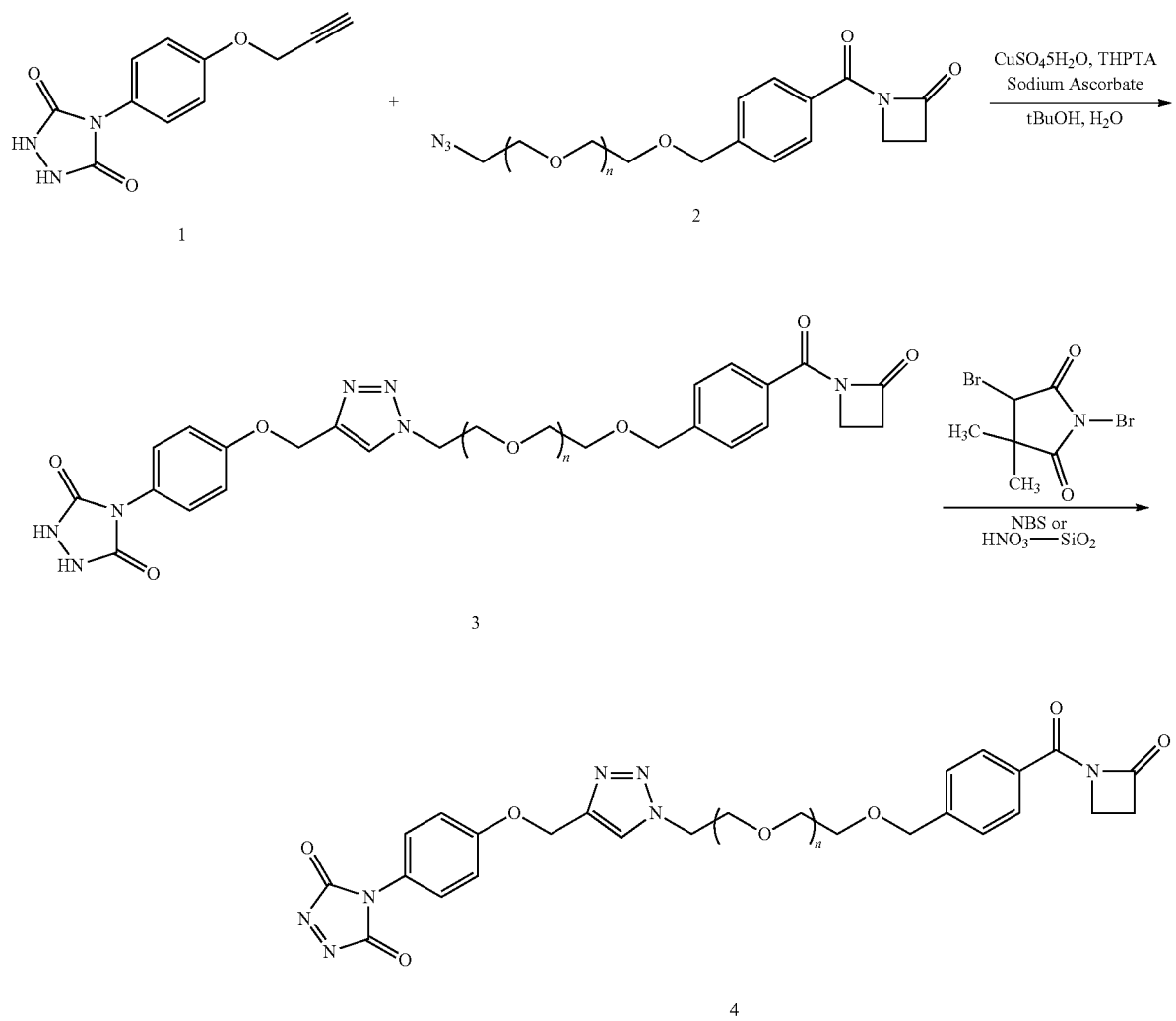

Scheme 7. PTAD linker to linker of phenolic group of compound/peptide or protein followed by addition of aldolase antibody that then reacts through the lactam A model for peptide labeling, a study was taken of N-acyl tyrosine methyl amide 1 modification with triazolediones 2, in mixed organic solvent/aqueous media necessitated by the solubility characteristics of 1. As shown in Scheme 7, peptide 1 reacted rapidly with 1.1 equivalents of PTAD in sodium phosphate buffer, pH 7/CH$_3$CN (1:1), (i.e. the reaction was complete within 5 minutes) to provide product 3a in 65% isolated yield. PTAD showed better modification result than 4-methyl-3H-1,2,4-triazole-3,5(4H)-dione (MTAD) 3b which modified amide 1 in 57% isolated yield.

Scheme 8. Model Tyrosine Ligation Reaction

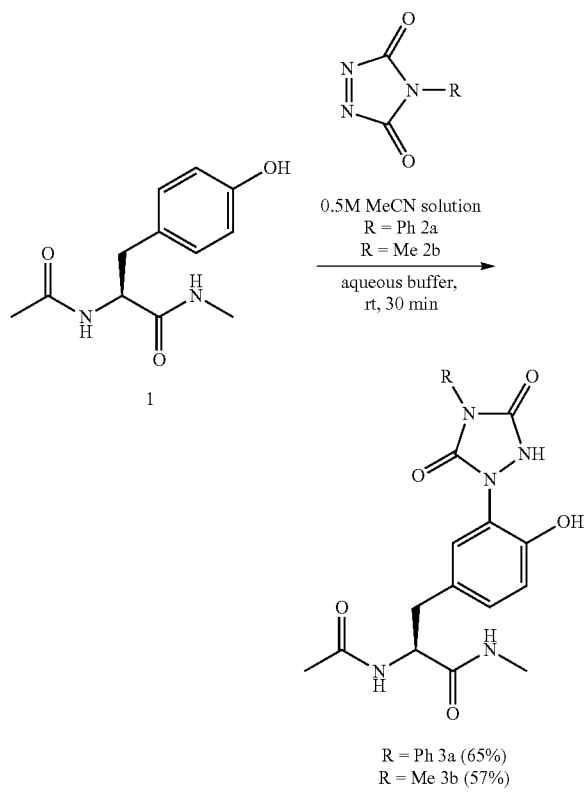

R = Ph 3a (65%)
R = Me 3b (57%)

As shown in Table 7, a detailed evaluation of N-acyl tyrosine methyl amide 1 modification with PTAD 2 was performed in several aqueous media over a wide range of pH. The conversion was calculated based on crude $^1$H NMR by comparison of the areas of aromatic signals. The reactions afforded labeled tyrosine 3 and any un-reacted starting material was recovered. No side products were observed. The reaction proceeded depending on pH over a wide rang, with the optimal pH being in the range of 7 to 8. By contrast, the buffer concentration did not significantly affect the reaction. The conversion is independent of buffer concentration where the buffer keeps enough buffering ability. The conversion was around 60% in the 20 mM reaction using pH 7 phosphate buffer over 50 mM concentration. The 6.7 mM reaction provided about 50% conversion in pH 7 phosphate buffer over 25 mM concentration. An increase in the excess of PTAD from 1.1 equivalents to 3.3 equivalents resulted in excellent conversion. Additional labeling did not occur to give double adduct on phenol. Acceptable conversion was obtained when the concentration of 1 was lowered from 20 mM to 2 mM. The reaction proceeded in buffer and basic conditions but did not proceed in water and brine condition or in organic solvent.

TABLE 7

| Entries | Buffer | PTAD (equiv) | Conc. (mM) | Conversion (%) |
|---|---|---|---|---|
| 1 | 50 mM pH 7 NaH$_2$PO$_4$—Na$_2$HPO$_4$/CH$_3$CN (1:1) | 1.1 | 20 | 60 |
| 2 | 200 mM pH 7 NaH$_2$PO$_4$—Na$_2$HPO$_4$/CH$_3$CN (1:1) | 1.1 | 20 | 61 |
| 3 | 200 mM pH 7 NaH$_2$PO$_4$—Na$_2$HPO$_4$/CH$_3$CN (1:1) | 2.2 | 20 | 87 |
| 4 | 200 mM pH 7 NaH$_2$PO$_4$—Na$_2$HPO$_4$/CH$_3$CN (1:1) | 3.3 | 20 | 93 |
| 5 | 100 mM pH 7 NaH$_2$PO$_4$—Na$_2$HPO$_4$/CH$_3$CN (1:1) | 1.1 | 20 | 69 |
| 6[a] | 100 mM pH 7 NaH$_2$PO$_4$—Na$_2$HPO$_4$/CH$_3$CN (1:1) | 1.1 | 20 | 79 |
| 7[b] | 100 mM pH 7 NaH$_2$PO$_4$—Na$_2$HPO$_4$/CH$_3$CN (1:1) | 2.2 | 20 | 91 |
| 8[c] | 100 mM pH 7 NaH$_2$PO$_4$—Na$_2$HPO$_4$/CH$_3$CN (1:1) | 3.3 | 20 | 96 |
| 9[c] | 200 mM pH 7 NaH$_2$PO$_4$—Na$_2$HPO$_4$/CH$_3$CN (1:1) | 3.3 | 20 | >99 |
| 10 | 100 mM pH 7 NaH$_2$PO$_4$—Na$_2$HPO$_4$/CH$_3$CN (1:1) | 3.3 | 2 | 67 |
| 11 | 200 mM pH 5 NaH$_2$PO$_4$/CH$_3$CN (1:1) | 1.1 | 20 | 3.8 |
| 12 | 200 mM pH 6 NaH$_2$PO$_4$—Na$_2$HPO$_4$/CH$_3$CN (1:1) | 1.1 | 20 | 30 |
| 13 | 200 mM pH 8 NaH$_2$PO$_4$—Na$_2$HPO$_4$/CH$_3$CN (1:1) | 1.1 | 20 | 69 |
| 14 | 200 mM pH 9 Na$_2$HPO$_4$/CH$_3$CN (1:1) | 1.1 | 20 | 67 |
| 15[d] | CH$_3$CN | 1.1 | 20 | No reaction |
| 16[d] | H$_2$O/CH$_3$CN (1:1) | 1.1 | 20 | No reaction |
| 17[d] | 100 mM NaCl/CH$_3$CN (1:1) | 1.1 | 20 | No reaction |
| 18 | 100 mM pH 7.4 HEPES buffer/CH$_3$CN (1:1) | 1.1 | 20 | 63 |
| 19 | 100 mM pH 7.4 Tris buffer/CH$_3$CN (1:1) | 1.1 | 20 | 35 |
| 20 | 100 mM Na$_2$CO$_3$/CH$_3$CN (1:1) | 1.1 | 20 | 43 |
| 21 | 100 mM Et$_3$N/CH$_3$CN (1:1) | 1.1 | 20 | 58 |

[a]0.1M PTAD solution was added in 5 aliqots with 10 sec. interval,
[b]0.2M PTAD solution was added in 5 aliqots with 10 sec. interval,
[c]0.3M PTAD solution was added in 5 aliqots with 10 sec. interval,
[d]reaction time 12 h.

A model for peptide labeling, a study was taken of N-acyl tyrosine methyl amide 1 modification with triazolediones 2, in mixed organic solvent/aqueous media necessitated by the solubility characteristics The N-acyl and C-methyl tyrosine amide, 4 and 6, were reacted with PTAD to evaluate effect of C-terminal and N-terminal substitution. As shown in Scheme 9, the reactions were performed using the same condition as Entry 5 in Table 7, and modified both peptides successfully. The modification of 4 gave better results than 6 resulting in a clean reaction without side products, while the modification of 6 resulted in a small amounts of side products in spite of the same conversion in crude $^1$H-NMR.

Scheme 9. Modification Of N-Acyl And
C-Methyl tyrosine Amide By The Tyrosine Ligation Reaction

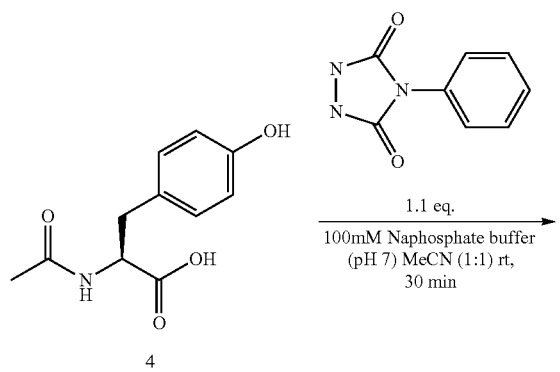

4

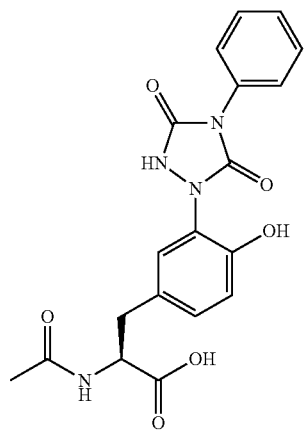

5
conversion 46%

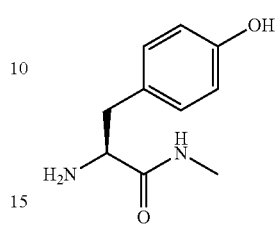

6

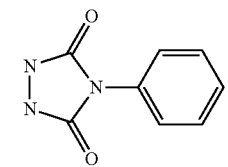

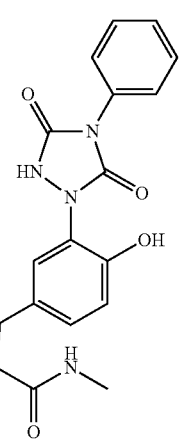

7
conversion <47%

To understand the tyrosine ligation reaction, the pKa of o-cresol and labeled p-cresol by ACD was calculated. As shown in Scheme 10, the calculation shows that the reaction generates more acidic compounds from less acidic ones in water. The pKa value of p-cresol is 10.2. The pKa value of labeled p-cresol is more acidic at 4.3. The reaction proceeds by counter cation relay from buffer to coupling compound. Starting from partial exchanging of proton to a counter cation such as Na$^+$, the cation is transferred to more acidic triazolidine ring. The coupling compound finally exists as a salt mainly with the cation in buffer or aqueous basic condition. The mechanism was well supported by the results of pH effect in Table 7 and the reaction with 4-methlanisole. PTAD cannot react with 4-methlanisole in any condition in Table 7. Based on this, more basic conditions should have given better conversion but the conversion plateaued at pH 8. The reason may be competitive reaction against water. The decomposition of PTAD is also accelerated depending on basicity. The tyrosine ligation reaction is conducted in delicate pH balance and reagent's reactivity and stability. This type of reaction has not been reported to occur in such mild aqueous media.

Scheme 10. Calculated pKa Of Labeling Phenol

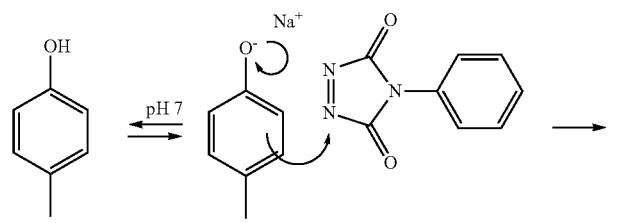

pKa = 10.2

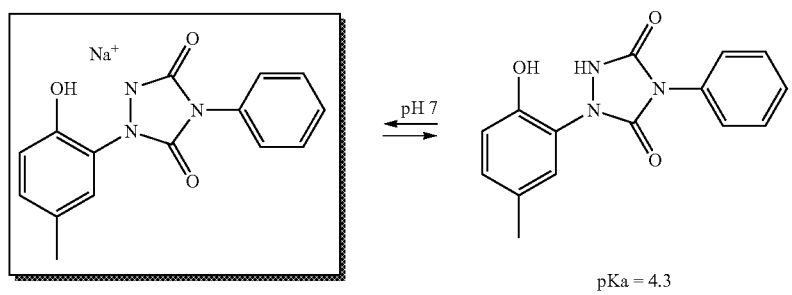

pKa = 4.3

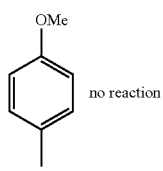

no reaction

The reaction of phenol derivatives with PTAD was investigated to find the scope and limitations for the tyrosine ligation reaction. As shown in Table 8, the reactions were performed using the same conditions as Entry 5 in Table 7. The reaction of phenol or o-cresol gave p-mono-adducts in low yields, because both p- and o-position modified di-adducts were produced. On the other hand, the reactions of o-disubstituted 2,6-dimethylphenol gave p-adduct as a single product 8d in 61% yield. The reaction with m-cresol, enhanced the orientation for o- and p-position, selectively provided p-adduct 8e in 77% yield and the isolated yield reached 96% yield by use of the excess of PTAD (2.2 eq.). Based on these results, the p-position seemed more reactive than the o-position against PTAD. In the case of p-substituted phenols, compounds having electron donor group provide o-adduct in 58-61% yields, whereas p-nitrophenol having strong electron withdrawing group gave no reaction because the anionic substrate generated in the buffer was strongly stabilized by delocalization of the electrons. The reaction of biaromatic compounds gave a mono-adducts in good yield and high selectivity. Interestingly, the reaction with qunidine derivative afforded single 5-position adduct in spite of the bulky environment. The substitution of PTAD with MTAD also gave a similar result.

TABLE 8

| Entry[a] | Substrate | $R_2$ | Selectivity | Yield (%) |
|---|---|---|---|---|
| 1 | OH-phenyl | Ph | para<br>para & ortho | 8a: 15<br>8a': 19 |

TABLE 8-continued
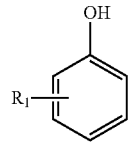
| Entry[a] | Substrate | R$_2$ | Selectivity | Yield (%) |
|---|---|---|---|---|
| 2 | 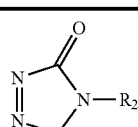 | Ph | para<br>para &<br>ortho | 8b: 11<br>8b': 24 |
| 3 | 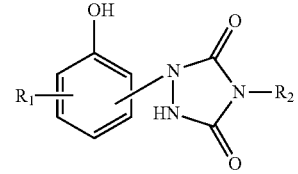 | Ph | para<br>para &<br>ortho | 8c: 35<br>8c': 11 |
| 4 | 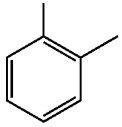 | Ph | para | 8d: 61 |
| 5 | 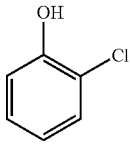 | Ph | para | 8e: 77<br>(96)[b] |
| 6 | 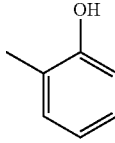 | Ph | ortho | 8f: 60 |
TABLE 8-continued
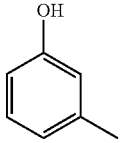
| Entry[a] | Substrate | R$_2$ | Selectivity | Yield (%) |
|---|---|---|---|---|
| 7 | 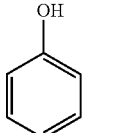 | Ph | ortho | 8g: 61 |
| 8 | 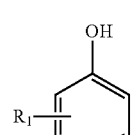 | Ph | ortho | 8h: 58 |
| 9 | 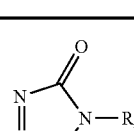 | Ph | — | No reaction |
| 10 | 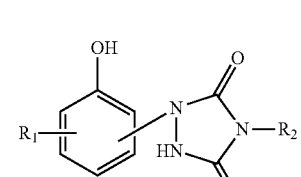 | Ph | 1-position | 8i: 89 |
| 11 |  | Ph | 5-position | 8j: 88 |

TABLE 8-continued

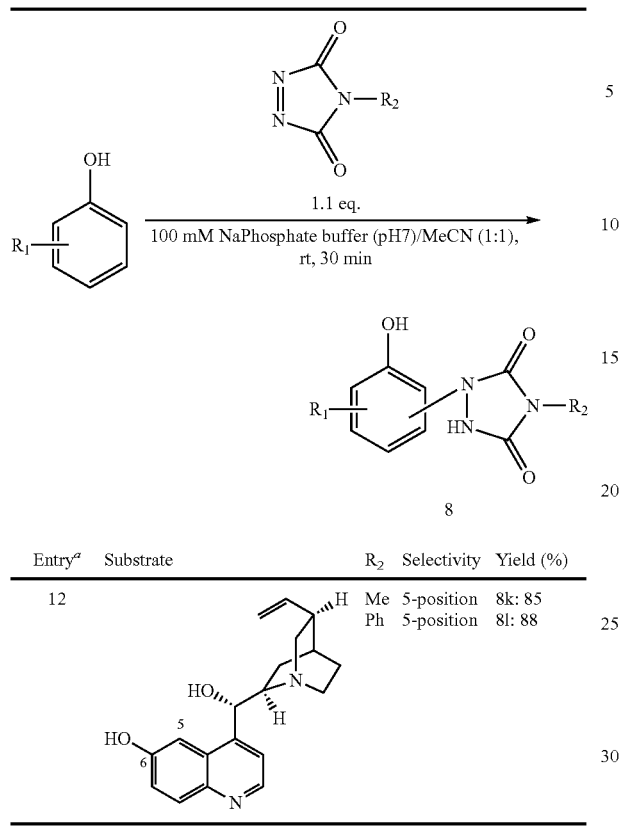

| Entry[a] | Substrate | R2 | Selectivity | Yield (%) |
|---|---|---|---|---|
| 12 | (cinchonidine structure) | Me<br>Ph | 5-position<br>5-position | 8k: 85<br>8l: 88 |

[a]The concentration of phenol derivatives was 20 mM and 0.3M PTAD solution was added in 6 aliqots with 10 sec. interval.
[b]PTAD of 2.2 eq. was used in the reaction.

The relative stability of the C—N bond formed in the products was studied using p-cresol as a model phenol. As shown in Scheme 11, p-cresol was reacted with PTAD in tetrahydrofuran in the presence of sodium hydride to provide adduct in 75% isolated yield. Compound 8f was subjected to both strong acidic and basic conditions for 24 hours at room temperature or high temperature (120° C.) for 1 h. The C—N bond was found stable under these conditions, and starting material was recovered in 89% following acid treatment and quantitatively recovered following base and heat treatments. This study suggests that the 1,2,4-triazolidine-3,5-dione linkage is hydrolytically and thermally stable, more robust than maleimide-type conjugation, which are prone to elimination, or Mannich-type conjugations where retro-Mannich reaction would be expected.

Scheme 11. Stability Evaluation

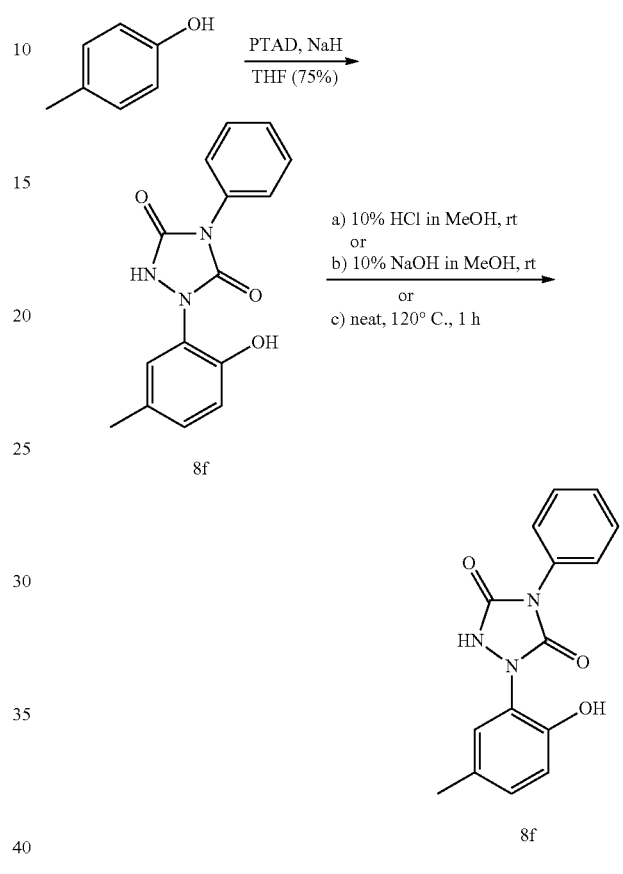

Given the labeling potential of PTAD on tyrosine in aqueous media, the design and preparation of PTAD analogs possessing a biomolecule reporter was studied. As shown in Scheme 12, the structures and preparations of PTAD are outlined below.

Scheme 12. Synthesis Of PTAD Derivatives
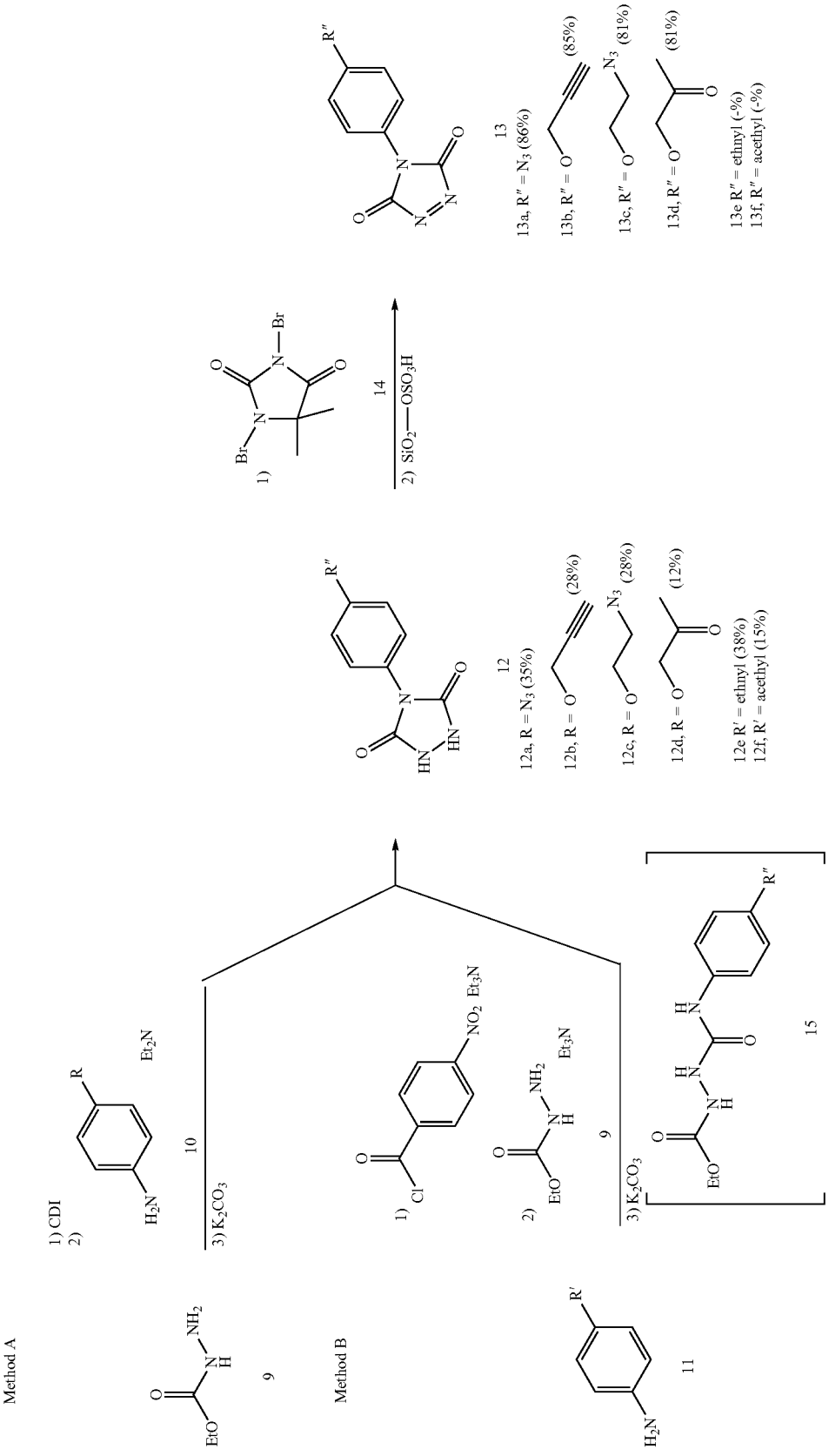

Two kinds of PTAD were designed. One is PTAD directly substituted by biomolecule reporter on phenyl ring like 13a, 13e, and 13f. The other is PTAD replaced by oxygen atom linker like 13b, 13c, and 13d. The coupling reaction between ethyl hydrazinecarboxyrate 9 and anilines 10 or 11 was performed by method A or B depending on nucleophilicity of aniline. The anilines were commercially available or synthesized from commercially available compounds by the methods in Scheme 13.

Scheme 13. Synthesis Of Anilines

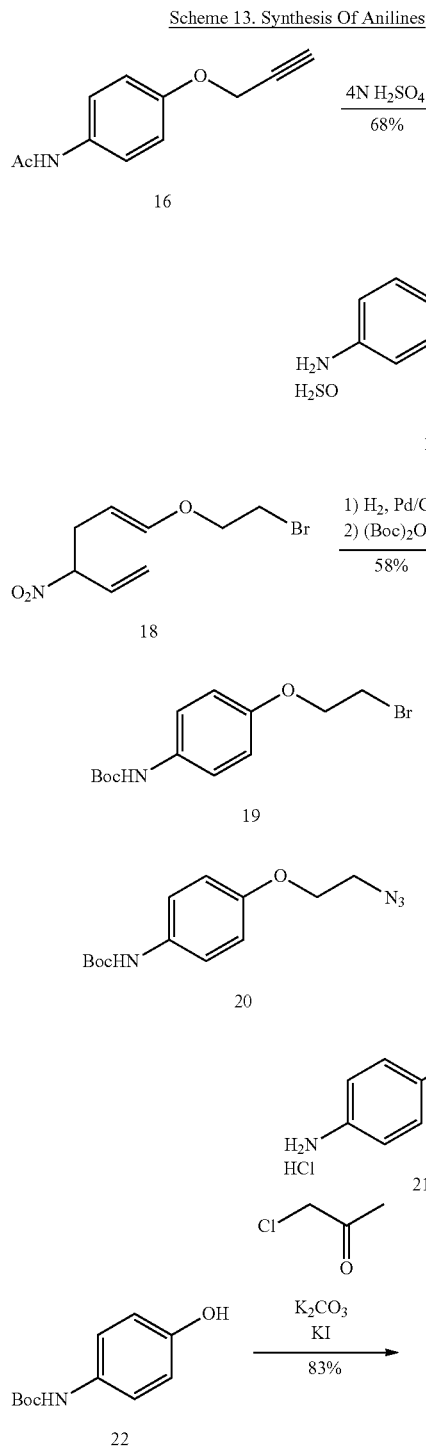

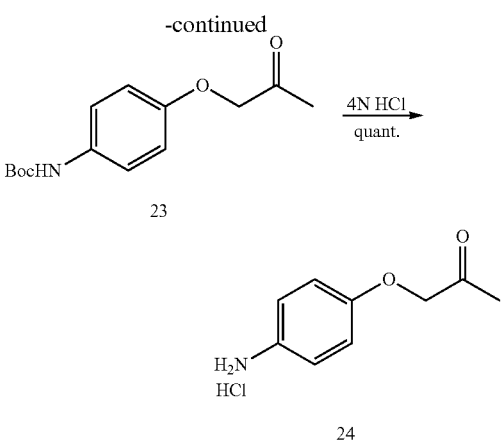

As shown above in Scheme 12 for Method A: after activation of 9 by treatment with CDI, aniline 10 was reacted with the activated ester in tetrahydrofuran at room temperature to afford coupling intermediate 15. Also shown in Scheme 12 for Method B: less nucleophilic aniline 11 was converted to corresponding activated ester using 4-nitrophenyl chloroformate, then reacted with 9 to afford coupling intermediate 15 in tetrahydrofuran at room temperature. Obtained intermediates 15 were cyclized in the presence of $K_2CO_3$ in methanol under reflux without isolation. Finally, triazolidine 12 was converted to desired triazole 13 by oxidization of N—N single bond to N—N double bond with 1,3-diboromo-5,5-dimethylhydantoin 14 according to a literature. Side products derived from 14 and un-reacted starting material were removed by scavenging with silica sulfuric acid ($SiO_2$—$OS_3H$). These reagents were unstable against silica-gel column chromatography purification. The generation of products could be monitored by color change in reaction mixture from colorless to specific deep red color. Reagents, 13a, 13b, 13c, and 13d, were obtained as isolable solids or oil at temperature while their solution were relatively unstable. The specific color in solution was gradually disappeared overnight. The products, 13e and 13f, were immediately degraded during isolation at room temperature. Reagents, 13a, 13b, 13c, and 13d were used for the next reaction without additional purification after confirmation of purity by $^1$H-NMR. The reagents, 13e and 13f, were used as 0.5 M $CH_3CN$ mixture solution for next reaction without any purification.

The reactivity of the prepared PTAD analogs was evaluated by the same operation as Entry 4 in Table 7. Electronically-neutral substituted reagents, 13a and 13e, gave the same result as PTAD. The tyrosine modification proceeded in the same conversion without side product. In contrast, large amounts of significant uncharacterized side products were generated in the modification by electronically-poor reagent 13f. The labeling compound couldn't be characterized in crude $^1$H-NMR analysis due to many peaks derived from side products. Among these reagents, electronically-rich substituted the reagents, 13c, 13b and 13d, could modify tyrosine peptide 1 in good conversion. PTAD analogs contain strong electrophilic acceptor in triazole ring. This result suggests that electron donating substitutions on the phenyl ring can make the acceptor stable against water maintaining enough reactivity toward phenol and the tyrosine ligation reaction could introduce biomolecule reporters into tyrosine peptide.

TABLE 9

| Entries[a] | Reagents | | Conversion[b] (%) |
|---|---|---|---|
| 1 |  | 13a | 69 |
| 2[c] |  | 13e | 67 |
| 3[c] |  | 13f | — |
| 4 |  | 13c | 76 |
| 5[d] |  | 13b | 85 |
| 6 |  | 13d | 73 |

[a]The reaction was performed in 100 mM pH 7 $NaH_2PO_4$—$Na_2HPO_4$/$CH_3CN$ (1:1) at room temperature for 30 minutes.
[b]conversion was determined by crude $^1$H-NMR.
[c]0.5M $CH_3CN$ mixture solution.
[d]100 mM pH 7 $NaH_2PO_4$—$Na_2HPO_4$/$CH_3CN$ (1:1.5).

To confirm reactivity of novel reagents for the tyrosine ligation reaction, the labeling of the small cyclic peptide (Ile3)-pressinoic acid (tocinoic acid) as a simple peptide model was studied. As shown in Scheme 14, the cyclic peptide reacted rapidly with these reagents in pH 7 phosphate buffer, and provided one modified pure products in good yield after purification by reversed phase HPLC. These compound structures were confirmed by HRMS and $^1$H NMR. The cyclic peptide has proton signals derived from phenol in aromatic area of $^1$H-NMR. After tyrosine modification, the characteristic aromatic proton signals of labeling phenol are appeared in $^1$H-NMR ([a]. Reversed phase HPLC purity (gradient of $CH_3CN$/0.1% TFA water, 0:100 to 100:0 over 30 minutes at UV 254 nm).

Scheme 14. Peptide Modification

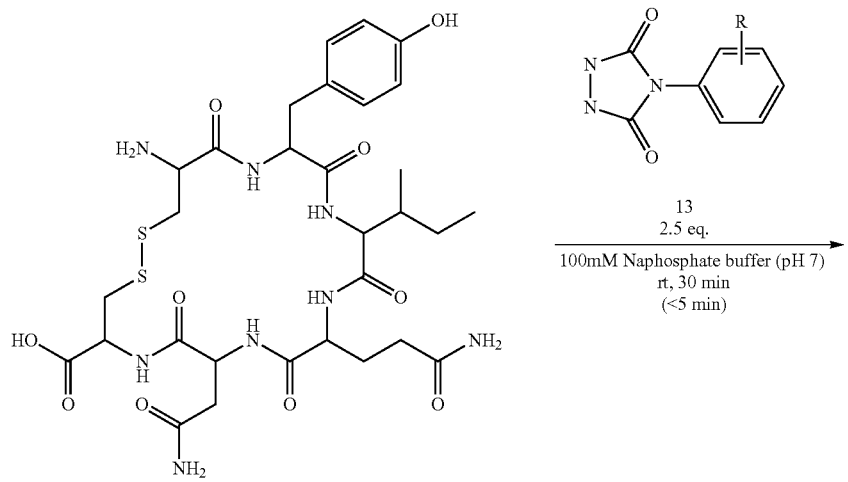

-continued

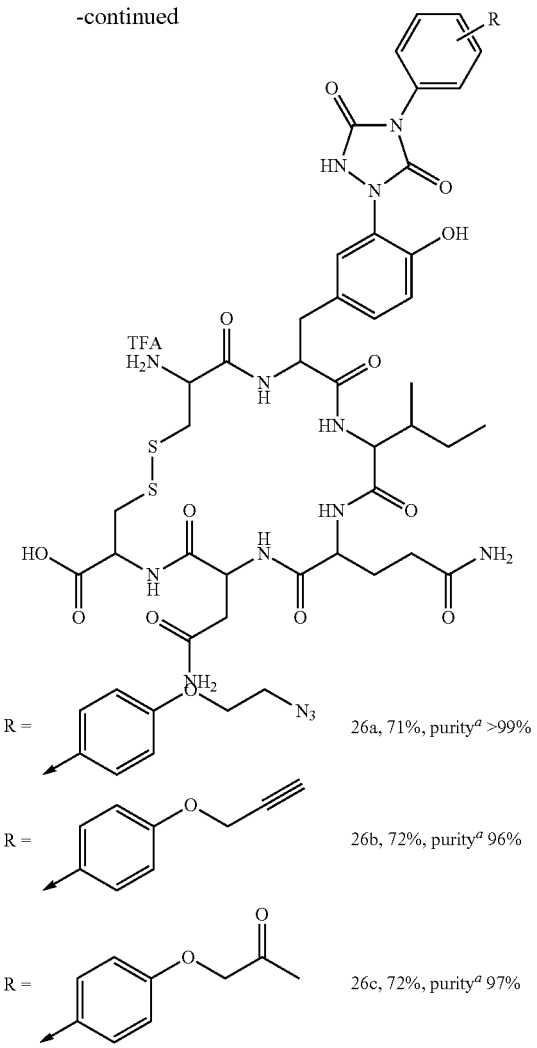

26a, 71%, purity$^a$ >99%

26b, 72%, purity$^a$ 96%

26c, 72%, purity$^a$ 97%

The potential of the tyrosine ligation reaction using these reagents for complicated peptide labeling was studied by designing a custom-synthesized peptide 27, H$_2$N-VWSQKRHFGY-CO$_2$H. As shown in Scheme 15, compound 27 has a tyrosine at the C-terminal containing reactive functional group such as Val, Trp, Ser, Glu, Lys, Arg, and His in its structure (a. Reversed phase HPLC purity (gradient of CH$_3$CN/0.1% TFA water, 0:100 to 100:0 over 30 minutes at UV 254 nm). The labeling was performed using 3.0 equivalent PTAD analog in pH 7 phosphate buffer at room temperature. After purification using reversed phase HPLC, the pure compounds were obtained in 60%, 61% and 63%. Significantly, only one type of one modified compound was observed in each modification in the monitoring of reaction mixture by LC-MS. HRMS and MS/MS data showed tyrosine selective modification.

Scheme 15. Peptide Modification

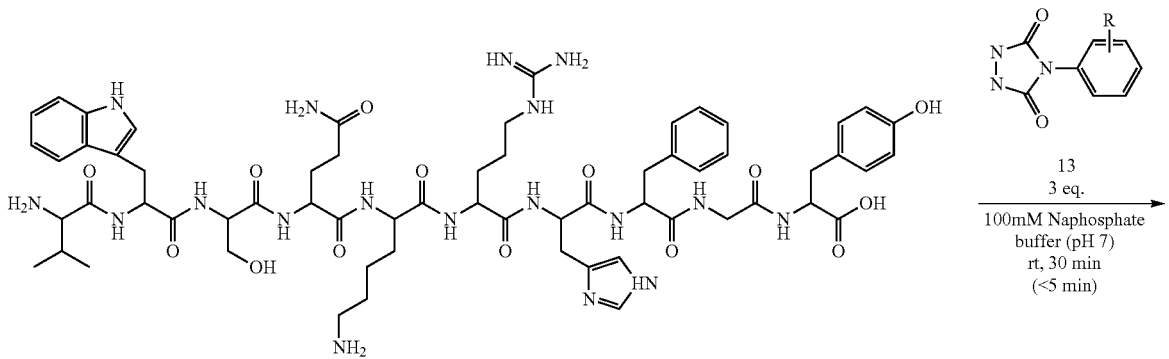

27

-continued

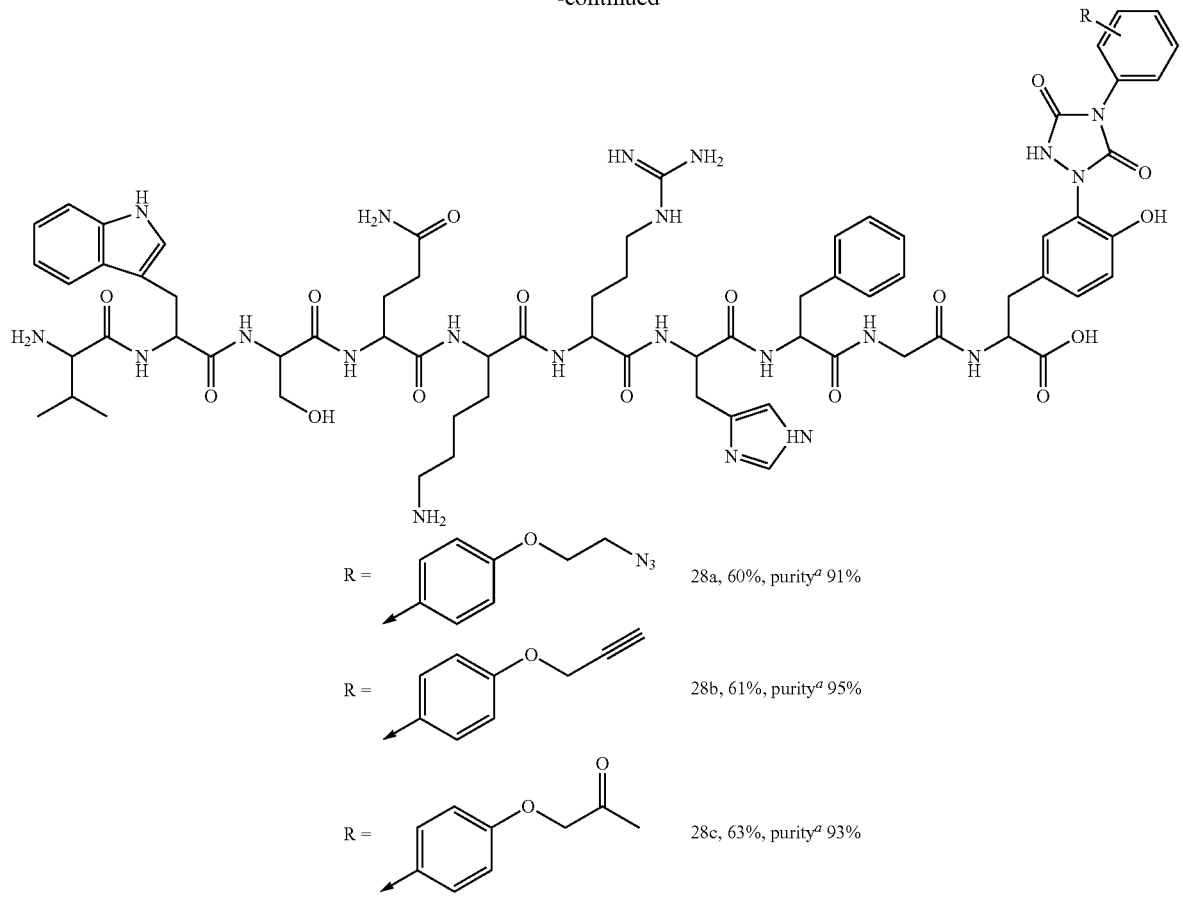

| R = | | 28a, 60%, purity[a] 91% |
| R = | | 28b, 61%, purity[a] 95% |
| R = | | 28c, 63%, purity[a] 93% |

As shown in Scheme 16, by MS/MS analysis, three products showed similar fragmentation pattern started at N-terminal and main all daughter ions contained the ions of modified tyrosine peptide. These experiments demonstrated the high chemoselectivity of the tyrosine ligation reaction and its application to peptide chemistry suggesting that PTAD analog should selectively introduce biomolecule reporter into tyrosine chain in complicated peptide without interference by the other amino acids.

Scheme 16. Peptide Fragmentation in MS/MS Analysis

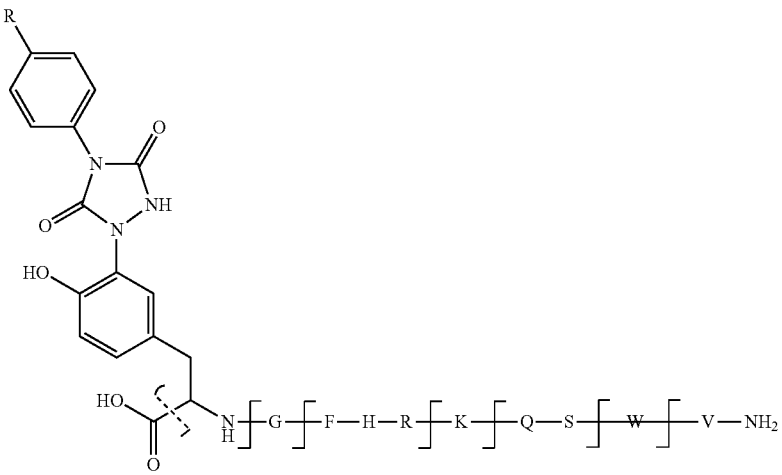

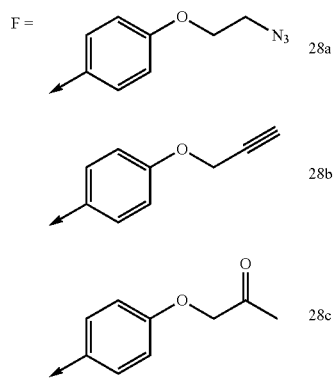

The tyrosine ligation reaction may be used to introduce a wide variety of multiple functionalities onto protein surfaces. Tri-functionalized albumins were prepared using bovine serum albumin (BSA) and human serum albumin (HSA) against tyrosine, lysine, and cysteine residues using PTAD analogues 13b-13d, N-[3-(dimethylamino)propyl]-N-ethyl-carbodiimide hydrocholide, EDC HCl, and maleimides derivative. As shown in Scheme 17, the first labeling of BSA and HSA were performed using 1.0 equivalent of 11-(dansy-lamino) undecanoic acid and 2.0 equivalents of EDC HCl against lysine residue in pH 6.0 water at 37° C. 14.5 hours. After the purification and MALDI TOF analysis, the modified BSA 29a and HSA 29b have 3.8 and 4.1 dansyl residues, respectively. The second tyrosine labeling for 29a and 29b were carried out using 110 equivalents of PTAD analogues 13b-13d against tyrosine residue in pH 7.4 100 mM sodium phosphate buffer at room temperature for 15 minutes. PTAD derivatives 13b, 13c, and 13d gave corresponding products, which have 4-8 modified residues. The final cysteine labeling for 30a-30c and 31a-31c were achieved at 1 mM fluorescein-5-mareimide in pH 7.0 SSC buffer at room temperature for 2 hours. These reactions gave a good cysteine modification.

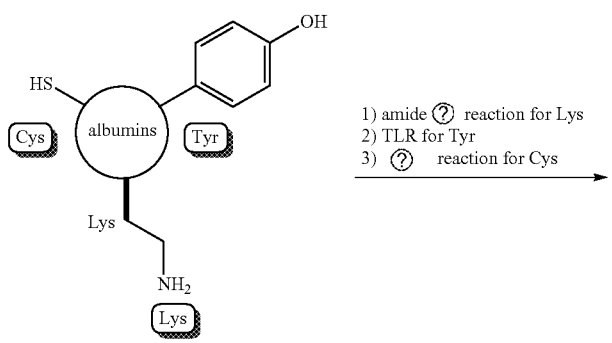

-continued

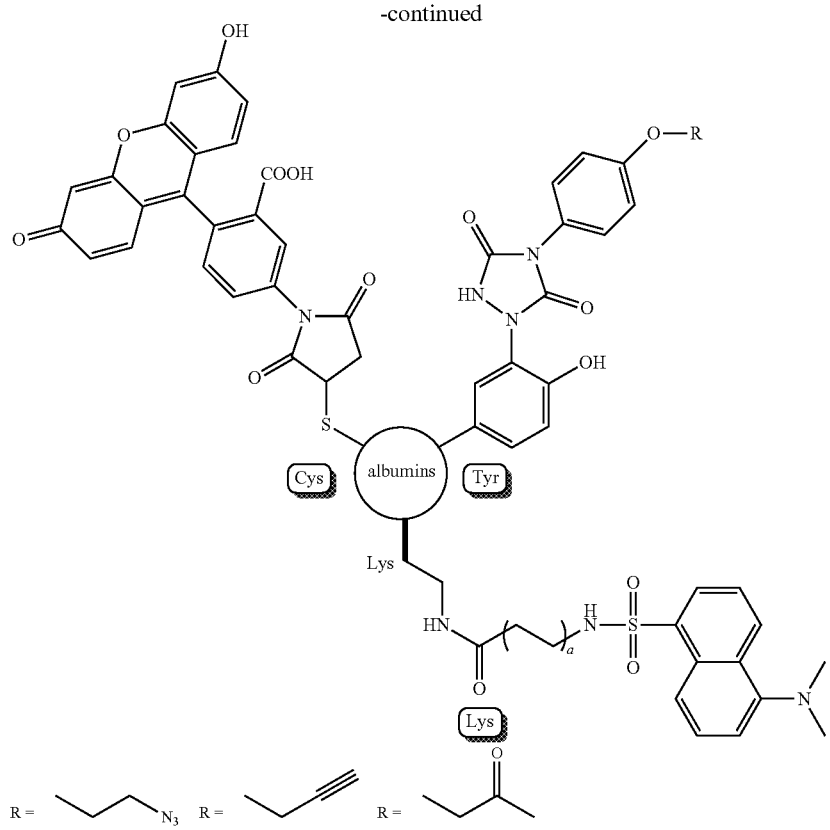

These results are summarized in Tables 10, 11, and 12. Moreover, fluorescence properties of 29a-29b, 32a-32c, and 33a-33c were determined under appropriate conditions. All modified proteins were showed suitable fluorescence densities.

TABLE 10

| Starting material | Number of modification (Product number) |
| --- | --- |
| BSA | 3.8 (29a) |
| HSA | 4.1 (29b) |

TABLE 11

| Source | Starting material | Reagent | Number of modification (Product number) |
| --- | --- | --- | --- |
| BSA | 29a | 13b | 7.4 (30a) |
|  |  | 13c | 8.3 (30b) |
|  |  | 13d | 3.9 (30c) |
| HSA | 29b | 13b | 6.7 (31a) |
|  |  | 13c | 6.5 (31b) |
|  |  | 13d | 4.6 (31c) |

TABLE 12

| Source | Starting material | Number of modification (Product number) |
| --- | --- | --- |
| BSA | 30a | 2.3 (32a) |
|  | 30b | 1.3 (32b) |
|  | 30c | 2.7 (32c) |

TABLE 12-continued

| Source | Starting material | Number of modification (Product number) |
| --- | --- | --- |
| HSA | 31a | 1.2 (33a) |
|  | 31b | 1.8 (33b) |
|  | 31c | 1.6 (33c) |

The above results indicate that the tyrosine ligation reaction is a highly efficient ligation strategy for proteins. The tri-functionalized albumins were prepared in a straightforward manner. Importantly, the reactions are highly chemoselective and proceed in water media without heavy metals. This is the first case in which two functional groups and other bioconjugatable groups, alkyne, azide, and ketone, were installed into a protein. Alkyne and azide on modified protein 32a 32b, and 33a-33b have been used as "click reaction" agents to study function of biomolecules. Additionally, azides of tri-functionalized albumins 32b and 33b can react with triphenylphosphine derivatives by the Staudinger ligation, which is a modification of the classic Staudinger reduction of azides with triphenylphosphine. Ketones of tri-functionalized albumins 32c and 33c have abilities of condensation with aminooxy compounds and hydrazide compounds to form stable oxime or hydrazone linkages, respectively.

Figure 19:
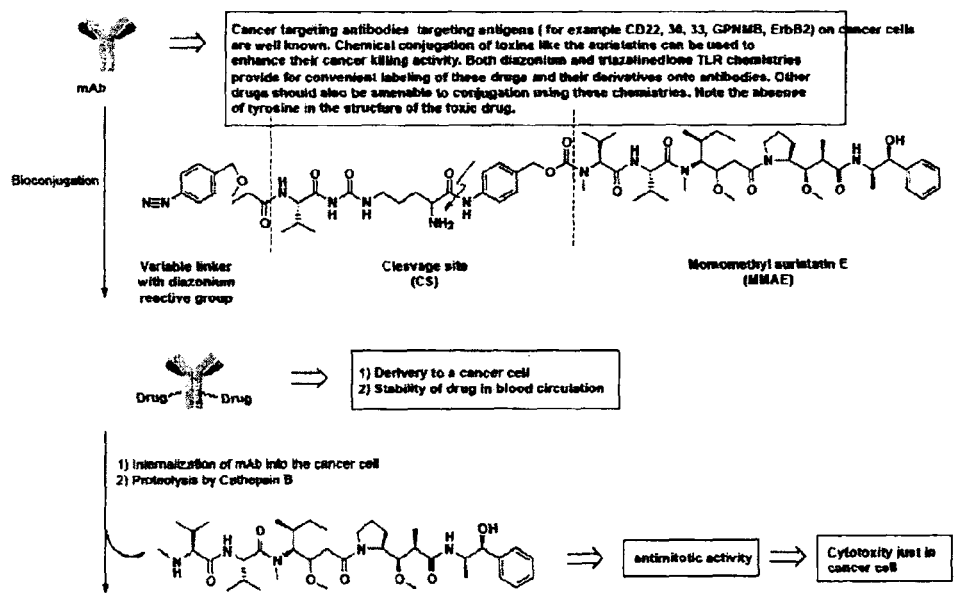
Figure 20:
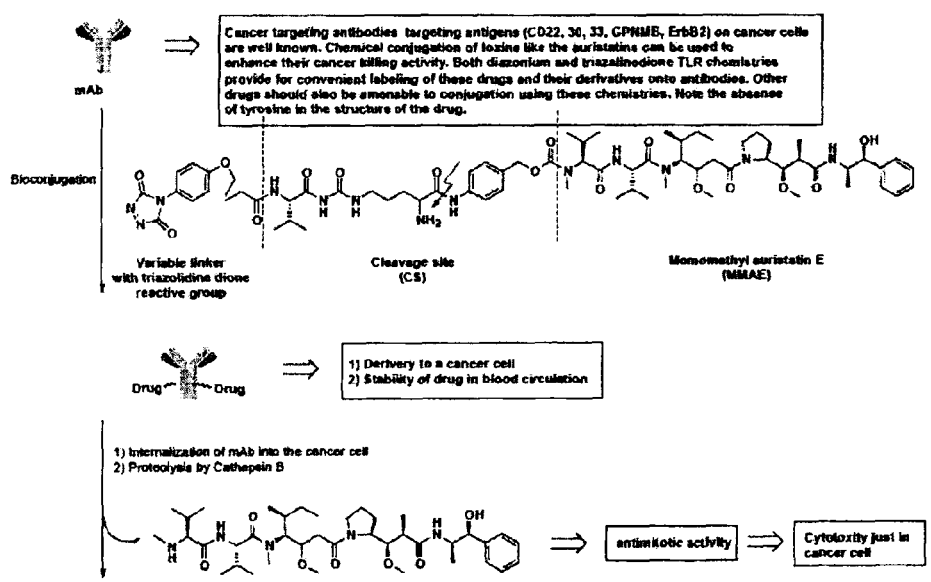
Figure 21:
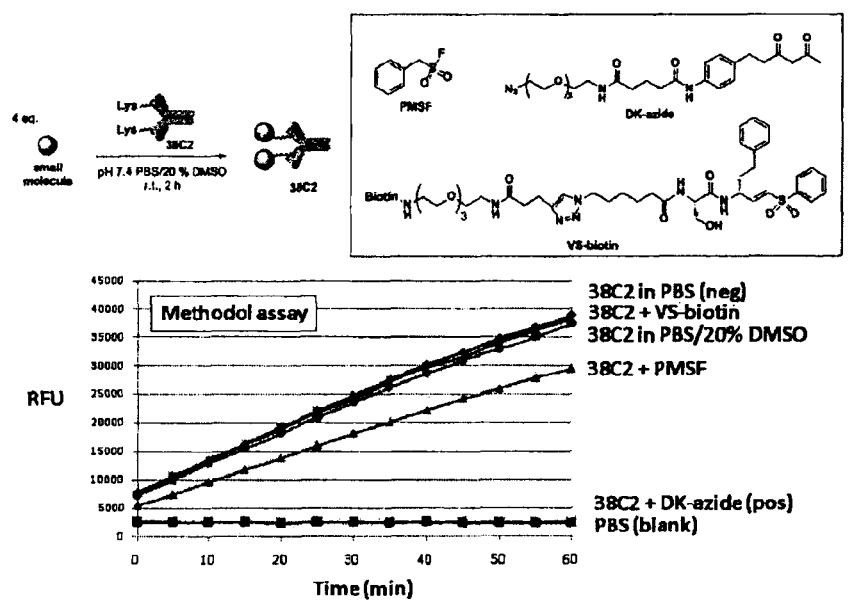
Figure 22:
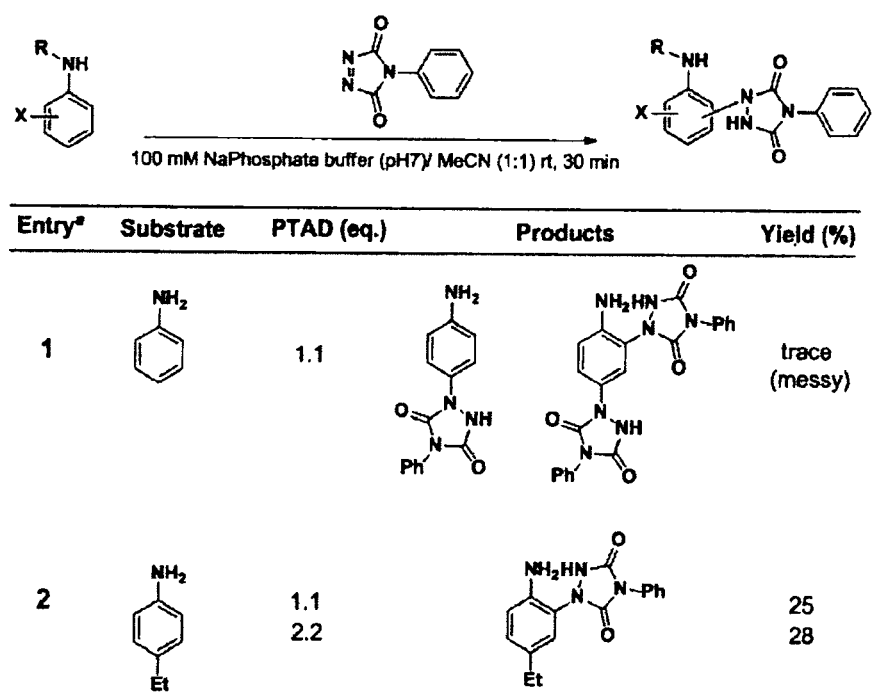

Cancer targeting antibodies targeting antigens (for example CD22, 30, 33, GPNMB, ErbB2) on cancer cells are well known. Chemical conjugation of toxins like the auristatins can be used to enhance their cancer killing activity. Examples of such drugs include, but are not limited to monomethyl auristatin E (MMAE), a synthetic antineoplastic agent. Because of its toxicity, it cannot be used as a drug itself; instead, it is linked to a monoclonal antibody (MAB) which directs it to the cancer cells. In International Nonproprietary Names for MMAE-MAB-conjugates, MMAE is referred to as vedotin. Monomethyl auristatin E is an antimitotic agent which inhibits cell division by blocking the polymerisation of tubulin. As shown in FIGS. 19 and 20, both diazonium and triazalinedione tyrosine ligation reaction chemistries provide for convenient labeling of these drugs and their derivatives onto antibodies. Other drugs should also be amenable to conjugation using these chemistries. Note the absence of tyrosine in the structure of the toxic drug. The linker to the monoclonal antibody may be stable in extracellular fluid, but is cleaved by cathepsin once the conjugate has entered a tumour cell, thus activating the antimitotic mechanism.

The present disclosure also provides compounds that bind to and activate the glucaon-like protein receptor (GLP-1R), which may be labeled according to the diazonium and tyrosine ligation reaction procedures onto antibodies. GLP-1R agonists promote insulin secretion and lower blood glucose levels by binding to and activating the glucagon-like protein 1 receptor (GLP-1R). Examples of GLP-1R agonists are set forth in WO 2008/081418, the disclosure of which is hereby incorporated by reference in its entirety.

GLP agonists bind to a membrane GLP receptor. As a consequence of this, insulin release from the pancreatic beta cells is increased. Endogenous GLP has a half life of only a few minutes; thus an analogue of GLP would not be practical. By contrast, compounds such as Exenatide (also Exendin-4, marketed as Byetta) is the first GLP-1 agonist approved for the treatment of type-2 diabetes. Exenatide is not an analogue of GLP, but rather a GLP agonist. Exenatide has only 53% homology with GLP, which increases its resistance to degradation by DPP-4 and extends its half-life. Typical reductions in A1C values are 0.5-1.0%. Other examples include Liraglutide, a once daily human analogue (97% homology), that is being developed by Novo Nordisk under the brand name Victoza. This product was approved by the European Medicines Agency (EMEA) on Jul. 3, 2009, and by the U.S. Food and Drug Administration (FDA) on Jan. 25, 2010; and Taspoglutide, which is presently in Phase III Clinical Trials with Hoffman-La Roche. These agents may also cause a decrease in gastric motility, responsible for the common side effect of nausea, and is probably the mechanism by which weight loss occurs.

New Approaches to HIV-1

Despite the successes of highly active anti-retroviral therapy (HAART), more than 2 million people die each year from HIV-1 infection and over 33 million individuals are infected worldwide. The failings of classical vaccine strategies are perhaps most obvious in the decades long quest for an HIV-1 vaccine. More than 25 years have passed since the discovery of HIV and 17 years have passed since the discovery of the broadly neutralizing antibody b12, yet an effective HIV vaccine remains elusive. Only the most modest signs of success have recently been reported from a large vaccine trial in Thailand. It is generally accepted that an effective HIV-1 vaccine should elicit potent T-cell mediated immunity and broadly neutralizing antibodies (bNABs), yet numerous attempts to achieve this goal have failed. Many (10-25%) infected individuals do eventually develop bNABS. Because of the genetic malleability of the HIV virus, most early antibodies generated against HIV are rendered useless. However, several studies have shown that transfer of sufficient quantities of broadly neutralizing antibodies can achieve sterilizing immunity against intravenous, vaginal, or rectal challenge in macaque models. Alternatively, the delivery of broadly neutralizing antibodies using gene-based approaches in animal models has also been shown to be effective in these models. This suggests that bNABs could be effective prophylactics and therapeutics. Unfortunately, even the most broadly neutralizing antibody is vulnerable to viral escape because a single amino-acid change on the target protein can alter the binding epitope. However, if a bNAB could be modified to inhibit HIV in multiple ways, the evolutionary hurdle for escape would be significantly elevated.

In vitro studies show that antibodies can mediate anti-viral effects by a number of mechanisms. The mechanisms of anti-viral activity by antibody can be conveniently divided into those acting against free virus particles and those acting against virally infected cells. Thus, the creation of antibodies that target both the free HIV virus for destruction and healthy cells for protection from infection is important. Probably the most dramatic anti-viral activity of antibody, and the one most well correlated generally with antibody protection in vivo, is neutralization of free virus particles. Neutralization is defined as the loss of infectivity which ensues when an antibody molecule binds to a virus particle, and usually occurs without the involvement of any other agency. The mechanism of neutralization has been much debated over the years and still remains controversial. It may be that different mechanisms are operative for different viruses under differing conditions. However, for several viruses including HIV-1, evidence supports that the mechanism is antibody binding causing steric interference with virus attachment and/or fusion. Binding to functional HIV spikes is described as necessary and sufficient for neutralization, which has important consequences for understanding the mechanisms of anti-viral activity responsible for protection in vivo. If in vitro neutralization is directly correlated to binding to functional spikes, the observation of a correlation between neutralization and protection does not necessarily mean that neutralization of free virus particles is the sole mechanism of protection. In principle, any mechanism that involves antibody binding to spikes can thus contribute to protective activity in vivo and provide the neutralization/protection correlation.

Figure 3:
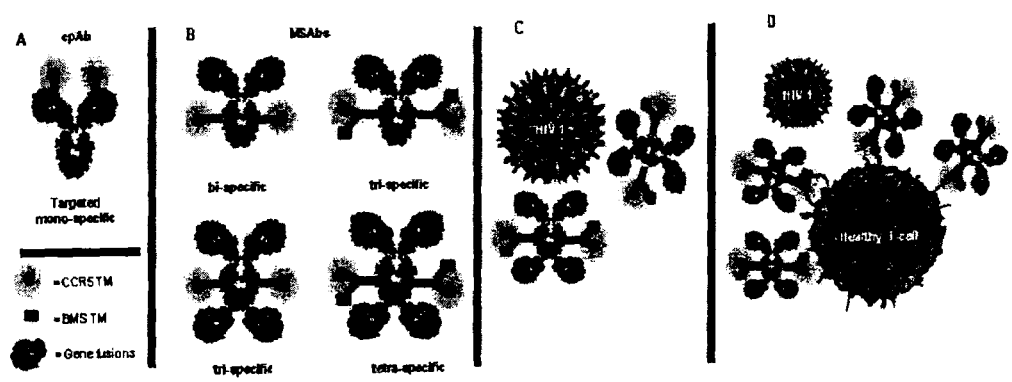
FIG. 3 illustrates the MSAbs structure and function: (A) bi-specific chemically programmed antibody (cpAb). (B) Multi-specific antibody formats to be created in this study (labeled IgG and IgG-scFv proteins are shown). The proposed MSAbs can display 4 different specificities for targeting virus and host cell receptors. (C) MSAbs targeting free virus, and (D) blocking entry receptors on healthy cells.
Figure 4:
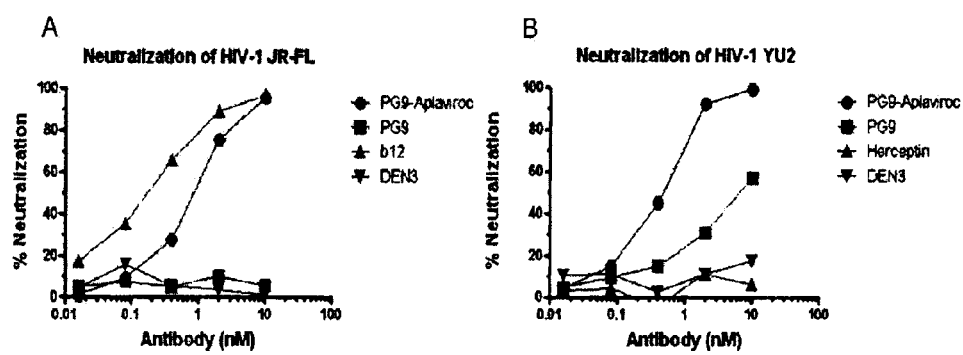
FIG. 4 illustrates the neutralization assay for Aplaviroc™ conjugated to PG9. Preliminary results show that chemical modification of PG9 with the CCR5 binder Aplaviroc —$CH_2CH=CHCH_2$—, —$CH_2C.ident.CCH_2$—, —$CH_2CH_2CH(CH_2CH_2CH_3)CH_2$—. Typically, an alkyl (or alkylene) group will have from 1 to 24 carbon atoms, with those groups having 10 or fewer carbon atoms being useful in the present disclosure. A "lower alkyl" or "lower alkylene" is a shorter chain alkyl or alkylene group, generally having eight or fewer carbon atoms.
Figure 5:
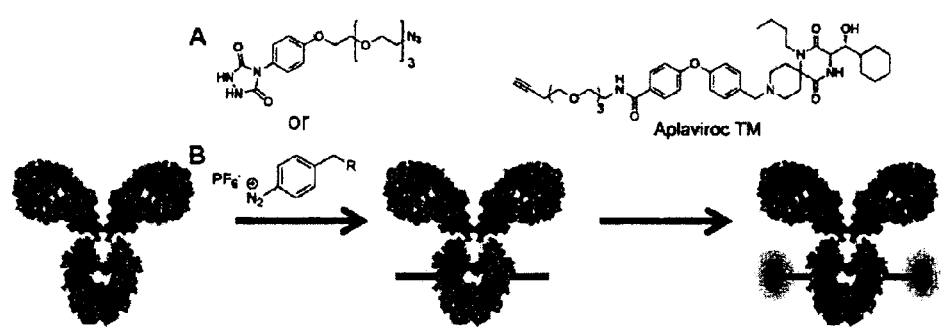
Figure 6:
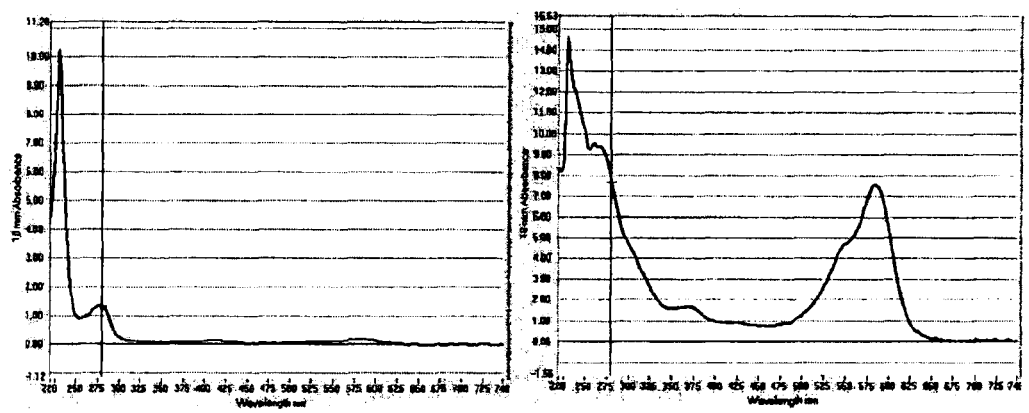

Recently, a new class of therapeutic molecules has been developed which demonstrates that covalent monoclonal antibodies can be programmed via their covalent reaction with designed ligands of a variety of specificities. Such chemically programmed antibodies possess potent biological activities in a variety of animal models of disease. Indeed, multiple human trials are ongoing to explore the efficacy of chemically programmed monoclonal antibodies in the treatment of cancer and diabetes. These studies have elucidated the many advantages of coupling active small molecules to antibodies. Using this approach, antibodies that are already effective at neutralizing HIV should allow for a single modified antibody to inhibit viral infection in as many as four ways. Current anti-HIV therapies rely mainly on targeting viral proteins involved in replication. Drug-resistant viral strains rapidly evolve in the face of this type of therapy. An alternative to the targeting of viral proteins is the targeting of host proteins required for viral entry and replication. Unlike viral proteins, host proteins are not under selective pressure to evolve to evade the therapeutic agent. The most advanced approaches in this area target the HIV-1 entry co-receptor CCR5. FDA approval of the CCR5 blocking drug Maraviroc™ in 2007 is one of the most recent breakthroughs in anti-HIV therapy. However as in all other HIV therapies, the virus can quickly evolve resistance to these compounds. This resistance is due to the ability of the virus to evolve envelope proteins that can use CCR5 receptors which are bound by the small molecules. If the CCR5 small molecule was appended to a much larger entity, such as an antibody, it is unlikely that the virus could find a means to escape this steric challenge. A multifunctional broadly neutralizing antibody (MSAb) is illustrated in FIG. 3, which possesses virus binding and co-receptor binding functionalities. The modified antibody will be quantitatively directed to neutralizing epitopes on the virus and a blocking epitope on the HIV-1 co-receptor CCR5 and/or CXCR4 thereby neutralizing virus and blocking viral entry. Alternatively, a small cocktail of modifying agents could be appended to a single MSAbs to block a collection of viral subtypes and co-receptor epitopes.

While conjugations of mAbs with toxins are well known, conjugation with small molecules that extend the binding capability of the parental antibody. An innovative approach that will allow for the creation of bi, tri, and tetra-specific antibodies with exceptionally broadly HIV neutralizing abilities. Many advantages of the chemically programmed antibodies (cpAb) approach are primarily seen in vivo. For small molecules and peptides, the cpAb approach has been shown to dramatically extend the pharmacokinetic lifetime of the targeting drug, thereby limiting the amount of small molecule drug required for therapeutic efficacy. Four cpAbs therapeutics are currently in human tails. In one case, the cpAb approach reduced the quantity of small molecule drug required for therapeutic activity by at least a 1000-fold. Such a dramatic reduction in the amount of small molecule drug required for therapeutic efficacy might serve to mitigate metabolic toxicity observed with anti-HIV drugs like Aplaviroc™. The fusion of two successful approaches stems from the chemically programmed antibody work applied to broadly neutralizing antibodies against HIV, which should make these antibodies much more potent. Mimicking the cocktail approach of small molecule anti-retroviral therapy on a single antibody may provide a myriad of advantages including increased patient compliance due to the greatly increased half-life for antibodies as compared to small molecules. Additionally, suitably modified broadly neutralizing antibodies may present an evolutionary challenge strong enough so that HIV will not be able to escape via mutation. This is supported by a recent report from Zhou et al in which they showed that HIV escape mutants selected by exposure to entry inhibitors were much more sensitive to bNABs. The two best bNABs (PG9 and VRCO1 in IgG and IgG-scFv formats) may be modified for extended in vivo half-lives and chemically modified with HIV fusion inhibitors (as targeting molecules (TMs)). These therapeutics should neutralize all known isolates of HIV-1. The innovative antibody conjugation chemistry developed here can be applied widely across therapeutic areas for the development of next generation therapies.

The synthesis of anti-HIV small molecules for MSAbs requires three parts: 1) targeting module (TM) that binds the desired target (i.e., CCR5, CXCR4, or gp120/CD4) 2) a reactive component that reacts with specific residues on the bNABs and 3) a linker molecule that links the targeting module with the reactive component. As shown in Scheme 18, two CCR5 (Aplaviroc™, Maraviroc™), a CXCR4 (GSK812397), and several HIV-1 envelope targeting molecules (BMS; one example shown) were identified, wherein there is sufficient structure activity relationships published to allow them to be appended on to a reactive moiety via a linker molecule.

Scheme 18. Anti-HIV TMs

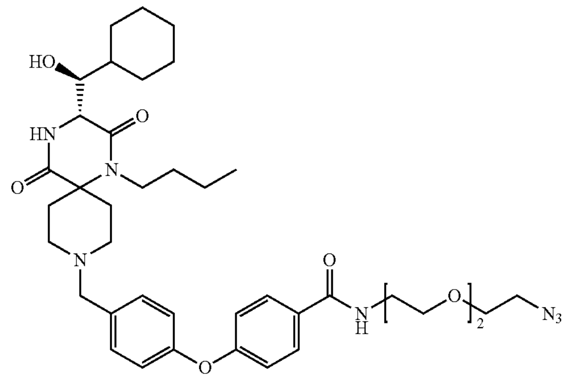

Aplaviroc based TM
(CCR5)

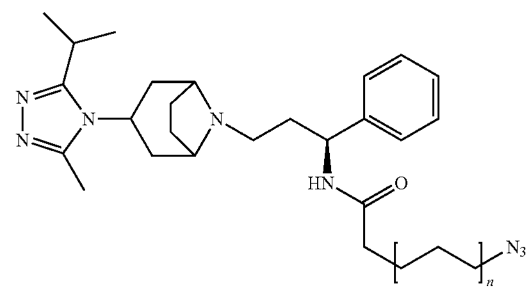

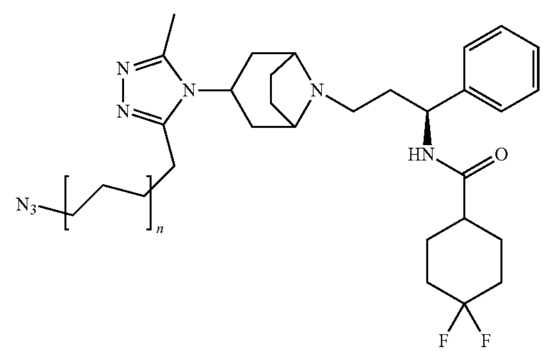

Maraviroc based TMs
(CCR5)

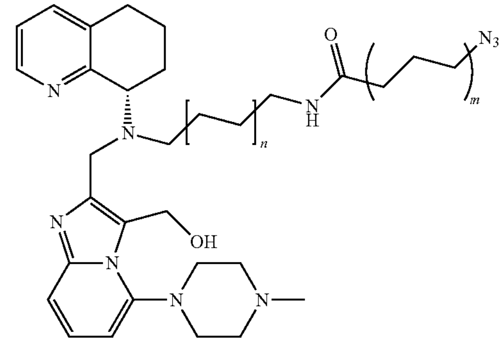

-continued

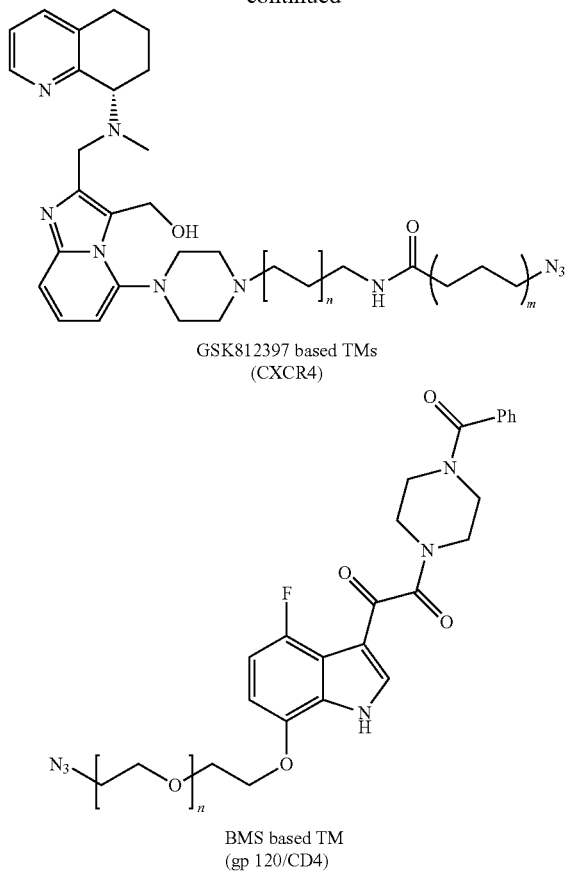
GSK812397 based TMs
(CXCR4)
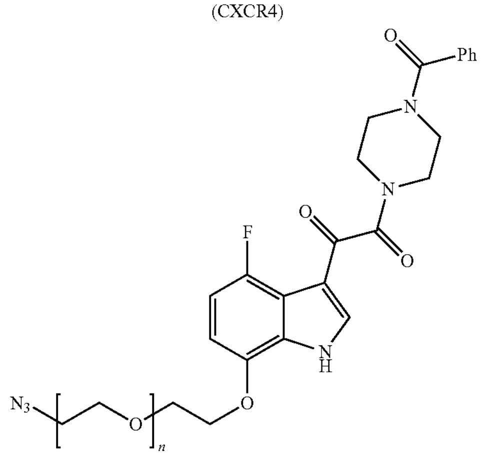
BMS based TM
(gp 120/CD4)

As part of a program to build novel long-lived and potent HIV therapeutics, chemically programmed antibodies using a small molecule drug that targets the CCR5 G-protein coupled receptor were developed. Chemically programmed antibodies (cpAbs) represent a new class of biologic drugs that acquire their specificity through chemistry rather than through biology. Aplaviroc™ was selected as the CCR5 targeting compound based on its extensive characterization and potent activity against a wide range of laboratory and primary isolates of HIV-1. Aplaviroc™ was the first anti-HIV CCR5 inhibitor developed, but clinical trials had to be halted because of toxicity issues. One major advantage of cpAbs, which can be extrapolated to the proposed MSAbs, is that conjugation of a small molecule to an antibody should allow for dosing at several orders of magnitude below that of the small molecule alone, thus reducing toxic effects.

We have recently reported a study in which the cpAb 38C2 was modified with Aplaviroc™. This modification allowed the non-neutralizing parent antibody to efficiently neutralize HIV and SIV. In order to create a chemically programmed antibody that targets CCR5, a derivative of Aplaviroc™ that allows for its attachment to the active site of the cpAb while maintaining CCR5 binding was designed. Homology modeling of the CCR5 receptor and docking studies of Aplaviroc™ into the putative binding pocket suggested that the carboxylic acid end points toward the solvent and is not crucial for interaction with the receptor. This modeling data, together with analysis of structure activity relationship (SAR) data of Aplaviroc™ derivatives led us to the carboxylic acid group of Aplaviroc™ could be conjugated to a linker to enable attachment to a chemically programmable antibody without compromising the binding activity of the parental molecule. In order to test this, a new synthetic strategy to access derivatives of Aplaviroc™ was designed.

In the study of the reported synthesis of Aplaviroc™, an important challenge that could be overcome with organocatalysis was noted. In this study, a simple organocatalytic methodology to produce anti-α-hydroxy-β-amino acids in two steps using commercially available and inexpensive proline catalysis. This method was employed in an expedient enantioselective synthesis of Aplaviroc™ and desired derivatives. Our recently published data suggests that both human and macaque CCR5 can be potently blocked using a novel chemically programmed antibody, thereby abrogating viral entry. As shown in FIG. 4, broadly neutralizing HIV antibodies such as PG9 become more potent and broadly acting following conjugation to Aplaviroc™ in the form of a MSAb. In this study, the diazonium chemistry noted below for the coupling of Aplaviroc™ to PG9 was used. This result also demonstrates that the combination of a CCR5 inhibitor with a Env targeting Ab does not facilitate infection by cross-linking virus and target cells.

To further explore CCR5 blockade using this approach, a Maraviroc™ based targeting modules was synthesized. Unlike Aplaviroc™ whose clinical development was halted due to metabolic toxicity, Maraviroc™ is an approved CCR5 inhibitor. No toxicity was expected in using this approach since Aplaviroc™ targeting modules were used at a dose (when conjugated) that was several orders of magnitude lower than when it is applied as a simple small molecule. However, a Maraviroc™ based targeting modules may be a significant alternative that may display enhanced breadth and potency and potentially better pharmacokinetics. A proposed synthetic scheme for two differentially linked Maraviroc™ based targeting modules is provided below.

As shown in Scheme 19, readily available benzyl protected tropinone is converted into the corresponding oxime followed by a sodium metal reduction that provides a separable mixture of endo- and exo-aminotropane 1. The separated exo-product 1 are coupled with acid 2 bearing a variable length TBS protected alkyl alcohol tail to provide intermediate 3. Chlorination with $PCl_5$ in dichloromethane at 0° C., followed by addition of acetyl hydrazide in tert-amyl alcohol and cyclization in the presence of acetic acid in tert-amyl alcohol, and removal of benzyl protection by hydrogenation provides triazole product 4. Protected amino aldehyde 5 may be prepared as previously described and used for the reductive amination with intermediate 4 followed by removal of Cbz with hydrogen in the presence of $Pd(OH)_2$ to give the desired amine 6. Finally, coupling with the 4,4-difluorocyclohexanecarbonyl chloride 7, and interconversion of TBS protected hydroxyl functionality into azide completes the synthesis of Maraviroc™ based targeting module 8. Alternative linker attachment position may be explored by coupling the amine intermediate 9 accessible via an established synthetic route with a selection of variable length alkylazido acid chlorides 10, to give another Maraviroc™ based targeting module 11.

Scheme 19. Synthesis of Two Differentially Linked Maraviro™ Targeting Modules
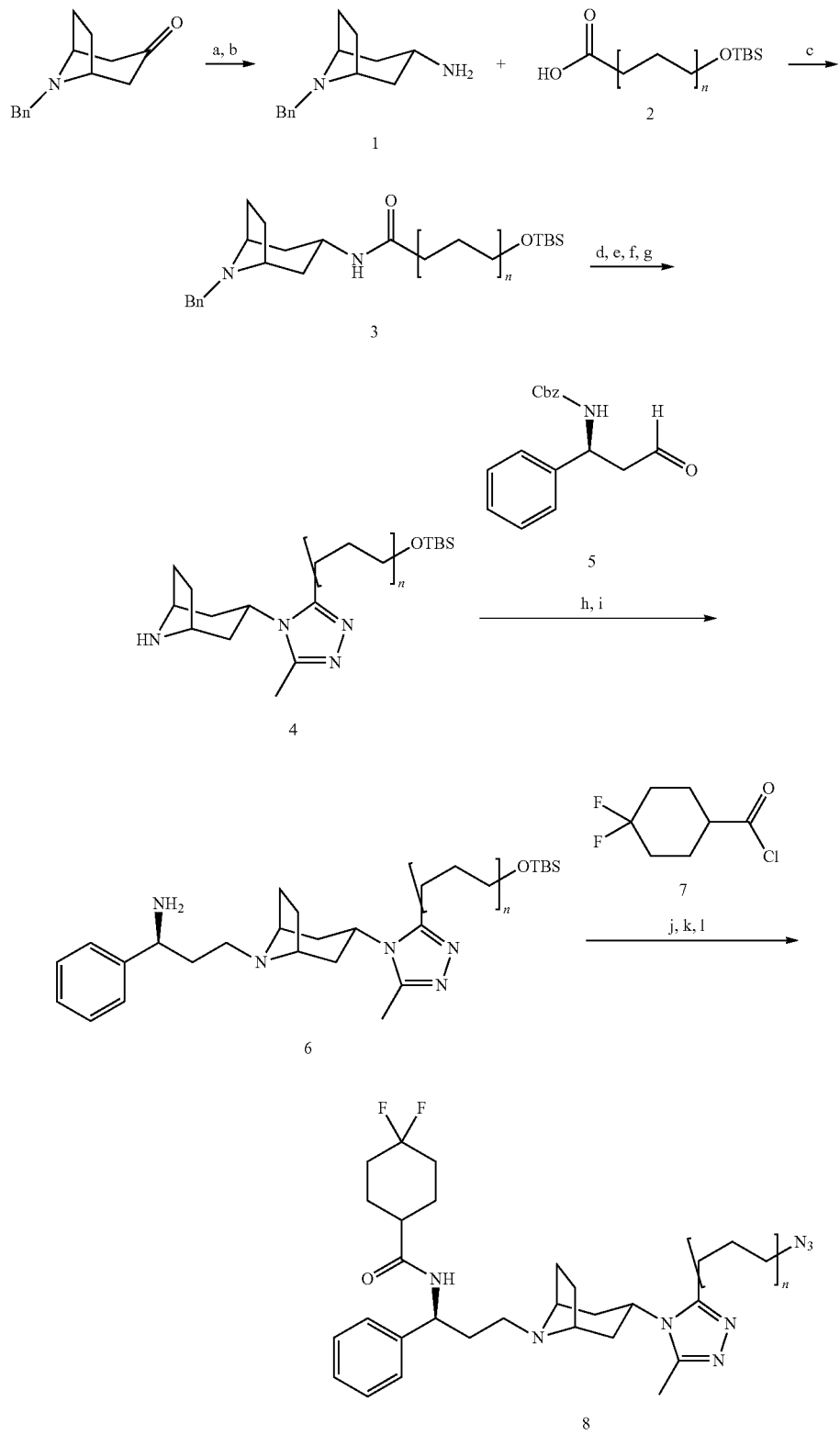
(a) NH₂OH·HCl, Py, EtOH; (b) Na, n-pentanol, reflux; (c) Et₃N, WSCDI, CH₂Cl₂; (d) PCl₅, CH₂Cl₂, 0° C.; (e) AcNHNH₂, tert-amyl, alcohol; (f) AcOH, tert-amyl alcohol; (g) p-TsOH, H₂, 10% Pd/C; (h) 23, p-TsOH, NaBH(OAc)₃, CH₂Cl₂, AcOH; (i) Pd(OH)₂, H₂, MeOH; (j) 25, Na₂CO₃ CH₂Cl₂; (k)TBAF; (l) i. TsCl, Et₃N; ii. NaN₃, DMF.

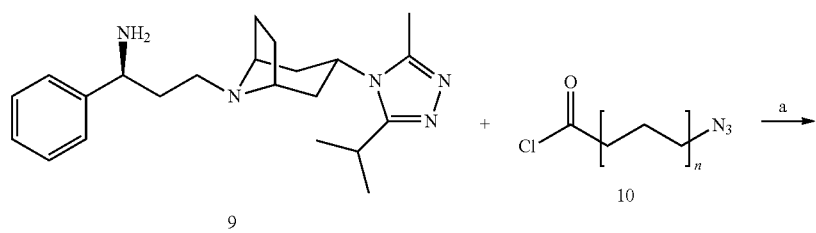

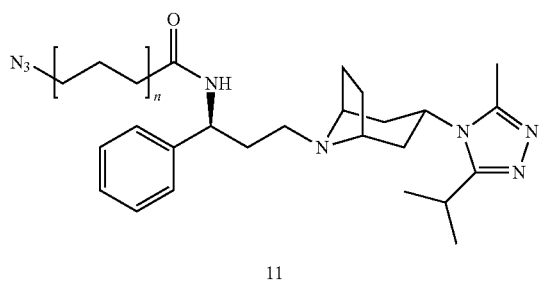

While evidence suggests that natural HIV-1 infection occurs primarily through the CCR5 receptor, viral adaptation to the CXCR4 co-receptor is associated with disease progression and AIDS. The development of potent small molecule CXCR4 inhibitors provides the opportunity to explore a MSAb that blocks both CCR5 and CXCR4. The investigation of CXCR4 is vital, because unlike CCR5, CXCR4 is widely expressed on many cell types and is implicated in homing and stem cell signaling. Thus, CXCR4 presents a difficult challenge as a therapeutic target. Antibodies targeted to CXCR4 through chemical modification of their Fc region may not be able to efficiently mediate antibody-dependant cell-mediated cytotoxicity (ADCC), but will still be effective in preventing viral entry. Two types of azide containing targeting modules may be synthesized based on the SAR data for CXCR4 antagonist GSK812397. As shown in Scheme 20, the synthetic plan is based on the process chemistry route to GSK812397.

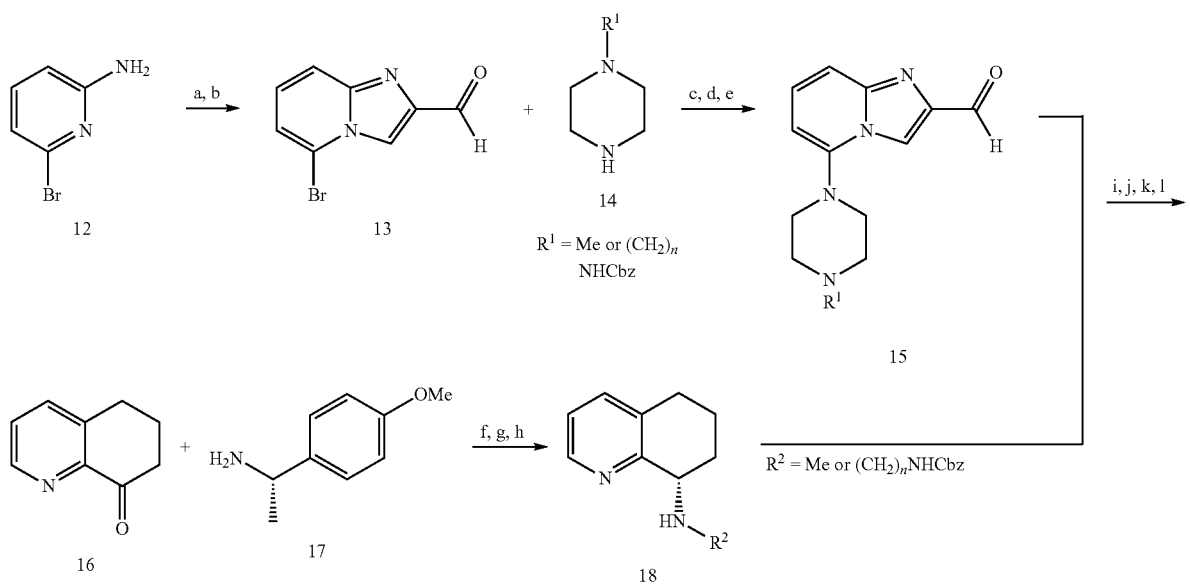

Scheme 20. Synthesis of (A) CXCR4 TMs and (B) BMS-based gp120 binding TM

-continued

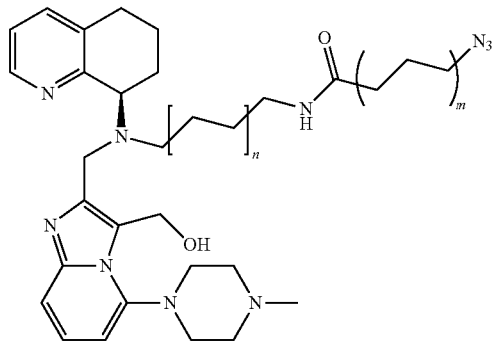

19 or

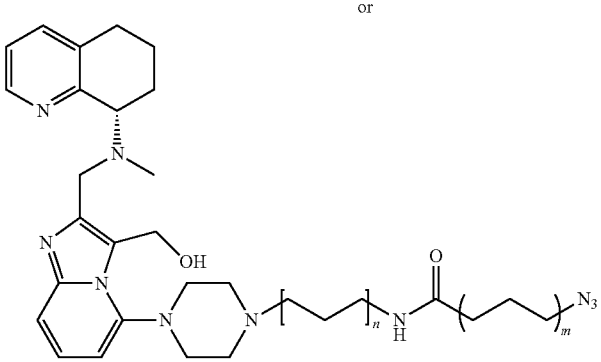

20

(a) 1,1,3-trichloroacetone, DME; (b) aq HCl; (c) n-BuLi, THF; (d) aq HCl; (e) aq NaOH; (f) NaBH(OAc)₃, CH₂Cl₂; (g) R²CHO, NaBH(OAc)₃, CH₂Cl₂; (h) TFA; (i) NaBH(OAc)₃, Et₃N, CH₂Cl₂; (j) CH₂O, H₂O; (k) 10% Pd/C, H₂; (l) NHS-azide linker, Et₃N.

B

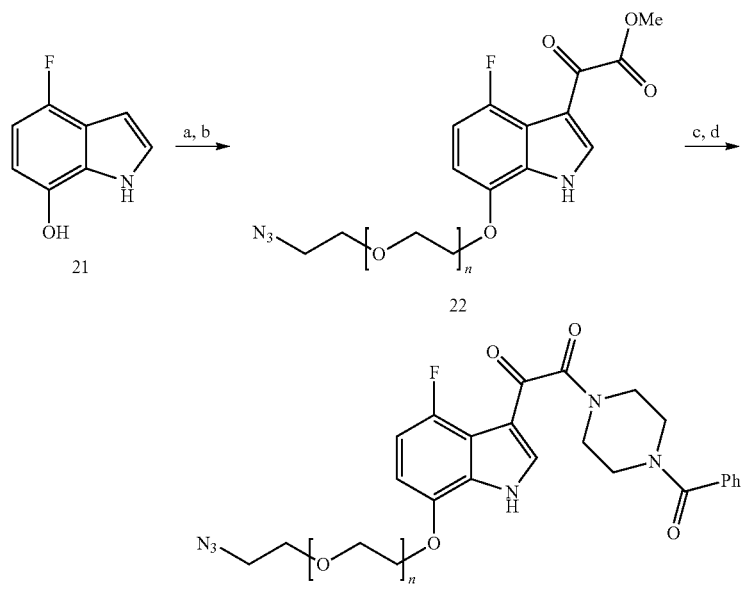

(a) N₃—PEGₙ—OTs, K₂CO₃; (b) EtO—C(O)—C(O)Cl, AlCl₃, CH₂Cl₂; (c) K₂CO₃, MeOH; (d) N-benzoylpiperazine, DEPBT, DIPEA, DMF 2-amino-6-bromopyridine 12 reacts with 1,1,3-trichloroacetone in DME, followed by cyclization in the presence of HCl to provide 5-bromoimidazo[1,2-a]pyridine-2-carbaldehyde 13. Subsequent reaction of 13 with N-alkyl substituted piperazine 14 provides the key intermediate 15. The piperazine ring may serve as one possible point of linker attachment.

The Cbz protected aminoalkyl chain may be used as one or the alkyl substituent's R¹. Readily available tetrahydroquinolinone 16 is subjected to reductive amination with chiral amine 17 to install the desired stereogenic center and the isolated enantiomerically pure product is provided by recrystallization. Subsequent reductive amination with alkyl aldehyde R²CHO followed by hydrolysis of p-methoxybenzyl auxiliary in the presence of TFA provides the desired intermediate 18. The R² substituent may serve as a second linker attachment point. Reductive amination coupling of intermediates 18 and 15, followed by installation of hydroxymethyl functionality in the imidazole ring, removal of Cbz and coupling with the NHS activated ester of the azide containing carboxylic acid provides the desired CXCR4 targeting modules 19 and 20.

Recently BMS reported an advanced analog of their previously discovered inhibitor of gp120/CD4 complex formation: BMS-378806. This new compound exhibits 60 pM activity, a promising pharmacokinetic profile, and is broadly neutralizing (including HIV-1 SF-162) The SAR study conducted by BMS suggests that position C7 would be the best point for linker attachment. The synthetic route is based on the literature synthesis of BMS-378806 and starts with commercially available indole 21. Indole 21 may be O-alkylated with azide-polyethylene-glycol linker of any desired length, followed by reaction with methyl 2-chloro-2-oxoacetate in the presence of aluminum trichloride to provide intermediate 22. Reaction with potassium carbonate in methanol followed by a DEPBT mediated coupling with N-benzoylpiperazine gives the desired azide containing targeting module 23. Variants of BMS-378806 are known in the literature and can be explored as alternative TMs.

Selective small molecule conjugation to proteins is a field of immense interest. While many procedures are available in the literature, the focus is on two that provide the best opportunity to specifically and quantitatively modify antibodies with anti-HIV compounds: Tyrosine ligation reactions based on 4-phenyl-3H-1,2,3-triazole-3,5(4H)-dione (PTAD)[34] or diazonium reaction and maleimide addition to free thiols of cysteine.

The creation of a novel click-like reaction that can specifically modify tyrosine residues known as the tyrosine ligation reaction, relies on the stability of cyclic diazodicarboxamides. Substituted phenols, such as tyrosine, can react with highly reactive electrophiles such as diazodicarboxlylates in organic solvents in the presence of activating protic or Lewis acid additives, and decompose rapidly in water. As shown in FIG. 5*a*, substituted 4-phenyl-3H-1,2,3-triazole-3,5(4H)-dione (PTAD), is not similarly activated, and shows good stability in aqueous media—providing an opportunity for reaction with water soluble proteins. This reagent is proficient for modifying proteins, including the human antibody Herceptin with a small molecule integrin TM, in mild aqueous conditions. The resulting conjugate retained the parental antibody erbB2 binding and was able to efficiently bind integrin providing for the first MSAb. This technique may be extended to modify PG9, VRCO1, and an IgG-scFv constructed from PG9 and VRC01.

An alternative to the tyrosine ligation reaction, is the use of diazonium based reagents to target tyrosine modification. Diazonium reagents have been extensively studied for selective modification of tyrosine in the context of bioconjugation and material science applications. Despite the great utility of this reaction it had not been extensively applied to the modification of functional proteins and/or antibodies due to several limitations of current methods. A practical chemical antibody modification method using a novel diazonium reagent has been developed. A bifunctional diazonium reagent was designed to have the following features: 1) improved reagent stability while maintaining high reactivity in aqueous buffer; and 2) abioorthogonal functionality for subsequent selective modification. As shown in FIG. 5B, the 4-formyl benzenediazonium with hexafluoro-phosphate ($PF6^-$) counterion was chosen as a suitable candidate, as it is known to be good stabilizing counterion. An electron-withdrawing group is essential for the stability of diazonium ion as it prevents cation formation at C4 and release of nitrogen gas. Furthermore, it activates the N—N triple bond as an electrophile. This procedure represents a significant advance in the ability to specifically modify tyrosines with diazonium-based reagents. Preliminary mass spectrometry studies indicate reproducible 2:1 labeling of targeting modules to antibody. This reagent and procedure represents a significant advance in the ability to specifically modify tyrosines with diazonium-based reagents. Preliminary results shown in FIG. 4 demonstrate the success of this technique. The reproducibility of site of labeling, stoichiometry, and synthetic compatibility may lead to the use of one or the other for the tyrosine ligation reaction.

EXAMPLES

For further illustration of various aspects of the present disclosure, several specific examples will now be described. It should be understood however that these examples are for illustrative purposes only, and are not intended to limit the scope of the present disclosure.

$^1H$ NMR and $^{13}C$ NMR spectra were recorded on Bruker DRX-600 (600 MHz), DRX-500 (500 MHz), Varian Inova-400 (400 MHz), or Varian MER-300 (300 MHz) spectrometers in the stated solvents using tetramethylsilane as an internal standard. Chemical shifts are reported in parts per million (ppm) on the δ scale from an internal standard (NMR descriptions: s, singlet; d, doublet; t, triplet; q, quartet; m, multiplet; br, broad). Coupling constants, J, are reported in Hertz. Mass spectroscopy was performed by the Scripps Research Institute Mass Spectrometer Center. Analytical thin-layer chromatography and flash column chromatography were performed on Merck Kieselgel 60 F254 silica gel plates and Silica Gel ZEOprep 60 ECO 40-63 Micron, respectively. Visualization was accomplished with anisaldehyde or $KMnO_4$. High performance liquid chromatography (HPLC) was performed on SHIMADZU GC-8A using VYDAC HPLC Column. LCMS ESI analysis was performed on Agilent 1100 with SB C-18 column, using 1-100% $CH_3CN$ gradient for 20 minutes method. Protein deconvolution was performed using TOF Protein Confirmation Software. Unless otherwise noted, all the materials were obtained from commercial suppliers, and were used without further purification. All solvents were commercially available grade. All reactions were carried out under nitrogen atmosphere unless otherwise mentioned. Amide starting materials, tyrosine 1, histidine, tryptophan, serine, cysteine, lysine and ($Ile^3$)-pressinoic acid 6, were commercially available compounds or prepared according to published procedures. All proteins were obtained from commercial sources: chymotrypsinogen A (ImmunO), BSA and myoglobin from equine heart (Sigma), Herceptin (Genentech). Cyclic RGD peptide was purchased from Peptides International Inc and stored at −20° C. Zeba spin desalting columns (7 k MWCO, product #89882) and mini slide-a-lyzer dialysis units (3.5 k MWCO, product #69550) were obtained from Pierce. Structural analysis of chymotrypsinogen A (entry 2CGA), myoglobin (entry 1DWR) were based on information from the Protein Data Bank. Sequence information for BSA was obtained from Swiss-PROT database (P02769). All reactions were carried out under argon atmosphere unless otherwise mentioned. Amide starting materials, tyrosine, histidine, tryptophan, serine, cystein, lysine, and ($Ile^3$)-pressinoic acid, were commercially available compounds or prepared according to published procedures. A peptide, H₂N-VWSQKRHFGY-CO₂H, was custom-synthesized by Abgent, Inc.

Example 1

Coupling of N-acyl tyrosine methylamide 1 with PTAD 2

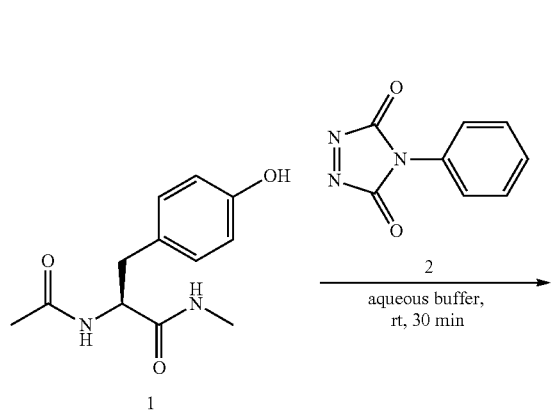

Example 2

Coupling of H-Gly-Gly-Tyr-OH 4 with PTAD 2

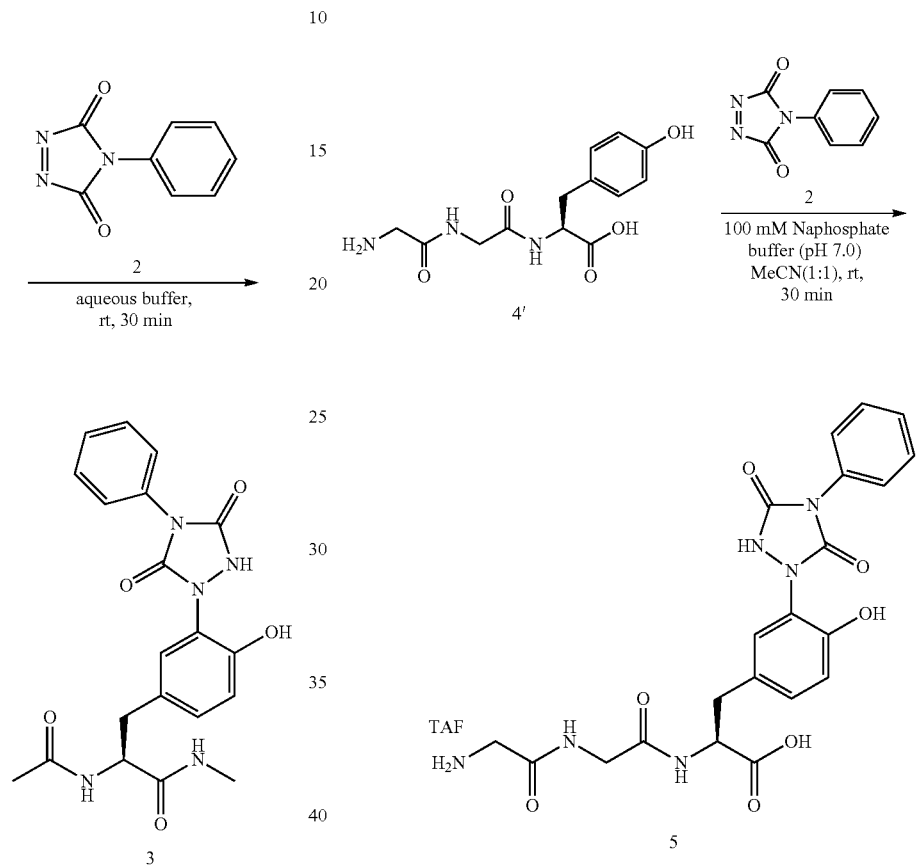

To a solution of N-acyl tyrosine methylamide 1 (14.2 mg, 0.060 mmol) in 100 mM pH 7.0 NaH$_2$PO$_4$/Na2HPO4 buffer (1.5 mL)-CH$_3$CN (1.5 mL) was added the 0.5 M solution of PTAD 2 (0.132 mL, 0.066 mmol) in CH$_3$CN at room temperature. The resulting solution was stirred at room temperature for 30 minutes. The reaction mixture was acidified with 12N HCl (0.249 mL) and concentrated in vacuo. The obtained crude material was purified by flash column chromatography (CHCl$_3$/CH$_3$OH) to give 3 (16.0 mg, 65%) as a white solid. $^1$H NMR (300 MHz, DMSO-d6): δ 11.57 (br, 1H), 8.06 (d, J=8.4 Hz, 1H), 7.90 (q, J=4.3 Hz, 1H), 7.74 (d, J=1.7 Hz, 1H), 7.63-7.51 (m, 2H), 7.43 (t, J=7.8 Hz, 2H), 7.34-7.21 (m, 1H), 6.83 (dd, J=8.2, 2.0 Hz, 1H), 6.68 (d, J=8.2 Hz, 1H), 4.33 (m, 1H), 2.85 (dd, J=13.5, 5.1 Hz, 1H), 2.63 (dd, J=13.7, 9.2 Hz, 1H), 2.55 (d, J=4.5 Hz, 3H), 1.78 (s, 3H). $^{13}$C NMR (150 MHz, DMSO-d6): δ 172.64, 170.02, 153.90, 150.86, 148.44, 135.37, 129.22, 129.02, 126.96, 126.48, 126.03, 122.72, 117.74, 55.47, 38.23, 26.51, 23.56. HRMS: calcd for C$_{20}$H$_{22}$N$_5$O$_5$ (MH$^+$) 412.1615. found 412.1615.

A 0.1M solution of PTAD 2 (1.00 mL, 0.100 mmol) in CH$_3$CN was added (0.200 mL×5 times, interval 1 minute) into a solution of H-Gly-Gly-Tyr-OH 4 (11.8 mg, 0.040 mmol) in 200 mM pH 7.0 NaH$_2$PO$_4$/Na$_2$HPO$_4$ buffer (1.0 mL)-CH$_3$CN (1.0 mL) at room temperature. The resulting solution was stirred at room temperature for 30 minutes. The reaction mixture was acidified with 12N HCl (0.166 mL) and then concentrated in vacuo. The obtained crude material was purified by reversed phase HPLC to give 5 (19.8 mg, 85%) as amorphous solid. $^1$H NMR (300 MHz, D$_2$O): δ 7.66-7.42 (m, 5H), 7.31 (d, J=2.1 Hz, 1H), 7.26 (dd, J=8.4, 2.2 Hz, 1H), 7.03 (d, J=8.4 Hz, 1H), 4.58 (dd, J=8.5, 5.2 Hz, 1H), 3.93 (d, J=2.5 Hz, 2H), 3.81 (s, 2H), 3.18 (dd, J=14.1 Hz, 5.2, 1H), 2.95 (dd, J=14.2 Hz, 8.7, 1H). $^{13}$C NMR (150 MHz, D$_2$O): δ 176.61, 171.16, 168.34, 163.83 (q, J$_{C-F}$=35.5), 154.49, 153.10, 152.08, 133.40, 130.90, 130.62, 130.41, 130.07, 127.92, 127.87, 121.55, 118.09, 117.09 (q, J$_{C-F}$=282.4), 55.74, 42.83, 41.13, 36.81. HRMS: calcd for C$_{21}$H$_{23}$N$_6$O$_7$ (MH$^+$) 471.1626. found 471.1626.

Example 3

Synthesis of Cyclized Linker 9'

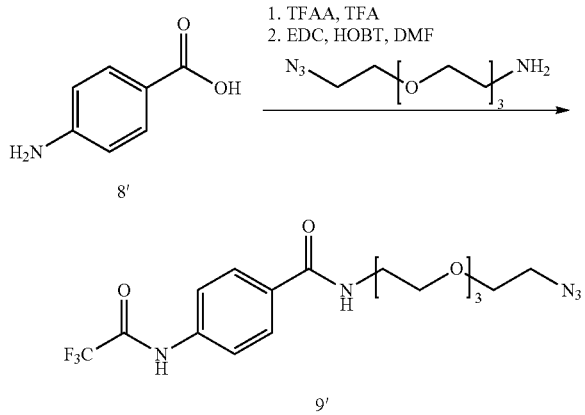

To a solution of 4-aminobenzoic acid (2.74 g, 20 mmol) in TFA (20 mL) was added TFAA (6.00 mL, 44 mmol) under ice-cooling. The resulting solution was stirred at room temperature overnight. The reaction mixture was added into ice-water. The resulting solids were collected by filtration, and washed with water and hexane to give 4-(2,2,2-trifluoroacetamido)-benzoic acid (6.15 g, quant.) as white solid. $^1$H NMR (300 MHz, DMSO-d6): δ 12.92 (br, 1H), 11.53 (s, 1H), 7.98 (d, J=8.6 Hz, 2H), 7.81 (d, J=8.2 Hz).

To a solution of 4-(2,2,2-trifluoroacetamido)benzoic acid (748 mg, 3.21 mmol) and 2-(2-(2-(2-azidoethoxy)ethoxy)ethoxy)ethanamine (700 mg, 3.21 mmol) in N,N-dimethylformamide (15 mL) was added EDC (738 mg, 3.85 mmol) and HOBT (520 mg, 3.85 mmol) at room temperature. The resulting solution was stirred at room temperature overnight. $CH_2Cl_2$ and water were added. The organic layer was separated and the aqueous layer was extracted twice with $CH_2Cl_2$. The combined organic layer was dried over $MgSO_4$, and concentrated in vacuo. The residue was purified by silica gel chromatography (ethyl acetate then $CHCl_3/CH_3OH$) to give 9' (1.44 g, quant.) as colorless oil. $^1$H NMR (300 MHz, CDCl$_3$): δ 8.38 (br, 1H), 7.84 (d, J=8.6 Hz, 2H), 7.68 (d, J=8.6 Hz, 2H), 6.87 (br, 1H), 3.69-3.61 (m, 14H), 3.35 (t, J=5.2 Hz, 2H). $^{13}$C NMR (75 MHz, DMSO-d6): δ 167.38, 155.50 (q, $J_{C-F}$=37.5), 139.10, 131.70, 128.39, 120.70, 115.93 (q, $J_{C-F}$=279.2), 50.82, 40.10. HRMS: calcd for $C_{17}H_{23}F_3N_5O_5$ (MH$^+$) 434.1646. found 434.1643.

Example 4

Synthesis of Cyclized Linker 10'

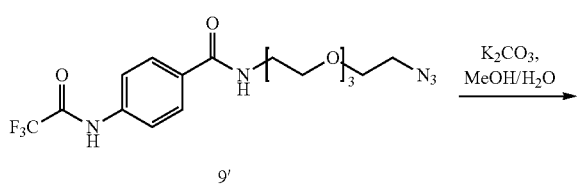

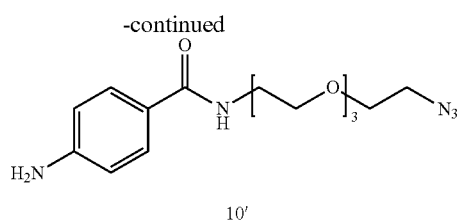

The solution of 9' (1.24 g, 2.86 mmol) and $K_2CO_3$ (1.19 g, 8.58 mmol) in methanol (15 mL) and water (5 mL) was stirred overnight under reflux. The volatile materials were evaporated in vacuo. The residue was purified by silica gel chromatography (ethyl acetate then $CHCl_3/CH_3OH$) to give 9' (709 mg, 80%) as orange oil. $^1$H NMR (300 MHz, CDCl$_3$): δ 7.61 (d, J=4.6 Hz, 2H), 6.64 (d, J=4.6 Hz, 2H), 6.54 (br, 1H), 3.67-3.60 (m, 14H), 3.33 (1, J=5.3 Hz, 2H). $^{13}$C NMR (75 MHz, DMSO-d6): δ 167.37, 163.33, 152.58, 129.69, 122.14, 113.54, 51.00, 36.76, 31.74. HRMS: calcd for $C_{15}H_{24}N_5O_4$ (MH$^+$) 338.1823. found 338.1826.

Example 5

Synthesis of Cyclized Linker 11'

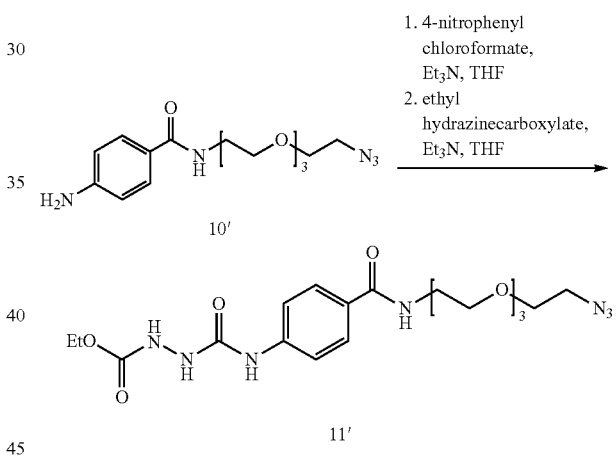

To a solution of 10' (200 mg, 0.593 mmol) and triethylamine (0.149 mL, 1.07 mmol) in tetrahydrofuran (5 mL) was added 4-nitrophenyl chloroformate (215 mg, 1.07 mmol) at −10° C. The resulting solution was stirred at room temperature. After 2 h, ethyl hydrazine-carboxylate (161 mg, 1.54 mmol) and triethylamine (0.215 mL, 1.54 mmol) were added at room temperature and stirred at 40° C. overnight. $CH_2Cl_2$ and water were added. The organic layer was separated and washed once with water. The resulting aqueous layer was combined and extracted twice with $CH_2Cl_2$. The combined organic layer was dried over $MgSO_4$, and concentrated in vacuo. The residue was purified by silica gel chromatography (ethyl acetate then $CHCl_3/CH_3OH$) to give 11' (235 mg, 85%) as pale green crystals. $^1$H NMR (600 MHz, DMSO-d6): δ 9.00 (br, 2H), 8.34-8.32 (m, 1H), 8.13 (br, 1H), 7.76 (d, J=8.6 Hz, 2H), 7.54 (br, 2H), 4.06 (q, J=7.0 Hz, 2H), 3.57-3.52 (m, 12H), 3.40-3.36 (m, 4H), 1.20 (t, J=7.1 Hz, 2H). $^{13}$C NMR (150 MHz, DMSO-d6): δ 166.78, 157.89, 156.32, 143.40, 129.14, 128.93, 128.44, 118.20, 70.75, 70.72, 70.62, 70.56, 70.20, 69.94, 61.52, 50.92, 15.50. HRMS: calcd for $C_{19}H_{30}N_7O_7$ (MH$^+$) 468.2201. found 468.2203.

Example 6

Synthesis of Cyclized Linker 8

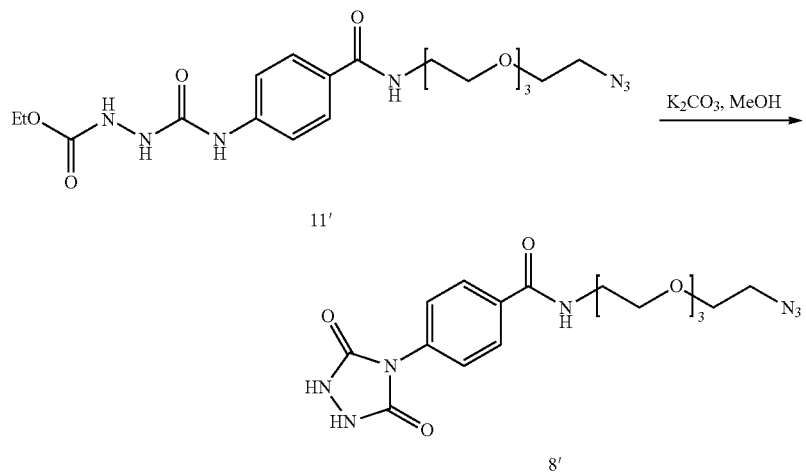

The suspension of 11' (200 mg, 0.427 mmol) and $K_2CO_3$ (177 mg, 1.28 mmol) in methanol (15 mL) was stirred overnight under reflux. The reaction mixture was acidified with 12N HCl (1.9 mL) and evaporated in vacuo. The residue was purified by silica gel chromatography ($CHCl_3/CH_3OH$) to give 8 (127 mg, 71%) as colorless oil. $^1$H NMR (500 MHz, $CDCl_3$): δ 9.34 (br, 2H), 7.91 (d, J=8.6 Hz, 2H), 7.80 (t, J=5.2 Hz, 1H), 7.57 (d, 8.6 Hz, 2H), 3.89-3.50 (m, 14H), 3.48-3.32 (m, 2H). $^{13}$C NMR (125 MHz, $CDCl_3$): δ 167.14, 153.32, 134.17, 133.36, 128.01, 124.81, 70.45, 70.17, 70.09, 70.03, 69.84, 69.73, 50.42, 50.39, 50.37, 39.84. HRMS: calcd for $C_{17}H_{24}N_7O_6(MH^+)$ 422.1782. found 422.1785.

Example 7

Synthesis of Cyclized Linker 12'

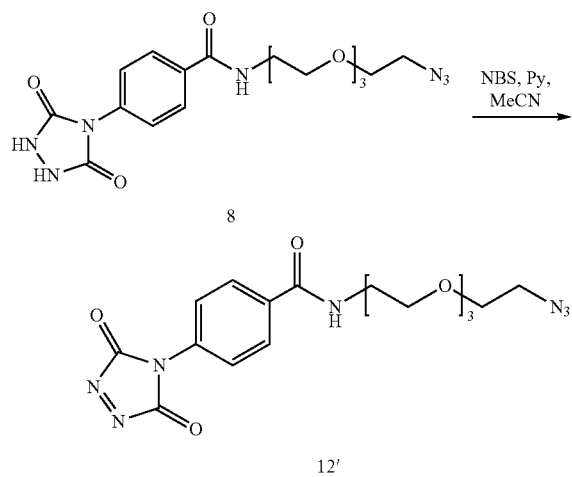

To a solution of 8 (3.17 mg, 0.00752 mmol) and Py (0.60 μL, 0.00737 mmol) in $CH_3CN$ (752 μL) was added NBS (1.31 mg, 0.00737 mmol) at room temperature. The resulting solution was stirred at room temperature for 5 minutes. The colorless solution immediately changed to cranberry red colored solution. This solution should be used for bioconjugation without isolation.

Example 8

Synthesis of Cyclized Linker 14'

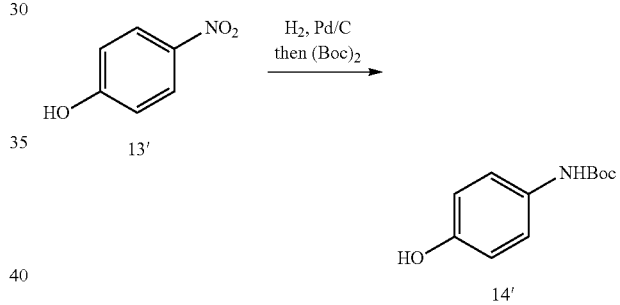

A suspension of 4-nitrophenol (3.00 g, 21.6 mmol) and 10% Pd/C (300 mg) in tetrahydrofuran (20 mL) was stirred at room temperature for 4 h under a hydrogen atmosphere. Hydrogen was replaced with argon, and a solution of (Boc)2O (3.76 g, 21.6 mmol) in tetrahydrofuran (10 mL) was added. After overnight, the catalyst was removed by passing through Celite®. Ethyl acetate and water were added. The organic layer was separated and washed once with water. The organic layer was dried over MgSO4, and concentrated in vacuo. The residue was purified by silica gel chromatography (hexane/ethyl acetate) to give commercially available 14' (3.37 g, 75%) as a white solid. $^1$H NMR (300 MHz, DMSO-d6): δ 9.02 (s, 1H), 8.97 (br, 1H), 7.20 (d, J=8.6 Hz, 2H), 6.63 (d, J=8.6 Hz, 2H), 1.45 (s, 9H).

Example 9

Synthesis of Cyclized Linker 15'

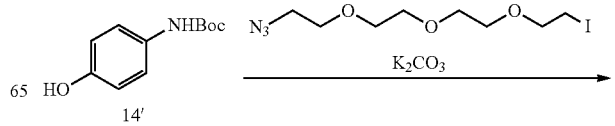

113
-continued

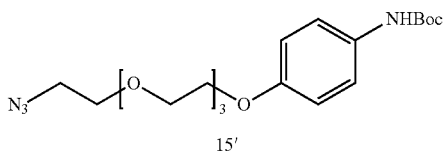

15'

To a solution of 2-(2-(2-azidoethoxy)ethoxy)ethanol (4.00 g, 18.2 mmol) and triethylamine (4.00 mL) in CH$_2$Cl$_2$ (80 mL) was added MesCl (1.84 mL, 23.7 mmol) under ice-cooling. The resulting solution was stirred at room temperature for 2 h. Ethyl acetate and saturated aqueous NaHCO$_3$ were added. The organic layer was separated and washed once with brine. The resulting aqueous layer was extracted once with ethyl acetate. The combined organic layer was dried over MgSO$_4$, and concentrated in vacuo to give mesylated compound (5.83 g). The suspension of mesylated compound (2.91 g, 9.79 mmol) and KI (2.44 g, 147 mmol) in N,N-dimethylformamide (40 mL) was stirred at 60° C. for 45 minutes. Ethyl acetate and brine were added. The organic layer was separated and washed once with brine. The resulting aqueous layer was extracted once with ethyl acetate. The combined organic layer was dried over MgSO$_4$, and concentrated in vacuo. The residue was purified by silica gel chromatography (hexane/ethyl acetate) to give 1-azido-2-(2-(2-iodoethyoxy)ethoxy)ethoxy)ethane (1.40 g, 2 steps yield 43%) as a colorless oil. $^1$H NMR (300 MHz, CDCl$_3$): δ 3.76 (t, J=6.8 Hz, 2H), 3.70-3.67 (m, 10H), 3.40 (t, J=5.2 Hz, 2H), 3.27 (t, J=7.1 Hz, 2H).

The suspension of 14' (128 mg, 0.614 mmol), 1-azido-2-(2-(2-iodoethyoxy)-thoxy)ethane (202 mg, 0.614 mmol) and K$_2$CO$_3$ (254 mg, 1.84 mmol) in N,N-dimethylformamide (5 mL) was stirred at 60° C. for 4 h. Ethyl acetate and water were added. The organic layer was separated and washed once with water. The resulting aqueous layer was combined and extracted once with ethyl acetate. The combined organic layer was dried over MgSO$_4$, and concentrated in vacuo. The residue was purified by silica gel chromatography (hexane/ethyl acetate) to give 15' (200 mg, 79%) as a colorless oil. $^1$H NMR (300 MHz, DMSO-d6): δ 9.12 (br, 1H), 7.33 (d, J=8.9 Hz, 2H), 6.83 (d, J=9.1 Hz, 2H), 4.04-4.00 (m, 2H), 3.59-3.53 (m, 2H), 3.61-3.53 (m, 10H), 3.40-3.36 (m, 2H), 1.46 (s, 9H). $^{13}$C NMR (150 MHz, DMSO-d6): δ 154.83, 153.12, 131.62, 120.37, 115.04, 70.82, 70.71, 70.70, 70.68, 70.03, 69.77, 67.76, 50.68, 28.37. HRMS: calcd for C$_{19}$H$_{31}$N$_4$O$_6$(MH$^+$) 411.2238. found 411.2219, Example 10

Synthesis of Cyclized Linker 16'

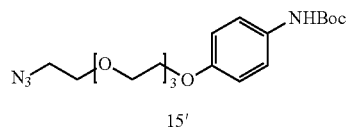

15'

1. 1.25 M HCl in MeOH
2. 4-nitrophenyl chloroformate, Et$_3$N, THF
3. ethyl hydrazinecarboxylate, Et$_3$N, THF 114
-continued

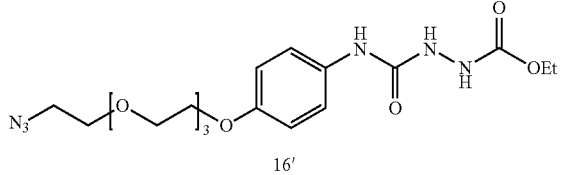

16'

A solution of 15' (165 mg, 0.402 mmol) in 1.25 M HCl/CH$_3$OH (4 mL) was stirred at 60° C. for 4 h. The solvent was evaporated in vacuo. The resulting compound was dissolved in tetrahydrofuran (10 mL) and 4-nitrophenyl chloroformate (782 mg, 3.88 mmol) and triethylamine (0.146 mL, 1.05 mmol) were added at –10° C. The resulting solution was stirred at room temperature overnight. Then ethyl hydrazinecarboxylate (146 mg, 0.724 mmol) and triethylamine 0.146 mL, 1.05 mmol) were added at room temperature and stirred at 40° C. for 3 h followed by addition of CH$_2$Cl$_2$ and water. The organic layer was separated and washed once with water. The resulting aqueous layer was combined and extracted once with CH$_2$Cl$_2$. The combined organic layer was dried over MgSO$_4$, and concentrated in vacuo. The residue was purified by silica gel chromatography (hexane/ethyl acetate) to give 16' (182 mg, quant.) as a colorless amorphous solid. $^1$H NMR (300 MHz, DMSO-d6): δ 8.88 (br, 1H), 8.53 (s, 1H), 7.90 (br, 1H), 7.34 (d, J=9.0 Hz, 2H), 6.84 (d, J=9.0 Hz, 2H), 4.06-4.02 (m, 4H), 3.73-3.70 (m, 2H), 3.61-3.55 (m, 10H), 3.40-3.36 (m, 2H), 1.21-1.15 (3H, m). $^{13}$C NMR (150 MHz, DMSO-d6): δ 157.63, 156.40, 155.16, 131.10, 121.89, 114.89, 70.77, 70.69, 70.63, 70.00, 69.77, 67.63, 62.45, 50.64, 14.40. HRMS: calcd for C$_{18}$H$_{29}$N$_6$O$_7$ (MH$^+$) 441.2092. found 441.2098.

Example 11

Synthesis of Cyclized Linker 7

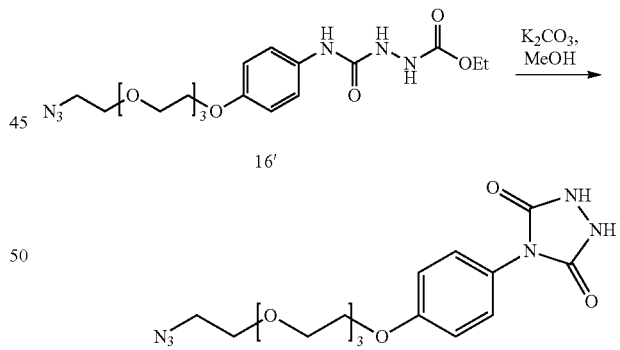

The suspension of 16' (150 mg, 0.341 mmol) and K$_2$CO$_3$ (141 mg, 1.02 mmol) in methanol (10 mL) was stirred overnight under reflux. The reaction mixture was acidified with 10% HCl up to pH 2 and evaporated in vacuo. The residue was purified by silica gel chromatography (ethyl acetate then CHCl$_3$/CH$_3$OH) to give 22 (63.8 mg, 47%) as a pale brown oil. $^1$H NMR (300 MHz, DMSO-d6): δ 10.4 (br, 1H), 7.32 (d, J=8.9 Hz, 2H), 7.03 (d, J=8.9 Hz, 2H), 4.14-4.11 (m, 2H), 3.78-3.74 (m, 2H), 3.61-3.55 (m, 10H), 3.40-3.36 (m, 2H). $^{13}$C NMR (125 MHz, DMSO-d6): δ 158.35, 154.58, 127.02, 124.16, 115.11, 70.96, 70.75, 70.70, 70.25, 69.91, 67.59, 50.77. HRMS: calcd for $C_{16}H_{23}N_6O_6$ (MH+) 395.1674. found 395.1680.

Example 12

Synthesis of Modified P-Cresol 4

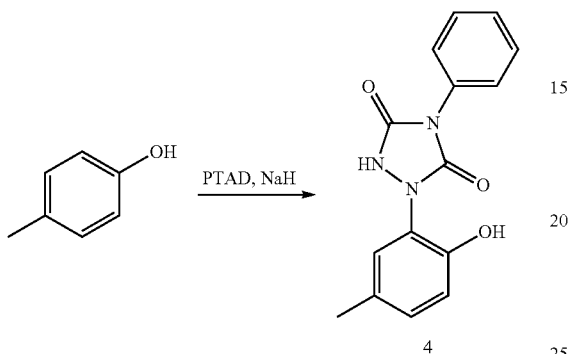

To a solution of p-cresol (80 mg, 0.740 mmol) in tetrahydrofuran (5 mL) was added NaH (35.5 mg, 0.885 mmol) at 0° C. After 20 minutes, PTAD (127 mg, 0.725 mmol) was added at 0° C. and stirred at room temperature for 3 h. Ethyl acetate and 10% HCl were added. The organic layer was separated and washed once with brine. The resulting aqueous layer was extracted once with ethyl acetate. The combined organic layer was dried over MgSO$_4$, and concentrated in vacuo. The residue was purified by silica gel chromatography (CHCl$_3$/ CH$_3$OH) to give 4 (158 mg, 75%) as white solids. $^1$H NMR (600 MHz, DMSO-d6): δ 9.86 (br, 1H), 7.53-7.49 (m, 4H), 7.43-7.40 (m, 1H), 7.19 (d, J=2.0 Hz, 1H), 7.10 (dd, J=8.3, 2.0 Hz, 1H), 6.87 (d, J=8.3 Hz, 1H), 2.24 (s, 3H). $^{13}$C NMR (150 MHz, DMSO-d6): δ 151.98, 151.64, 151.46, 131.86, 130.98, 129.56, 128.80, 127.91, 127.72, 126.03, 122.89, 116.57, 19.67. HRMS: calcd for $C_{15}H_{14}N_3O_3$ (MH+) 284.1030. found 284.1028.

Example 13

Stability Study of a Modified P-Cresol Under Hydrolysis Condition

The solution of compound 4 (10 mg, 0.0353 mmol) in 10% HCl (0.5 mL) in methanol (1.5 mL) and in 10% NaOH (0.5 mL) in methanol (1.5 mL) was stirred at room temperature for 12 h, respectively. Ethyl acetate and water were added. In the case of basic condition, ethyl acetate was added after acidification with 10% HCl up to pH 3. The organic layer was separated and washed once with water. The resulting aqueous layer was extracted once with ethyl acetate. The combined organic layer was dried over MgSO$_4$, and concentrated in vacuo. The residue was purified by silica gel chromatography using ethyl acetate to recover 4 as white solid. The recovery of 4; 8.9 mg (89%) after acidic conditions and 10.2 mg (quant.) after basic conditions.

Example 14

Stability Study of a Modified P-Cresol Under Thermal Conditions

Compound 4 (4.00 mg, 0.0141 mmol) was heated at 120° C. for 1 h according to the literature. The recovery of 4 was 4.00 mg (quant.). The decomposition wasn't detected by $^1$H NMR at all.

Example 15

General Procedure for Optimization of Tyrosine Modification with PTAD

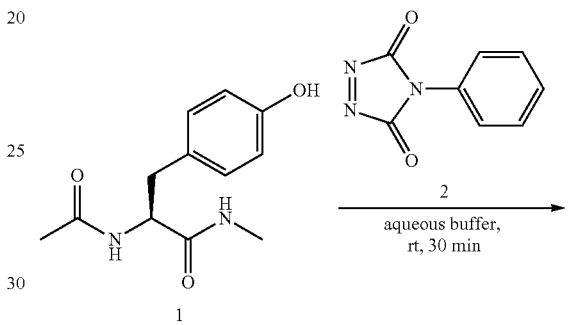

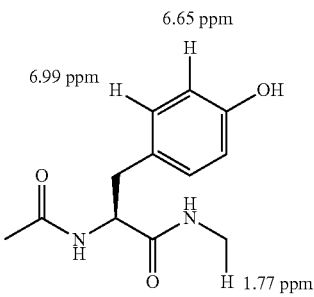

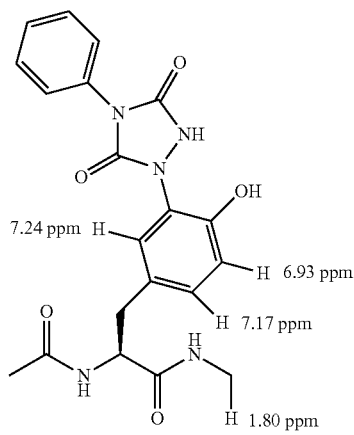

To a solution of N-acyl tyrosine methylaminde 1 (4.73 mg, 0.020 mmol, 1.0 equivalents) in aqueous solvent (0.5 mL)-

CH₃CN (0.5 mL) was added the 0.5 M solution of PTAD 2 (0.044 mL, 0.022 mmol, 1.1 equivalents) in CH₃CN at room temperature. The final concentration of 1 was adjusted to 2 or 20 mM. The resulting solution was stirred at room temperature for 30 minutes. After the reaction, the reaction mixture was acidified with 12N HCl (0.083 mL) to generate the sodium salt of 3 and then concentrated in vacuo. The obtained crude organic materials were dissolved in DMSO-d6 and were analyzed by 300 MHz $^1$H NMR to determine the conversion. The conversion was calculated by comparison of the areas of aromatic signals. Occasionally, the broad peak derived from phosphoric acid was overlapping with aromatic signals depended on concentration of solvent. In this case, as shown in Table 2, entry 4, the comparison of the areas of methyl signals were used to calculate the conversion using $^1$H NMR of the mixture of the reaction.

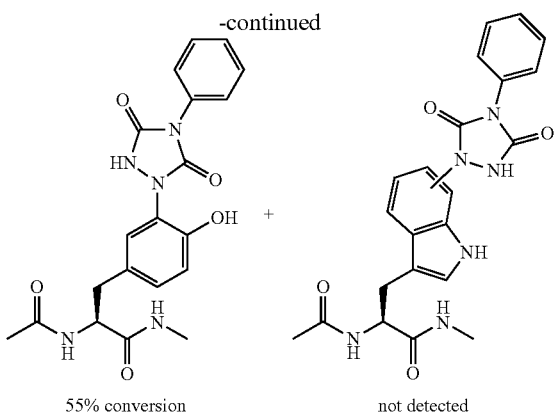

55% conversion  not detected

TABLE 2

| Entry | Buffer | PTAD (equivalent) | Conc. (mM) | Conversion (%) |
|---|---|---|---|---|
| 1 | 200 mM pH 7 NaH₂PO₄—Na₂HPO₄—CH₃CN (1:1) | 1.1 | 20 | 61 |
| 2 | 200 mM pH 7 NaH₂PO₄—Na₂HPO₄—CH₃CN (1:1) | 2.2 | 20 | 87 |
| 3 | 200 mM pH 7 NaH₂PO₄—Na₂HPO₄—CH₃CN (1:1) | 3.3 | 20 | 93 |
| 4 | 100 mM pH 7 NaH₂PO₄—Na₂HPO₄—CH₃CN (1:1) | 1.1 | 20 | 69 (65[a]) |
| 5[b] | 100 mM pH 7 NaH₂PO₄—Na₂HPO₄—CH₃CN (1:1) | 1.1 | 20 | 79 |
| 6[c] | 100 mM pH 7 NaH₂PO₄—Na₂HPO₄—CH₃CN (1:1) | 2.2 | 20 | 91 |
| 7[d] | 100 mM pH 7 NaH₂PO₄—Na₂HPO₄—CH₃CN (1:1) | 3.3 | 20 | 96 |
| 8[d] | 200 mM pH 7 NaH₂PO₄—Na₂HPO₄—CH₃CN (1:1) | 3.3 | 20 | >99 |
| 9 | 100 mM pH 7 NaH₂PO₄—Na₂HPO₄—CH₃CN (1:1) | 3.3 | 2 | 67 |
| 10[e] | CH₃CN | 1.1 | 20 | 0 |
| 11[e] | H₂O—CH₃CN (1:1) | 1.1 | 20 | 0 |
| 12 | 100 mM NaCl—CH₃CN (1:1) | 1.1 | 20 | 0 |
| 13 | 100 mM pH 7.4 HEPES buffer —CH₃CN (1:1) | 1.1 | 20 | 63 |
| 14 | 100 mM pH 7.4 Tris buffe-CH₃CN (1:1) | 1.1 | 20 | 35 |
| 15 | 100 mM Na₂CO₃—CH₃CN (1:1) | 1.1 | 20 | 43 |
| 16 | 100 mM Triethylamine-CH₃CN (1:1) | 1.1 | 20 | 58 |

[a] isolated yield.
[b] 0.1M PTAD solution was added in 5 aliqots with 10 sec. interval.
[c] 0.2M PTAD solution was added in 5 aliqots with 10 sec. interval.
[d] 0.3M PTAD solution was added in 5 aliqots with 10 sec. interval.
[e] reaction time 12 h.

Example 16

Selectivity Study of Amino Acids with PTAD

N-acyl methyl amides of tyrosine, histidine, tryptophan, serine, cysteine, lysine were used for selectivity study and competition study.

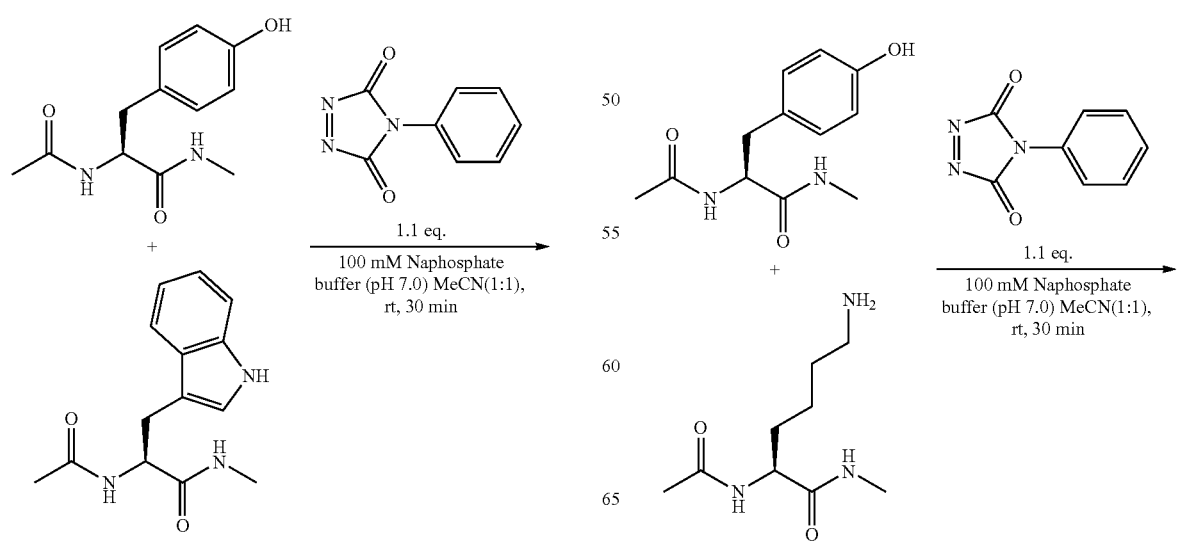

-continued

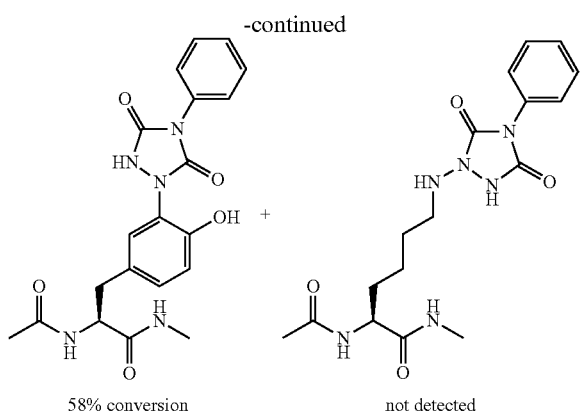

58% conversion      not detected

To a solution of N-acyl methyl amide (0.020 mmol, 1.0 equivalents) or mixed two N-acyl methyl amides (0.020 mmol each, 1.0 equivalents) in 100 mM Na phosphate buffer (pH 7.0, 0.5 mL)-CH$_3$CN (0.5 mL) was added the 0.5 M solution of PTAD 2 (0.044 mL, 0.022 mmol, 1.1 equivalents) in CH$_3$CN at room temperature. The final concentration of amino acid was adjusted to 20 mM. The resulting solution was stirred at room temperature for 30 minutes. The reaction mixture was acidified with 12N HCl in order to avoid generation of Na salts of amino acid(s) and then concentrated in vacuo. The obtained crude organic materials were dissolved in DMSO-d6. These solutions were analyzed by 300 MHz $^1$H NMR or LC-MS. The conversion of 1 was calculated by $^1$H NMR according to the procedure in section 6.

This procedure has shown that histidine, serine, cystein were not modified by PTAD, while modification of tryptophan and lysine could be detected by $^1$H NMR and LC-MS analysis. The modified tryptophans, with molecular weight increase of 175 vs nonmodified tryptophan, were detected by LC-MS analysis as three isomer peaks after the reaction. $^1$H NMR also showed detectable additional peaks derived from modified compounds (structures were not assigned). In the case of lysine, LC-MS analysis has shown same modification as previously observed for typtophan. Similarly, additional peaks of modified product were observed in $^1$H NMR. Tryptophan and lysine therefore were selected for competition experiments with tyrosine. It was determined that tryptophan and lysine did not interfere with the modification of tyrosine. The conversions were 55% and 58%, respectively. Furthermore, peaks corresponding to the modification of tryptophan or lysine were not detected in the $^1$H NMR spectrograph.

In the case of six amino acids mixed reaction, the concentration was adjusted to 6.67 mM in order to not disturb buffer capacity by the total amount of substrates (0.020 mmol×6 amino acids=0.12 mmol). The conversion of 1 was calculated from $^1$H NMR according to the procedure in section 6.

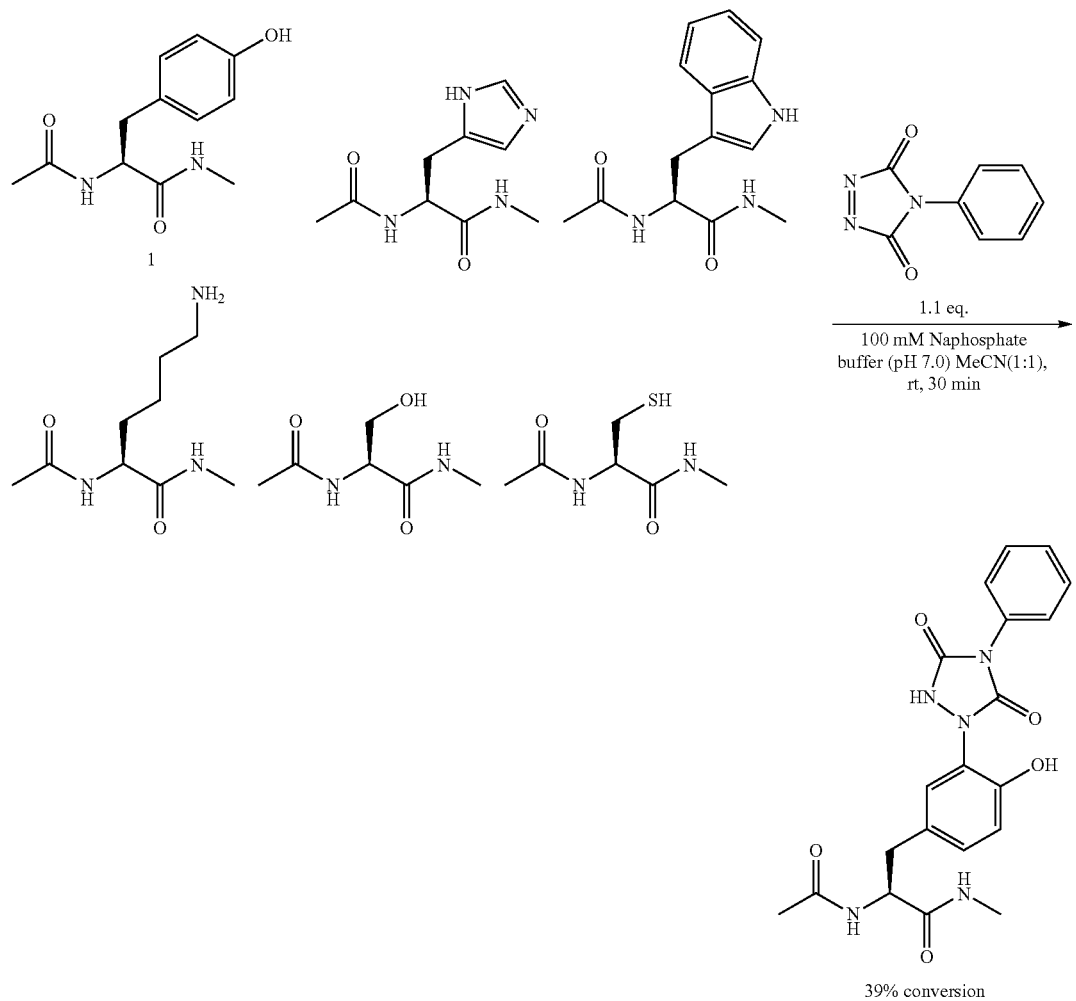

39% conversion

Example 17

Modification of Tocinoic Acid with PTAD

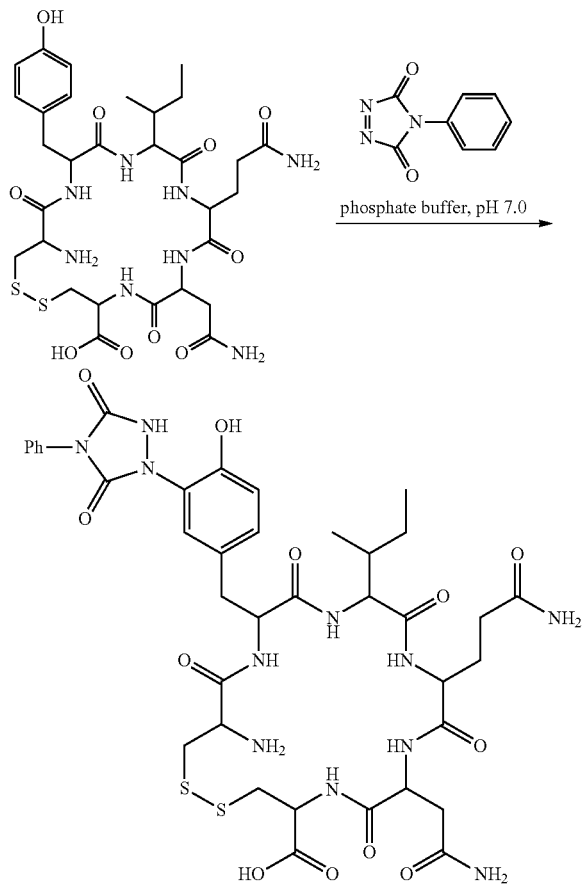

Chemical Formula: $C_{38}H_{49}N_{11}O_{12}S_2$
Exact Mass: 915.3004

To a 1.7 mL microcentrifuge tube was added 338 μL of (Ile3)-pressinoic acid (20.0 mM solution in 0.1M phosphate buffer pH 7.0; 1.0 equivalent, followed by addition of total of 12.16 μL of PTAD (100 mM solution in $CH_3CN$; 3.0 equivalent. Addition was done in aliquots of 1 equivalent with the interval of 2 minutes between additions. The mixture was vortexed briefly to mix the reaction components, then allowed to stand at room temperature for 1 h. The crude reaction mixture was analyzed directly by ESI-LC/MS (see trace at 210 nm and corresponding MS below) and has shown 96% conversion. The product was isolated as TFA salt using HPLC (gradient of 10% to 95% $CH_3CN/H_2O$, 0.1% TFA over 60 minutes, $R_t$ 27.12 minutes) to give 5.1 mg (83%) of Tyr modified tocinoic acid as a white solid. $^1H$ NMR (500 MHz, Methanol-d4) δ 8.82 (d, J=5.1, 1H), 8.42 (s, 1H), 8.26 (d, J=8.4, 1H), 8.19 (d, J=7.8, 1H), 7.58-7.50 (m, 4H), 7.46 (ddd, J=11.2, 6.0, 2.7, 1H), 7.39 (d, J=2.2, 1H), 7.33 (dd, J=8.4, 2.1, 1H), 6.95 (d, J=8.4, 1H), 4.81 (dd, J=10.4, 5.3, 1H), 4.73 (dd, J=9.0, 4.7, 1H), 4.21 (t, J=4.9, 1H), 4.18-4.12 (m, 1H), 3.98 (s, 0H), 3.81-3.75 (m, 1H), 3.46-3.43 (m, 1H), 3.39 (dt, J=13.6, 4.5, 2H), 3.25 (dd, J=15.2, 5.3, 1H), 3.08 (dd, J=14.1, 9.2, 1H), 3.01 (dd, J=16.1, 5.7, 1H), 2.86 (dd, J=13.8, 10.2, 2H), 2.69 (dd, J=16.0, 5.2, 2H), 2.41 (dtd, J=22.7, 16.6, 6.2, 3H), 2.15-2.07 (m, 2H), 2.03 (s, 1H), 1.93 (d, J=10.9, 2H), 1.48 (s, 3H), 1.29 (s, 2H), 1.16 (dd, J=14.5, 6.9, 5H), 0.98 (d, J=6.8, 3H), 0.93 (t, J=7.4, 3H). $^{13}C$ NMR (151 MHz, DMSO-$d_6$) δ 174.87, 173.05, 172.95, 172.10, 172.08, 171.66, 168.11, 159.02, 158.83, 154.55, 153.67, 153.15, 152.50, 148.24, 147.61, 132.82, 132.25, 130.69, 129.96, 129.31, 128.92, 127.10, 123.98, 121.18, 117.75, 108.97, 102.65, 56.56, 55.59, 53.98, 52.26, 51.35, 49.57, 41.70, 41.28, 40.99, 37.46, 37.19, 36.54, 32.17, 27.23, 25.14, 16.30, 11.84, 1.09. HRMS expected for $C_{38}H_{49}N_{11}O_{12}S_2[M+H]^+$ 916.3082; $[M+Na]^+$ 938.2901. found 916.3088; 938.2907.

Example 18

Protein Modification with Rhodamine Containing Reagents

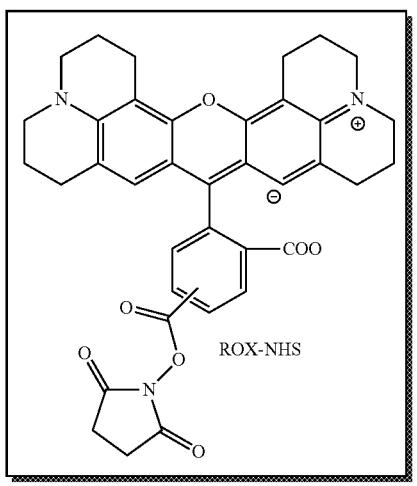

ROX-NHS

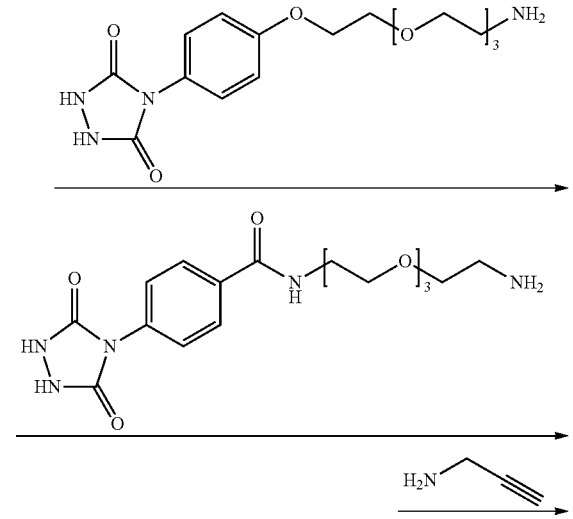

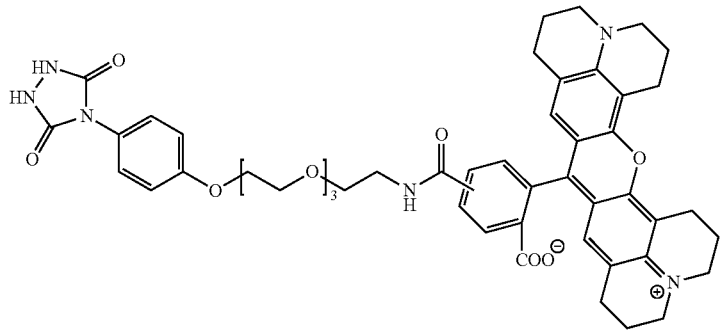

precursor 9

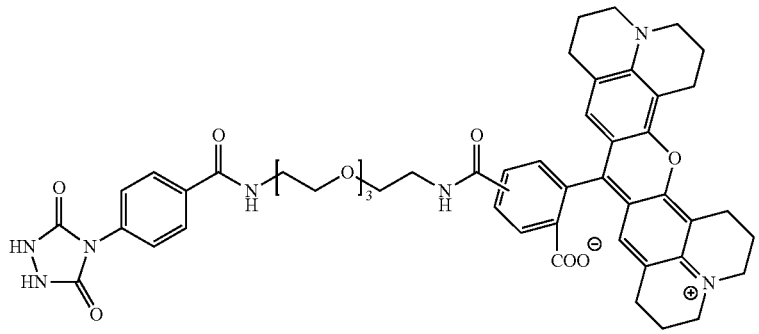

precursor 10

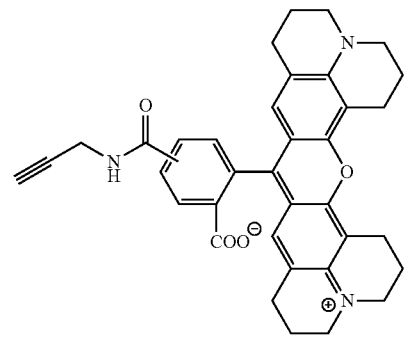

11

To the solution of NHS-activated 5-(and 6-) carboxy-X-rhodamine (ROX) (0.5 mg, 0.79 µM, 1.0 equivalent in CH₃CN (0.1 ml) was added amine (0.79 µM, 1.0 equivalent and TEA (0.068 µL, 87 µM, 1.1 equivalent. The reaction mixture was stirred overnight and the solvent was removed in vacuo to provide deep purple glassy solid. The crude product was stored at 4° C. and used without purification. A small aliqot was analyzed by LCMS and HRMS that confirmed complete conversion of the reaction. Precursor for Linker 9. HRMS: calcd for $C_{49}H_{52}N_6O_{10}$ (MH⁺) 885.3817. found 885.3815. Precursor for Linker 10. HRMS: calcd for $C_{50}H_{51}N_7O_{10}$ (MH⁺) 912.3932. found 912.3930. ROX alkyne 11. HRMS: calcd for $C_{36}H_{33}N_3O_4$ (MH⁺) 572.2549. found 572.2546.

Example 19

General Oxidation Procedure

To the 1.7 ml microcentrifuge tube was added solution of rhodamine linker precursor in N,N-dimethylformamide (1.0 equivalent and pyridine (0.98 equivalent followed by vortexing and addition of NBS (0.98 equivalent. The amount of the total N,N-dimethylformamide used for the reaction was calculated in accord with the desired oxidized reagent stock solution concentration (stock solution concentrations used 100 mM, 500 mM and 1.0M). The reaction mixture was vortexed briefly to mix all the components and kept on ice. The reagent was used for protein modification reaction immediately.

Example 20

General Procedure for Protein Modification

To the 1.7 ml microcentrifuge tube was added protein solution (30 μM in phosphate buffer pH 7.4, 99₄) followed by addition of rhodamine reagent (100 mM in N,N-dimethylformamide, 1 μL). The reaction mixture was vortexed briefly and allowed to stand at room temperature for 15 min before the unreacted small molecules were removed using Zeba spin desalting column (7 k MWCO) two to three times followed by 24 h dialysis in PBS.

Example 21

Calculation of Conversion Based on UV-VIS Spectra

Conversion of protein modification reactions was calculated essentially as described.[5] Chymotrypsinogen A $\epsilon$ (280 nm)=50585 $M^{-1}cm^{-1}$; Myoglobin $\epsilon$ (280 nm)=13980 $M^{-1}cm^{-1}$; BSA $\epsilon$ (280 nm)=49915 $M^{-1}cm^{-1}$ (determined from EXPASY Swiss-Prot database); ROX $\epsilon$ (575 nm)=82000 $M^{-1}cm^{-1}$ (AnaSpec technical data for the product). Correction Factor for 5-(and 6-) carboxy-X-rhodamine (ROX)=0.17. The UV-vis spectra of unmodified BSA vs rhodamine labeled BSA, shows a distinct rhodamine absorbance peak at 575 nm.

Example 22 pH Study

BSA was used as a model protein for the pH study. Buffers were prepared according to published procedures[7] and used for the preparation of 30 μM BSA solution. Modification reactions were performed as described above. As shown below in Table 3 and in FIG. 7, the results for pH effect in protein modification are provided.

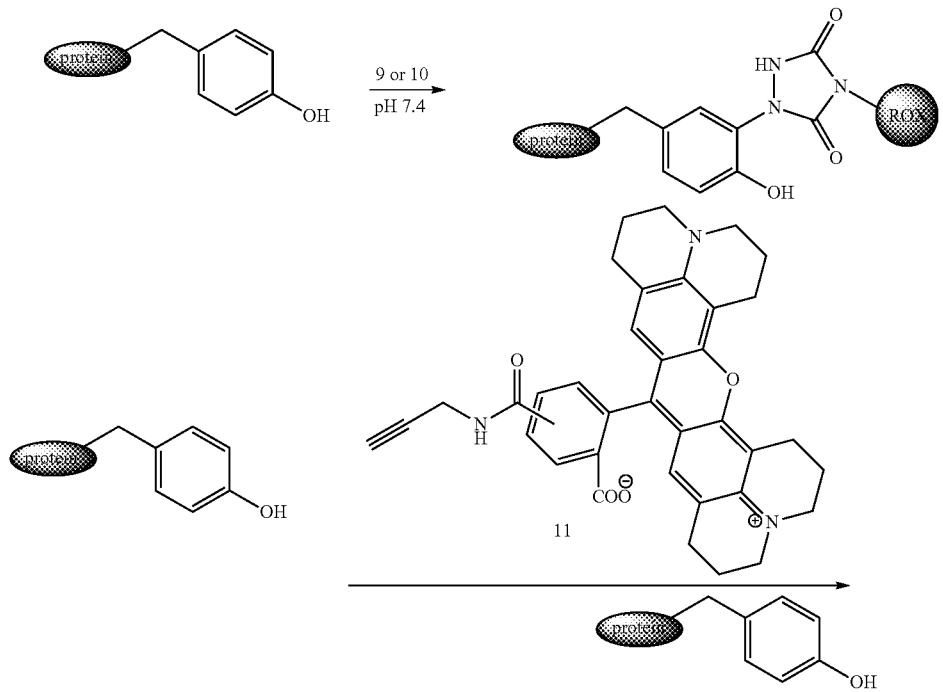

TABLE 3

| # | Buffer, pH | Conversion in rxn#1, % | Conversion in rxn#2, % | Average conversion, % |
|---|---|---|---|---|
| 1 | 10% AcOH, pH 2.0 | 44 | 44 | 44 |
| 2 | KCl/HCl, pH 2.0 | 50 | 57 | 54 |
| 3 | Phosphate buffer/citric acid, pH 3.0 | 37 | 37 | 37 |
| 4 | Phosphate buffer/citric acid, pH 4.0 | 55 | 56 | 56 |
| 5 | Phosphate buffer, pH 5.0 | 65 | 63 | 64 |
| 6 | Phosphate buffer, pH 6.0 | 71 | 76 | 74 |
| 7 | Phosphate buffer, pH 7.0 | 83 | 87 | 85 |
| 8 | Phosphate buffer, pH 8.0 | 93 | 98 | 96 |
| 9 | Phosphate buffer/NaOH, pH 9.0 | 97 | 98 | 98 |
| 10 | Phosphate buffer/NaOH, pH 10.0 | 85 | 85 | 85 |

Figure 7:
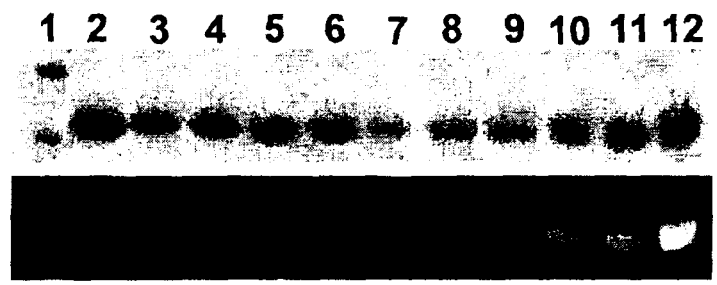

FIG. 7 provides SDS-PAGE gel for the pH study products: 1. MW ladder; 2. Unmodified BSA; 3. rxn #1 from the table above; 4. rxn #2; 5. rxn #3; 6. rxn #4; 7. rxn #5; 8. rxn #6; 9. rxn #7; 10. rxn #8; 11. rxn #9; rxn #10.

Example 23

Different Protein Modification Study

As shown below in Table 4, the different protein modifications using proteins cymottrypsinogen A, myoglobin, BSA, and reagents 9 and 10 is provided.

TABLE 4

| # | Protein[a] | Reagent conc. mM | Reagent 9, Av. Conv %[b] | Reagent 10, Av. Conv %[b] |
|---|---|---|---|---|
| 1 | Chymotrypsinogen A | 1 | 56 | 35 |
| 2 | Chymotrypsinogen A | 5 | 72 | 54 |
| 3 | Chymotrypsinogen A | 10 | 81 | 60 |
| 4 | Myoglobin | 1 | 6 | 13 |
| 5 | Myoglobin | 5 | 6 | 13 |
| 6 | Myoglobin | 10 | 8 | 16 |
| 7 | BSA | 1 | 85 | 53 |
| 8 | BSA | 5 | 96 | 65 |
| 9 | BSA | 10 | 96 | 68 |
| 10 | Chymotrypsinogen A[c] | 10 | 3 | 3 |
| 11 | Myoglobin[c] | 10 | 3 | 3 |
| 12 | BSA[c] | 10 | 4 | 4 |

[a] 30 µM protein solution in 0.1M phosphate buffer pH 7.4 was used.
[b] Average conversion of two independent experiments is shown.
[c] Reagent 11 was used as negative control.

Example 24

Activity Assay of Modified Chymoytrypsinogen A

Figure 8:
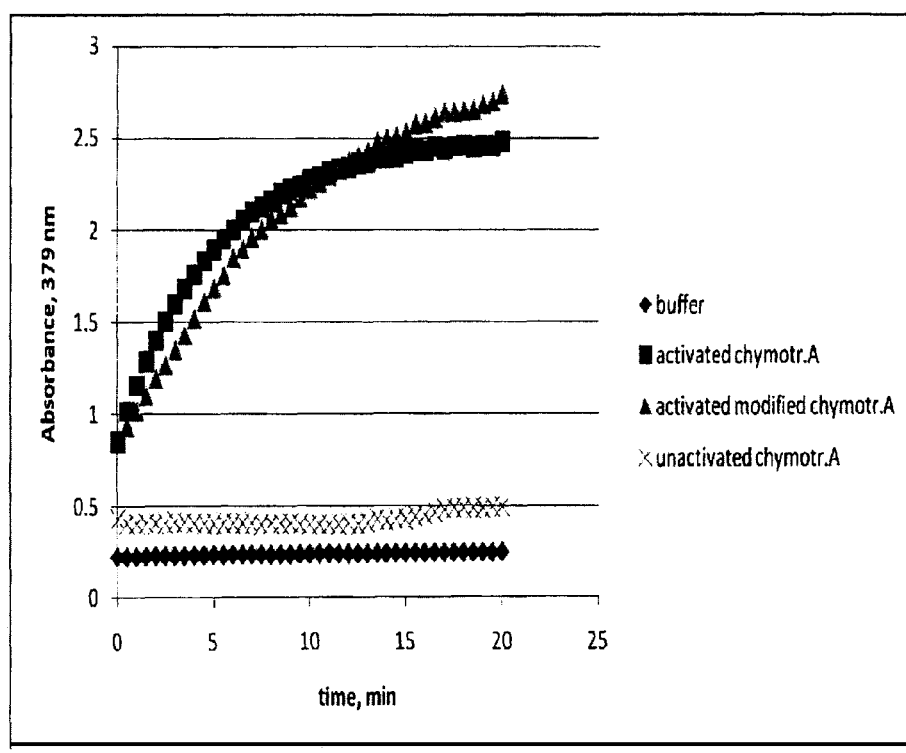

Activity assay was performed essentially as described by Francis et al. In brief, an 114 µL aliquot of a reaction mixture for the modification of chymotrypsinogen (1.0 mg/mL, 38 µM total protein content) was treated with 2.6 µL of a solution of sequencing grade modified trypsin (Promega, 20 µg reconstituted with 200 µL of 50 mM acid). The activation of the zymogen was allowed to proceed for 10 minutes at room temperature before being purified and performing buffer exchange into 0.1M Tris buffer (pH 7.6) using Zeba spin desalting column (Pierce). 40 µL aliquots of the activated protease were then added to 160 of 0.5 mM chymotrypsin substrate I, colorimetric (Suc-GGF-pNA, Calbiochem 230912) in 50 mM $CaCl_2$, 20 mM Tris buffer, pH 7.6 (dark red squares). An analogous procedure was followed for reagent modified chymotripsinogen A samples (light green triangles). In a negative control experiment, the enzyme was not activated with trypsin before addition of the tripeptide substrate (light blue crosses), or the substrate was monitored with addition of only Tris buffer (blue diamonds). The progress of the reaction was monitored by UV-Vis spectrophotometry at 379 nm every 30 sec for 20 minutes. Each measurement was done in duplicate and the average value was plotted. FIG. 8 provides the modified chymotrypsinogen A activity assay. Average of two measurements is shown. Error bars are omitted for clarity.

Example 25

Tryptic Digest Procedure

Tryptic digest was performed essentially as described.[5] In brief, 100 µL of the dialyzed protein reaction mixture was added to 36 mg of solid urea. The resulting solution was briefly vortexed and then heated at 65° C. in a water bath for 30 minutes. The denatured protein sample was diluted with 500 µL of 50 mM NH4HCO3 buffer, pH 7.8, and then treated with 20 µL of a solution of sequencing grade modified trypsin (Promega, 20 µg reconstituted with 200 µL of 50 mM acetic acid). The digest mixture was then incubated at 37° C. for 12 h. The crude digest mixture was desalted using a µC18 Pep-Clean tip with a CH3CN:H2O, 0.1% formic acid solvent system. The desalted protein mixture was then analyzed by LC-ESI MS. PAWS program (Genomic Solutions Inc.; http://bioinformatics.genomicsolutions.com/Paws.html) was used to predict tryptic digest fragments from protein sequences and potential modification adducts.

Example 26

Preparation of RGD Modified Herceptin

The preparation of RGD modified herceptin is outlined below.

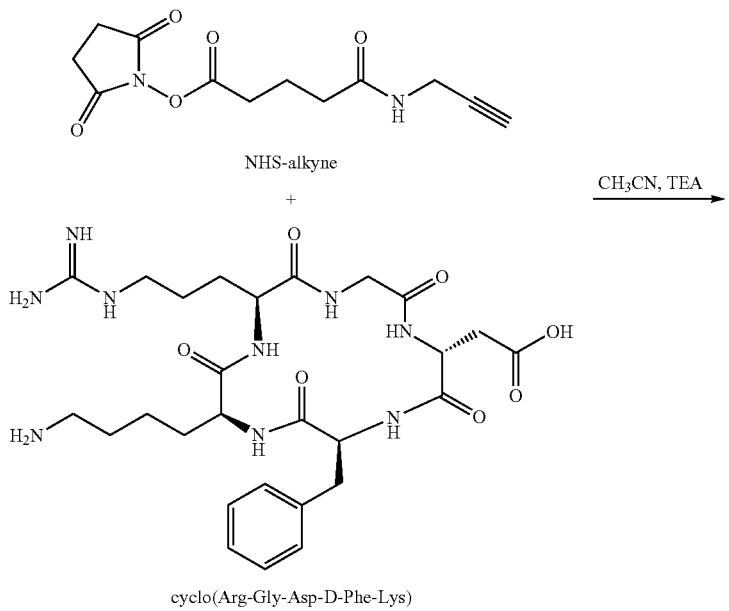

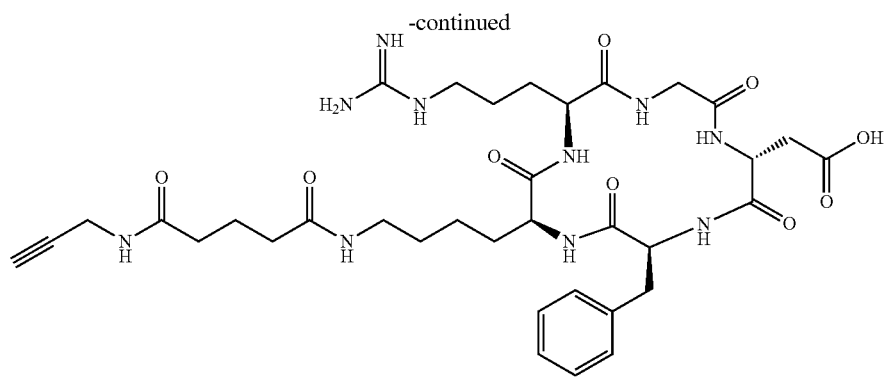

12

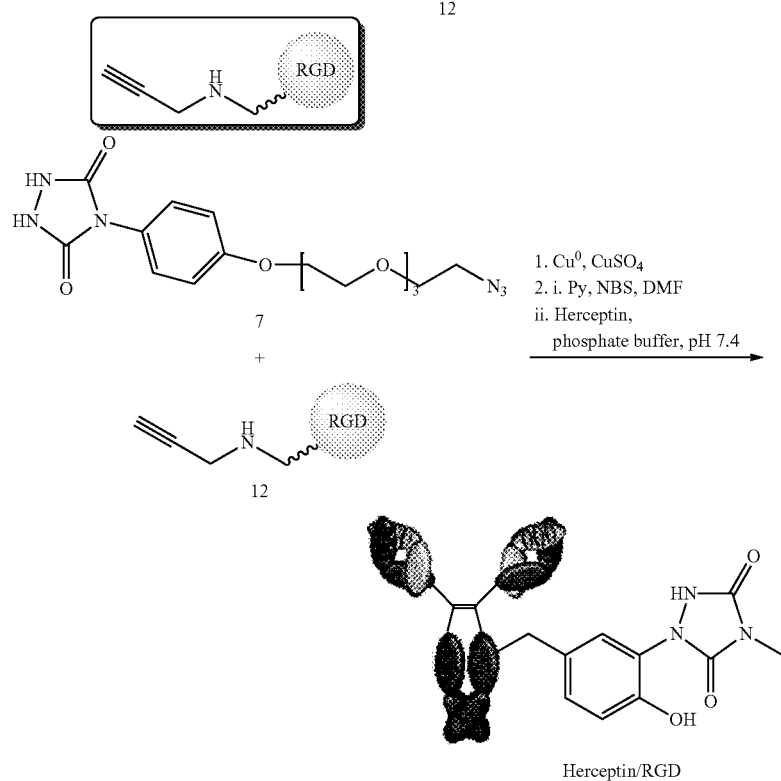

Herceptin/RGD

Example 27

Preparation of RGD Conjugated Diazodicarboxamide Reagent

To a 1.7 mL microcentrifuge tube were added 200 μL of cyclic RGD peptide solution in N,N-dimethylformamide (10.0 μM solution, 2 nM, 1 equivalent followed by addition of 20 μL of NHS-activated alkyne solution (0.1 mM solution in N,N-dimethylformamide, 2 nM, 1 equivalent and 22 μL of triethyl amine solution (0.1 mM solution in N,N-dimethylformamide, 2.2 nM 1.1 equivalent. The reaction mixture was vortexed occasionally and kept at room temperature for 12 h. A small aliquot was analyzed by FIRMS and confirmed complete conversion of starting material to the desired product 12. HRMS: [M+H]$^+$ calcd. for $C_{35}H_{50}N_{10}O_9$ 755.3840. found 755.3839. The product was used in the next step without purification.

To a 1.7 mL microcentrifuge were added 100 μl of RGD alkyne 12 (10.0 μM solution, 1.0 nM, 1 equivalent, azide linker 7 (1 eqiuv), a small piece of copper wire and 14 copper sulphate (0.1 μM solution in $^t$BuOH:H$_2$O 1:1; 0.1 nM, 0.1 equivalent. The reaction mixture was vortexed occasionally on the course of 8 h and kept at 37° C. A small aliqot (2 μL) was analyzed by LCMS-ESI and HRMS and confirmed reaction completion. HRMS: [M+H]$^+$ calcd. for $C_{51}H_{72}N_{16}O_{15}$ 1149.5441. found 1149.5439. Copper wire was removed and copper ions were scavenged with Cu absorbing polymer resin ("CupriSorb", Seachem), the resin was filtered and resulting reagent solution was used for the next oxidation step without additional purification. Oxidation was done exactly as previously described with 0.98 equivalent of pyridine and 0.98 equivalent NBS.

Example 28

Preparation of the Antibody Conjugate

To the solution of herceptin in phosphate buffer pH 7.4 (1 mg/ml, 90 μL, 0.612 μM total protein content) was added reagent RGD containing cyclic diazodicarboxamide reagent prepared immediately before use as previously described (10 µL of 0.1 mM solution in N,N-dimethylformamide). Reaction mixture was vortexed briefly and allowed to stay at room temperature for 15 minutes. Excess of unreacted small molecules was removed by first desalting the reaction mixture with Zeba spin desalting column (7 k MWCO) two times followed by dialysis for 24 hr in PBS. The purified Herceptin construct was characterized by MALDI-TOF MS and its biological activity was evaluated in ELISA assays.

Example 29

ELISA Procedures and Results

Figure 9:
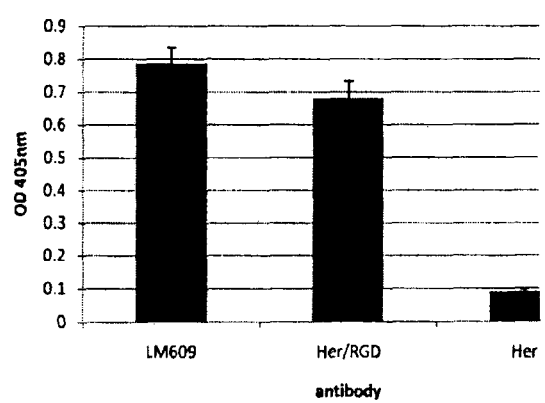

Integrin ELISA. Integrin αvβ3 binding ELISA was performed exactly as described.[8] All measurements were done in triplicate and the average normalized result is shown in FIG. 9, which provides the normalized integrin αvβ3 binding ELISA.

Example 30

ErbB2 ELISA

Figure 10:
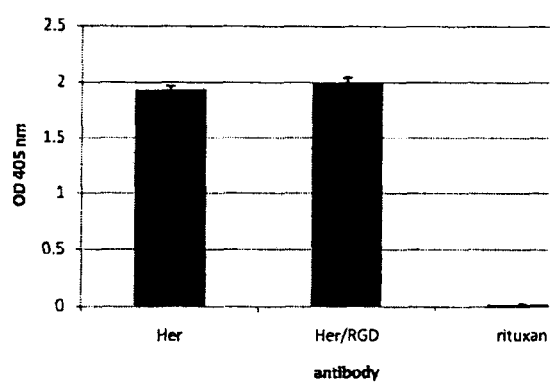

Erb B2 binding ELISA was performed as described.[9] In brief, Costar 96-well ELISA plates (Corning, Acton, Mass.) were coated with 25 ng of antigen (human ErbB2 or BSA) in 25 µL of PBS pH 7.4 and incubated overnight at 4° C. The plate was washed with PBS containing 0.01% tween-20 (100 µL×3). After blocking with 100 µL of 3% BSA/PBS, 0.01% tween-20 for 1 h at 37° C. and washing (100 µL of PBS containing 0.01% tween-20×5), 100 ng/504/well of herceptin or herceptin/RGD construct or rituxan solution was added and the plates were incubated for 1 hr at 37° C. The plate was thoroughly washed with PBS/0.01% tween (100 µL×5) followed by addition of 100 µL/well of secondary antibody solution (donkey anti-Human HRP, diluted 1:1000). The plate was incubated for 1 h at 37° C. and washed with PBS/0.01% tween (100 µL×5). Upon addition of the ABTS developing solution and incubation at room temperature for 20 minutes the absorbance was read at 405 nm. All measurements were done in triplicate and an average normalized result is shown in FIG. 10.

Example 31

General Procedure for Coupling of N-Acyl Tyrosine Methylamide 1 with Diazonium Salt 2

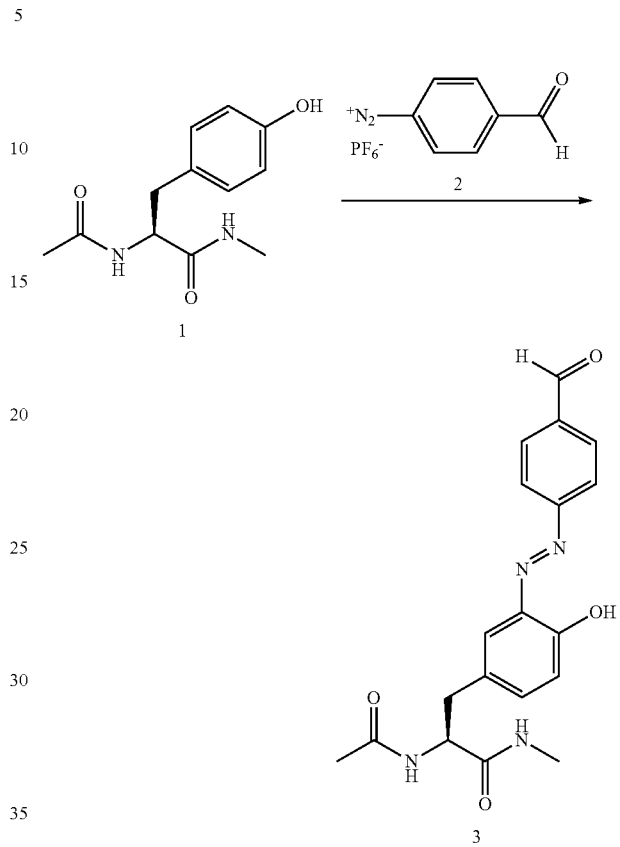

To a solution of N-acyl tyrosine methylamide 1 (20 mg, 0.0846 mmol) in 100 mM pH 7.0 NaH$_2$PO$_4$/Na$_2$HPO4 buffer (2.83 mL)-DMSO (1.41 mL) was added the diazonium salt 2 (25.9 mg, 0.0931 mmol) at room temperature. The resulting solution was stirred at room temperature for 45 minutes. After the reaction, water (2.82 mL) was added. The generated solid was filtrated, washed with water and ethyl acetate to provide 3 (31.0 mg, 99%) as a yellow solid. ESIMS: calcd for C$_{19}$H$_{20}$N$_4$O$_4$ (MH$^+$) 369.2. found 369.2. As shown below in Table 5, a summary of the various buffer conditions, times and yields.

TABLE 5

| Entry | Buffer | X$^-$ | Time | Isolated yield (%) |
|---|---|---|---|---|
| 1 | 67% 100 mM NaH$_2$PO$_4$—NaH$_2$PO$_4$, pH 5, CH$_3$CN | PF$_6$— | 12 h | 9 |
| 2 | 67% 100 mM NaH$_2$PO$_4$—NaH$_2$PO$_4$, pH 6, CH$_3$CN | PF$_6$— | 12 h | 33 |
| 3 | 67% 100 mM NaH$_2$PO$_4$—NaH$_2$PO$_4$, pH 7, CH$_3$CN | PF$_6$— | 45 min | 99 |
| 4[a] | 67% 100 mM NaH$_2$PO$_4$—NaH$_2$PO$_4$, pH 7, CH$_3$CN | PF$_6$— | 45 min | 93 |
| 5[b] | 67% 100 mM NaH$_2$PO$_4$—NaH$_2$PO$_4$, pH 7, CH$_3$CN | PF$_6$— | 45 min | 91 |
| 6 | 67% 100 mM NaH$_2$PO$_4$—NaH$_2$PO$_4$, pH 8, CH$_3$CN | PF$_6$— | 5 min | 96 |
| 7 | 67% 100 mM NaH$_2$PO$_4$—NaH$_2$PO$_4$, pH 7, CH$_3$CN | [c]BF$_4$— | 45 min | 84 |
| 8[b] | 67% 100 mM NaH$_2$PO$_4$—NaH$_2$PO$_4$, pH 7•CH$_3$CN | [c]BF$_4$— | 45 min | 63 |

[a]The reagent was used after stocking at 4° C. for 3 months under air.
[b]The reagent was used after stocking at room temperature for a week under air.
[c]Helv. Chim. Acta 2002, 85, 108-114.

Example 32

Coupling of Compound 3 with Ethoxyamine Hydrochloride 4

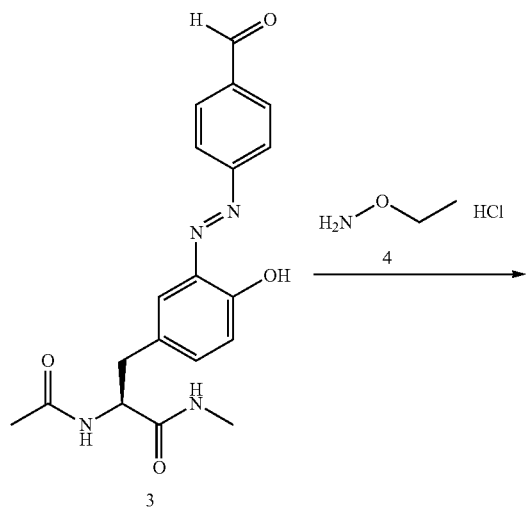

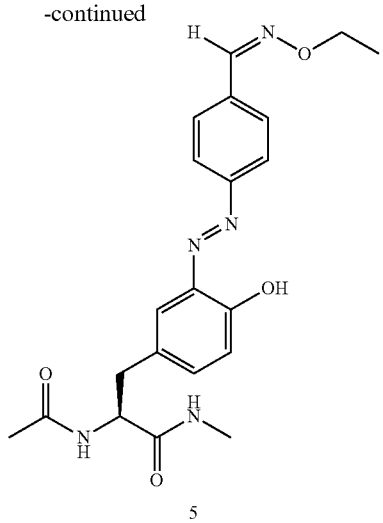

To a suspension of compound 3 (15 mg, 0.041 mmol) in 100 mM pH 7.0 NaH$_2$PO$_4$/Na$_2$HPO4 buffer (0.531 mL)-DMSO (1.54 mL) was added ethoxyamine hydrochloride 4 (4.37 mg, 0.045 mmol) at room temperature. The resulting suspension was stirred at room temperature for 2 h. After the reaction, water (4.00 mL) was added. The generated solid was filtrated then washed with water and ethyl acetate to give 5 (17.2 mg, quant.) as a yellow solid. ESIMS: calcd for C$_{21}$H$_{25}$N$_5$O$_4$(MH$^+$) 412.2. found 412.2. As shown below in Table 6, a summary of the various buffer conditions, times and yields is provided.

TABLE 6

| Entry | Buffer | Time | Isolated Yield (%) |
|---|---|---|---|
| 1 | 25% 100 mM NaH$_2$PO$_4$—Na$_2$HPO$_4$, pH 5, CH$_3$CN | 30 min | Quant.[a] |
| 2 | 25% 100 mM NaH$_2$PO$_4$—Na$_2$HPO$_4$, pH 6, CH$_3$CN | 1 h | Quant. |
| 3 | 25% 100 mM NaH$_2$PO$_4$—Na$_2$HPO$_4$, pH 7, CH$_3$CN | 2 h | Quant. |
| 4 | 25% 100 mM NaH$_2$PO$_4$—Na$_2$HPO$_4$, pH 8, CH$_3$CN | 2 h | Quant. |

[a]quantitative yield.

Example 33

General Procedure for Three Component Reaction—Method 1

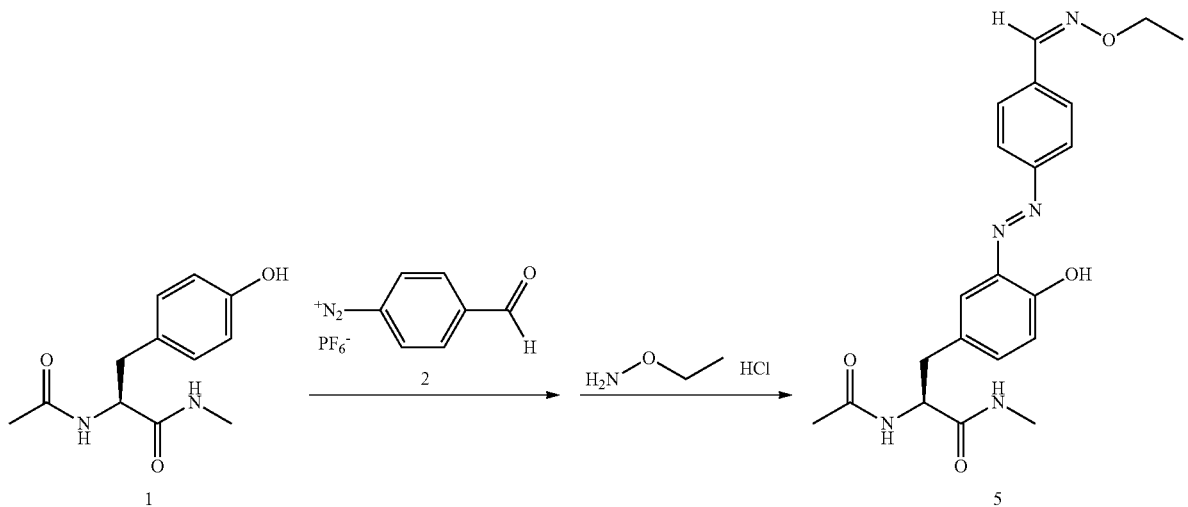

To a solution of N-acyl tyrosine methylamide 1 (20 mg, 0.0846 mmol) in 100 mM pH 7.0 NaH$_2$PO$_4$/Na$_2$HPO4 buffer (2.83 mL)-DMSO (1.41 mL) was added the diazonium salt 2 (25.9 mg, 0.0931 mmol) at room temperature. The resulting solution was stirred at room temperature for 1 h. After adding DMSO (1.41 mL), ethoxyamine hydrochloride 4 (8.25 mg, 0.0846 mmol) was added at room temperature. The resulting suspension was stirred at room temperature for 2 h. The generated solid was filtrated then washed with water and ethyl acetate to provide 5 (32.5 mg, 93%) as a yellow solid. ESIMS: calcd for C$_{21}$H$_{25}$N$_5$O$_4$ (MH$^+$) 412.2. found 412.2.

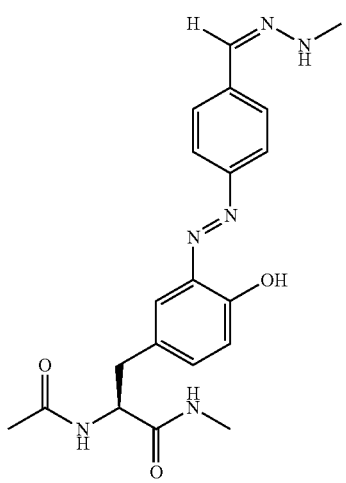

6

Compound 6 was prepared in a similar fashion from methylhydrazine (4.50 μL, 0.0846 mmol), and was obtained as yellow solid (30.7 mg, 92%). ESIMS: calcd for C$_{20}$H$_{24}$N$_6$O$_3$ (MH$^+$) 397.2. found 397.2.

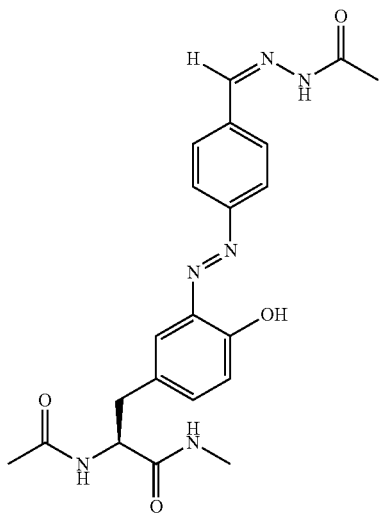

7

Compound 7 was prepared in a similar fashion as follows. To a solution of N-acyl tyrosine methylamide 1 (9.69 mg, 0.041 mmol) in 100 mM pH 7.0 NaH$_2$PO$_4$/Na$_2$HPO4 buffer (1.37 mL)-DMSO (0.686 mL) was added the diazonium salt 2 (12.5 mg, 0.045 mmol) at room temperature. The resulting solution was stirred at room temperature for 1 h. After adding DMSO (2.05 mL), acetic hydrazine (3.33 mg, 0.045 mmol) was added at room temperature. The resulting suspension was stirred at room temperature overnight. Ethyl acetate and brine were added. The organic layer was separated and the aqueous layer was extracted once with ethyl acetate. The combined organic layer was concentrated in vacuo. The residue was washed with water and ethyl acetate to give 7 (14.8 mg, 85%) as yellow solid. ESIMS: calcd for C$_{21}$H$_{24}$N$_6$O$_4$ (MH$^+$) 425.2. found 425.2.

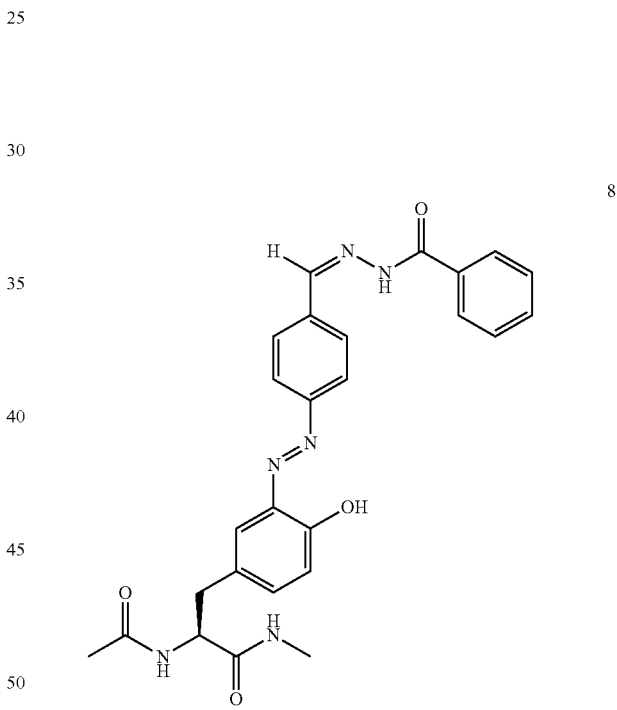

8

Compound 8 was prepared in a similar fashion as follows. Compound 8 was prepared from benzhydrazine (6.13 mg, 0.045 mmol), and was obtained as yellow solid (17.4 mg, 87%). ESIMS: calcd for C$_{26}$H$_{26}$N$_6$O$_4$ (MH$^+$) 487.2. found 487.2.

Example 34

General Procedure for Three Component Reaction—Method 2

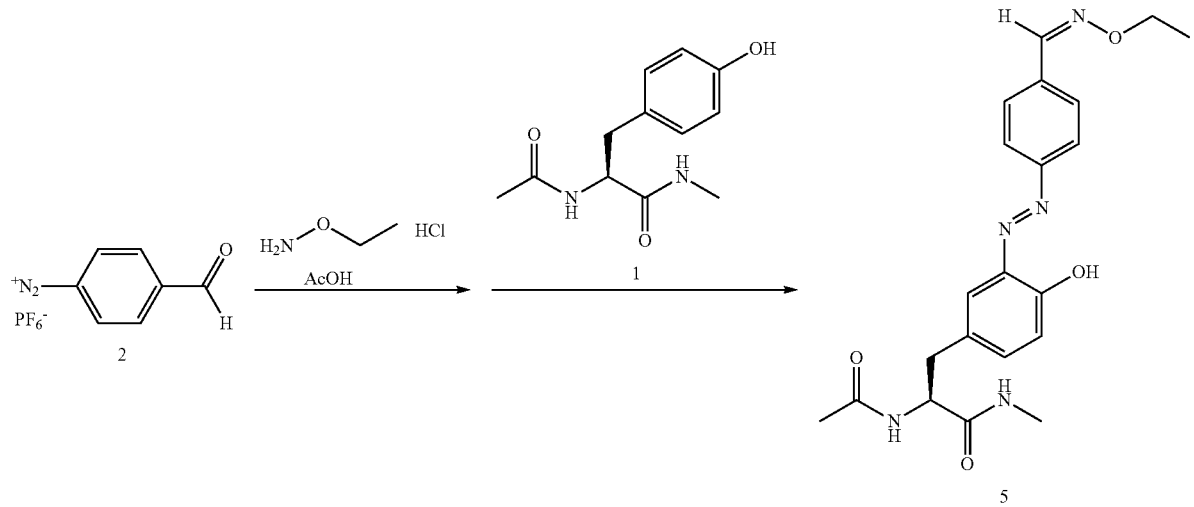

To a solution of diazonium salt 2 (25.9 mg, 0.0931 mmol) in DMSO (1.41 mL) were added the ethoxyamine hydrochloride 4 (9.95 mg, 0.102 mmol) and AcOH (5.32 µL, 0.0931 mmol) at room temperature. The resulting solution was stirred at room temperature for 2 h, and was added to the solution of N-acyl tyrosine methylamide 1 (20.0 mg, 0.0847 mmol) in 138 mM pH 8.0 NaH$_2$PO$_4$/Na$_2$HPO4 buffer (4.25 mL)-DMSO (0.686 mL). After the reaction, water (4.00 mL) was added. The generated solid was filtrated then washed with water and ethyl acetate to give 5 (15.8 mg, 45%) as a yellow solid. ESIMS: calcd for C$_{21}$H$_{25}$N$_5$O$_4$ (MH$^+$) 412.2. found 412.2.

Example 35

Synthesis of Diazonium Salt 2

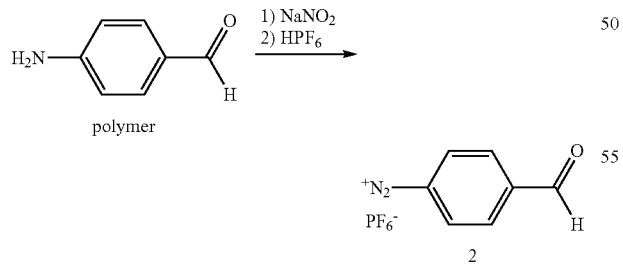

To a suspension of 4-aminobenzaldehyde polymer (5.00 g, 41.3 mmol) in 12N HCl (85 mL) was added the solution of NaNO$_2$ (3.42 g, 49.5 mmol) in water (67 mL) at −10° C. The resulting solution was stirred at −10° C. After 1.5 h, 60% HPF$_6$ in water (10.3 mL, 70.2 mmol) was added at −10° C. and stirred for 30 minutes. Then the reaction mixture was stirred at room temperature for 30 minutes. The resulting solids were collected by filtration, and washed with water and ethyl acetate to give 2 (14.8 mg, 85%) as a white solid. $^1$H NMR (300 MHz, DMSO-d6): δ 10.2 (s, 1H), 8.85 (d, J=5.2 Hz, 2H), 8.39 (d, J=5.0 Hz, 2H).

Example 36

General Method for Protein Modification with Diazonium Salt 2

To the 0.5 ml Eppendorf tube containing 99 µL of protein solution (30 µM solution in 0.1M phosphate buffer) was added 1 µL or reagent solution (100 mM solution in CH$_3$CN or DMF) and reaction mixture was vortexed briefly. Reaction was kept at room temperature for 30 minutes and the conversion was followed by visual observation in FIG. 1 and UV-vis measurement at 340 nm that corresponds to the absorbance of diazene functionality. The reaction products 9 were purified using Zeba Spin desalting column (7,000 Da MWC, Pierce) and the buffer was exchanged to PBS pH 5.0.

Figure 11:
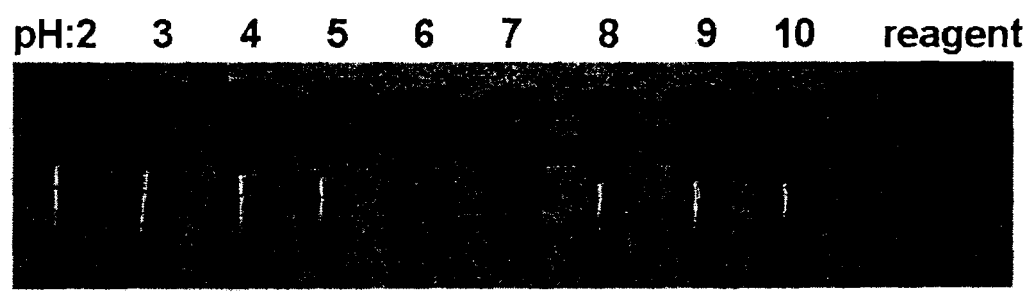

As shown below and in FIG. 11, in order to assess influence of the pH, model reaction with BSA and diazonium salt 2 was performed at pH 2-10:

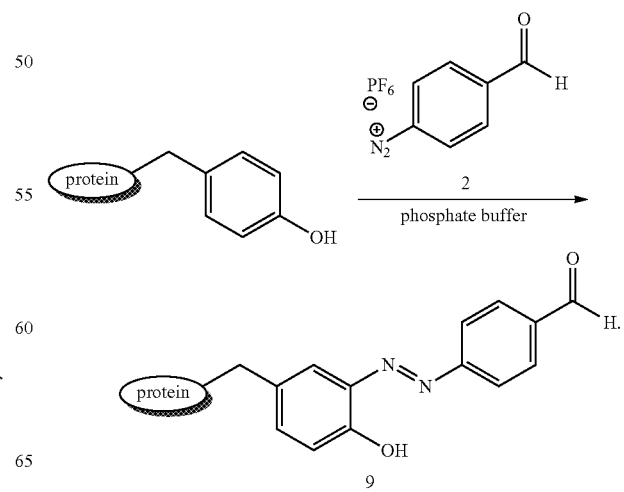

Figure 12:
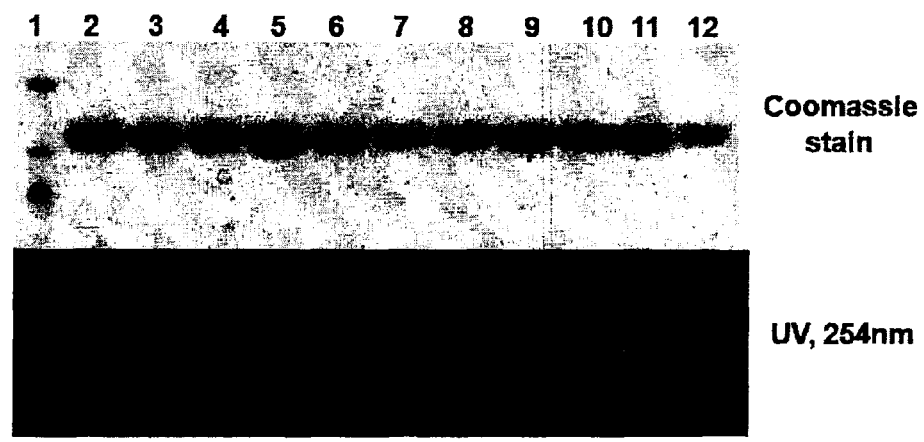
Figure 13:
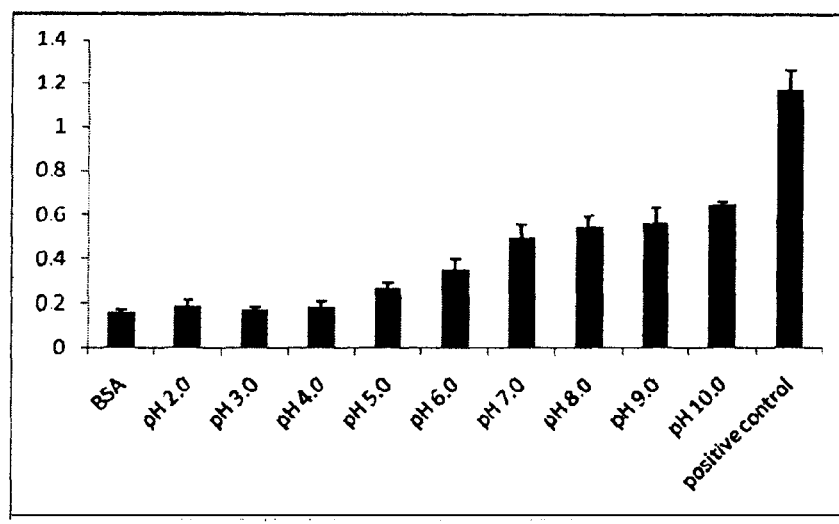

Similarly, as shown below and in FIGS. 12 and 13, the reaction of BSA with biotin and rhodamine derivatives of diazonium salt 2, compounds 12 and 13 respectively, was done at pH 2-10 and characterized by SDS-PAGE gel and ELISA:

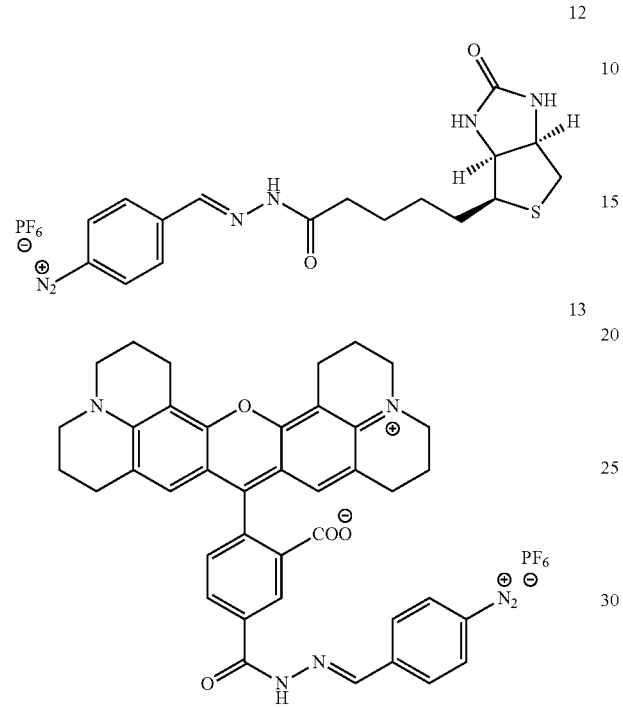

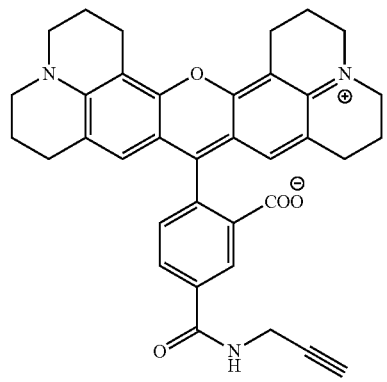

Example 37

Procedure for the Modification of the Aldehyde Modified Protein

Figure 14:
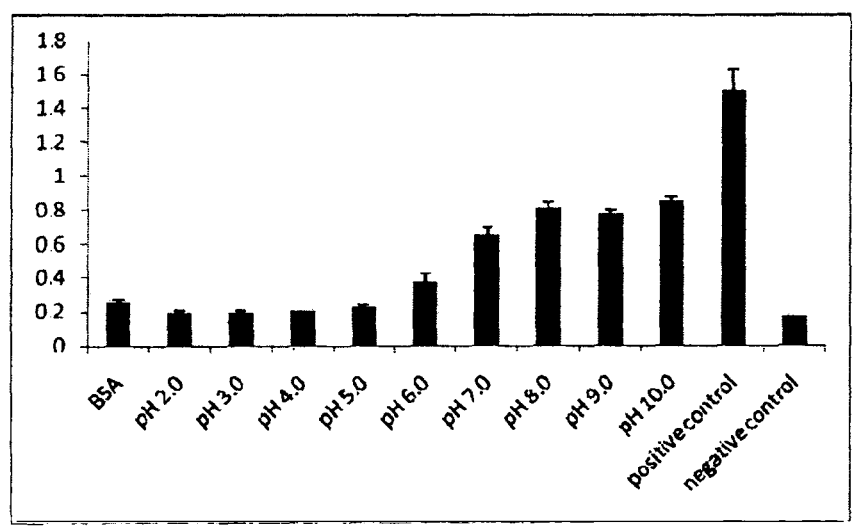
Figure 15:
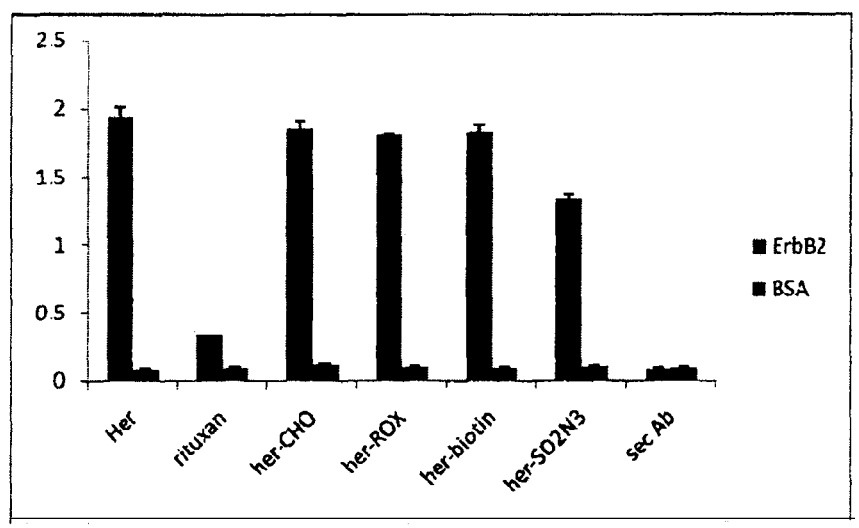
Figure 16:
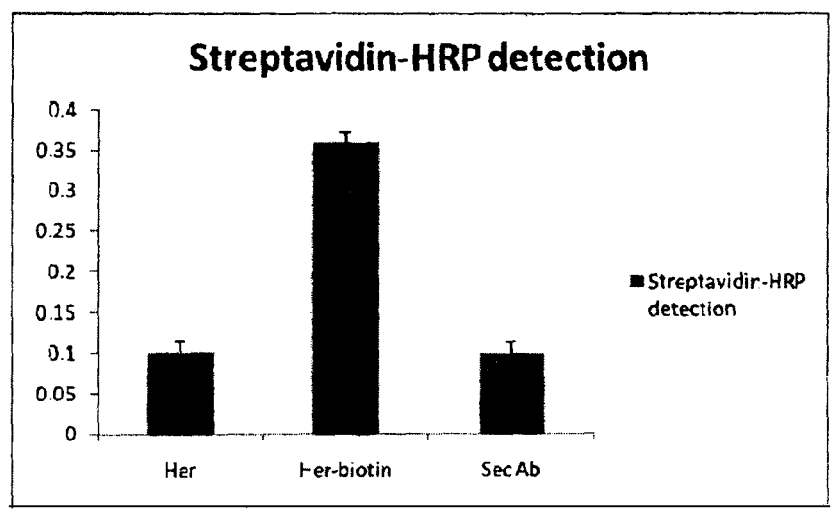
Figure 17:
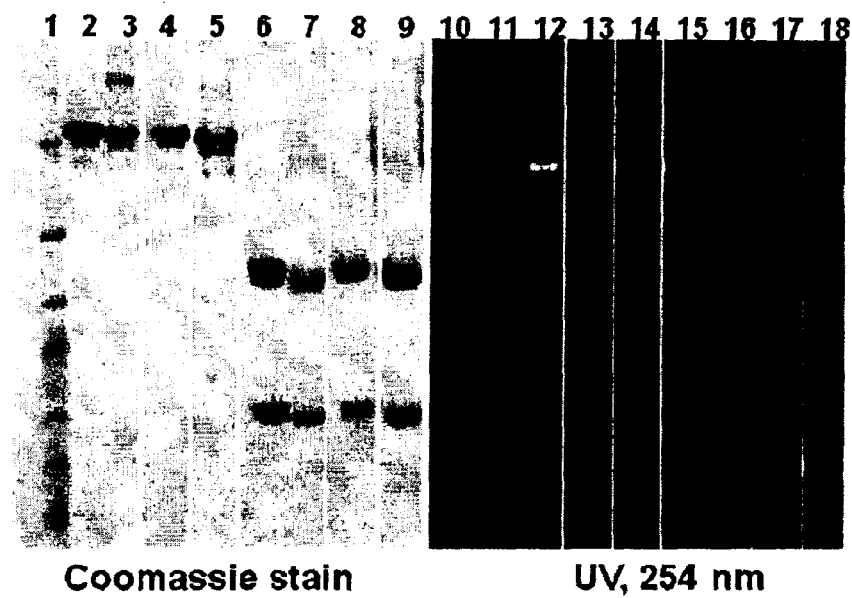
Figure 18:
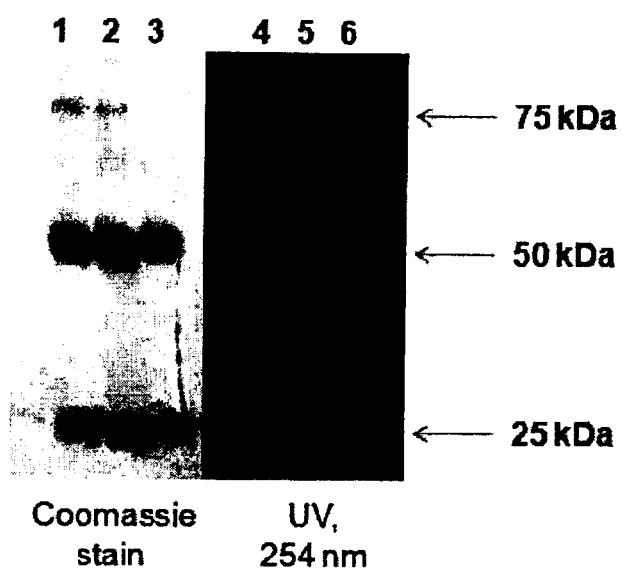

In the 1.5 mL Eppendorf tube 99 mL of 30 mM solution of BSA-aldehyde 9 in 0.1 m PBS pH 5 was treated with biotin hydrazide (1 mL of 100 mM solution in DMSO), over night 4° C., followed by removal of the excess of small molecule by Zeba Spin Desalting column. As shown below and in FIG. 14, the reaction products were tested in streptavidin capture ELISA to determine the degree of biotinylation in a qualitative manner:

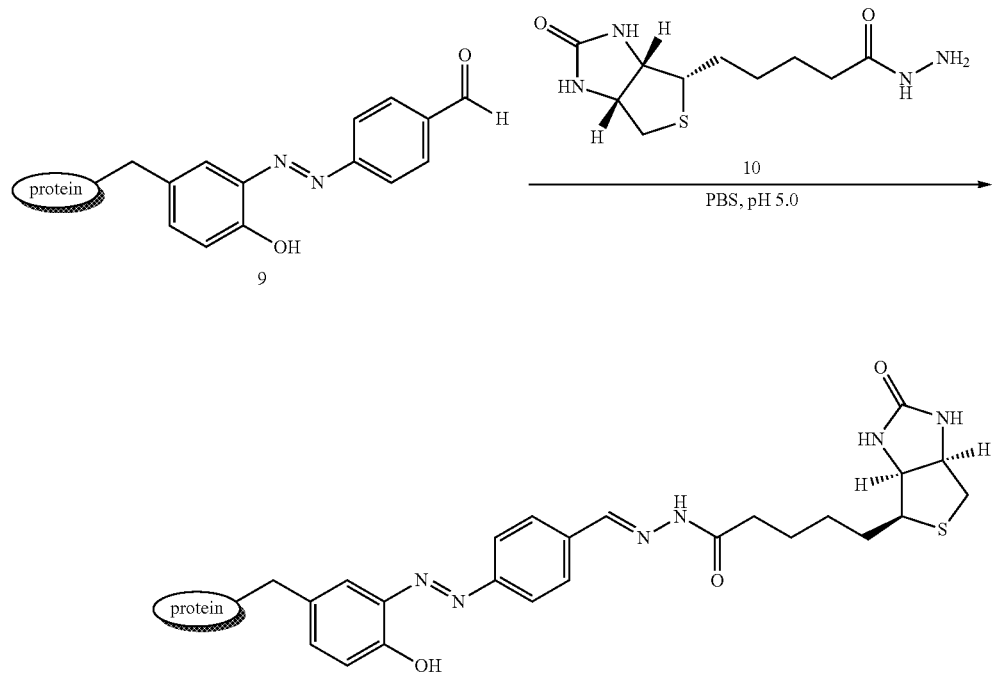

Example 38

Modification and Tryptic Digest Procedure for Human Serum Albumin (HSA)

In the 0.5 mL Eppendorf tube 99 μL of the 30 μM solution of HSA (0.1M phosphate buffer, pH 8.0) was treated with diazonium reagent (1-5 μL in DMF or CH$_3$CN, 10 equivalents, 0.1 mM final concentration) for 30 minutes at room temperature. Excess of small molecules removed using Zeba Spin Desalting column followed by a 24 h dialysis.

The tryptic digest was performed as follows. 100 μL of the dialyzed protein reaction mixture was added to 36 mg of solid urea. The resulting solution was briefly vortexed and then heated at 65° C. in a water bath for 30 minutes. The denatured protein sample was diluted with 500 μL of 50 mM NH4HCO3 buffer, pH 7.8, and then treated with 20 μL of a solution of sequencing grade modified trypsin (Promega, 20 μg reconstituted with 200 μL of 50 mM acetic acid). The digest mixture was then incubated at 37° C. for 12 h. The crude digest mixture was desalted using a μC18 PepClean tip with a CH3CN:H2O, 0.1% formic acid solvent system. The desalted protein mixture was then analyzed by LC-ESI MS. Human serum albumin was found to be modified at Y17 based on the analysis of tryptic digest fragments.

Example 39

General Procedure for the Modification of Human Antibodies

In the 0.5 mL Eppendorf tube 99 μL of the 10 μM solution of human antibody (0.1M phosphate buffer, pH 8.0) was treated with diazonium reagent (1-5 μL in DMF or CH$_3$CN, 10 equivalents, 0.1 mM final concentration) for 30 minutes at room temperature. Excess of small molecules removed using Zeba Spin Desalting column followed by a 24 h dialysis. In the reactions with rhodamine containing reagent the desalting was done 3 times.

Example 40

Chymotrypsinogen/Trypsin Digest Procedure for Modified Human Antibodies

50 μL of the dialyzed protein reaction mixture was added to 18 mg of solid urea. The resulting solution was briefly vortexed and then heated at 65° C. in a water bath for 30 minutes. The denatured protein sample was diluted with 250 μL of 50 mM NH$_4$HCO$_3$ buffer, pH 7.8, and then treated with 5 μL of a solution of sequencing grade modified trypsin (Promega, 20 μg reconstituted with 200 μL of 50 mM acetic acid) and 2 μL of chymotrypsin (1 μM solution in PBS). The digest mixture was then incubated at 37° C. for 12 h. The crude digest mixture was then analyzed by LC-ESI MS.

All human antibodies were found to be modified at the tyrosine in Fc region of heavy chain at the reaction times of 30 minutes or less at room temperature. The modification positions determined by LCMS-ESI analysis of thrypsin/chymotrypsinogen digest were as follows: 1. Herceptin is modified at Y304; 2. Rituxan is modified at Y300; 3. Erbitux is modified at Y305. Prolonged reaction times led to additional modification of the light chain.

Example 41

Synthesis of Aniline Derivatives 2, 3, and 4

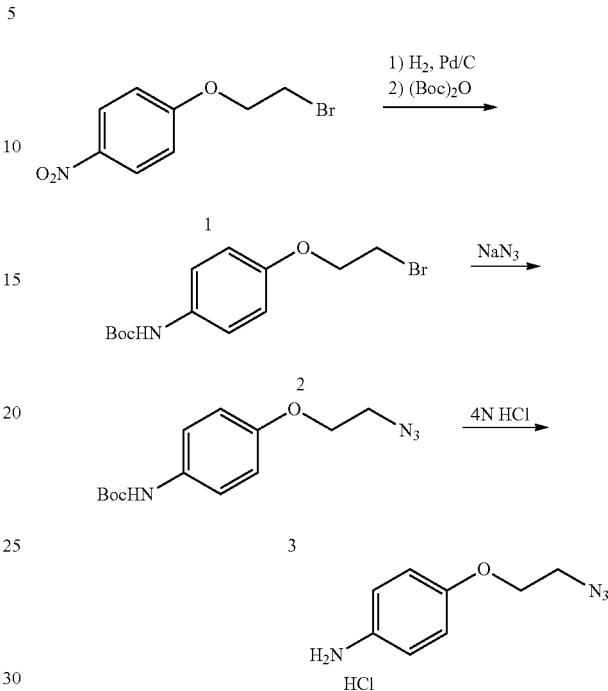

Synthesis of 4-N-Boc-(2-bromoethoxy)benzene (2)

A suspension of 1-(2-bromoethoxy)-4-nitrobenzene 1 (1.00 g, 4.06 mmol) and 10% Pd/C (100 mg) in tetrahydrofuran (20 mL) was stirred at room temperature for 3 h under a hydrogen atmosphere. Hydrogen was replaced with argon, and a solution of (Boc)$_2$O (708 mg, 4.06 mmol) in tetrahydrofuran (5 mL) was added. After overnight, the catalyst was removed by passing through Celite®. After evaporation, the obtained solids were washed with hexane/diethyl ether to give 2 (742 mg, 58%) as white solids. $^1$H NMR (300 MHz, CDCl$_3$): δ 7.28-7.25 (m, 2H), 6.87-6.84 (m, 2H), 6.41 (br, 1H), 4.25 (t, J=6.0 Hz, 2H), 3.61 (t, J=6.0 Hz, 2H), 1.51 (s, 9H). $^{13}$C NMR (75 MHz, CDCl$_3$): δ 154.36, 153.39, 132.52, 120.80, 115.66, 80.67, 68.65, 29.53, 28.69. HRMS: calcd for C$_{13}$H$_{18}$BrNNaO$_3$(MNa$^+$) 338.0362. found 338.0366.

Synthesis of 4-N-Boc-(2-azidoethoxy)benzene (3)

A suspension of compound 2 (1.64 g, 5.19 mmol) and NaN$_3$ (1.68 g, 25.9 mmol) in DMF (25 mL) was stirred at 50° C. for 3 h. Ethyl acetate and water were added. The organic layer was separated and washed once with water. The resulting aqueous layer was extracted once with ethyl acetate. The combined organic layer was dried over MgSO$_4$, and concentrated in vacuo. The residue was purified by short silica gel chromatography (hexane/ethyl acetate) and washing with hexane/diethyl ether to give 3 (1.24 g, 86%) as white crystals. $^1$H NMR (300 MHz, CDCl$_3$): δ 7.29-7.26 (m, 2H), 6.87-6.84 (m, 2H), 6.43 (br, 1H), 4.11 (t, J=6.0 Hz, 2H), 3.57 (t, J=6.0 Hz, 2H), 1.51 (s, 9H). $^{13}$C NMR (75 MHz, CDCl$_3$): δ 154.51, 153.41, 132.42, 120.75, 115.36, 80.63, 67.64, 50.49, 28.67. HRMS: calcd for C$_{13}$H$_{18}$N$_4$NaO$_3$(MNa$^+$) 301.1271. found 301.1258.

Synthesis of 4-(2-Azidoethoxy)aniline hydrochloride (4)

A solution of compound 3 (500 mg, 1.80 mmol) in 4 M HCl/dioxane (10 mL) was stirred at room temperature for 3 h. After evaporated solvent, the obtained solids were washed with ethyl acetate to give 4 (335 mg, 87%). $^1$H NMR (300 MHz, DMSO-d6): δ 10.4 (br, 2H), 7.38-7.33 (m, 2H), 7.08-7.03 (m, 2H), 4.18 (t, J=3.0 Hz, 2H), 3.65 (t, J=3.0 Hz, 2H). $^{13}$C NMR (75 MHz, DMSO-d6): δ 158.38, 125.62, 125.55, 116.37, 68.09, 50.46. HRMS: calcd for $C_8H_{11}N_4O$ (MH$^+$) 179.0972. found 179.0925.

Example 42

Synthesis of 4-Propargyloxy Aniline Sulfate (6)

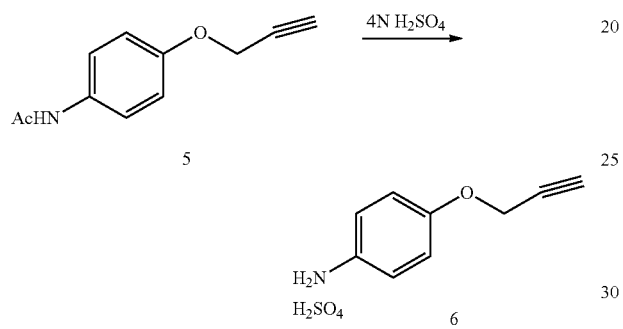

A solution of N-(4-(propargyloxy)phenyl)acetamide 5 (650 mg, 3.44 mmol) in 4 M $H_2SO_4$ (10 mL) was stirred under reflux for 3 h. The generated white crystals were filtrated and washed with diethyl ether to give 6 (577 mg, 68%). $^1$H NMR (300 MHz, DMSO-d6): δ 8.18 (br, 2H), 6.97-6.90 (m, 4H), 4.73 (d, J=3.0 Hz, 2H), 3.55 (t, J=3.0 Hz, 1H). $^{13}$C NMR (75 MHz, DMSO-d6): δ 153.92, 134.71, 120.94, 117.17, 80.61, 79.20, 57.06. HRMS: calcd for $C_9H_{10}NO$ (MH$^+$) 148.0757. found 148.0754.

Example 43

Synthesis of 4-N-boc-(2-oxopropoxy)benzene (8) and 4-(2-oxopropoxy)aniline hydrochloride (9)

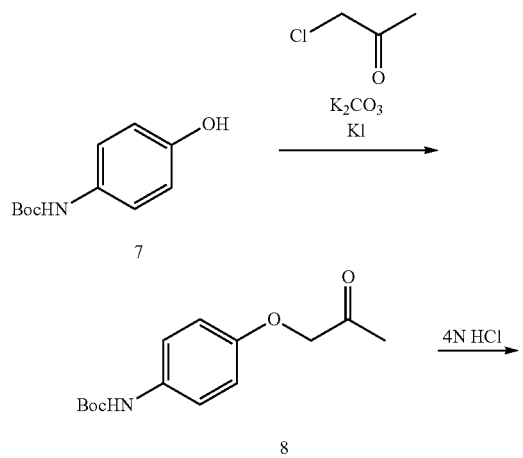

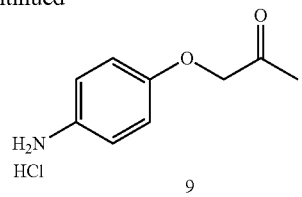

Synthesis of 4-N-boc-(2-oxopropoxy)benzene (8)

To a suspension of 4-N-Boc-aminophenol 7 (4.00 g, 18.2 mmol), $K_2CO_3$ (3.05 g, 22.1 mmol) and KI (1.22 g, 7.36 mmol) in acetone (40 mL) was added chloroacetone (0.703 mL, 8.83 mmol) under reflux. After 2 h, additional chloroacetone (0.703 mL, 8.83 mmol) was added. The resulting suspension was stirred under reflux for 2 h. Ethyl acetate and water were added. The organic layer was separated and washed once with water. The resulting aqueous layer was extracted once with ethyl acetate. The combined organic layer was dried over MgSO$_4$, and concentrated in vacuo. The generated white solids were washed with hexane/diethyl ether to give 8 (1.63 g, 83%). $^1$H NMR (300 MHz, DMSO-d6): δ 9.13 (br, 1H), 7.33-730 (m, 2H), 6.82-6.78 (m, 2H), 4.71 (s, 2H), 2.13 (s, 3H), 1.45 (s, 9H). $^{13}$C NMR (75 MHz, CDCl$_3$): δ 206.25, 153.96, 153.37, 132.78, 120.81, 115.23, 80.65, 73.72, 28.65, 26.92. HRMS: calcd for $C_{14}H_{20}NNaO_4$ (MNa$^+$) 288.1206. found 288.1199.

Synthesis of 4-(2-Oxopropoxy)aniline hydrochloride (9)

A solution of compound 8 (400 mg, 1.51 mmol) in 4 M HCl/dioxane (10 mL) was stirred at room temperature for 3 h. After evaporated solvent, the obtained pale brown solids were washed with ethyl acetate to give 9 (303 mg, quant.). $^1$H NMR (300 MHz, DMSO-d6): δ 10.3 (br, 2H), 7.35-7.32 (m, 2H), 7.02-6.99 (m, 2H), 4.87 (s, 2H), 2.16 (s, 3H). $^{13}$C NMR (75 MHz, DMSO-d6): δ 204.68, 158.20, 125.42, 116.32, 73.17, 27.20. HRMS: calcd for $C_9H_{12}NO_2$ (MH$^+$) 166.0863. found 166.0867.

Example 44

Synthesis of 1,2,4-triazolidine-3,5-diones—General Procedure A1

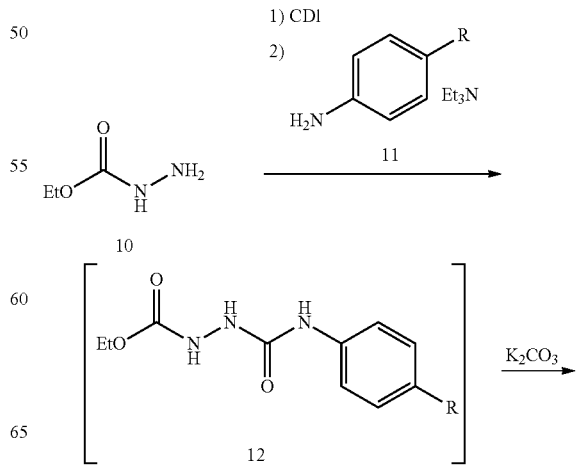

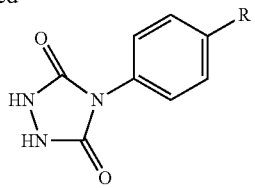

13

To a 0.2 M solution of ethyl hydrazinecarboxylate 10 (1.0 eq.) in tetrahydrofuran was added 1,1'-carbonyldiimidazole (CDI, 1.0 eq.) at room temperature. The resulting solution was stirred at room temperature. After 2 h, aniline 11 (1.0 eq.) and triethylamine (2.0 eq.) were added at room temperature and stirred overnight. Ethyl acetate and 10% HCl were added. The organic layer was separated and washed once with 10% HCl and water. The resulting aqueous layer was extracted once with ethyl acetate. The combined organic layer was dried over MgSO$_4$, and concentrated in vacuo. The obtained crude solids were dissolved in methanol after washing with ethyl acetate. K$_2$CO$_3$ (3.0 eq.) was added into the 0.2 M solution. The equivalent was calculated based on obtained crude solids. The suspension was stirred under reflux for 3 h. The reaction mixture was acidified with 12N HCl to pH 2 and then concentrated in vacuo. The generated white solids were washed with water and ethyl acetate to give 13.

Example 45

Synthesis of 4-(4-Azidophenyl)-1,2,4-Triazolidine-3,5-dione (13a)

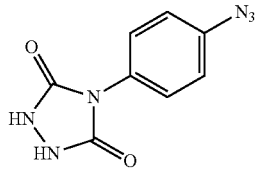

13a

Compound 13a was prepared from 4-azidoaniline hydrochloride, and was obtained as white solids (2 steps, 35%). $^1$H NMR (300 MHz, DMSO-d6): δ 10.5 (br, 2H), 7.50 (d, J=9.0 Hz, 2H), 7.23 (d, J=9.0 Hz, 2H). $^{13}$C NMR (75 MHz, DMSO-d6): δ 154.25, 139.59, 129.76, 128.53, 120.47. HRMS: calcd for C$_8$H$_7$N$_6$O$_2$ (MH$^+$) 219.0625. found 219.0617.

Example 46

Synthesis of 4-(4-Propargyloxyphenyl)-1,2,4-Triazolidine-3,5-dione (13c)

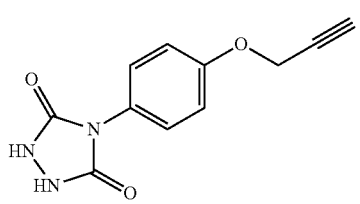

13c

Compound 13c was prepared from 6, and was obtained as white solids (2 steps, 28%). $^1$H NMR (300 MHz, DMSO-d6): δ 10.6 (br, 2H), 7.60-7.57 (m, 2H), 7.54-7.50 (m, 2H), 4.27 (s, 1H). $^{13}$C NMR (75 MHz, DMSO-d6): δ 158.83, 133.36, 133.07, 126.67, 121.59, 83.81, 82.41. HRMS: calcd for C$_{10}$H$_8$N$_3$O$_2$ (MH$^+$) 202.0611. found 202.0619.

Example 47

Synthesis of 1,2,4-triazolidine-3,5-diones—General Procedure A-2

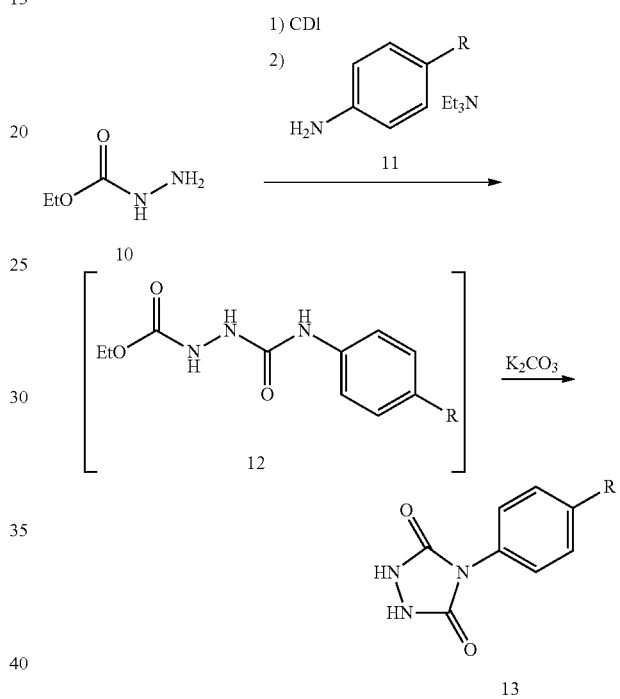

To a 0.2 M solution of ethyl hydrazinecarboxylate 10 (1.0 eq.) in tetrahydrofuran was added CDI (1.0 eq.) at room temperature. The resulting solution was stirred at room temperature. After 2 h, aniline 11 (1.0 eq.) and triethylamine (2.0 eq.) were added at room temperature and stirred overnight. Ethyl acetate and 10% HCl were added. The organic layer was separated and washed once with 10% HCl and water. The resulting aqueous layer was extracted once with ethyl acetate. The combined organic layer was dried over MgSO$_4$, and concentrated in vacuo. The obtained crude solids were dissolved in methanol after washing with ethyl acetate. K$_2$CO$_3$ (3.0 eq.) was added into the 0.2 M solution. The equivalent was calculated based on obtained crude solids. The suspension was stirred under reflux for 3 h. Ethyl acetate and 10% HCl were added. The organic layer was separated and washed once with 10% HCl. The resulting aqueous layer was extracted once with ethyl acetate. The combined organic layer was dried over MgSO$_4$, and concentrated in vacuo. The generated white solids were washed with ethyl acetate to give 13.

Example 48

Synthesis of 4-(4-(2-Azidoethoxy)phenyl)-1,2,4-Triazolidine-3,5-dione (13b)

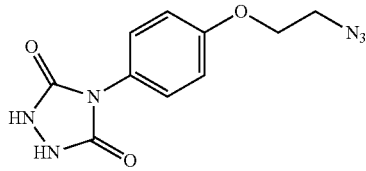

13b

Compound 13b was prepared from 4, and was obtained as white solids (2 steps, 28%). $^1$H NMR (300 MHz, DMSO-d6): δ 10.4 (br, 2H), 7.36-7.33 (m, 2H), 7.07-7.03 (m, 2H), 4.21 (t, J=6 Hz, 2H), 3.66 (t, J=6 Hz, 2H). $^{13}$C NMR (75 MHz, DMSO-d6): δ 158.16, 154.63, 128.67, 125.85, 115.63, 68.03, 50.44. HRMS: calcd for $C_{10}H_{11}N_6O_3$ (MH$^+$) 263.0887. found 263.0889.

Example 49

Synthesis of 4-(4-(2-Oxopropoxy)phenyl)-1,2,4-Triazolidine-3,5-dione (13d)

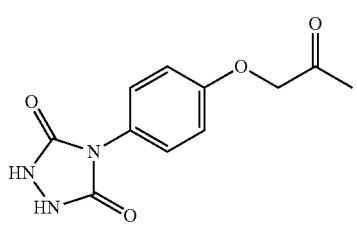

13d

Compound 13d was prepared from 9, and was obtained as white solids (2 steps, 12%). This compound was purified by washing ethyl acetate after passing through short column chromatography (CHCl$_3$/CH$_3$OH) and then evaporating solvent. $^1$H NMR (300 MHz, DMSO-d6): δ 10.4 (br, 2H), 7.31-7.27 (m, 2H), 7.02-6.95 (m, 2H), 4.87 (s, 2H), 2.16 (s, 3H). $^{13}$C NMR (75 MHz, DMSO-d6): δ 204.81, 157.96, 154.67, 128.57, 125.75, 115.57, 73.13, 27.16. HRMS: calcd for $C_{11}H_{12}N_3O_4$ (MH$^+$) 250.0822. found 250.0826.

Example 50

Synthesis of 1,2,4-triazolidine-3,5-diones—General Procedure B

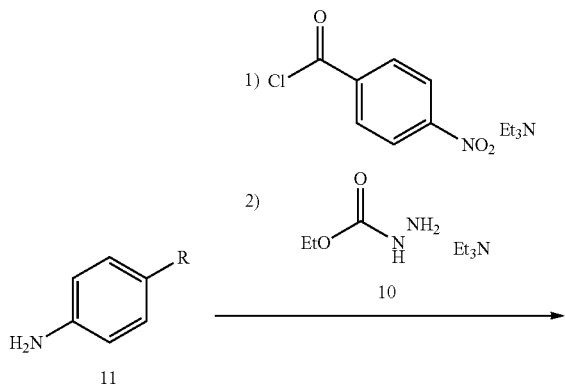

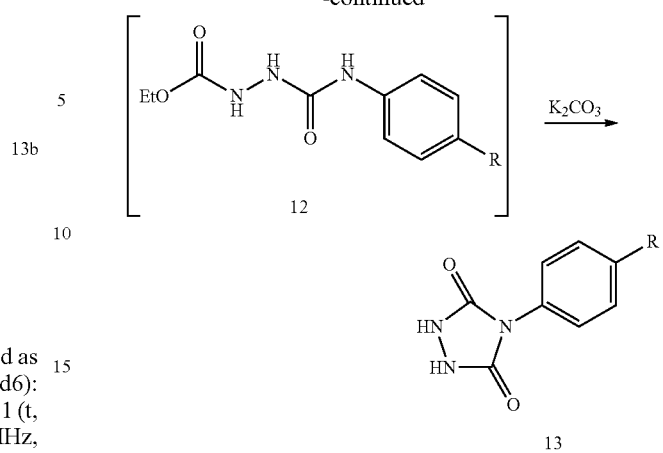

To a 0.5 M solution of compound 11 (1.0 eq.) and triethylamine (1.8 eq.) in tetrahydrofuran (5 mL) was added 4-nitrophenyl chloroformate (1.8 eq.) at 0° C. The resulting solution was stirred at room temperature overnight. Ethyl hydrazinecarboxylate (2.6 eq.) and triethylamine (2.6 eq.) were added at room temperature and stirred at 40° C. for 4 h. Ethyl acetate and water were added. The organic layer was separated and washed once with water. The resulting aqueous layer was combined and extracted twice with ethyl acetate. The combined organic layer was dried over MgSO$_4$, and concentrated in vacuo. The obtained crude solids were dissolved in methanol after washing with ethyl acetate. K$_2$CO$_3$ (3.0 eq.) was added into the 0.2 M solution. The equivalent was calculated based on obtained crude solids. The suspension was stirred under reflux for 3 h. The reaction mixture was acidified with 12N HCl to pH 2 and then concentrated in vacuo. The generated white solids were washed with water and diethyl ether to give 13.

Example 51

Synthesis of 4-(4-ethynylphenyl)-1,2,4-triazolidine-3,5-dione (13e)

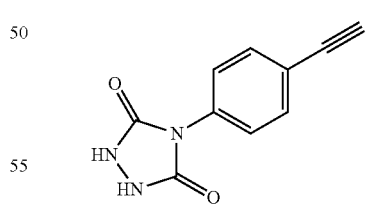

13e

Compound 13e was prepared from 4-ethynylaniline hydrochloride, and was obtained as white solids (2 steps, 38%). $^1$H NMR (300 MHz, DMSO-d6): δ 10.6 (br, 2H), 7.60-7.57 (m, 2H), 7.54-7.50 (m, 2H), 4.27 (s, 1H). $^{13}$C NMR (75 MHz, DMSO-d6): δ 153.83, 133.36, 133.07, 126.67, 121.59, 83.81, 82.41. HRMS: calcd for $C_{10}H_8N_3O_2$ (MH$^+$) 202.0611. found 202.0619.

Example 52

Synthesis of 4-(4-acetylphenyl)-1,2,4-triazolidine-3,5-dione (13f)

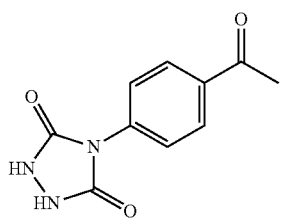

Compound 13f was prepared from 4'-aminoacetophenone, and was obtained as white solids (2 steps, 15%) was obtained as white solids (2 steps, 38%). $^1$H NMR (300 MHz, DMSO-d6): δ 10.7 (br, 2H), 8.09-8.06 (m, 2H), 7.71-7.68 (m, 2H), 2.62 (s, 3H). $^{13}$C NMR (75 MHz, DMSO-d6): δ 198.18, 153.67, 137.09, 136.26, 129.74, 126.17, 27.76. HRMS: calcd for $C_{10}H_{10}N_3O_3(MH^+)$ 220.0717. found 220.0713.

Example 53

General Procedure for the Oxidation of 3H-1,2,4-triazole-3,5(4H)-diones

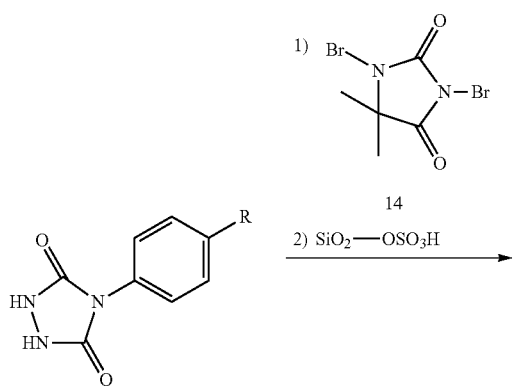

To a 0.05 M solution of compound 13 (1.0 eq.) in $CH_2Cl_2$ was added 1,3-dibromo-5,5-dimethylhydantoin (1.0 eq.) at room temperature. The resulting solution was stirred at room temperature. After 2 h, silica sulfuric acid ($SiO_2$—$OSO_3H$, 4 times weight to starting material) was added at room temperature and stirred at room temperature. After 30 minutes, the silica sulfuric acid was removed by filtration. The volatile materials were evaporated in vacuo to give 15. The obtained material was relatively unstable against light and humidity in solution at temperature. Therefore, it was used for next reaction without additional purification after confirmation of purity by $^1$H-NMR (see NMR chart section).

Example 54

Synthesis of 4-(4-azidophenyl)-3H-1,2,4-triazole-3,5(4H)-dione (15a)

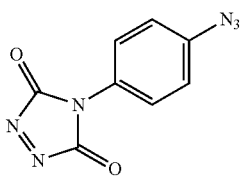 [SMILES: [N-]=[N+]=Nc1ccc(N2C(=O)N=NC2=O)cc1]

Compound 15a was prepared from 13a (40 mg, 0.183 mmol), and was obtained as deep red solids (34.1 mg, 86%). $^1$H NMR (300 MHz, $CDCl_3$): δ 7.51-7.46 (m, 2H), 7.22-7.17 (m, 2H).

Example 55

Synthesis of 4-(4-(2-azidoethoxy)phenyl)-3H-1,2,4-triazole-3,5(4H)-dione (15b)

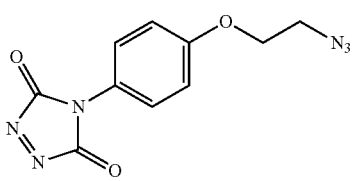 [SMILES: [N-]=[N+]=NCCOc1ccc(N2C(=O)N=NC2=O)cc1]

Compound 15b was prepared from 13b (49.0 mg, 0.187 mmol), and was obtained as deep red oil (39.6 mg, 81%). $^1$H NMR (300 MHz, $CDCl_3$): δ 7.40-7.35 (m, 2H), 7.10-7.06 (m, 2H), 4.20 (t, J=3.0 Hz, 2H), 3.64 (t, J=3.0 Hz, 2H).

Example 56

Synthesis of 4-(4-(propargyloxy)phenyl)-3H-1,2,4-triazole-3,5(4H)-dione (15c)

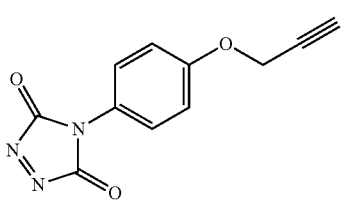 [SMILES: C#CCOc1ccc(N2C(=O)N=NC2=O)cc1]

Compound 15c was prepared from 13c (50.0 mg, 0.216 mmol), and was obtained as deep red solids (42.0 mg, 85%). $^1$H NMR (300 MHz, $CDCl_3$): δ 7.41-7.37 (m, 2H), 7.15-7.12 (m, 2H), 4.75 (d, J=3.0 Hz, 2H), 3.64 (t, J=3.0 Hz, 1H).

Example 57

Synthesis of 4-(4-(2-oxopropoxy)phenyl)-3H-1,2,4-triazole-3,5(4H)-dione (15d)

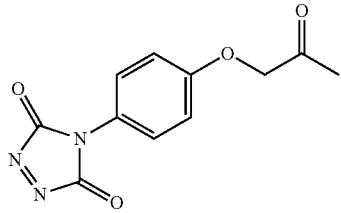 [SMILES: CC(=O)COc1ccc(N2C(=O)N=NC2=O)cc1]

15d

Compound 15d was prepared from 13d (47.0 mg, 0.189 mmol), and was obtained as deep purple solids (34.9 mg, 81%). $^1$H NMR (300 MHz, CDCl$_3$): δ 7.42-7.38 (m, 2H), 7.05-7.02 (m, 2H), 4.61 (s, 2H), 2.31 (s, 3H).

Example 58

Synthesis of 4-(4-ethynylphenyl)-3H-1,2,4-triazole-3,5(4H)-dione (15e)

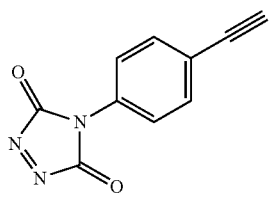

15e

To a solution of compound 13e (4.43 mg, 0.022 mmol) in CH$_3$CN (44 μL) was added 1,3-dibromo-5,5-dimethylhydantoin (6.29 mg, 0.022 mmol) at room temperature. The resulting solution was stirred at room temperature for 10 minutes. The obtained material was easily degraded at temperature. Therefore, the 0.5 M CH$_3$CN mixture reaction solution was used for next reaction without purification after confirmation of reaction color changing from clear to material specific deep red.

Example 59

Procedure for Coupling N-Acyl Tyrosine Methylamide with PTAD: Compound (18a) and (18b)

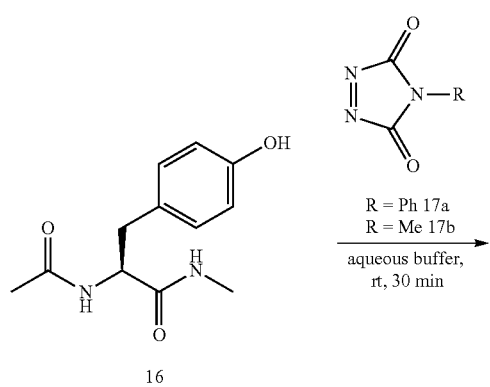

R = Ph 17a
R = Me 17b aqueous buffer, rt, 30 min

16

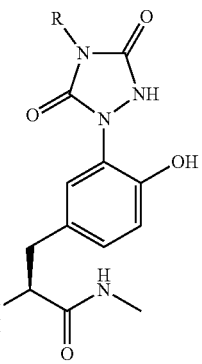

R = Ph 18a
R = Me 18b

Synthesis of Compound (18a)

To a solution of tyrosine 16 (14.2 mg, 0.060 mmol) in 100 mM pH 7.0 NaH$_2$PO$_4$/Na$_2$HPO$_4$ buffer (1.5 mL)-CH$_3$CN (1.5 mL) was added the 0.5 M solution of PTAD 17 (0.132 mL, 0.066 mmol) in CH$_3$CN at room temperature. The resulting solution was stirred at room temperature for 30 minutes. The reaction mixture was acidified with 12N HCl (0.249 mL) and then concentrated in vacuo. The obtained crude material was purified by flash column chromato-graphy (CHCl$_3$/CH$_3$OH) to give 18a (16.0 mg, 65%) as a white solid. $^1$H NMR (300 MHz, DMSO-d6): δ 11.57 (br, 1H), 8.06 (d, J=8.4 Hz, 1H), 7.90 (q, J=4.3 Hz, 1H), 7.74 (d, J=1.7 Hz, 1H), 7.63-7.51 (m, 2H), 7.43 (t, J=7.8 Hz, 2H), 7.34-7.21 (m, 1H), 6.83 (dd, J=8.2, 2.0 Hz, 1H), 6.68 (d, J=8.2 Hz, 1H), 4.33 (m, 1H), 2.85 (dd, J=13.5, 5.1 Hz, 1H), 2.63 (dd, J=13.7, 9.2 Hz, 1H), 2.55 (d, J=4.5 Hz, 3H), 1.78 (s, 3H). $^{13}$C NMR (150 MHz, DMSO-d6): δ 172.64, 170.02, 153.90, 150.86, 148.44, 135.37, 129.22, 129.02, 126.96, 126.48, 126.03, 122.72, 117.74, 55.47, 38.23, 26.51, 23.56. HRMS: calcd for C$_{20}$H$_{22}$N$_5$O$_5$ (MH$^+$) 412.1615. found 412.1615.

Synthesis of Compound (18b)

Compound 18b was prepared from tyrosine 16 (14.2 mg, 0.060 mmol) and 0.5 M solution of MTAD 17b (0.438 mL, 0.132 mmol), and was obtained as white amorphous solid (11.9 mg, 57%). $^1$H NMR (300 MHz, DMSO-d6): δ 10.51 (br, 1H), 8.05 (d, J=8.4 Hz, 1H), 7.86 (q, J=4.4 Hz, 1H), 7.21 (s, 1H), 7.02 (dd, J=1.9, 8.4 Hz, 1H), 6.77 (d, J=8.3 Hz, 1H), 4.28 (m, 1H), 2.92 (s, 3H), 2.82 (dd, J=13.8, 4.8 Hz, 1H), 2.60 (dd, J=13.5, 9.9 Hz, 1H), 2.53 (d, J=4.5 Hz, 3H), 1.75 (s, 3H). $^{13}$C NMR (75 MHz, DMSO-d6): δ 172.28, 169.81, 154.68, 153.39, 152.07, 150.78, 130.59, 129.42, 124.27, 117.14, 54.98, 37.38, 26.20, 25.44, 23.22. HRMS: calcd for C$_{15}$H$_{19}$N$_5$O$_5$ (MH$^+$) 350.1459. found 350.1460.

Example 60

Procedure for Modification of Tocinoic Acid with PTAD Analogs: Compound (20b), Compound (20c), and Compound (20d)

Synthesis of Compound (20b)

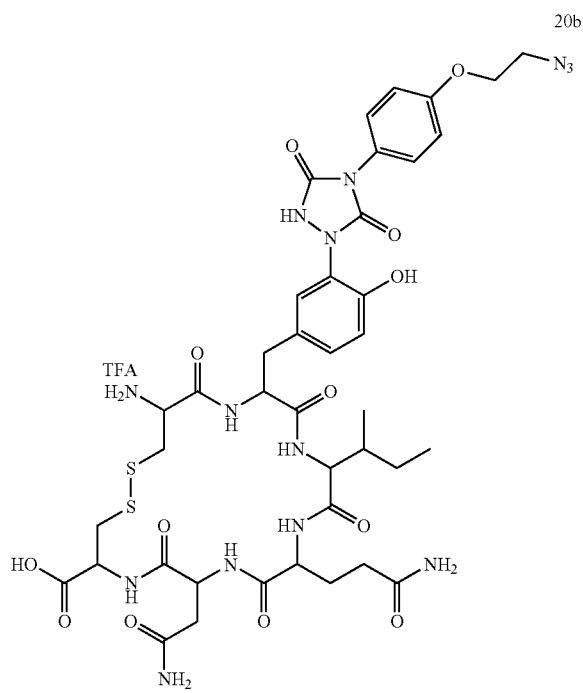 [SMILES: CCC(C)C1NC(=O)C(Cc2ccc(O)c(-n3[nH]c(=O)n(-c4ccc(OCCN=[N+]=[N-])cc4)c3=O)c2)NC(=O)C(N)CSSCC(C(=O)O)NC(=O)C(CC(N)=O)NC(=O)C(CCC(N)=O)NC1=O ; "TFA"]

20b

Compound 20b was prepared from (Ile3)-pressonic acid 19 (3.0 mg, 4.05 mmol) and 15b (2.6 mg, 10.1 mmol), and was obtained as white amorphous solid (3.20 mg, 71%). Reversed phase HPLC condition for isolation (mobile phase; $CH_3CN$/0.1% TFA water, 30:70, Rt; 14.4 minutes, detection; UV 254 nm). HRMS: calcd for $C_{40}H_{52}N_{14}O_{13}S_2$ ($MH^+$) 1001.3352. found 1001.3337. Reversed phase HPLC purity>99.9% (mobile phase; gradient of $CH_3CN$/0.1% TFA water, 0:100 to 100:0 over 30 minutes, Rt; 16.6 minutes, detection; UV 254 nm).

Synthesis of compound (20c)

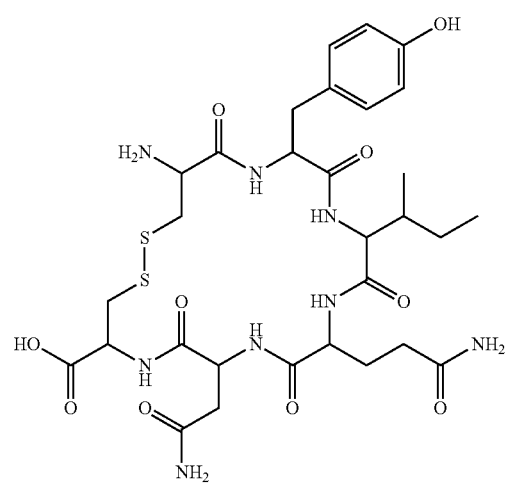

19

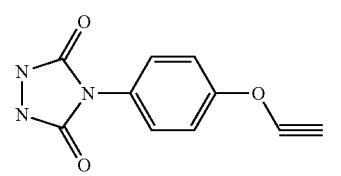

15c

100mM Naphosphate buffer (pH 7)

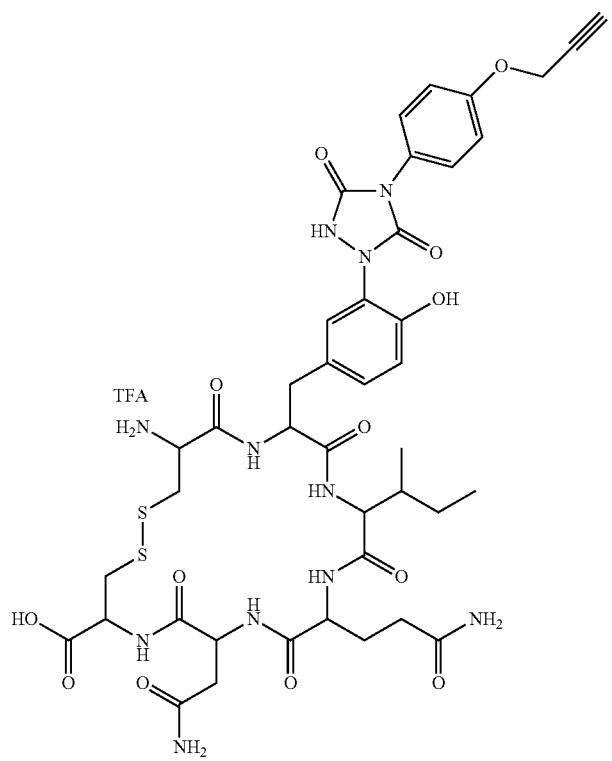

20c

To a 20 mM solution of (Ile3)-pressonic acid 19 (33.8 μL, 6.75 μmol) in 100 mM pH 7.0 NaH$_2$PO$_4$/Na$_2$HPO$_4$ buffer was 100 mM solution of PTAD 15c (169 μL, 16.9.μmol) in CH$_3$CN was added (56.3 μL×3 times, interval 1 minute) at room temperature. The resulting solution was stirred at room temperature for 30 minutes. The reaction mixture was diluted by CH$_3$CN (500 μL)-water (500 μL). The obtained crude material was purified by reversed phase HPLC (mobile phase; CH$_3$CN/0.1% TFA water, 30:70, Rt; 13.0 minutes, detection; UV 254 nm) to give 20c (5.20 mg, 72%) as white amorphous solid. HRMS: calcd for C$_{41}$H$_{51}$N$_{11}$O$_{13}$S$_2$ (MH$^+$) 970.3182. found 970.3177. Reversed phase HPLC purity 96.6% (mobile phase; gradient of CH$_3$CN/0.1% TFA water, 0:100 to 100:0 over 30 minutes, Rt; 16.3 minutes, detection; UV 254 nm). Blank peaks at UV 245 nm.

Synthesis of compound (20d)

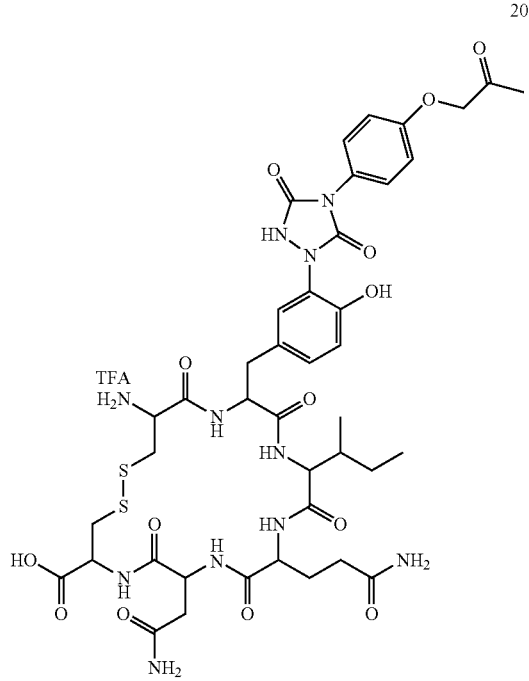

Compound 20d was prepared from (Ile3)-pressonic acid 19 (3 mg, 4.05 μmol) and 15d (2.5 mg, 10.1 μmol), and was obtained as white amorphous solid (3.20 mg, 72%). Reversed phase HPLC condition for isolation (mobile phase; CH₃CN/0.1% TFA water, 30:70, Rt; 10.6 minutes, detection; UV 254 nm). HRMS: calcd for $C_{41}H_{53}N_{11}O_{14}S_2$ (MH⁺) 988.3287. found 988.3272, Reversed phase HPLC purity 97.1% (mobile phase; gradient of CH₃CN/0.1% TFA water, 0:100 to 100:0 over 30 minutes, Rt; 15.4 minutes, detection; UV 254 nm).

Example 61

Procedure for Modification of Custom-Synthesized Peptide with PTAD Analogs: General Procedure for Labeling: Compound (22b), Compound (22c), and Compound (22d)

Compound (22b)

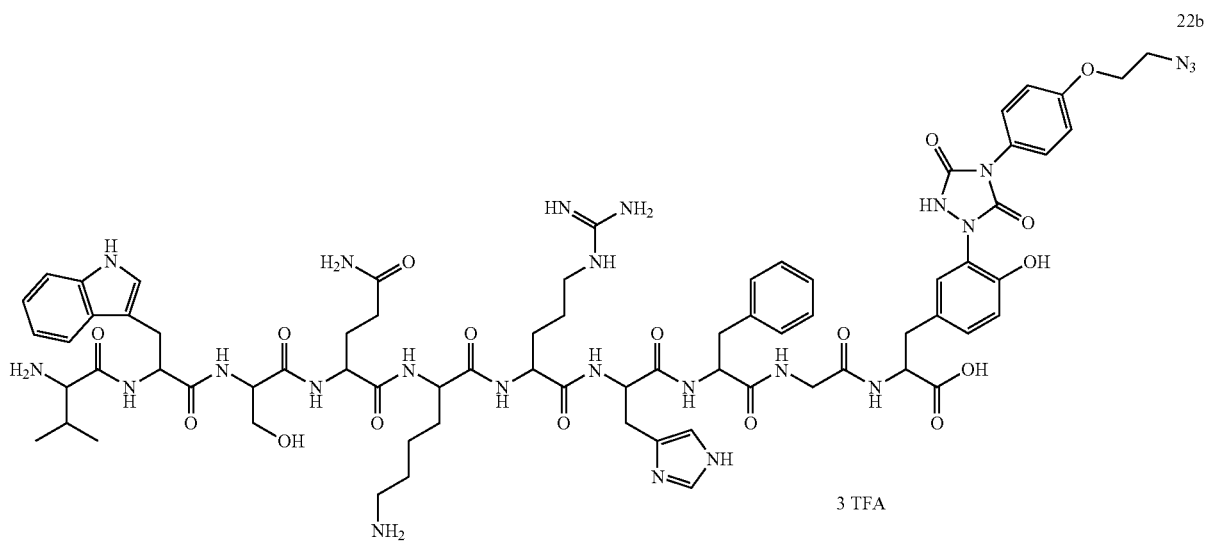 [SMILES: CC(C)C(N)C(=O)NC(Cc1c[nH]c2ccccc12)C(=O)NC(CO)C(=O)NC(CCC(N)=O)C(=O)NC(CCCCN)C(=O)NC(CCCNC(=N)N)C(=O)NC(Cc1c[nH]cn1)C(=O)NC(Cc1ccccc1)C(=O)NCC(=O)NC(Cc1ccc(O)c(-n2[nH]c(=O)n(-c3ccc(OCCN=[N+]=[N-])cc3)c2=O)c1)C(=O)O ; "3 TFA"]

Compound 22b was prepared from custom-synthesized peptide 21 (5 mg, 3.82 mmol) and 15b (2.99 mg, 11.5 mmol), and was obtained as white amorphous solid (4.40 mg, 60%). Reversed phase HPLC condition for isolation (mobile phase; gradient of $CH_3CN/0.1\%$ TFA water, 30:70 to 50:50 over 30 minutes, Rt; 15.6 minutes, detection; UV 254 nm). HRMS: calcd for $C_{72}H_{94}N_{24}O_{17}$ $(MH^+)$ 1567.7301. found 1567.7236. Reversed phase HPLC purity 91.3% (mobile phase; gradient of $CH_3CN/0.1\%$ TFA water, 0:100 to 100:0 over 30 minutes, Rt; 15.9 minutes, detection; UV 254 nm).

Compound (22c)

μmol) in $CH_3CN$ was added (9.55 μl×12 times, interval 1 minute) at room temperature. The resulting solution was stirred at room temperature for 30 minutes. The crude reaction was analyzed directly by ESI-LC/MS at 254 nm UV absorption and corresponding MS. The reaction mixture was diluted by $CH_3CN$ (1.00 mL). The obtained crude material was purified by reversed phase HPLC (mobile phase; gradient of $CH_3CN/0.1\%$ TFA water, 30:70 to 50:50 over 30 minutes, Rt; 14.5 minutes, detection; UV 254 nm) to give 22c (4.40 mg, 61%) as white amorphous solid. HRMS: calcd for $C_{73}H_{93}N_{21}O_{17}$ $(MH^+)$ 1536.7131. found 1536.7125.

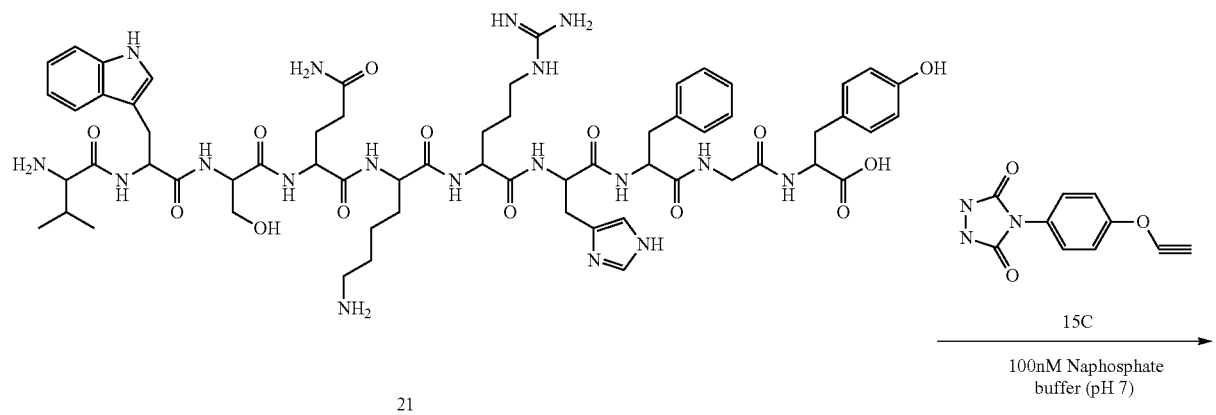

21

15C
100nM Naphosphate buffer (pH 7)

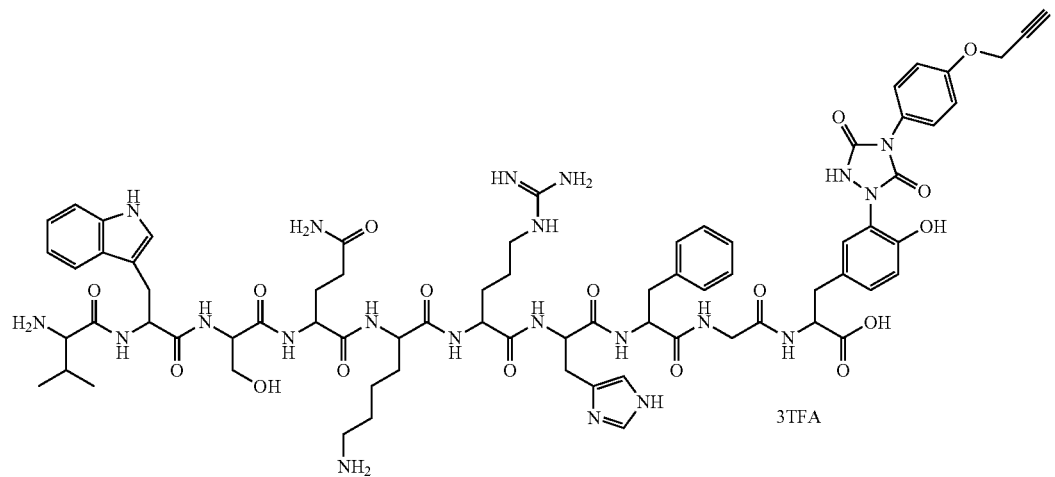

22C

To a 2 mM solution of custom-synthesized peptide 21 (1.82 mL, 3.82 μmol) in 100 mM pH 7.0 $NaH_2PO_4/Na_2HPO_4$ buffer was 100 mM solution of PTAD 15c (114 μL, 11.5

Reversed phase HPLC purity 95.1% (mobile phase; gradient of $CH_3CN/0.1\%$ TFA water, 0:100 to 100:0 over 30 minutes, Rt; 15.8 minutes, detection; UV 254 nm).

Compound (22d)

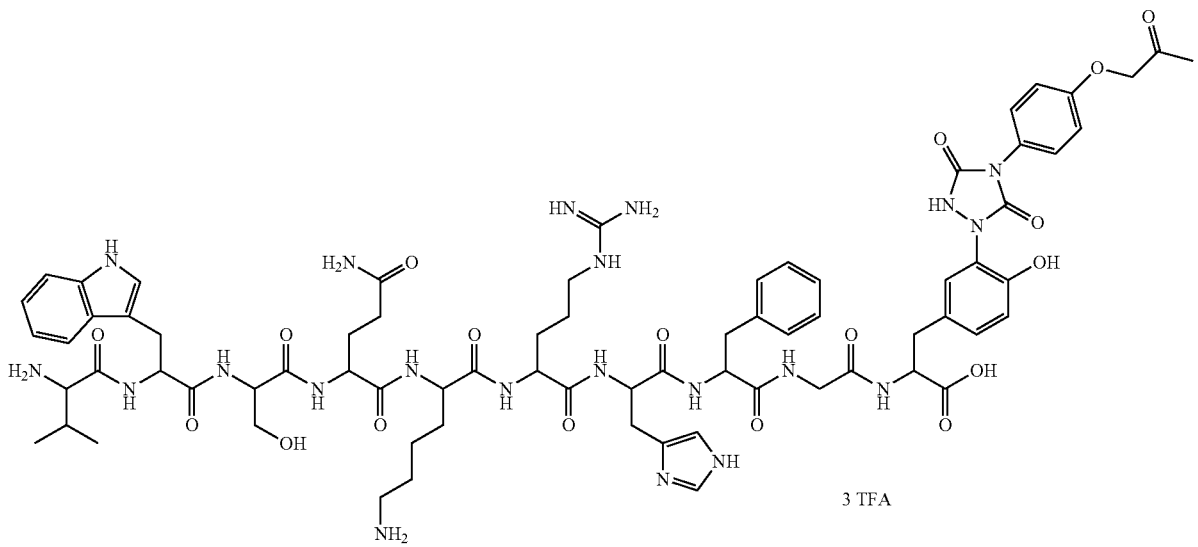

Compound 22d was prepared from custom-synthesized peptide 21 (5 mg, 3.82 µmol) and 15b (2.84 mg, 11.5 µmol), and was obtained as white amorphous solid (4.60 mg, 63%). Reversed phase HPLC condition for isolation (mobile phase; gradient of $CH_3CN/0.1\%$ TFA water, 30:70 to 50:50 over 30 minutes, Rt; 14.8 minutes, detection; UV 254 nm). HRMS: calcd for $C_{73}H_{95}N_{21}O_{18}$ ($MH^+$) 1554.7236. found 1554.7220. Reversed phase HPLC purity 93.6% (mobile phase; gradient of $CH_3CN/0.1\%$ TFA water, 0:100 to 100:0 over 30 minutes, Rt; 15.2 minutes, detection; UV 254 nm).

Example 62

Synthesis of a Modified P-Cresol: 1-(2-hydroxy-5-methylphenyl)-4-phenyl-1,2,4-triazolidine-3,5-dione (23)

To a solution of p-cresol (80 mg, 0.740 mmol) in tetrahydrofuran (5 mL) was added NaH (35.5 mg, 0.885 mmol) at 0° C. After 20 minutes, PTAD (127 mg, 0.725 mmol) was added at 0° C. and stirred at room temperature for 3 h. Ethyl acetate and 10% HCl were added. The organic layer was separated and washed once with brine. The resulting aqueous layer was extracted once with ethyl acetate. The combined organic layer was dried over $MgSO_4$, and concentrated in vacuo. The residue was purified by silica gel chromatography ($CHCl_3/CH_3OH$) to give 23 (158 mg, 75%) as white solids (see detail;). $^1H$ NMR (600 MHz, DMSO-d6): δ 9.86 (br, 1H), 7.53-7.49 (m, 4H), 7.43-7.40 (m, 1H), 7.19 (d, J=2.0 Hz, 1H), 7.10 (dd, J=8.3, 2.0 Hz, 1H), 6.87 (d, J=8.3 Hz, 1H), 2.24 (s, 3H). $^{13}C$ NMR (150 MHz, DMSO-d6): δ 151.98, 151.64, 151.46, 131.86, 130.98, 129.56, 128.80, 127.91, 127.72, 126.03, 122.89, 116.57, 19.67. HRMS: calcd for $C_{15}H_{14}N_3O_3$ ($MH^+$) 284.1030. found 284.1028.

Example 63

Stability Study of a Modified P-Cresol in Hydrolysis Condition

A solution of compound 23 (10 mg, 0.0353 mmol) in 10% HCl (0.5 mL) in methanol (1.5 mL) and in 10% NaOH (0.5 mL) in methanol (1.5 mL) was stirred at room temperature for 12 h, respectively. Ethyl acetate and water were added. In the case of basic condition, ethyl acetate was added after acidification with 10% HCl up to pH 3. The organic layer was separated and washed once with water. The resulting aqueous layer was extracted once with ethyl acetate. The combined organic layer was dried over $MgSO_4$, and concentrated in vacuo. The residue was purified by silica gel chromatography (ethyl acetate) to recover 23 as white solids. The recovery of 23; 8.9 mg (89%) in acidic condition and 10.2 mg (quant.) in basic condition.

Example 64

Stability Study of a Modified P-Cresol in Thermal Condition

Compound 23 (4.00 mg, 0.0141 mmol) was heated at 120° C. for 1 h according to literature. The recovery of 23 was 4.00 mg (quant.). The decomposition wasn't detected by $^1H$ NMR.

Example 65

Optimization of Tyrosine Modification with PTAD: General Procedure

To a solution of tyrosine 24 (4.73 mg, 0.020 mmol, 1.0 equivalents) in aqueous solvent (0.5 mL)—$CH_3CN$ (0.5 mL) was added the 0.5 M solution of PTAD 25 (0.044 mL, 0.022 mmol, 1.1 equivalents) in $CH_3CN$ at room temperature. The final concentration of tyrosine 24 was adjusted to 2 or 20 mM. The resulting solution was stirred at room temperature for 30 minutes. After the reaction, the reaction mixture was acidified with 12N HCl (0.083 mL) not to generate Na salt of 26 and then concentrated in vacuo. The obtained crude organic materials were dissolved in DMSO-d6 and were analyzed by 300 MHz $^1H$ NMR to determine the conversion. The conversion was calculated by comparison of the areas of aromatic signals. Occasionally, the broad peak derived from phosphoric acid was overlapped on aromatic signals depended on concentration of solvent. In this case, the comparison of the areas of methyl signals also could give the conversion.

Example 66

Effect of Buffer Concentration

Figure 23:
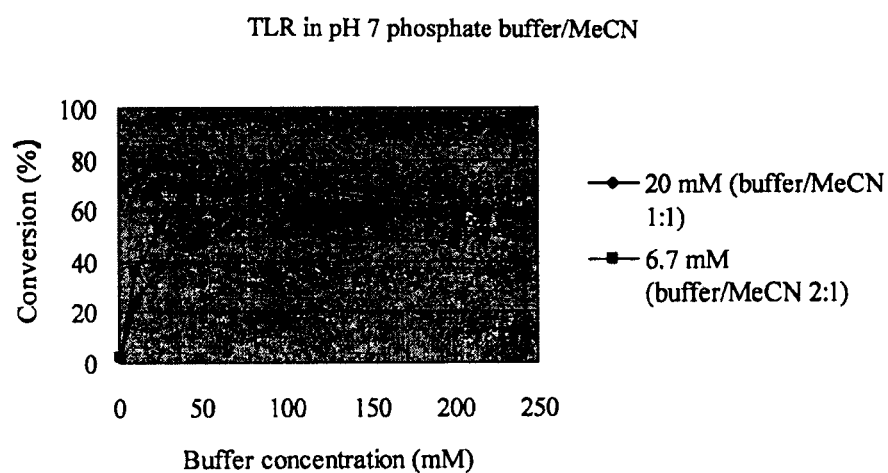

The reactions in pH 7 100 mM sodium phosphate buffer and the calculations of their conversion were performed according to the procedure in Example 65. The results are shown in FIG. 23.

Example 67

Synthesis of 1-(4-hydroxyphenyl)-4-phenyl-1,2,4-triazolidine-3,5-dione (27)

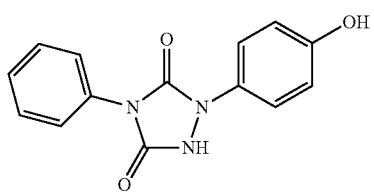

To a solution of phenol (11.3 mg, 0.120 mmol) in 100 mM pH 7.0 $NaH_2PO_4/Na_2HPO_4$ buffer (3.0 mL)-$CH_3CN$ (3.0 mL) was slowly dropped the 0.3 M solution of PTAD 17a (0.442 mL, 0.132 mmol) in $CH_3CN$ at room temperature. The resulting solution was stirred at room temperature for 30 minutes. The reaction mixture was acidified with 1M HCl and extracted with ethyl acetate twice. The organic layer was dried over $Na_2SO_4$ and concentrated in vacuo. The obtained crude material was purified by flash column chromatography (ethyl acetate) to give para-adduct 27 (4.8 mg, 15%) and para-ortho-di-adduct 27' (10.1 mg, 19%) as a white solid. $^1$H NMR (300 MHz, DMSO-d6): δ 11.35 (br, 1H), 9.60 (s, 1H), 7.53-7.35 (m, 7H), 6.83 (m, 2H), $^{13}$C NMR (75 MHz, DMSO-d6): δ 156.11, 152.73, 150.41, 132.22, 129.22, 128.78, 128.66, 127.19, 122.99, 116.22. HRMS: calcd for $C_{14}H_{11}N_3O_3$ (MH$^+$) 270.0873. found 270.0873.

Example 68

Synthesis of 2,4-di(4-phenyl-1,2,4-triazolidine-3,5-dione)-phenol (27')

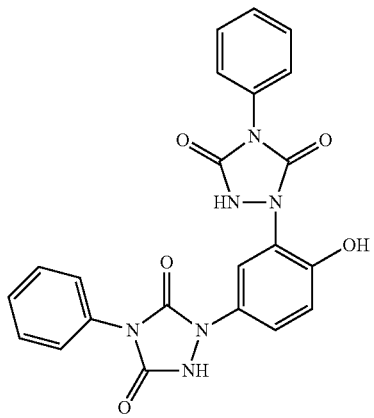

$^1$H NMR (300 MHz, Methanol-d4): 8.04 (d, J=3.0 Hz, 1H), 7.60 (dd, J=2.1, 9.0 Hz, 1H), 7.50-7.33 (m, 10H), 6.96 (d, J=9.0 Hz, 1H). $^{13}$C NMR (75 MHz, Methanol-d4): δ 155.53, 155.37, 150.97, 150.43, 146.23, 133.51, 133.31, 130.63, 129.05, 128.75, 128.67, 127.52, 127.31, 126.56, 125.23, 118.07, 114.30. HRMS: calcd for $C_{22}H_{16}N_6O_5$ (MH$^+$) 445.1255. found 445.1239.

Example 69

Synthesis of 1-(4-hydroxy-3-methylphenyl)-4-phenyl-1,2,4-triazolidine-3,5-dione (28)

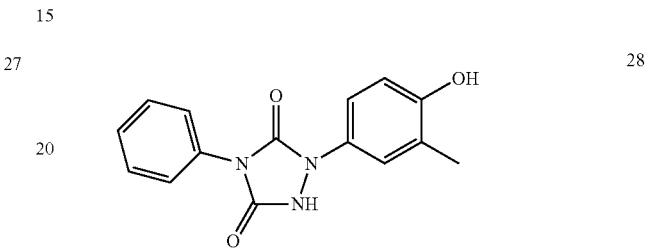

Compound 28 and 28' were prepared from o-cresol in the same manner of compound 27, and was obtained as white solids (11% and 24%). $^1$H NMR (300 MHz, DMSO-d6): δ 11.32 (br s, 1H), 9.51 (s, 1H), 7.50-7.47 (m, 4H), 7.41 (m, 1H), 7.29 (d, J=2.4 Hz, 1H), 7.19 (dd, J=2.4, 8.9 Hz, 1H), 6.82 (d, J=8.7 Hz, 1H), 2.13 (s, 3H). $^{13}$C NMR (75 MHz, DMSO-d6): δ 154.34, 152.63, 150.35, 132.34, 129.55, 127.15, 125.27, 124.02, 120.33, 115.30, 16.76. HRMS: calcd for $C_{15}H_{13}N_3O_3$ (MH$^+$) 284.1030. found 284.1028.

Example 70

Synthesis of 2,4-di(4-phenyl-1,2,4-triazolidine-3,5-dione)-6-methylphenol (28')

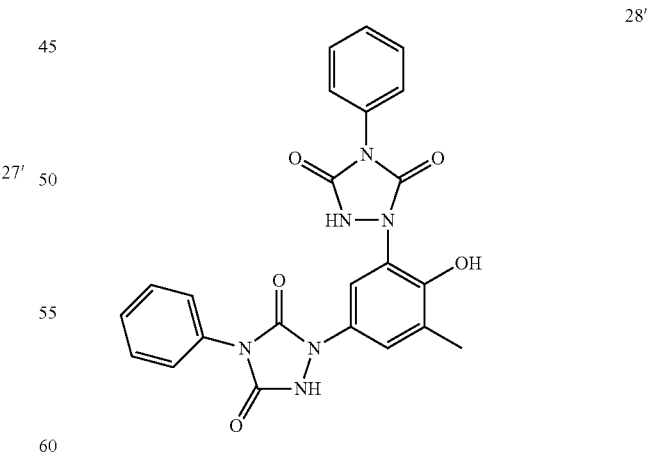

$^1$H NMR (300 MHz, Methanol-d4): δ 7.87 (s, 1H), 7.51-7.30 (m, 11H), 2.27 (s, 3H). $^{13}$C NMR (75 MHz, Methanol-d4): δ 155.41, 155.21, 150.72, 150.28, 133.52, 133.37, 129.68, 128.69, 128.62, 127.44, 127.25, 126.57, 126.53, 126.38, 126.07, 119.28, 111.54, 15.71. HRMS: calcd for $C_{23}H_{18}N_6O_5$ (MH$^+$) 459.1411. found 459.1432.

Example 71

Synthesis of 1-(3-chloro-4-hydroxyphenyl)-4-phenyl-1,2,4-triazolidine-3,5-dione (29)

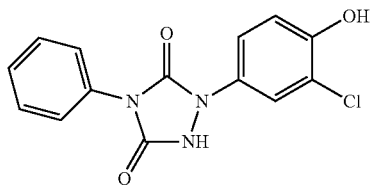

Compound 29 and 29' were prepared from 2-chlorophenol in the same manner of compound 27, and was obtained as white solids (11% and 24%). $^1$H NMR (300 MHz, Methanol-d4): δ 7.60 (d, J=2.4 Hz, 1H), 7.52-7.41 (m, 5H), 7.38 (dd, J=2.7, 8.9 Hz, 1H), 6.99 (d, J=8.8 Hz, 1H). $^{13}$C NMR (75 MHz, Methanol-d4): δ 153.15, 151.83, 150.55, 131.58, 128.97, 128.86, 128.37, 126.38, 122.42, 120.78, 120.38, 116.52. HRMS: calcd for $C_{14}H_{10}ClN_3O_3$ (MH$^+$) 304.0483. found 304.0498.

Example 72

Synthesis of 2,4-di(4-phenyl-1,2,4-triazolidine-3,5-dione)-6-chlorophenol (29')

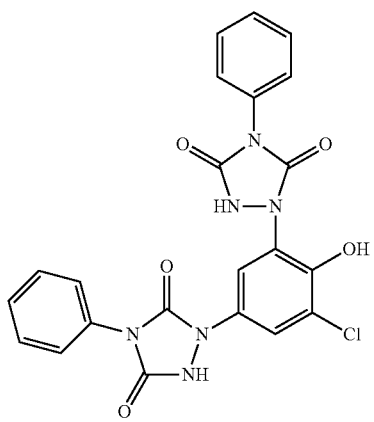

$^1$H NMR (300 MHz, Methanol-d4): δ 8.09 (br s, 1H), 7.79 (br s, 1H), 7.58-7.41 (m, 8H), 7.38-7.32 (m, 2H). $^{13}$C NMR (75 MHz, DMSO-d6): δ 154.06, 153.49, 150.52, 150.50, 135.24, 134.99, 131.54, 128.96, 128.87, 127.29, 126.79, 126.51, 126.29, 126.22, 121.06, 114.33, 109.22. HRMS: calcd for $C_{22}H_{15}ClN_6O_5$ (MH$^+$) 479.0865. found 479.0874.

Example 73

Synthesis of 1-(4-hydroxy-3,5-dimethylphenyl)-4-phenyl-1,2,4-triazolidine-3,5-dione (30)

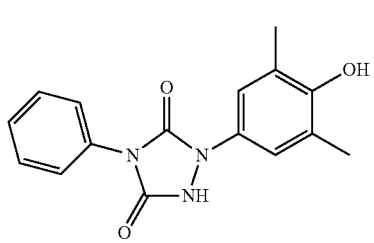

Compound 30 was prepared from 2,6-dimethylphenol in the same manner of compound 27, and was obtained as white solids (61%). $^1$H NMR (300 MHz, DMSO-d6): δ 11.32 (br s, 1H), 8.42 (s, 1H), 7.53-7.39 (m, 5H), 7.14 (d, J=1.8 Hz, 1H). $^{13}$C NMR (75 MHz, DMSO-d6): δ 152.07, 151.38, 129.58, 127.13, 125.61, 121.94, 121.48, 17.43. HRMS: calcd for $C_{16}H_{15}N_3O_3$ (MH$^+$) 298.1186. found 298.1184.

Example 74

Synthesis of 1-(4-hydroxy-2-methylphenyl)-4-phenyl-1,2,4-triazolidine-3,5-dione (31)

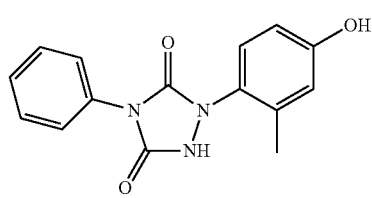

Compound 31 was prepared from 2,6-dimethylphenol in the same manner of compound 27, and was obtained as white solids (77%). $^1$H NMR (300 MHz, DMSO-d6): δ 11.22 (br s, 1H), 9.78 (s, 1H), 7.50-7.49 (m, 4H), 7.40 (m, 1H), 7.25 (d, J=8.4 Hz, 1H), 6.71 (d, J=2.4 Hz, 1H), 6.68 (dd, J=2.4, 8.7 Hz, 1H), 2.19 (s, 3H). $^{13}$C NMR (75 MHz, DMSO-d6): δ 158.65, 152.58, 138.57, 132.52, 129.57, 126.99, 126.51, 117.72, 114.19, 18.17. HRMS: calcd for $C_{15}H_{13}N_3O_3$ (MH$^+$) 284.1030. found 284.1027.

Example 75

Synthesis of 1-(2-hydroxy-5-methylphenyl)-4-phenyl-1,2,4-triazolidine-3,5-dione (32)

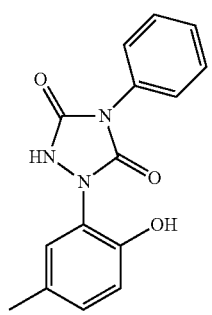

Compound 32 was prepared from p-cresol in the same manner of compound 27, and was obtained as white solids (60%).

Example 76

Synthesis of 1-(2-hydroxy-5-methoxyphenyl)-4-phenyl-1,2,4-triazolidine-3,5-dione (33)

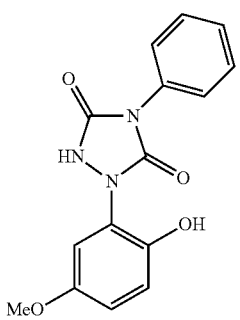

33

Compound 33 was prepared from p-anisolel in the same manner of compound 27, and was obtained as white solids (61%). $^1$H NMR (300 MHz, Methanol-d4): δ 7.53-7.41 (m, 4H), 7.40 (m, 1H), 7.16 (dd, J=1.5, 2.9 Hz, 1H), 6.88 (d, J=9.6 Hz, 1H), 6.80 (dd, J=3.0, 9.0 Hz, 1H), 3.75 (s, 3H). $^{13}$C NMR (75 MHz, Methanol-d4): δ 153.19, 152.28, 153.90, 147.13, 131.91, 128.95, 128.26, 126.40, 123.28, 117.55, 116.43, 112.75, 55.16. HRMS: calcd for $C_{15}H_{13}N_3O_4$ (MH$^+$) 300.0979. found 300.0985.

Example 77

Synthesis of 1-(2-hydroxy-5-chlorophenyl)-4-phenyl-1,2,4-triazolidine-3,5-dione (34)

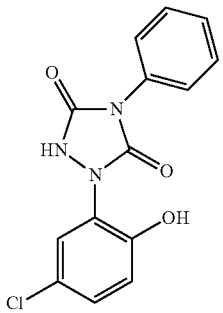

34

Compound 34 was prepared from 4-chlorophenol in the same manner of compound 27, and was obtained as white solids (56%). $^1$H NMR (300 MHz, Methanol-d4): δ 7.75 (d, J=3.0 Hz, 1H), 7.52-7.46 (m, 4H), 7.38 (m, 1H), 7.08 (dd, J=1.8, 8.7 Hz, 1H), 6.88 (d, J=8.7 Hz, 1H). $^{13}$C NMR (75 MHz, DMSO-d6): δ 153.70, 152.32, 132.28, 129.63, 128.93, 128.19, 127.12, 126.41, 126.23, 124.62, 123.70, 118.20. HRMS: calcd for $C_{14}H_{10}ClN_3O_3$ (MH$^+$) 304.0483. found 304.0487.

Example 78

Synthesis of 1-(2-hydroxynaphtyl)-4-phenyl-1,2,4-triazolidine-3,5-dione (35)

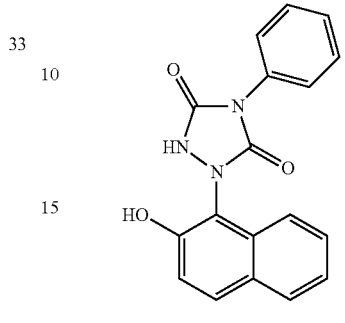

35

Compound 35 was prepared from 2-naphthol in the same manner of compound 27, and was obtained as white solids (89%). $^1$H NMR (300 MHz, DMSO-d6): δ 10.94 (br s, 1H), 7.95 (d, J=9.0 Hz, 1H), 7.89 (d, J=8.1 Hz, 1H), 7.80 (d, J=8.4 Hz, 1H), 7.58-7.50 (m, 5H), 7.44-7.35 (m, 2H), 7.27 (dd, J=2.4, 9.0 Hz, 1H). $^{13}$C NMR (75 MHz, DMSO-d6): δ 154.39, 152.93, 152.16, 133.29, 132.99, 132.18, 129.59, 128.77, 128.58, 128.45, 128.29, 126.88, 124.19, 121.90, 119.38, 114.74. HRMS: calcd for $C_{18}H_{13}N_3O_3$ (MH$^+$) 320.103. found 320.1032.

Example 79

Synthesis of 6-hydroxy-5-(4-phenyl-1,2,4-triazolidine-3,5-dione)-quinoline (36)

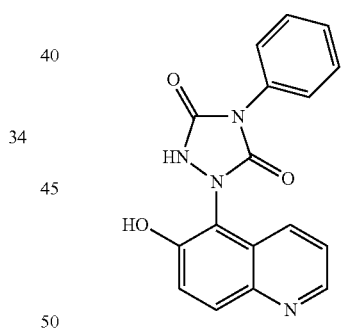

36

To a solution of 6-quinolinol (8.7 mg, 0.060 mmol) in 100 mM pH 7.0 NaH$_2$PO$_4$/Na$_2$HPO$_4$ buffer (1.5 mL)-CH$_3$CN (1.5 mL) was slowly dropped the 0.3 M solution of PTAD 17a (0.220 mL, 0.066 mmol) in CH$_3$CN at room temperature. The resulting solution was stirred at room temperature for 30 minutes. The reaction mixture was acidified with AcOH 500 μL and concentrated in vacuo. The obtained crude material was purified by flash column chromatography (20% methanol in CH$_2$Cl$_2$) to give 36 (16.9 mg, 88%) as a thin yellow solid. $^1$H NMR (300 MHz, DMSO-d6): δ 11.07 (br, 1H), 8.76 (dd, J=1.5, 4.2 Hz, 1H), 8.30 (d, J=8.6 Hz, 1H), 8.05 (d, J=9.2 Hz, 1H), 7.58-7.50 (m, 6H), 7.41 (m, 1H). $^{13}$C NMR (75 MHz, DMSO-d6): δ 154.45, 153.09, 152.34, 148.53, 143.40, 133.15, 132.33, 129.58, 128.57, 128.48, 126.88, 123.17, 122.74, 114.38. HRMS: calcd for $C_{17}H_{12}N_4O_3$ (MH$^+$) 321.0982. found 321.0986.

Example 80

Synthesis of 6-hydroxy-5-(4-methyl-1,2,4-triazolidine-3,5-dione)-quinidine (37)

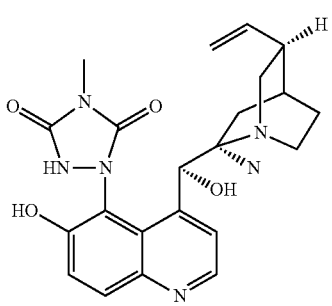

37

To a solution of deprotected quinidine (18.6 mg, 0.060 mmol) in 100 mM pH 7.0 $NaH_2PO_4/Na_2HPO_4$ buffer (1.5 mL)-$CH_3CN$ (1.5 mL) was slowly dropped the 0.3 M solution of MTAD 17b (0.214 mL, 0.66 mmol) in $CH_3CN$ at room temperature. The resulting solution was stirred at room temperature for 30 minutes. The reaction mixture was acidified with AcOH and directly concentrated in vacuo. The obtained crude material was purified by flash column chromatography (20% methanol in $CH_2Cl_2$) to give 5-position-adduct 37 (85%) as a colorless crystals. $^1H$ NMR (300 MHz, DMSO-d6): δ 13.23 (br s, 1H), 10.31 (br s, 1H), 8.51 (d, J=4.2 Hz, 1H), 7.95 (d, J=9.1 Hz, 1H), 7.88 (br s, 1H), 7.47 (d, J=9.3 Hz, 1H), 7.21 (br s, 1H), 6.03 (br s, 1H), 5.69 (m, 1H), 4.99 (s, 1H), 4.94 (d, J=8.8 Hz, 1H), 3.67 (m, 1H), 3.52 (m, 1H), 3.33-2.90 (m, 6H), 2.42 (m, 1H), 1.62 (m, 2H), 1.44-1.33 (m, 2H). $^{13}C$ NMR (75 MHz, DMSO-d6+$CDCl_3$): δ 158.34, 154.87, 146.39, 144.38, 143.50, 136.63, 131.86, 129.02, 128.98, 126.24, 124.99, 121.45, 120.97, 120.12, 116.48, 115.23, 66.64, 59.95, 37.23, 27.58, 25.58, 22.58, 18.64. HRMS: calcd for $C_{22}H_{25}N_5O_4$ ($MH^+$) 424.1979. found 424.1968.

Example 81

Synthesis of 6-hydroxy-5-(4-methyl-1,2,4-triazolidine-3,5-dione)-quinidine (38)

38

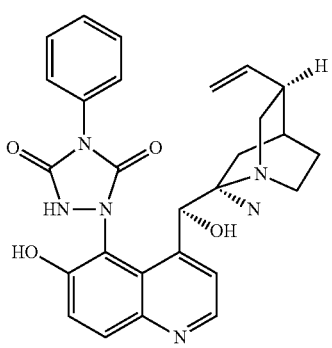

Compound 38 was prepared from deprotected quinidine with 0.3 M PTAD 17a in a similar manner to that described for the preparation of 37, (88%, colorless crystals). $^1H$ NMR (300 MHz, Methanol-d4): δ 8.52 (d, J=4.5 Hz, 1H), 8.05 (d, J=8.7 Hz, 1H), 7.74 (dd, J=2.2, 7.4 Hz, 2H), 7.56 (d, J=9.1 Hz, 1H), 7.51 (d, J=4.2 Hz, 1H), 7.40-7.38 (m, 3H), 6.70 (d, J=2.4 Hz, 1H), 5.79 (m, 1H), 5.10 (d, J=5.7 Hz, 1H), 5.06 (d, J=0.7 Hz, 1H), 4.08 (m, 1H), 3.63 (m, 1H), 3.38-3.23 (m, 1H), 2.99 (m, 1H), 2.50 (m, 1H), 1.74-1.61 (m, 4H), 0.48 (m, 1H). $^{13}C$ NMR (75 MHz, Methanol-d4): δ 157.02, 154.85, 146.51, 144.41, 143.49, 136.61, 133.77, 131.95, 128.83, 128.31, 127.73, 124.97, 121.28, 116.12, 115.67, 66.68, 59.38, 48.89, 42.55, 37.04, 27.58, 22.41, 22.30, 18.61. HRMS: calcd for $C_{27}H_{27}N_5O_4$($MH^+$) 486.2136. found 486.2132.

While the present disclosure has been particularly shown and described with reference to several embodiments thereof, it will be understood by those of ordinary skill in the art that various changes in form and details may be made thereto without departing from the principles and spirit of the present disclosure, the proper scope of which is defined in the following claims and their equivalents.

What is claimed is:
1. A method of chemoselectively modifying a moiety containing the amino acid tyrosine, the method comprising the step of reacting a compound of Formula X with a compound of Formula XI to provide a compound of Formula XII, thereby modifying the moiety containing the amino acid tyrosine:

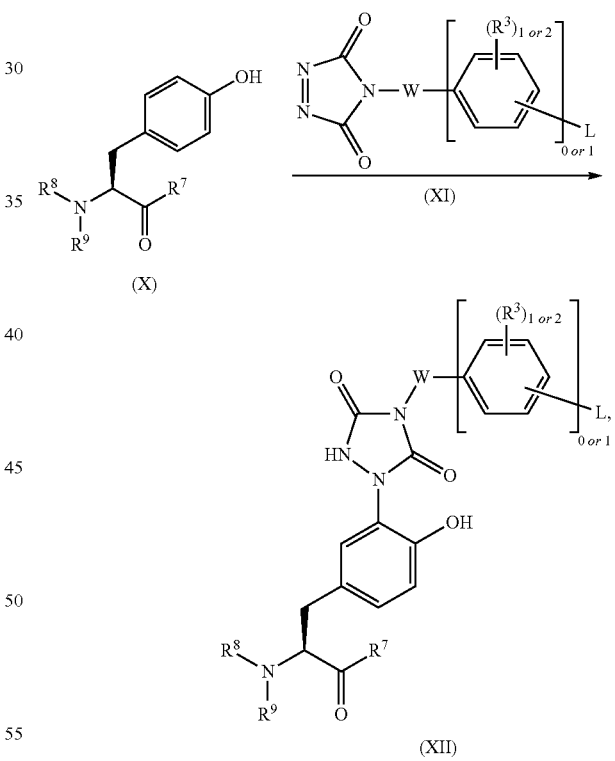

wherein:
W is independently a direct bond or is O;
$R^3$ is independently hydrogen, halogen, carboxyl, cyano, nitro, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy; substituted or unsubstituted alkylaryl, or substituted or unsubstituted alkylheteroaryl, or two R³ groups form a cyclic or heterocyclic ring, wherein each R³ is optionally independently substituted with 1 to 3 groups selected from halogen, carboxyl, cyano, nitro, amino, alkyl, alkenyl, alkynyl, perfluoroalkyl, thioalkyl, alkoxy, aryloxy, aryl, alkylaryl, heteroaryl, and alkylheteroaryl;

L is independently H, $N_3$, $CH_3$, C≡CH, C≡$CN_3$, CH=$CHN_3$, $CH_2CH_2N_3$, $O(CH_2)N_3$, $C_6H_5$, $COCH_3$, $OCH_2$C≡CH, $OCH_2COCH_3$, $OCOCF_3$, or X—[$CH_2CH_2$—Y]$_n$—($CH_2$)$_q$—$N_3$;

X and Y are each independently $CH_2$, O, NH, S, NHCO or CONH;

n and q are each independently an integer from 0 to 12;

$R^7$, $R^8$ and $R^9$ are each independently hydrogen, hydroxyl, amino, substituted or unsubstituted alkyl, substituted or unsubstituted thioalkyl, perfluoroalkyl, substituted or unsubstituted alkoxy, substituted or unsubstituted aryl, substituted or unsubstituted aryloxy, substituted or unsubstituted heteroaryl, substituted or unsubstituted heteroaryloxy, substituted or unsubstituted alkylaryl, substituted or unsubstituted alkylheteroaryl, or $R^7$, $R^8$ and $R^9$ are in a tyrosine residue of a peptide or a protein.

2. The method of claim 1, wherein the compound of Formula X has Formula XIII, XIV, XV, or XVI:

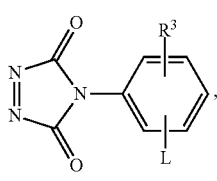
(XIII)

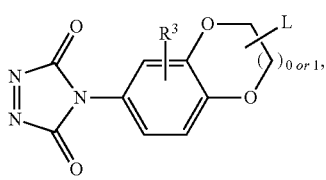
(XIV)

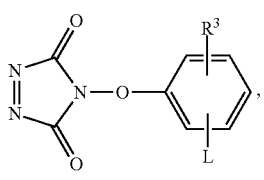
(XV)

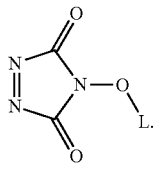
(XVI)

3. The method of claim 1, wherein the compound of Formula XI has Formula XVII:

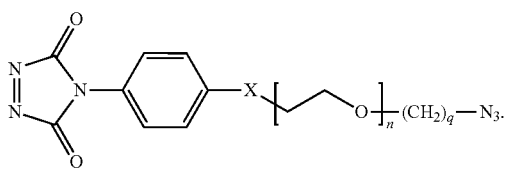
(XVII)

4. The method of claim 3, wherein the compound of Formula XVII has Formula XVIII or Formula XIX:

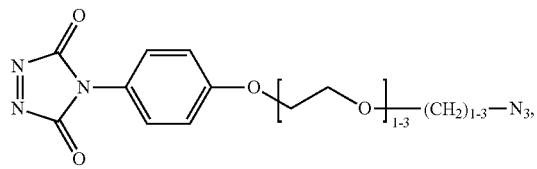
(XVIII)

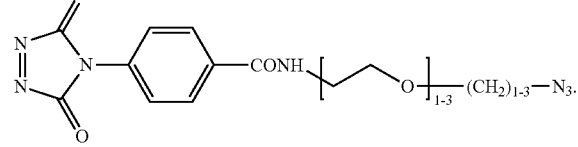
(XIX)

5. The method of claim 1, wherein the compound of Formula XI is any one of the following compounds:

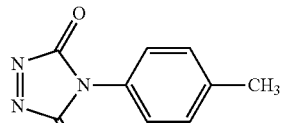

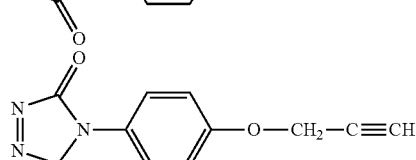

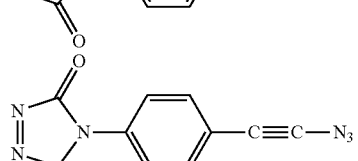

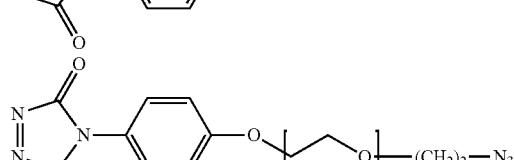

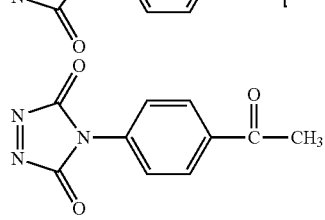

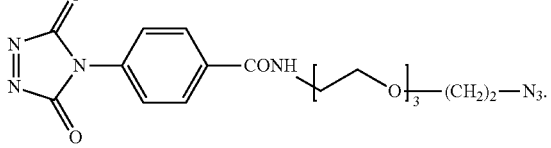

6. The method of claim 1, wherein the reaction occurs in an aqueous media at a pH between 2 and 10.

7. The method of claim 6, wherein the aqueous media is a phosphate buffer at about a pH of 7.4.

8. The method of claim 1, wherein the reaction occurs in a mixed organic/aqueous media.

* * * * *